(12) United States Patent
Cowsert et al.

(10) Patent No.: US 6,743,909 B2
(45) Date of Patent: Jun. 1, 2004

(54) ANTISENSE MODULATION OF PTPN12 EXPRESSION

(75) Inventors: Lex M. Cowsert, San Mateo, CA (US); Kenneth W. Dobie, Del Mar, CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 16 days.

(21) Appl. No.: 10/172,911

(22) Filed: Jun. 17, 2002

(65) Prior Publication Data

US 2003/0232434 A1 Dec. 18, 2003

(51) Int. Cl.$^7$ .................. C12N 15/85; A61K 48/00; C12Q 1/68; C07H 21/04
(52) U.S. Cl. .................. 536/24.5; 435/91.1; 435/325; 435/375; 435/366; 536/23.1; 536/24.3; 536/24.33; 514/44
(58) Field of Search .................. 435/375, 6, 91.1, 435/325; 536/24.1, 24.5, 23.1, 24.3, 24.33; 514/44

(56) References Cited

U.S. PATENT DOCUMENTS 5,801,154 A * 9/1998 Baracchini et al. ............ 514/44
6,087,109 A * 7/2000 Waldman ........................ 435/6

FOREIGN PATENT DOCUMENTS

WO     WO 98/54318     * 5/1998

OTHER PUBLICATIONS

Davidson et al. PTP–PEST, a scaffold protein tyrosine phosphatase, negatively regulates lymphocyte activation by targeting a unique set of substrates. EMBO Journal, 2001. vol. 20:3414–3426.*

Fritz et al. Cationic Polystyrene Nonoparticles: Preparation and Characterization of a Model Drug Carrier System for Antisense Oligonucleotides. Journal of Colloid and Interface Science, 1997; 195:272–288.*

Takekawa et al. Chromosomal localization of the protein tyrosine phosphatase G1 gene and characterizationof the aberrant transcripts in human colon cancer cells. FEBS Letters, 1994 vol. 339:222–228.*

Charest et al., *Coupling of the murine protein tyrosine phosphatase PEST to the epidermal growth factor (EGF) receptor through a Src homology 3 (SH3) domain–mediated association with Grb2*, Oncogene, 1997, 14:1643–1651.

Cool et al. , *cDNA isolated from a human T–cell library encodes a member of the protein–tyrosine–phosphatase family*, Proc. Natl. Acad. Sci. U S A, 1989, 86:5257–5261.

Garton et al., *Association of PTP–PEST with the SH3 domain of p130cas; a novel mechanism of protein tyrosine phosphatase substrate recognition*, Oncogene, 1997, 15:877–885.

Garton et al., *Identification of p130cas as a substrate for the cytosolic protein tyrosine phosphatase PTP–PEST*, Mol. Cell Biol., 1996, 16:6408–6418.

Goldstein et al., *Regulation of the insulin signalling pathway by cellular protein– tyrosine phosphatases*, Mol. Cell. Biochem., 1998, 182:91–99.

Nishiya et al., *Hic–5, a paxillin homolog, binds to the protein–tyrosine phosphatase PEST (PTP–PEST) through its LIM 3 domain*, J. Biol. Chem., 1999, 274:9847–9853.

Song et al., *Role of paxillin in metabolic oxidative stress––induced cytoskeletal reorganization: involvement of SAPK signal transduction pathway and PTP–PEST gene expression*, Free Radical Biol. Med., 2000, 29:61–70.

Takekawa et al., *Chromosomal localization of the protein tyrosine phosphatase G1 gene and characterization of the aberrant transcripts in human colon cancer cells*, FEBS Lett., 1994, 339:222–228.

Takekawa et al., *Cloning and characterization of a human cDNA encoding a novel putative cytoplasmic protein–tyrosine–phosphatase*, Biochem. Biophys. Res. Commun., 1992, 189:1223–1230.

Yang et al., *Cloning and expression of PTP–PEST. A novel, human, nontransmembrane protein tyrosine phosphatase*, J. Biol. Chem., 1993, 268:6622–6628.

Zhang, *Protein–tyrosine phosphatases: biological function, structural characteristics, and mechanism of catalysis*, Critical Review in Biochemistry and Molecular Biology, 1998, 33:1–52.

* cited by examiner

*Primary Examiner*—Karen A. Lacourciere
*Assistant Examiner*—Terra C. Gibbs
(74) *Attorney, Agent, or Firm*—Licata & Tyrrell P.C.

(57) ABSTRACT

Antisense compounds, compositions and methods are provided for modulating the expression of PTPN12. The compositions comprise antisense compounds, particularly antisense oligonucleotides, targeted to nucleic acids encoding PTPN12. Methods of using these compounds for modulation of PTPN12 expression and for treatment of diseases associated with expression of PTPN12 are provided.

12 Claims, No Drawings

SEQUENCE LISTING

<160> NUMBER OF SEQ ID NOS: 123

<210> SEQ ID NO 1
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 1

```
tccgtcatcg ctcctcaggg                                           20

<210> SEQ ID NO 2
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 2
gtgcgcgcga gcccgaaatc                                           20

<210> SEQ ID NO 3
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 3
atgcattctg cccccaagga                                           20

<210> SEQ ID NO 4
<211> LENGTH: 3160
<212> TYPE: DNA
<213> ORGANISM: H. sapiens
<220> FEATURE:
<220> FEATURE:
<221> NAME/KEY: CDS
<222> LOCATION: (30)...(2372)

<400> SEQUENCE: 4
```

| | | | | | | | | |
|---|---|---|---|---|---|---|---|---|
| agcgaccgca gccgggggga cgcgggagg | atg Met 1 | gag Glu | caa Gln | gtg Val | gag Glu 5 | atc Ile | ctg Leu | agg Arg | 53 |
| aaa Lys | ttc Phe 10 | atc Ile | cag Gln | agg Arg | gtc Val | cag Gln 15 | gcc Ala | atg Met | aag Lys | agt Ser | cct Pro | gac Asp 20 | cac His | aat Asn | ggg Gly | 101 |
| gag Glu 25 | gac Asp | aac Asn | ttc Phe | gcc Ala | cgg Arg 30 | gac Asp | ttc Phe | atg Met | cgg Arg | tta Leu 35 | aga Arg | aga Arg | ttg Leu | tct Ser | acc Thr 40 | 149 |
| aaa Lys | tat Tyr | aga Arg | aca Thr | gaa Glu 45 | aag Lys | ata Ile | tat Tyr | ccc Pro | aca Thr 50 | gcc Ala | act Thr | gga Gly | gaa Glu | aaa Lys 55 | gaa Glu | 197 |
| gaa Glu | aat Asn | gtt Val | aaa Lys 60 | aag Lys | aac Asn | aga Arg | tac Tyr | aag Lys 65 | gac Asp | ata Ile | ctg Leu | cca Pro | ttt Phe 70 | gat Asp | cac His | 245 |
| agc Ser | cga Arg | gtt Val 75 | aaa Lys | ttg Leu | aca Thr | tta Leu | aag Lys 80 | act Thr | cct Pro | tca Ser | caa Gln | gat Asp 85 | tca Ser | gac Asp | tat Tyr | 293 |
| atc Ile | aat Asn 90 | gca Ala | aat Asn | ttt Phe | ata Ile | aag Lys 95 | ggc Gly | gtc Val | tat Tyr | ggg Gly | cca Pro 100 | aaa Lys | gca Ala | tat Tyr | gta Val | 341 |
| gca Ala | act Thr 105 | caa Gln | gga Gly | cct Pro | tta Leu | gca Ala 110 | aat Asn | aca Thr | gta Val | ata Ile | gat Asp 115 | ttt Phe | tgg Trp | agg Arg | atg Met 120 | 389 |
| ata Ile | tgg Trp | gag Glu | tat Tyr | aat Asn 125 | gtt Val | gtg Val | atc Ile | att Ile | gta Val 130 | atg Met | gcc Ala | tgc Cys | cga Arg | gaa Glu 135 | ttt Phe | 437 |
| gag Glu | atg Met | gga Gly | agg Arg 140 | aaa Lys | aaa Lys | tgt Cys | gag Glu | cgc Arg 145 | tat Tyr | tgg Trp | cct Pro | ttg Leu | tat Tyr 150 | gga Gly | gaa Glu | 485 |
| gac Asp | ccc Pro | ata Ile | acg Thr | ttt Phe | gca Ala | cca Pro | ttt Phe | aaa Lys | att Ile | tct Ser | tgt Cys | gag Glu | gat Asp | gaa Glu | caa Gln | 533 |

```
Asp Pro Ile Thr Phe Ala Pro Phe Lys Ile Ser Cys Glu Asp Glu Gln
        155                 160                 165 gca aga aca gac tac ttc atc agg aca ctc tta ctt gaa ttt caa aat    581
Ala Arg Thr Asp Tyr Phe Ile Arg Thr Leu Leu Leu Glu Phe Gln Asn
        170                 175                 180 gaa tct cgt agg ctg tat cag ttt cat tat gtg aac tgg cca gac cat    629
Glu Ser Arg Arg Leu Tyr Gln Phe His Tyr Val Asn Trp Pro Asp His
185                 190                 195                 200 gat gtt cct tca tca ttt gat tct att ctg gac atg ata agc tta atg    677
Asp Val Pro Ser Ser Phe Asp Ser Ile Leu Asp Met Ile Ser Leu Met
                        205                 210                 215 agg aaa tat caa gaa cat gaa gat gtt cct att tgt att cat tgc agt    725
Arg Lys Tyr Gln Glu His Glu Asp Val Pro Ile Cys Ile His Cys Ser
                220                 225                 230 gca ggc tgt gga aga aca ggt gcc att tgt gcc ata gat tat acg tgg    773
Ala Gly Cys Gly Arg Thr Gly Ala Ile Cys Ala Ile Asp Tyr Thr Trp
            235                 240                 245 aat tta cta aaa gct ggg aaa ata cca gag gaa ttt aat gta ttt aat    821
Asn Leu Leu Lys Ala Gly Lys Ile Pro Glu Glu Phe Asn Val Phe Asn
        250                 255                 260 tta ata caa gaa atg aga aca caa agg cat tct gca gta caa aca aag    869
Leu Ile Gln Glu Met Arg Thr Gln Arg His Ser Ala Val Gln Thr Lys
265                 270                 275                 280 gag caa tat gaa ctt gtt cat aga gct att gcc caa ctg ttt gaa aaa    917
Glu Gln Tyr Glu Leu Val His Arg Ala Ile Ala Gln Leu Phe Glu Lys
                        285                 290                 295 cag cta caa cta tat gaa att cat gga gct cag aaa att gct gat gga    965
Gln Leu Gln Leu Tyr Glu Ile His Gly Ala Gln Lys Ile Ala Asp Gly
                300                 305                 310 gtg aat gaa att aac act gaa aac atg atc agc tcc ata gag cct gaa   1013
Val Asn Glu Ile Asn Thr Glu Asn Met Ile Ser Ser Ile Glu Pro Glu
            315                 320                 325 aaa caa gat tct cct cct cca aaa cca cca agg acc cgc agt tgc ctt   1061
Lys Gln Asp Ser Pro Pro Pro Lys Pro Pro Arg Thr Arg Ser Cys Leu
        330                 335                 340 gtt gaa ggg gat gct aaa gaa gaa ata ctg cag cca ccg gaa cct cat   1109
Val Glu Gly Asp Ala Lys Glu Glu Ile Leu Gln Pro Pro Glu Pro His
345                 350                 355                 360 cca gtg cca ccc atc ttg aca cct tct ccc cct tca gct ttt cca aca   1157
Pro Val Pro Pro Ile Leu Thr Pro Ser Pro Pro Ser Ala Phe Pro Thr
                        365                 370                 375 gtc act act gtg tgg cag gac aat gat aga tac cat cca aag cca gtg   1205
Val Thr Thr Val Trp Gln Asp Asn Asp Arg Tyr His Pro Lys Pro Val
                380                 385                 390 ttg cat atg gtt tca tca gaa caa cat tca gca gac ctc aac aga aac   1253
Leu His Met Val Ser Ser Glu Gln His Ser Ala Asp Leu Asn Arg Asn
            395                 400                 405 tat agt aaa tca aca gaa ctt cca ggg aaa aat gaa tca aca att gaa   1301
Tyr Ser Lys Ser Thr Glu Leu Pro Gly Lys Asn Glu Ser Thr Ile Glu
        410                 415                 420 cag ata gat aaa aaa ttg gaa cga aat tta agt ttt gag att aag aag   1349
Gln Ile Asp Lys Lys Leu Glu Arg Asn Leu Ser Phe Glu Ile Lys Lys
425                 430                 435                 440 gtc cct ctc caa gag gga cca aaa agt ttt gat ggg aac aca ctt ttg   1397
Val Pro Leu Gln Glu Gly Pro Lys Ser Phe Asp Gly Asn Thr Leu Leu
                        445                 450                 455 aat agg gga cat gca att aaa att aaa tct gct tca cct tgt ata gct   1445
Asn Arg Gly His Ala Ile Lys Ile Lys Ser Ala Ser Pro Cys Ile Ala
                460                 465                 470
```

```
gat aaa atc tct aag cca cag gaa tta agt tca gat cta aat gtc ggt    1493
Asp Lys Ile Ser Lys Pro Gln Glu Leu Ser Ser Asp Leu Asn Val Gly
        475                 480                 485 gat act tcc cag aat tct tgt gtg gac tgc agt gta aca caa tca aac    1541
Asp Thr Ser Gln Asn Ser Cys Val Asp Cys Ser Val Thr Gln Ser Asn
    490                 495                 500 aaa gtt tca gtt act cca cca gaa gaa tcc cag aat tca gac aca cct    1589
Lys Val Ser Val Thr Pro Pro Glu Glu Ser Gln Asn Ser Asp Thr Pro
505                 510                 515                 520 cca agg cca gac cgc ttg cct ctt gat gag aaa gga cat gta acg tgg    1637
Pro Arg Pro Asp Arg Leu Pro Leu Asp Glu Lys Gly His Val Thr Trp
            525                 530                 535 tca ttt cat gga cct gaa aat gcc ata ccc ata cct gat tta tct gaa    1685
Ser Phe His Gly Pro Glu Asn Ala Ile Pro Ile Pro Asp Leu Ser Glu
        540                 545                 550 ggc aat tcc tca gat atc aac tat caa act agg aaa act gtg agt tta    1733
Gly Asn Ser Ser Asp Ile Asn Tyr Gln Thr Arg Lys Thr Val Ser Leu
    555                 560                 565 aca cca agt cct aca aca caa gtt gaa aca cct gat ctt gtg gat cat    1781
Thr Pro Ser Pro Thr Thr Gln Val Glu Thr Pro Asp Leu Val Asp His
570                 575                 580 gat aac act tca cca ctc ttc aga aca ccc ctc agt ttt act aat cca    1829
Asp Asn Thr Ser Pro Leu Phe Arg Thr Pro Leu Ser Phe Thr Asn Pro
585                 590                 595                 600 ctt cac tct gat gac tca gac tca gat gaa aga aac tct gat ggt gct    1877
Leu His Ser Asp Asp Ser Asp Ser Asp Glu Arg Asn Ser Asp Gly Ala
            605                 610                 615 gtg acc cag aat aaa act aat att tca aca gca agt gcc aca gtt tct    1925
Val Thr Gln Asn Lys Thr Asn Ile Ser Thr Ala Ser Ala Thr Val Ser
        620                 625                 630 gct gcc act agt act gaa agc att tct act agg aaa gta ttg cca atg    1973
Ala Ala Thr Ser Thr Glu Ser Ile Ser Thr Arg Lys Val Leu Pro Met
    635                 640                 645 tcc att gct aga cat aat ata gca gga aca aca cat tca ggt gct gaa    2021
Ser Ile Ala Arg His Asn Ile Ala Gly Thr Thr His Ser Gly Ala Glu
650                 655                 660 aaa gat gtt gat gtt agt gaa gat tca cct cct ccc cta cct gaa aga    2069
Lys Asp Val Asp Val Ser Glu Asp Ser Pro Pro Pro Leu Pro Glu Arg
665                 670                 675                 680 act cct gaa tcg ttt gtg tta gca agt gaa cat aat aca cct gta aga    2117
Thr Pro Glu Ser Phe Val Leu Ala Ser Glu His Asn Thr Pro Val Arg
            685                 690                 695 tcg gaa tgg agt gaa ctt caa agt cag gaa cga tct gaa caa aaa aag    2165
Ser Glu Trp Ser Glu Leu Gln Ser Gln Glu Arg Ser Glu Gln Lys Lys
        700                 705                 710 tct gaa ggc ttg ata acc tct gaa aat gag aaa tgt gat cat cca gcg    2213
Ser Glu Gly Leu Ile Thr Ser Glu Asn Glu Lys Cys Asp His Pro Ala
    715                 720                 725 gga ggt att cac tat gaa atg tgc ata gaa tgt cca cct act ttc agt    2261
Gly Gly Ile His Tyr Glu Met Cys Ile Glu Cys Pro Pro Thr Phe Ser
730                 735                 740 gac aag aga gaa caa ata tca gaa aat cca aca gaa gcc aca gat att    2309
Asp Lys Arg Glu Gln Ile Ser Glu Asn Pro Thr Glu Ala Thr Asp Ile
745                 750                 755                 760 ggt ttt ggt aat cga tgt gga aaa ccc aaa gga cca aga gat cca cct    2357
Gly Phe Gly Asn Arg Cys Gly Lys Pro Lys Gly Pro Arg Asp Pro Pro
            765                 770                 775 tca gaa tgg aca tga ttcagggagc tagaagacac tttaagttat actggaaaat    2412
Ser Glu Trp Thr
            780
```

-continued

```
tcaggtgcca ctgaaagcca gatttatagt attccatctt taatatgtgg gactaacagc    2472
agtgtagatt gttaccttaa tattttttgc tgggaccatc tacctgcctt atactacact    2532
taggaaaaag tattacatat ggtttatttt gaaacttcaa gtattattgc cttaatgtct    2592
cttaaccctg ttacacgctg cttgtagaca tgttaatata gtaataccct tatgatatat    2652
tgagtttaag gactactctt tttctgtttt atcatgtatg cattattttg tatatgtaca    2712
gggcaagtag gtatataatt tgataaagtt gcaattgaaa tattattaac agaagatgta    2772
agaaatttct gcatggtcta aatctttgtg tactttattt gtaaattatt tgccctggag    2832
ttttagaaaa tagtttctga attttaaact tgctggattc atgcagccag ctttgcaggt    2892
tatcagagat caaagattgt aataataatt ttgtaaattg taagcaaaaa gttattttta    2952
tattatatac agtctaattg ttcatcctaa ttgttcctgt tttcatctag tcagagattc    3012
agtaagtgcc ttggaacaat attgaattct cttagcttgt gtgtgtttct ttaatatttg    3072
aactcaagtg ggattagaag actatcaaaa tacatgtatg tttcagatat ttgacctgtc    3132
attaaaaaaa acaaacagtt ttacagtg                                       3160

<210> SEQ ID NO 5
<211> LENGTH: 17
<212> TYPE: DNA
<213> ORGANISM: Artificial Sequence
<220> FEATURE:
<223> OTHER INFORMATION: PCR Primer

<400> SEQUENCE: 5
tgcagccacc ggaacct                                                     17

<210> SEQ ID NO 6
<211> LENGTH: 26
<212> TYPE: DNA
<213> ORGANISM: Artificial Sequence
<220> FEATURE:
<223> OTHER INFORMATION: PCR Primer

<400> SEQUENCE: 6
agtagtgact gttggaaaag ctgaag                                           26

<210> SEQ ID NO 7
<211> LENGTH: 27
<212> TYPE: DNA
<213> ORGANISM: Artificial Sequence
<220> FEATURE:
<223> OTHER INFORMATION: PCR Probe

<400> SEQUENCE: 7
atccagtgcc acccatcttg acacctt                                          27

<210> SEQ ID NO 8
<211> LENGTH: 19
<212> TYPE: DNA
<213> ORGANISM: Artificial Sequence
<220> FEATURE:
<223> OTHER INFORMATION: PCR Primer

<400> SEQUENCE: 8
gaaggtgaag gtcggagtc                                                   19

<210> SEQ ID NO 9
<211> LENGTH: 20
<212> TYPE: DNA
```

<213> ORGANISM: Artificial Sequence
<220> FEATURE:
<223> OTHER INFORMATION: PCR Primer

<400> SEQUENCE: 9
gaagatggtg atgggatttc                                                    20

<210> SEQ ID NO 10
<211> LENGTH: 20
<212> TYPE: DNA
<213> ORGANISM: Artificial Sequence
<220> FEATURE:
<223> OTHER INFORMATION: PCR Probe

<400> SEQUENCE: 10
caagcttccc gttctcagcc                                                    20

<210> SEQ ID NO 11
<211> LENGTH: 137000
<212> TYPE: DNA
<213> ORGANISM: Homo sapiens
<220> FEATURE:

<400> SEQUENCE: 11
gtatatgttg taaatcgaag gtatcatagg ctttatgatt aacagttcaa attctaaaat        60
ttaaatgcct gtgtctaaat gtcaactctg ccacttgcat gctatgtgac cttggatatc       120
tgtaaatcag aatgaatgat aattaattta tagagttgtt atatgtatta attcaaatga       180
aataatgcat ataaaggatc aaaaatgtta gctactatta ccattcatta actatagaaa       240
tcagtcatct aacattgcat ttagtggcag accaacatac aagagaacat tgttctcttt       300
ctacttcttc accactcctg tcttattttg gtctgcaaaa tatcctaagg tggaggtaca       360
tcttcattag gccatgggat cctttctttg atgggacttt aacaagcatc tttgaagaaa       420
cactcatgaa actaagttta taacaatgac ttttttttgtt aagtgatgaa cccagcaata       480
tctgtttgct gccttttaaa aaagtctaat gagcttacct gtagcaaata aaaacacaaa       540
gagctgaccc aaggacattg aaggcaactt ctcaacagga aaatctagac aaaaattatt       600
attattatta ttattattat ttttgagaca gggtctcact gttgcacagg ctggagtaca       660
ggggtgcgat cttggcttat tgcattctct gcttcccagg ctcgggtgat tcttccacct       720
cagcctcccc agtagctggg actacaggca agcaccacac aatcagctag ttttaaaaaa       780
atttttttta cagagatgag gtttcaccac gttggccagg ctggtctcaa actcctggac       840
tcacgcagtc cgcctgcctc agcctcccaa aatgctggga ttacaggcgt gagccactgc       900
tccggcctca ctctaattaa ttttaaaacc tcatcacatt ggcagcattc tttttcaaaa       960
atgataacct tgtgtacgc ccaatgcaga ataatccatt catttgtaat tactttctta      1020
aaaacctgta ttatgttagt agattcctac ccattcttca aagcacagct aagataatat      1080
ctcccctgtg agactggcac caatatttct tccatttccc agaaagaact agtccctccc      1140 tccatttta cttaaatggt aactcagaat tagcagtatt tatttataca gcacttaaca      1200
tcaacaatca tttccttgtt tgtttgtttt ctcctgttgg aatggagctt acaaaggatg      1260
tcttattctg cagaatattc tttgtattta gttttggtcc aactgatttc tattttgtgc      1320
ttggcctgcc ctcctttgta gagtctatgc ttttcccatt gggacatct ttcccttttt      1380 tgaaagaaag attgaaacta caacttggct tcttgagtct gtcaactaca tggcttattt      1440
attcattttc ttaactcaac ttgcttctta gcacacattt attttagatg gtgacccttta      1500

-continued

| | | | | |
|---|---|---|---|---|
| tttttttttat | ttttatttttt | attttttgag | acagggtctt | gttctgttgc ccaggctgga | 1560 |
| gtgcagtggt | gtcgcagctc | actgcagccc | cgacctcctg | ggctcaagca atcttcccac | 1620 |
| ctcagcctcc | ttgagtagct | aggactacag | gcatatgcca | ccatgcctgg ctaatttttt | 1680 |
| tattttttaat | ttttttgtag | agatgggttt | ctttctgctg | cccaggctgt tctcaaattc | 1740 |
| ctgggctcag | gcaacccacc | cactacagcc | tcccaaagtg | ctgggattgc aactgtgagc | 1800 |
| caccacgcct | ggactgatgg | tgacattttt | aaaagcctct | tggctttctt tagtttggaa | 1860 |
| attgaggaag | agatggttag | ttgactcttt | acaccctccc | tcgtatgaca atagaaactc | 1920 |
| caattttcag | tgagcaattg | atgacccaag | gaaaagactg | cttttctcag caactcctgc | 1980 |
| aaatgagtat | gaccctgtaa | ctaatttatt | gccaatgata | gatgcgtgtc aatgccctcc | 2040 |
| acccaaaaat | cacaggagta | tgctagtggt | tgaataaggt | gggtttactc cttgttatga | 2100 |
| gagagaacat | gcaccatggg | gaactatggg | tgtctcagta | aaaagagtat tagaaaggct | 2160 |
| ttaaataaga | tttgccttgc | tttaggtggt | tttaggaagg | gctgaaggaa ccagggcttt | 2220 |
| actctggatt | ggatgccatc | aggaagcaag | ggcaattcta | tgactgggta tattaaaaca | 2280 |
| ttgtcgggga | aatgaaacat | agtcaaagct | gtaattggta | acaaaccata ttaggcaaaa | 2340 |
| tagggagatg | tttggtcact | ttacagtttg | gacaatgttc | atgttttttgt ctgtattcag | 2400 |
| gcataattat | ggtgtagttt | tgtgtttata | tcgatccatc | atggtcacag aatggctttg | 2460 |
| tcaaatgttg | gtattctttg | caattgcata | tatttaatag | gacaacacca agttttactg | 2520 |
| tgactgctcg | ggcagctctt | agatgtcagg | tgctgttttt | ctcattcatt ttttgagaca | 2580 |
| gcatctccct | ctgtcaccca | ggctggagtg | cagtggcaca | ctcacagctc actgcagcct | 2640 |
| cgacctcctg | ggctcaagtg | atcctcatac | ttcagcctcc | ctagtagctg ggactacagg | 2700 |
| tgtgtgccac | tacacccggc | taattttttat | attttttgta | gagacaaggt ttcactatgt | 2760 |
| tacccaggct | ggccttgaac | ttctgggttc | aagtgatcca | gtcaccttgg cttcccaaag | 2820 |
| tgctgggata | agcatggtga | gccactgtac | ctggccatgc | ttttctcttt cttataggta | 2880 |
| agcaaagtat | ggcagttcat | ggaaaccgtc | tttataagag | agctgatggg tcctttgccc | 2940 |
| ccgattattc | ttttcttcct | tcagacagac | tggaatatgg | ttgtgatggc tggagtagcc | 3000 |
| cagctgaaac | aagaggtgac | cttgggaatg | gaagctacaa | gagtaccagg ccacctcagc | 3060 |
| tctagactaa | gccattgttt | tttgtttttt | tttttttttt | tttttttact cacagctgaa | 3120 |
| gctattcctg | actgatacag | gaatctagtg | gtaagttctt | ttttcagtgg gtttaaggtt | 3180 |
| ggtttcatat | ctttaagctg | gacagattgt | cagataaatg | acttaagagt cagaactaat | 3240 |
| tacctttgta | caaatggaag | gacatcatga | atctgtatca | ttgtaagtaa aatactatga | 3300 |
| cttgatgatg | actatttgct | gagatactgt | gacttttcta | atatatgatg ataataacag | 3360 |
| taatgacact | tatattctcc | acggctgttg | agattaacac | ttttggccat agtacattga | 3420 |
| tttaggtttt | aaaacatgac | actagaaaga | ctaaaataat | taatttaatt aataagttta | 3480 |
| aacatgagaa | aaaacaaact | agttaaattt | actcaatttg | gtcaaaatgt ctgttttcaa | 3540 |
| tatgctatat | cccttgatag | ttttctgtta | cctgaagata | ttttcaagtt gtcttttttat | 3600 |
| tttttttaatt | acagacatac | atagttgttt | tatagtctgt | ggatctgttt ctaatatctg | 3660 |
| ctgtttcctt | tgaatcttgc | ttacagggcc | agacttcctt | atgtacctca atatctttgt | 3720 |
| gcattgctca | ttgtaattga | aaatttgttt | tatttttatt | tggggggggg ggcgggggtta | 3780 |
| ggctccattc | tacaaaacag | aatgaaaagg | ccaagatggg | cgaattacct aaggtcagaa | 3840 |
| gtttgagact | agcctggcca | acatggtgaa | acccgtctc | tacaaaagat cgaaaactca | 3900 |

```
gccaggcatg gtggcaggtg cctgtaatcc cagctactcg tgaggctgag gcaggagaat    3960
cacttgaacc caggaggcag aggttgcagt gagcagagat cacaccactg cactccagcc    4020
tgggtgacaa gagcaagact ccatctcaaa caaaaaaaca aaatatcaac cctggccagg    4080
cacagtggct cacgcctgta atcccagcac tttgggaggc tgaggcaggc ggatcacgag    4140
gtcaggagat caagaccatc ctggctaaca ttggtgaaac cccgtctcta ctaaaaatac    4200
aaaaaattag ccaggcgtgg tggcgggcac ctgtagtccc agctactcag gaggctgagg    4260
caggagaatg gcgtgagcct gggaggcgga gcttgcaatg agctgagatc acgccactgc    4320
actccagcct gggcgacaga gtgagactcc gtctcaaaac aaaaacaaaa acaaaacaaa    4380
aaaacaaccc cattaaaaaa tggtcgagtt tccatggtga gatggtcaac aagcctgtaa    4440
gttcctcagc tacgactacc aggtacctcg ggttcctccc tcctccgaga gaccgccgag    4500
gtgcgggctg tgagagaggg agcgtggagc ctccgaggcc gaggactcgg tcccagtttg    4560
gacagataga agatcctgcc gagtgcctgt gattgcaggc acgcgccgcc acgcctgact    4620
ggttttggtg gagacggggt ttcgctgtgt tggccgggcc ggtctccagc cctaaccgc    4680
gagtgatccg cccgccttgg cctcccgagg tgccgggatt gcagagggag tctcgttcac    4740
tcagtgctca atggtgccca ggctggagtg cagtggcgtg gtctcggctc actacaacct    4800
acacctccca gccgcctgcc ttggcctccc agagtgccga gattgcagcc tctgcccggc    4860
cgccaccccg tctgggaagt gaggagtgtc tctgcctggc cgccatcgt ctgggatgtg    4920
aggagcccct ctgcctggct gcccagtctg gaaagtgagg agcgtctccg cccggccgcc    4980
atcccatcta ggaagtgagg agcgcctctt cccagccgcc atcacatcta ggaagtgagg    5040
agcgtctctg cccggccgcc catcgtctga gatgtgggga gcgcctctgc cccgccgccc    5100
catctgggat gtgaggagcg cctctgcccg gccgagaccc cgtctgggag gtgaggagcg    5160
tctctgcccg gccgccccgt ctgagaagtg aggagaccct ctgcctggca accacccgt    5220
ctgaaaagtg aggagcccct ctgcccggca gccgccccgt ctgggaggtg aggagcctct    5280
ccgcccggca gccaccctgt ccgggaggga ggtgggggg gtcagccccc cgcccggcca    5340
gctgccccat ccgggaggga ggtgggggt cagccccgc ccggccagcc gtgccatccg    5400
ggagggaggt gggggggtca gccccccgcc tggccagccg tgccgtccgg gagggaggtg    5460
gggggtcag ccccctgccc ggccagccgc ccgtccggg aggtgagggg cgcctctgcc    5520
cgcccacccc tactgggaag tgaggagccc ctcagcccgg ccagccaccc cgtccaggag    5580
ggagatgggg ggtcagcccc cccacccggc cagccgcccc gtccgggagg gaggtggggg    5640
ggtcagcccc ccgcctggcc agccgccccg tctgggaggg aggtgggggg gtcagccctc    5700
cgcctggcca gccgcccgt ctgggaggtg aggggcgcct ctgcccggcc gccctactg    5760
ggaagtgagg agccctctg cccggccagc cgccccgtct gggagggagg tgggggggtc    5820
agccccccc ccggccagcc gccctgtccg ggagggaggt gggggggtca gccctccgcc    5880
cagccagccc cccgtctgg gaggtgaggg gcgcctctgc ccggccgccc ctactgggaa    5940
gtgaggagcc cctctgcccg gccagccgcc ccgtccggga gggaggtggg gggtcagcc    6000
ctctgcccgg ccggccgccc cgtccggag gcgagggcg cctctgcccg gccgcccta    6060
ctgggaagtg aggagcccct ctgcccggcc accacccgt ctgggaggtg tgcccaacag    6120
ctcattgaga acgggccagg atgacaatgg cggctttgtg gaatagaaag gcgggaaagg    6180
tggggaaaag attgagaaat cggatggttg ccgtgtctgt gtagaaagaa gtagacatgg    6240
```

```
gagactttc atttttgttct gcactaagaa aaattcttct gccttgggat cctgttgatc      6300 tgtgaccttα cccccaaccc tgtgctctct gaaacatgtg ctgtgtccac tcagggttaa      6360
atggattaag ggcggtgcaa gatgtgcttt gttaaacaga tgcttgaagg cagcatgctc      6420
gttaagagtc atcaccaatc cctgatctca agtaatcagg gacacaaaca ctgcggaagg      6480
ccgcagggtc ctctgcctag gaaaaccaga gacctttgtt cacttgttta tctgctgacc      6540
ttccctccac tactgtccca tgaccctgcc aaatccccct ctgtgagaaa cacccaagaa      6600
ttatcaataa aaaaataaat taaaaaaaaa aatggtcaaa ggacatgaac agagacttct      6660
caaaagaata tacacatgtg gccaacaagc atatgaaaaa cactcagtat caccagttaa      6720
tagagaaatg caaatcaaaa tcaaaaccag ggtgagatac catctcgcac cagtcaaaat      6780 ggctatttt aaaagtgaa aaaataacat gttggtgaag ttgttaagaa aagagaatgc       6840
ttatacactg ctggtggaaa tgtaaattag ttctgccact atggaaatta gtttggagat      6900
ttctcaaaga acttaaaaca gaactaccat tcaacccagt aatctcatta ttgggtatat      6960
atccaaagga atataaatta ttctaccata aagacacatt tcctatctca aaaaaaaaaa     7020 aaaaagaca catgtactca catatacttt gcagcaattt tcacaatggc aaagacatgg      7080
aatcaaccta gatgtccatc aacagtggac tggattaaaa aaatgtggta catatacact      7140
gaggaatact acagagccat aaaaaagaat gaaatcatgt tctttgcagc atgggtgcaa      7200
ctggaggcca ttgtcctaag cgaattaatg caggaacaga aaaccaaacc ccaaatgttc      7260
tcatatatag gtgggagcta aacaatgagt acacatggac acaagaggg gaaaacaag      7320 acactgggtt ttacttgagg gtgaaggatg ggaggagggt gagaagtgaa aaactatcag      7380
gtactatgct caccacgtgg gtgatgaaat catttgtacc ctaaacccca gcaacaaaca      7440
atttacccat gtaacaaacc tgcatgtgta ccccctgcac ctgaaagaaa gtttgaaga      7500 aaaaaatttt actcttacat tgtaagtctt gaaatatttc cttaattat ttttattgct      7560 ttccgtgctt gtattttaga ggtcatgctt ctttcattac attgtaaatg ccaacttttt     7620
gtgaaatttt tttctcgtct ctaatgaatt catagatatg aaaaaagaa ctattgttg      7680 acatcacata gtagcttatg ttattatctt tttcatgaat gtgtcttatt tcctctatta     7740
agtattaaac acctaaagga aatcatgtct tatacatctt tgcattctcc atagtatccc     7800
actcaattta ttggtgggtt aattgtgttt ccaaagtttt gtgaaactct gtgacaatta     7860
tttcaagcat aaaaccagtt tagcaagcat tgtgaaaaat agaacacact aatatgtatg     7920
gaataacagg aagacattgc cacgctatgg ttttccctcc tatatgtact ctacattttg     7980
agtgtgctag atactttaca gaatgaagag ctgattttca tgaagttaag attattcagt     8040
gcctgagtat ccaatttgaa gactacctat gtcttttaga cattatattt cccattaata     8100
cctccagtga atgtcagctg ggaaaatgag aggaaactca agttagctga tggaagcttc     8160
ctattaatag ctctgtagaa aagtatggta gggagtttga aattattatt gaagatgaaa     8220
atgaggaaat acccatagat cgattagctg tacttgagac gtgtttatt aaacatgtac      8280 attctaacga tagtattttt attcagaggg acctttgata aagagaacc tagatgagac     8340 aacaagtaa tttttatatc cagtgaccat acactcctga tttttcagaa cagttcccat     8400
tttaaatatt atgtctgtta ttaatgccca acatgtccta ccatgtatcc tgatttatga     8460
cataaatatg tcacaatatt tataggaaca tttgagacac ttttgaaagg tctcctggtg     8520
aacttcatct aggtacttcc aatagacatt aagtggattt tagcaattgc tccacaatcc     8580
ttcctaagaa attttacaac ttcatataaa catatagaat aaaacctctt gtgctatcca     8640
```

-continued

```
tttggagtta atggaaccac cgttcattca gtgggaaact gagaatcatg agtcctccct    8700
ctcagcctct tcacccagta agtcgctttt tatagcttga atgtttgtat tcccctcaaa    8760
attcatatgc tgaaactcca accccccattg tgatggtatg aggaggtggg gcctttggca   8820
agtaattagg tttagatgaa gtcatgaggg tggaggcccc atgataggat tagtgccctt    8880
ataagaagag gaagggaaac cagagctcct tctctcttta aggatacagt aagaaggtgg    8940
ccatctacaa gccaggaaga aagccctcac caagaattga atctgcttgt gccttgatct    9000
tggactttcc agcttccaga ataatgaaaa ataaatgtct gagtttaagc cacccaggct    9060
atggcatttg gttaaggcag cccgagctaa gacatttcta tatcttgtac catcccttcc    9120
caattggcct caccatttat cctccacagt aagccagaat ggtctctgaa agagcaaata    9180
cgttcatgtt aactccacct taagataatc ttccatgact ccccattgct gcagcagggg    9240
gagtaagctc aaatgtctgc agggatagct aggtaaccta aatatggagg ggtgagcctg    9300
aggagacaga agactagaga atgtacgtct ttttaaagac attcaaattc aagaaaaaaa    9360
aacctacatc aaacaaagaa tatttgtggg caagattcct cctgtggggt gagagtttta    9420
attattttaa cttgttagca tagtagaaca agtatcttca ttatctggct cctataaaca    9480
aagataatct tccgtgactc cccattgctg cagcagggga gtaagctca aatgtctgca    9540
gggatagcta ggtaacctaa atatggaggg gtgagcctga ggagacagaa gactagagaa    9600
tgtacgtctt tttaaagaca ttcaaattca agaaaaaaaa acctacatca aacaaagaat    9660
atttgtgggc aagattcctc ctgtggggtg agagttttaa ttattttaac ttgttagcat    9720
agtagaacaa gtatcttcat tatctggctc ctataaacat acatcatcct ctccaattat    9780
tctcagttgt gtgctcctct ctgaaattgc caagcatttt tgcccatgcc tcttcctctg    9840
tccagaatgt cctactggtg aatttctact cattcttgaa ggcttattac ctctgagaag    9900
ttttccttga tatacctaag ctgaaattag tacttttctt ctgcattcca gaacacatat    9960
tcatatgctg tttagatata caacttatct cactgctgta attagctttt atgtctgttt   10020
catctaaaca ccacacacat agctcatggt gagtgttgaa ttcatcttga tgtccccagc   10080
attttacgtg gtacctacgc acaggcactt ggaaaacatg ctggatagac agatggcctg   10140
cttaactaaa tgaaatgatt gatccaaaca gtattttaga agaagtgcag ttttcaacat   10200
ttcaagtgta cagagtaggt ccactcgcct acaaagtgtt gccaagtgga agccactgtc   10260
agaaatgtat taatgacaga caagtcttag gtatgattgg catcctcatt tatgtgaaga   10320
aatgaagcca aaggaaagca cccttagacc aaccttcttc cctccccaac cacatggaaa   10380
gaacttgcat gctaatggtc aaaagttgga gctgggagtc agagattcct ggtagaattt   10440
cagcattacc atctagaaac agtgaaactt caggcaactt acttaatctc tctaaatctg   10500
atcatcttgt ttgtaaaata agcttgataa tagtacttaa tgagaaaaaa tatgtaaagc   10560
atttggtata gtatctggca cacagtaagc actcatcaca tattgataat tctggtagga   10620
tggtattttg agatattcac atttttttctc ccttcatttt cccctttctt tctacatctc   10680
acaaaattca aagagctagc cttttgttca ctgtctcagg ggaggcatta acatggta     10740
gaaagaagac aagcttgtaa gttttctgcc tttttatttcc gaaagtcctg gagaggttga   10800
gaagattcaa gtacaaagta tcatggccaa aaatgaggag aatttcccca agataaaaac   10860
aaaatatctg caggctgaag atgaagaaca ggaggtctac aaataggtct gtatttctag   10920
gaaaagagga aacttaggct ttgcttcctg agcagagact ggtagaaagg tgcaagtcca   10980
```

-continued

```
gtgaaggaat aactacatgg tgtgttgggg caaacaggga cagaggcaac ctcacaagaa      11040
tttccatact caagtgcttc atgaaacagc aggattcctg tgcttctggg gtatcatgta      11100
agcaaaagac aacatttaga cctaaaggag ccatgcttta ttagttacat attctgtata      11160
acaaattacc acttgaaaac ttagttaaaa caacaaacat tatctcacat agtttctgtt      11220
ggtagggaat tcaggagctt cttagctagg ttgttgtggc tcagtctctc atgaggttgt      11280
agtcaaaata tcagccctgg ctgcagtcat atgaaggcct gactagggct agagaaccca      11340
cttctaagat ggctcattca catagctggc aagttggtgc tggctcttgg taggaggctt      11400
cagtttctca ccatgtggat ctctccatag gaatgcttga gtatcctcat gaaaagtagc      11460
tggcttcact cagggagaga catccaagag aacaagtcag acatcaccgt gtcttttcgg      11520
atctagtgtc acaagtcaca caccatcact ccctgaatt ttatcacaaa gaccaacctt       11580
ggtatgacat gggaggacac aacacaaggg tgtgaatatc aggaggtgag aatcactggg      11640
ggctatcttg gaaggcacca cacatgacaa atggggtggc aattgtctca gttgtactgc      11700
ttaattagct gaacaagatg ccataataat acctgcagc ttggccaggt gtaagggacc        11760
agaacctaga ataactgggg gaggacagag gcataaagga ttgctctttt ttttgtcagt      11820
caggtgggat tataggcaca aaacagaatt taaacaatta gagaaagtaa tgtagtactt      11880
attgcacatt ttagttttatg aataatagta gcaattatca ttattattat aaatgaagga    11940
gtaactgtat tgttgcatca ttttccccaa gtggttcagg gtgactccag ttccactagg     12000
tcagtaattc tcaatcttgc aaatataata gaatcaactg gaatagctt ctgatttaat       12060
tgatttggag cagggccatg gagcttccga tttaactgat ttggagcagg gcctgggcat     12120
cagtattttt ttaagcccca tagttgattc taatacgtaa ccaagactga gatccaatgc     12180
tttatgcaaa ttcaagacct tcttgctact tcaaccatct atgattctat caggagcttg     12240
ccatatagga agctggctaa ttctccctat taactgcctg ggattgtttt cttcataaac     12300
actggaaaca cttgtcagta acagtctact tgagagagca gagcaaaggt taaagtttgc     12360
taaaacaaa caaaacagaa ccaagggat ctcagttggc attgtattct ctaacataat        12420
gcaactctgc ctcttgtccc tatcatcttc agcaactagt caacatttaa gccttgcgca     12480
tcaacaataa tctcataatc tctctcccac acacgcacac ctccatgctt cctcctcttt     12540
tattgcattc ttatttgact tctttaaggt atccgacact taaaatatat ttatctccct     12600
ggacttacaa gacctatctc tagttctttc cctacttctc tgacaacttc ttattgtcct     12660
ttgctagctt ctcttttctct acctgcctct taaatgatag tgttctctaa gattctgttc    12720
cttgttctct tttgatccca ttctatattg ttttccttgg gcaaaactca ctcccagcag     12780
ttccatctac catctatttta ctgacaactc caagatcttt atttttccagt ccatactttt   12840
cttgtgttcc agacctgcat ttgtagtttc ctgttaatta agctacctca aaccctgaat     12900
gctccttcag gttctccacg ccacctctcg aactgcttct cctcctttaa ttcatatctg     12960
aatagcacaa tacttcttat tttttaacct gatggtttta tttgcttgtt ttttccccca      13020
gctttataga gatataattg acaaaaattg tatatattca aagtgtacaa tgtgatgttt     13080
tgatatatgt atacattgtg aaataatttc cacaatcaag ctaattaaca tatccatata     13140
agcatatgga gagatctact ctcttagcag gcaccatgct tctaatcatt taaggtagaa     13200
accaggaatc accccagaac agaggtgcaa cctgcttatt tactaaactt gttttttattt    13260
ggtccaggaa gtacttttaa aaactttggg ccaaatttta agatttggga gatttcacat     13320
aagaatacag gtttaggctt ctcttttaaaa aacagaagat gatgaggcaa cacttcatcc    13380
```

-continued

```
tacctgcatg gaacaactgg ctggagatga gcagcagatg agctcctggt tcatgtagtc    13440
ttcacagtga ccataaagga tgctgaagct cctttcattc atttatatac acttgcctgg    13500
ctcttgaata tatctcagat tgtgacttct ctccttactc atacctctca ccatagctcc    13560
ctctacaatt gattaggaag ccctacagat tctagcactt ctctaatctg tcttcctcct    13620
cttcatcttg attgctacgt tcttagttca ggatcttgac tttgcttata tggagtatgt    13680
aacagtctac ttctagctcc gtcattaatc cattgcttat aaaccagtaa aatgaagtga    13740
tgttattatc ctgcctaaag gccttcactg ttctctact acctacaaga taaagttcaa    13800
attcctctag tacatggtac caggccatcc atgccctgac ccctgcccac cactccagcc    13860
ttatctcact tcattcccac agtaggtagt ctatgcttta cccctgccaa acaattctgc    13920
taaccaggtg gattatttca aatctctgaa tcatgttgct ctttatgcct taaaaaatat    13980
cttaatgcta cctaccaccc acttggccca cacaaccaca ttcttaactt cagagatttg    14040
gttcaagtgt tactttctct ttaaagactt ttctacctca ttcccaatct cataggtaaa    14100
aagaccatta cactcccacc tccatccccg accccgaccc ccgtccctc taagactgct    14160 atcctggcga ctataacata ttattgtatc tacttgttac ttgtttgtat tccttttctat    14220 tagaaggcaa attccttaaa agtagtggct atcccttata tatccttata tttctagatc    14280
catgcttagc gcatatagct gcttaataaa tattgcctga acgaattaag gattacttca    14340
aatgattact tacaagtcag ttgttgtctt aaataggttg atcatctttc tgtaatcatg    14400
tttatactat atcacggatc tgcttttact cagggattat gcaagggtaa acattttagc    14460
tcagttcaag caaattaact caattttttga aacagtagga gttcagatcg atgacatata    14520
ttttatttgt gttaacaatg tttcaccagt tttattcttt tttttttttt tttgagatgg    14580
agtattgctc tgtcgcccag gctggagtgc agtggcacga tctcggctca ctgcaagctc    14640
cacctcccgg gttcacacca ttctcctgcc tcagtctcgg gagtagctgg gactacaggc    14700
acacactgcc acgcccggct aatttttgt atttttagta gagacggggt ttcaccatgt    14760
tagccaggat gatctcgatc tcctgacctt gtgatctgcc ggcctcagcc tcccaaagtg    14820
ctgggattat aggcgtgagc caccatgccc ggccttacca gttttattct taagaaagat    14880
atcacatatt gccctaata cctgggggca atatgattga taaataattt tataatttag    14940
gctattatac catatgtagg agacatatca gtgtgactta tgggtatggc ttataaataa    15000
cactaggtca gagctgtcaa ttctcttaat gaagaaaaga atacaacaga acttggctgg    15060
gcacaatggc tcacacctgt aatcccagca ctttgggagg ctgaggcggg tggatcgcct    15120
gagttcagga gtttgagacc agcctggcca aaatgctgaa accccatctc tactaaaaat    15180
acaaaaatta gcagggtatg gtggcaggtg cccgtaatcc cagctactca ggaggctgaa    15240
gcaggagaat cgctaaccca ggaggcagag gttgcagtga gctgagatcg cgccattgca    15300
tcccagcctg ggcgacagag cgagacttct tctcaaaaat aaataaataa ataaatataa    15360
aaataataaa aaatataaaa attatatata tatatatata gagagagaga gagagaacct    15420
aatatgtgct ggcactgttt taaactctag ggatgctgct gcctttctaa acaggccgag    15480
gggatgaggg aagcgagtac aatataccag cctggaaaac atgaaaggga gcccagggct    15540
gattatgtag catgtcaaaa caaatgtcat tttgctgagg aattggacaa tttttttttc    15600
accagtacca acccatatgt ggcggccctg ctcatgaagt ttaaatttca gtgtgtctgt    15660
aggggtgagg taaagggcag gtcagcaggc aaccaaaaaa taagtagttg tccagggatc    15720
```

-continued

```
agtgagtccc ctaagaaaaa taagacaggg aagagatatt aggagtaccg ggggacagag   15780
gtacaatttt aaattgggtg ataaggcaaa gcctcactga gcaggtggca tttaagcaaa   15840
gagccgaagg aggggaggaa atgagcatgt ggatacctga tggaagagca ttccacagag   15900
aaaacaaaca gcaaatgcag acagaggtcc aggggtgggc atatgctgga gcttgcatgg   15960
aaaagcaggg aagccagtgg ttagtgggca gagcaaggga gtggagagca gaacagccaa   16020
cagtagattc aattactgag gaaatctagg aaagaaagt ggctgggtca gaatatgtag    16080
ggtagtgttt ctctaggcta acagacccag tgccccttt atataataaa tattttatac    16140
ttttcccttc atatgctgaa attaaattta tggatattat aactatatac aaaactaact   16200
tcaaaataac taatataatg ctaaacctgt aatataaatg agaaatgcat gaaagcaatt   16260
tataataata tatattttaa tatgtaaatg tgcagacatg aacaccataa agatataat    16320 gaaataggtg tttacacctt tatgtagaat cacataaatg tggtagctac aaatgcagac   16380
tgatagagga atgttgactt cttgtctcaa atgccatgaa tagtgaagct gatgctgtct   16440
ctgacatgtt tttccagaat agcaaacctc tgacaaaatt ctgaacaaaa taccattttg   16500
ttctcaactt acatcacagt tacatttctg gaaaatcaag tgtacattaa aactatgcta   16560
aaaatatttt gtgtttatat atatgtaatt agtttctagg ctcagatatt tataaacagg   16620 ttttcacct tcaagaatat ccaacgggct attcaaaggt catgcagaag gcacatgaga    16680 gaacttttg tggtgatggg aatgttttat gccttgatta ttgtggtggt tacacagata    16740
tataaatgtg tcaaacatca aattgtacac ttaaaatggg tacattttac ttttgataaa   16800
ccatacctca aaaatggatt attattatta tcattatttt ttgagacaga gttttgctct    16860
tgttgtccag gctggaatgc aatggcatga tctcggctca ctgcaacctc cacctcctgg   16920
gttcaagcga ttctctcctg cctcagcctc ccgagtagc tgggactaca ggcacgcacc    16980
accacgccca tttaattttt ttttgtattt ttagtagaga cgagggttca ccacgttggc    17040
caggcttgtc tcgaactctt gacctcaggt gatctgcccg ccttggcctc ccaaagtgct   17100
gggattacag tgtgagccac cacgcctggc caaaaatgga tttttttaaaa aactcatacg   17160 ggaggatgag ggacaattct ttatagtgag ggagtatgta taatggtcta gcagcccaga   17220
cccccacata ctcaatgcta ccacttaatt atggtacaac caaaaatact cccacaaatt   17280
tccaaaacat accttagcaa taccacttct actgagaata ttgcacgcca tgtcttagtg   17340
agatgggaag ccaactggag ggttctgagc caagaagtga ggtgacctga catgttttaa   17400
aaggactgct ttaactcttt caggcagagg caggaaaggg ctgatgcaga gagaccaatc   17460
agaaggctat catgaaaggc aggtgagaga tgatattggc ttggacaaag gcagttgcag   17520
tggtcatcat gagacatatc agaaaagaac ttcagaagtt tcgagtccca aaagacatgt   17580
tggaaacaga aagagttcaa aaaatgtgta ttagattaca agaagtaaat agcagtaatt   17640
ttcaagattc tcaacaatcc tcacgtaaca ctacttcatt attaaatgaa attaaatgaa   17700
attaaaaaac actttgggat tctagctgtg tcattttaca tccaaatata atgaaacgtt   17760
attttctgga aaaatgagat tcagcaaaaa tgtccttttg aaaaatgtta ccataggccg   17820
ggcatggtgg ctcacgcctg taatcccaga actttgggag gccaaggtgg gtggatcacc   17880
tgaggtcagg agtttgagac caacatggtg aaaccctgtc tctactgaaa atacaaaaat   17940
tagctgggca tggggtgag cgcctgtaat cccagctact ggaggccg aggcagaaga     18000 atcactttaa ccctggaggt ggagcttgca gtgagccgag atcgcaccac tgcactccag   18060
cctgggtgac aatagtgaaa ctctgtctca aaaaaaaaaa aaaagttacc atagaaaagt   18120
```

-continued

```
atacttccca cactaaaatt taaatttaat aagcagggtt gcaacatagg aaggttctgg    18180
tgaaacactt catcttggct gtttctgtga taatttagct cttgcaatac cttgagttca    18240
gtgtaatgaa tatcagttcc tcatttgagt ttttcaaagt gtagaagttc agaaaattat    18300
gctggatttg ttttaagact agaacctatt acgttgaatt tttttaagct ccgagatggc    18360
agataatttc ttccaatttg tcctgttctc ttaaaattgg aggatagtta attgagggtt    18420
tcagttagtt aacctcaggt gaactaaagt tctatgttta gtacttcaaa tccttccttt    18480
aaaaatgtca aaagtattta tgtatgtata aatgatttc tgaggtttgc tttaaaataa     18540
tccagcgggg agagagtgga agggatttag atgaaaccag attgatgctg tatcgataat    18600
tatcaaaggg tgttcatttt acgattctct ttacttttac acatttgaca ttttccataa    18660
caaaaagttt tgttttgttg ttgttgttgt tgttgttgtt ttgagacagg gtctcactct    18720
gttgcccagg ctggagtgca gtggcgtgat caaggctcac cacagactca acctcccag    18780
gctcaggcga tcctcctacc gcagcctccc aagtagctgg actatgggcg catgccacca    18840
agcccagcta atttttttgta gatatggggt ttcaccatgt tgcccaggct ggtctcgaac    18900
tcctagactc aagcgatccg catgcctcag cctcccaaag tgctgaaatt acaggcgtga    18960
gccaccatgc ctggccttca cattctttaa aagttttttct ttttcttttt tttttttataa   19020
ttagtgtatt ttactttagc tattttgttc actgaaaata tatgtagaaa ttgtggccag    19080
gcacagtggc tcacacttgt aatcccagca ctttgggagg ctgaggcagt tggattactt    19140
gagcctagga gttcgaggcc agcctgggca acatgatgaa accctgtctc tacaaaaata    19200
cacaaaaaat tagctgggct tggtggcatg tgcctatagt ctcaactact tgggaggttg    19260
aggctggagg attgcctgag cttgggaggt tgaggctgag gtgagccaag atcgcattac    19320
tgcactccag cctggctggc agagtatgac cctgtctcaa aaaaaaaaaa aaaaaaaaa     19380
attaaatgca agttctgaga tttagtattt tttgagtatt actatgtacc agacttttac    19440
tatgaacttg ggagagattt attagctaca gggatagatc tctacattaa ggagctcata    19500
acctagatat ataaacaaac cagtataagg caatgtaagg actaaaatat tgtgttaaat    19560
gtataaagtg ttacaggagg aaagaaagag agaaataggc aaagggctga gtagacattc    19620
ctccaaagat atacaaatag ccaagaagca catcaaaaga tgctcaacat cattaatcat    19680
taggaaaatg catatcaaaa ccataatgag gtaccacttc gtacccagta ggatggccaa    19740
aaattttta aaggaaaata acaagtgttg gcaaggatga gaataaatta gaaccctttgt   19800
acaatttctg gtgagaatgt aaaatgcagc ttctgtagaa aacagtttgg ttctccacag    19860
aaaaccatga tcataggaac actattcaca actcctcaaa agtgaacact gcccaaaagt    19920
ccatcaatgg atgaaagaat aaacaaaatg tagtatatac ttataatgca atattattca    19980
gctttaaaaa ggcagaaaat cctttcatac gctataacat ggatgaacct tcaagacatt    20040
acactaaatg aaattagcca gtcacaaaaa gacaaataaa tgtgagccca cctgtatgag    20100
gtatctaaaa tagttatatt catagaaaca aagtagaatg gtagttactg ggagctagaa    20160
ggacagggaa atcaaggaac attgtttaat gagtatacat attcagtttt gcaagatgaa    20220
aagtttctgg agatctgttg cacaacaatg caaatatatt taacactaat gaacacttaa    20280
aaatggttaa gatagtaaat tttgttatgt gattttacca gaattttttt aaaggcaaga    20340
tactactcag cataaagtta tacatgcact ggaacaataa aaattctaaa tacaagataa    20400
tggttatttc tggggagaga aaggaaggac tctataggca tctcaactct atccatactg    20460
```

-continued

```
ttttcttact gaaaatctga ggcaaatatg aaaatattaa gatttgaaac aaaacattat    20520
gcaagtgaaa gaagccagac acaagaggcc acatactatt atatatgatt ccatttttat    20580
atgaaatata cagaataggt aaatccatat agacagaatg cagattggtg attgccagga    20640
tgttagggga ggaaggagta gggagtaact gtttaatggg aatagggctt tcttttgggg    20700
acacgaaaat gtcttagaac tagatagatg tggtagttgc acaatattgt gaatgtacta    20760
aatgccactg aattgttaac tttaaaatga ttaattacat attatataaa tttcacttca    20820
attaaaacaa actaaggaaa gggagaattt caagaaggaa tggtattcac tgaaaagggt    20880
caaatgctgc acaagggtta agaaggatgt acactaagag gtcatgagat ttggcaagta    20940
ggaagtcctt taggagatat gtgccagtag tcagactgtt gtgggttgca tgagatgggc    21000
agtagtttgt gggagtcttg agcattttgt aggataagga gagtcactga aggggaaaag    21060
actgacaata aaggagagga gatatttgta cagcaagagt aggaagagac ataaaagggt    21120
agagagggtc aacagaatcc taatagtgga gagaaatgag taagttatag gggtaaattt    21180
gtgatttccc aatttcactt ggaaaggaga aactgagtta aaacttgata actccatttt    21240
tctaagaatg aagaagcagg gtgtagggct tgaagcgagt gataaagcca tgggagctga    21300
ccaaaaatgg acaaaaggc tgtctgagca gctttgaggg cttagtaga aatcataaat     21360
atctccctcg cacacacaaa cccacaatta aaaagttcaa ctgttaaagg tattgcatga    21420
ttaatagtat gtctcacaaa ttgctcatta gaaataaaac cactgcctag actcatctgt    21480
atgacacatg atactggatt tgtgaaatat tatgaatata cttaaaaata gtattcatgt    21540
aacacaacag aaagatcact cagtgagaac tacagaaaga tagcaaattg aaatctactg    21600
aagaaatatt aaataccaaa cattcagcta gaaaagaaa tgaaatatct ctaggagaca     21660
acttactact gaagaaagat ataaataaat atttcaccag aattttgaaa taatggaact    21720
atttaaaaat tgacaaggaa agggcagttg atgattgcct tgataaatta catagttaat    21780
ttctttgaaa aaaaaaaaaa aaaggatatg ccctaaagtt taaaataaac tattttaaaa    21840
gtatactttt aaaaagtaac tggtagagca tattaaatgg aaattaaaaa caattttaaa    21900
accataaaat gcttgctaat tgaaaactaa gactaatcgt aactagctat taacagtaaa    21960
tacctttaa caaattttca actactgagc caggtgcagt ggctcatgcc tgtcatctca     22020
gcactttggg aggccaaggc aggcagattg cttgagctca ggagtttgaa gccagcctag    22080
gcaacgtggc gaaactctct acaaaaaata caaaaattag ctgggtgtgg tggcgtgtgc    22140
ctgtggtctt ggatactcgg gaggctgagg tgggtggatc acttgagtcc cagaggtcaa    22200
ggctgcagtg agccatgact gtgtcactgc attccaacct gggtgacaga gtgagagacc    22260
ctgtcttaaa acaaaacaaa aaccaaagtt tcaactactg aatgaacttg aatataacta    22320
aaaaatcggc aggcgcctgt agtcccagct actcgggagg ctgaggcagg agaatggcgt    22380
gaacccggga ggcagagctt gcagtgagcc gagatcatgc cactgcactc cagcctgggt    22440
gacagagtga gactccatct caaaataaat aaataaataa aagaaatgtg atattcactg    22500
acaaggtaag gtaaccatca aatgatgaca tataatatgc acattaggtg ccttctagaa    22560
ttctatggc attagaagat ttttgcataa tattacagca attcttggaa atgaaatttc     22620
cctctataga ttttagttta gacttgtata gctgctaacg acaccaatta tttgtttgac    22680
tataggctaa ataacagagt tgaaagaaat ctctgctttc tagttgccaa cacagaaaca    22740
tgaagtgcaa gattttcaca gaatagtgaa tatgataaaa atataaaatc atggaacttt    22800
aaatatactt ttttaactgc agtacaatat atctaacata aaatttatca ttttaaccat    22860
```

```
ttttaagtgt atagctcagt aacattaagt acattcacat tgttgtgcaa ccatcaccac    22920
taaccatttt ttatcatctc aaactatata ttttatttat ttatattgtg gtgaaaaaca    22980
catacatttg ccatcttaac catttttaag tgtatagttt actagtatta agtatacctg    23040
tattgattca cattgttgtg aaacagatct ccagaacgtt tttatcttgc aaatctgaaa    23100
atctatgccc attaaactcc ccttttccct tctgccccca acccctggta accaccattc    23160
tattttgttt ctatgagttt aactacttta gatacctcaa ataagtggaa gcacattttt    23220
tttaatctaa aattattagt ggtcactgaa gaaaagggat tttttgcttg ttttgttttg    23280
ctgatagttt ggcctgacct caatcaataa agtgaatgaa ttttatatgg cacaattata    23340
tttcataagc cttgttaatg atccattctt gaatacagaa accaaatgtc atcatgttga    23400
aaaacgacta attagatggt caggtagtat ttgactttga agttatttat aaaattttaa    23460
tttttctttg aatgttaaat gaaacagcat aagaagtatg atatagaaag gtcagagaac    23520
agggtggatt taatgactgt attctcttgc agttagcatt aattattact gtatgtagcc    23580
tttgttgtgt aacactctta agttttcatt gagtggagaa ttatctgggt tttagttcta    23640
gttctgccat ctatgtgatc ttgggcaaat aatttaattt ctctaaagtt atgcattatt    23700
atccttacta gtattctaat gcatatataa agaatatagg gtcgggtgcg gtggctcatg    23760
cctgtaatcc caacacttcg ggaagttgag gcaggtggat cacctaaggt caggagttag    23820
agaccagcct ggccaacatg ctgaaacccc gtctctacca aaaaagaaa agaaaaaaaa    23880 attagccagg catggcagtg cacacctata atcccagcta cttgggaggc tgaggcagga    23940
gaatcacttg aaccctggag gtggaggtta cagtgagcca agattatact actgtactcc    24000
agcctgggga caaagagaga ctccttctca aaaaaaaaa aaaaaaata tatatata     24060 tatatataaa ataatacctg acctacctac ttaagggtag agttataagg ataaacagga    24120
tgtgatatat gaaaaagctc tgacatatta agctttgaaa tacacattga atattagaga    24180
gatttcatcc cttccaaact tctcttcatt tttatgtgtc ttctgaaaat tttatgttac    24240
cgtaggaaac taaaaagtta tgctccctta ctgccagttt cctatttatt agatgacaca    24300
tttcaacaaa aaactcagat taaaaaatgg tcaacatttg ctgtgactat ggctagaaag    24360
aaggaataaa taggatacca ggataaacaa gaatttccct agcttctcat tcactctctc    24420
ataacctccc acccaaaagt ctatcttaaa tatagtttca gagtatggag aggactgagg    24480
aatgcagaat gaaatgacag gttaatatta gaaatgccat tgtgggagac tctcaggaat    24540
gatttcaacc ttcacctgca gtttcactta aatcacacca ggtatagaat cattgtgact    24600
cagtggttta tgcaacaatc tggaaactca ggacctgtaa gctttggcca tgtgtctgac    24660
atttgttttc cacaagtaag ctaatcatgt tcactcactg tgcttcattt agctttatc     24720 tattaatgaa gaaaatgata tgaaattact tcccagggtt gtaaaaaaaa aaaaagaac     24780 agaactcaca aagagctata aaatgctgtg aaagccataa caaggtagc ttgtatgagt     24840 atagatgtga aaacacccca aaagttaaaa tttccacaca tttaaagcat taattttacc    24900
tgagctaagg gaaaaaaaag gtaatatgaa catgaaacaa gtagatcatc ctgaaacctc    24960
ttttggatta ttagttttaa attccttccc actcagacct tcacaaaagt agtaagaaga    25020 gagattttt taaaaatgaa atttagcttt cttctcattc ctcctgtatt tacccagagt     25080
gatgtagcta gtgagtagga aaagggccta aagagatgag gaaggaggta aaaaagcaca    25140
agacccagaa atcattaacg gtctttaacc agttattatt ttgtgtttg tttttctttt     25200
```

```
cttttttgaga cagagtcttg ctttgttgcc tagggtggaa ttcagtggca tcagagttca   25260
ctgcagcctc aacctcaacc tccgaggttc aagcaatcct cccacctcag cctcccaagt   25320
agctgggact acaggtatgc accaccacgc ctgggtaatt taaaaatttt ttttgtagag   25380
actgggtctc actgtgttgc ctaggctgtt ctcaaactcc tgggctcaag caattctcct   25440
gtctcagcct cccacagtgc tgggattgca ggtgtgagcc gttgcgcctg gcctattttg   25500
tgttttctat gagtaagtat atagtacacc actgctgaaa cattatctca ttaagccagc   25560
accaggtggc tttcctaaaa gaggaaactg atgcttagac agcttaagtg acttaccctg   25620
aacaagaaat ggaacaggtt tttgaacctt catttctctg acttcagagc ccacgctctt   25680
tattactgcc ctattctgtt tcaagaaaag caaaatttac ttatggaata aatgtcaact   25740
gaacctctcc taaaagtttta tcggaagtca ggttactctg gagattctcc ccatctcccc   25800
catggccata tgggttatgt tgtgacatac ccacatattg ctgcatgtct gcttaatgtt   25860
cttttctttc ctttaaaagt ttattttatt ttactttata gatacggggt ttcgccatgt   25920
tggccaggct ggtctcgaac tcctggcctc aagtgatgtg ctcgcctcag cctcccgaaa   25980
tgctgggctt acaggcgtga gccactgagt gcatcctaat gttctcttcc taatcagatt   26040
ctttatactt tctactctct ctcaaggctt caaatcgcta attctacccc atggcataca   26100
ttcagcttct gcccttgctg cataatgact tactcttttct aggtttccaa attcagattc   26160
ctaagagtga gaactgattg cccagacca tcttcttata ccaggacata ggttgctggc   26220
cagtctgtat gggctgatta acttctcaac tgcccaaaca cgtggctgtg acagaggata   26280
ggcagagcag taaatttccc tgagactata gtataggtag gtgagctttc taaagctgga   26340
cctaccatgt gccatttttta aaaatctccc aaacaagatc tgcctccttc cacccagctt   26400
ttttttctga cagggtct tgctctgttg cccaagctag agtgcagcgg tacaatcatg   26460
gctcactcca gcttggaact ccggggctta agcaatcctc ctgcctcagc ctcccgacta   26520
gctgggatta caggcacaca tcaccacgcc tgggtaattt ttgtattttt agtagagaca   26580
gggtttcatc gtgttggcca ggctggtctc gaactcctga cctcaagtga tctgcccgcc   26640
ttggcctccc aaagtgttgg gattacaggc gtgagccagg gcacccagcc tgcatttctt   26700
actttttatt ttatttttt tgagacggag tcttgctctg tcactcaggc tggagtgcag   26760
tggcgtgatc tcagctcact gcaagctctg cctcctgggt tcacgccatt ctcctgcctc   26820
agcctccgga gtagctggga ctacaggctc agccaccac gcccggctaa ttattcgtat   26880
tttttttttt taagtagaga cggggtttca ccgtgttagc caggatggtc tcgatctcct   26940
gacctcgtga tctgcccgcc ttggcctccc aaagtgctgg gattacatgc gtgagccacc   27000
gtgcccggcc acttcttact tttatttttg ttgtttcatg tattggctcc taatatctct   27060
cattcccttc tctctcattc acaatttatc agaaaagtac cagattacta ttttcctcat   27120
ttccataatt ttgcttctat cctcagaaac ctcttgtggc tcccatgcct acagtatcaa   27180
cattctccag agcctagtct actttggagc tttcacatct atacaaatgt tctacttcaa   27240
acttctgctt tgctgtcttc atgcttatca cttctcttgc ctgggcgttc tacttcctgt   27300
tcaaacctaa tttaacttac cctttaaggt ctacctctgt gaccaccca tgctgacagc   27360 ccggtccaca attctctctc ctcagaactg ttaaatcact tattatctgt atcactcttt   27420
cacatttatt aacttaaagt aactaagagt ttattgtttt tcctgtctcc tgaactaaga   27480
tattcattcc ttaggagtag gagccatctc tataacattt ttgtatctga cacacacagc   27540
ataaaccctc atatgttgat atgttaaaaa gccatatgta gattgaaaca agacctaaat   27600
```

```
gtattgaaaa gaagaaaaag ccactttgag aggccgaggt gggtggatca cgaggtcagg    27660
agatcgagac catcctggct aacatggtga acccctgtct ctactaaaaa tacaaaaaaa    27720
ttagtcaggc atggggcgg gcgcctgtag tccaagctac tcgggaggct gaggcaggag    27780
aatggcatgg aacccgggag gtggagcttg cagtgagccg agatcacgcc actgcactcc    27840
agcctgggcg acagagtgag actttgtctc aaaaaaaaaa aaaaaagaa gaagaagaag    27900 aagaagaaga aaaagctagc aaggtaccaa ggaaagcact gctaagcctt ccaaagaac     27960 tgaaatcctg gcggggcttg gtggttcacg cctgtaatcc cagcactttg ggaggccgag    28020
gtgggttaat catttgaggt cagggggttcg agactagcct ggccaacgtt gtgaaacccc    28080
atctctacta aaaattcaaa aaattagcc gggcgtggtg gcaggcacct gtaagcccag    28140
ctactgggag gctgaggcag gagaatcact tgaaccagga ggctcaggtt gcagtgagcc    28200
gagatcgcgc cactgcactc cagcctgtgc gactaaggaa gactccatct caaaaagaa    28260 aaaaaagaa aaaaagaat tgaaatcctt ggagatagtt tacataaatt ttcccaaacc    28320
tagcagtaga tgccaaaggt agccgctgag aactcaagaa actctcaagt gttgcaagaa    28380
agagagagaa gcttgccaat aagacgaaac attttaaaaa agactaaaaa caccagccaa    28440
aatgggactc aataccttaa acaagtaaca cttcttaccc aacactatac caaaccgtac    28500
tagactgtta cacaacttgt tcagcatatc ttctttaccg atcattgtct ggttggtaca    28560 ttctttgaa ccatcaaaag cagaggcact tctgatcatc cttccatttc tcttcctaca    28620
gtcgaatttc tctcccattt ctgaggggaa agggccatct acaataagca tgatcaagcc    28680
ctgattctgg catttcctca catcccgtga aactcagtct cagtatctgg ttaaagtaaa    28740
atactgcggg ccctttttc aaataaagtt taccttagaa attaaactat tcctctaagt    28800
gaatttttga aatacagagc aaaactgtat ctctttgcat gcacacacat atataaatgc    28860
ataggaaaaa atttggaagg gcataacttg aagtgcattt ttttcttttt tctttttttt    28920
gtttttttgt ttttgttttg ttttgttttg tttttattg atcattcttg ggtgtttctc    28980
acagaggggg atttggcagg gtcataggac aatagtggag ggaaggtcag cagataaaca    29040
agtgaacaaa ggtctttggt ttcctaggc agaggaccct gcggccttcc gcagcgtttg    29100
tgtccctggg tacttgagat tagggagtgg tgatgactct taatgagcat gctgccttca    29160
agcatctgtt taacaaagca catcttgcac cgcccttcat ccatttaact ctgagtggac    29220
acagcacatg tttcagagag cacagggttg ggggtaaggt cacagatcaa caggatccca    29280
aggcagaaga attttctta gtacagaaca aaatgaaaag tctcccatgt ctacttctac    29340
acagacacgg caaccatccg acttctcaat cttttcccca cctttccccc ctttctattc    29400
cacaaagccg ccattgtcat cctggccgtt ctcaatgagc tgctgggcac acctcccaga    29460
cggggtggtg gccgggcaga ggggctcctc acttcccagt aggggcggcc gggcagaggc    29520
gcccctcacc tcccggaagg gacggctggc cgggcggggg gccgaccccc ccacctccca    29580
cccggacggg gcggctggcc aggcagaggg gctccccacc tccagtaggg gcggccggg    29640 cagaggcgcc cctcacctcc cggacgggac ggctggccgg gcgggggct gaccccccca    29700 cctccctccc ggacggggcg gctggccggg caggggctg accccccac ctccctccg     29760 gactgggcgg ctggccgggc gggggctga ccccccccac ctccctcccg gactgggcgg    29820
ctggccgggc gggggctga cccccccacc tccctcccgg acgggcggc tggccggca    29880 gagggactcc tcacttccca gtaggggcgg ccgggcagag gcgcccctca cctcctggac    29940
```

-continued

```
ggggcggctg gcgggcgggg ggctgacccc cccacctccc tcccggacgg ggcgactggc    30000
cgggcgggtc tgacccccc  acctccctcc ggacggggcg actggcctgg ccggcggctg    30060
accccccac  ctccctcccg gacggggcgg ctggcctggc gggggctga  ccccccccac    30120
ctccctccgg acagggtgg  ctgccaggcg agacgctcc  tcacttccca gacggggtgg    30180
ctgccgggcg gaggtctcc  tcacttctca gacggggcag ccgggcagag acgctcctca    30240
cctcccagac ggggtggcag ccgggcaggg gcgctcctca catcccagac ggggcggcgg    30300
ggcagaggcg ctccccacat cccagacgat gggcggccgg gcagagacgc tcctcacttc    30360
ctagatgtga tggcggccgg aagaggcgct cctcacttcc cagatgggat ggcggccggg    30420
cagagaggct cctcacttcc tagatgtgat ggcggccagg cagagacgct cctcacttcc    30480
cagacgggt  ggcggccggg cagaggctgc aatctcggca ctttgggagg ccaaggcagg    30540
cggctggaag gtggaggttg tagcgagccg agatcacgcc actgcactcc agcctgggca    30600
ccattgagca ctgagtgaac cagactccgt ctgcaatccc ggcacctcgg gaggccgagg    30660
ctggcggatc actcgcggtt aggagctgga accagcccg  gccaacacag cgaaaccccg    30720
tttccaccaa aaaaatacga aaaccagtca ggcgtggcgg cgcgcgcctg caattgcagg    30780
cactccgcag gcggaggcag gagaatcagg cagggaggct cttttttttt tttagagaca    30840
gagtttcgct cttgttgccc aggctggagt gcaatggcgt gatctcgctc aatgcaacct    30900
ccgcctcctg ggttcaagca attctcctgc ctcagcctcc tgactagctg ggattacagg    30960
catgcgtcac cacgcccggc taattttttg tattttagt  aaagacgggg ttggtttcac    31020
catattggcc aggctggtct tgaactcctg acctcaggtg atccgcccgc ctcggcctcc    31080
caaagggttg ggattacagg tgtgaaccat cgcgcctggc cttttattt  ttattttttg    31140
agacagactc tcgctctttc acccaggctg gagtgtggtg gcacgacctc ggctcactgc    31200
aatctccgcc tctcaggttc aggcgattct tctgcctcag cctctggagt acctgggact    31260
acaggcgtgc accaccacac ccggctttgt attttttagca gagacagggt ttcaccatat    31320
cggccaggtt ggtctcgaac tcctgacctc aagtgatcca cccaactcgg cctcccgaag    31380
tgctaggatt acaggtgtga gccactgcac ctggtctgaa gtgcatattt ctggagtgga    31440
tgtattagtt ggattatttt aacagaaata ttttcctttt tttgaagaag taaataaact    31500
atatcctgtt acacctattt tcttttcttt tttttttttt tgagacaggg cctcactccc    31560
gtcgcccagg ttggggtgca atggtgtgat cacagctcac tgcaacctcc gcctcccggg    31620
ttcaggtgat cctcccatct cggcctccca aagtgctggg attacaggcg tgagccaccg    31680
cgcccggcct acacctattt tcttcaatga gttttttcact aaattccata gtgctcctaa    31740
ctttcatctg agaaagtatt ctaccactga tatttcctat tataaccaaa ttcgctgacc    31800
aatctgctct gtaaaaaaag gtttgtgggt ataaatgacg aaagtcagtt catggatcaa    31860
atccttcagt tctgtcacat tgtgagaggc cactgttgtg aaagtaaaat aacttctagt    31920
tacggctctg ctaagaatac gctgggggat gtcaggaagt cgctttattt gtaaaatgat    31980
gagttagacc agaatatatt ctctgataga agtttacaaa gatgaataaa gatttatagg    32040
ctaggcgcgg tggctcacgc ctaaaatccc aacactttcg gaagctgagg atccctagtg    32100
cacaggaatt cgagatcagc ctgggcaacc tggtgagacc cccttctcta ccaaaaataa    32160
ataaataaat aaaataaaa  ttttttaaaat gtattagctg ggcttggtga cgtagtgagg    32220
caggaggatg ccttgagccc aggagttcaa ggctgcagcg agccgtgatc atagcactgc    32280
actttggcat gggagataga gcaagacctt agctctaaaa aaaaaaaaa  aaaaaaatta    32340
```

-continued

| | | | | | |
|---|---|---|---|---|---|
| atagatttat | aaagtccatt | ctatggagga | aagtctctta | ttcagttatg | aactgctgcg | 32400 |
| aacctaaagg | caggaaggca | aattcccttc | agttcggcaa | acacgaagac | cccacattcg | 32460 |
| cgtcgtctgt | gaagaaggca | ctccgaacct | caggcgctca | ctcgccaggt | ttaagaggat | 32520 |
| gagcaaagaa | taaagtcct | ctcacccagg | aagcgtttcg | cttcccttag | ctggagccac | 32580 |
| gctccaaggt | gccaaagcct | aattgctgtc | cactctcacc | aatccgttag | caagatgagc | 32640 |
| atctacctgc | tgcgaacgtg | gcggtgacac | tactacagct | cccagcctgc | ctcccgcccg | 32700 |
| cccccactcc | tggactccac | agaccgtgac | ttgtagtccc | agcccacggc | tggcggcggt | 32760 |
| gcgggactcc | tgaaaactgc | ttttcctccc | tagtaggcgg | tgagaccgca | aattccatca | 32820 |
| gaatcctact | ctgacccact | agggcttggc | ccgctcagag | tcgcattccc | tcctccaaat | 32880 |
| gaaccaactc | tcctcccagc | gatactccga | cctctgagca | cccgggcgg | ggccacgccc | 32940 |
| cggaaatgga | gtcaggtctc | caggccgccc | gctgaagtgc | cttccagcca | ctccaagcgg | 33000 |
| ggctggggcc | ggcggggcgg | gcttggggc | gtggccggga | ggcgggcggg | gatgcatctg | 33060 |
| cgggcgcagc | gcttggggcg | gagccgcagc | gcgaggccgc | gcatctgggt | ggcggcgggg | 33120 |
| acgcgcccgt | ggggagaggc | ggctgcggct | gcggctgcgg | ctgctggcgg | ggggtggggg | 33180 |
| ggaggaggaa | ccgggaaggg | ggggcagggc | gagcggagag | ctagctgtgt | tcctgaggcg | 33240 |
| gcggcggcgg | cggcggcggc | ggcggcgtct | ccgacggagg | aggagggcgg | ggaaggagga | 33300 |
| tggagcaagc | tggggggttgg | ggttggcgct | agcgcagcgg | ctcgcctggt | actgtgggag | 33360 |
| agcggcggct | gctcctggaa | gttgtggtgt | cgggagccca | gccggtgccg | ccgcagccgc | 33420 |
| cgcctagggc | ggtggggagg | aggagggagc | cgcggggctt | ggcggggtcg | ggagggaggg | 33480 |
| acgtgctggg | ggaacgagct | ggggaagacg | gagcgggctc | tgtgccgggc | gggcgggcgg | 33540 |
| cgggggggcc | agcgaccgca | gccgggggga | cgcgggagga | tggagcaagt | ggagatcctg | 33600 |
| aggaaattca | tccagagggt | ccaggccatg | aagagtcctg | accacaatgg | ggaggacaac | 33660 |
| ttcgcccggg | acttcatggt | gagtctctcc | cctcgctgtc | gcgttttctt | gccggcgccg | 33720 |
| gagcccatcg | ccgcctctcc | cggccgggcc | gccagtgctt | tgtgtacctc | tgtgaggaga | 33780 |
| ggggcggagg | gggcgcgcac | cagccgggtg | agccgggtgg | tctcggaggc | cagcgggagg | 33840 |
| cgagagcgcc | tccccccgtg | gcctcctttc | ttctcccatg | ttcgcgaccc | ccgcgcgggt | 33900 |
| tcccgggacg | cgaagggagc | ggccgcgcgg | ccgagcccgc | agcctgcacc | gtggctcgcg | 33960 |
| accacctatt | gtttaccggg | ccgggagccg | taggcaagtg | aggtgcaggc | cggggggggg | 34020 |
| ggctcgcgtt | tccacacctc | cccgcgcagt | tcgctcctcc | caggagggtc | gaggcaaggt | 34080 |
| atctggctgt | gaccgggagg | agtgcagatc | gtggctgaca | gaggaacggg | ggtattgagg | 34140 |
| ttggcactaa | ctcctgggat | ccctttgctc | tagctggtct | caaagcgggc | agggtaggac | 34200 |
| ttaggccgtt | tctggggtcg | cagtcatgat | ctccaacgct | tgggaaagga | ttgcccataa | 34260 |
| ggaatctcat | gggtttacct | aatttccatt | tacccgcgtc | ccgcttctcc | tctcctgagg | 34320 |
| cccaggtttg | agtggtcttt | ggggtccgtg | tgactatagg | ttcaggggat | aagtgtgggt | 34380 |
| ggggaatta | tcctgaagga | agccagccga | cttcggactc | cccagggat | attgccgaag | 34440 |
| gcggagggga | tgtgactatc | acttcctatc | cgggtgggg | gtgggaact | tgggaacaat | 34500 |
| agtcctggtg | gggcggaggc | gacgctacgg | gccgaagccc | tgaactggga | gataaccttc | 34560 |
| ccagcgcccc | cccgcctccg | ccaccccta | ctttccgccc | tctgcttgtg | caggcagtct | 34620 |
| tgagaggagg | tgaaggttaa | aagtcttgtt | catgaaattg | ctctagatac | actattgctt | 34680 |

-continued

```
tagcacactg tgaggggtc agatccgaag gcgtgagacc agaagtcgac ttcctacgtt    34740
acccaccccc ccaaccccg ccctttttat ttttctgctg acaatgttc cctctagggt     34800
tgtttcccgg cttaggaggc ggtggttgcg gctgctgctc ctacggatat tgcgcaagac   34860
tggggcgttg gaaaccctgt aggtctgggg aatgaaaaag gaagtgggac tttgggaagt   34920
ggttgctcct tagtcttggc gggggttggg aatgggaaat aagctgggga aaattttttat  34980
cttgggtaag gtacacctcg aagaataatc acttaattct gaaatctgat tatgagaagg   35040
atacacagtt aatgcctgta aaatgaatgg gcagcaaaca ttggctagtt tttattttt    35100
gtttaaaaag tacagtagtt tttatggtgg aggtgatatg acttagtagt gaatactttt   35160
tcacgtttta aagagactgg tctagtaaag ctttagcgtt aaattttttaa cagcttataa  35220
aataggccct tgaccataca cagtattata ctagcatcgt tgagctttgt gattcccgcc   35280
tccccagacc aataatagag gacgaagta aagttttctc agtatctttt gaagattgaa    35340
aatataagtt aaataatcta acttattcct tattaaaaat aaaaatattg cttatattta   35400
aacatttgct cttgatattt agcctatgta tttttgaaaa attacttttt gatctgaaag   35460
ggttaaggaa aacggcattt tcccttttta ctattgagag tttttattgt cttggtatct   35520
tttgaatggt gtcatttaca gcaattggat ggagtccctt ttttactact ttctagcaaa   35580
agtagaagaa aatactttga atatttaaga tgtttaaaac tagttttttt gggttttgtt   35640
gtttggttgg ttggttggtt ggttttttttt ttgagacgga gtctcgctct acgtctgtc   35700
gccccggctg gagtgcagcg gcgcaatctc agctcactgc aacctctgcc tcccagattc   35760
aagcgatgct cctgcctcag cctcctgagt agctgagatt ataggcacgt gccaccacgc   35820
ccggctaatt tttgtccgaa gtagccggga ctacaggcgc aagctaccac gccctgctaa   35880
ttttgtattt ttagtagaga tggggtttcg ccatatttgc aggctgctct cgaactcctc   35940
atctcaagtg atccatctgc tttggcctcc caaagtgctg ggattacagg cgtgagccac   36000
catgcccggc ctaaaactag ttttttaccg tcttactttg gttatggaag aagagatggt   36060
gtggtccctg tcatttctt gtttgcatgc tagtcacctt gttatcccta ggcatatacc    36120
gtcaggaagg agcattgttt ggtgatgcgg gccatcagga caggttgccc agcctctgaa   36180
ctcctgtact ggagaagtgg ccttagggtt catgctttgg ggatgagtca gggattccta   36240
ttggagagtt catttctttc tttctttctt tctttctttt ttttttgaga tgtaacacct   36300
cgctgtgtcg cccaggttgg agtgcagtgg ctcaatctcg gctcactgca tcctccacct   36360
cccaggttca agcgattctc ctgcctcagc ctcctgagta gctgagatta caggcgcatg   36420
ccaccacgcc tggctaattt ttgtattttt agtagagatg gatttcacc atattggcca    36480
gactggtctt gaactttcat ctgactgact ttgtgatctg cccgcctcag cctcccaaag   36540
tgctaggatt acaggcatga gccaccgaga gttcatttct ccaagagtaa atgagtttcc   36600
ttttcttcc atgataccta ggtatagcta ggtgattcta cattagagat ttgatgacta    36660
aggctattct tttataggc tttttttttt tttaatttcc tgacttgata agcaatagct    36720
gtaattaaga cagccggtag ttggtgctgc ttttccct gactggaagg ctggagagga     36780
actatgttct cctggcatgg aaagagaaaa aaaagattag cttatagatt ctattatttt   36840
taaattctga tgtcgattaa aaatgcattt taaattctta acattttatg actgagcctt   36900
agagataatg tagctgatat aactgttcca tcataaaata atgtttattc caaatttgga   36960
aattaataga ataataataa tgccttacac ttagaccaca gttcaaatga acactccact   37020
tgcctgactg gtgatgatgc tcttttcgct ctatccagct gtcctacagt cctgtcattt   37080
```

-continued

```
aaaggctacc tctgttaata ttttttggtt ttgttttgtt ttgttgtttt gttctgtttt      37140
tgagacaggg tctcactctg tcacccaggc tggagtgcat ggttgcgatc ctggctcacg      37200
gcagcgtcgg tctccctggg ctcaggtgat cctcccactt cagcctccag agtagctggg      37260
gctatgggcc cacccacca agccctgctg attttttgtat tttttgtaga gacagggttt      37320
ccccatgttg cccaggctgg tctcaaactc ctgggctcaa gcaatccacc tgcctcagcc      37380
tcaaagtgct ggggttacag gtgtgagcca ccgtagccgg cctactactt ggtaactatc      37440
ttatatctta attttgtttc tttatgtttg agtatttagg tcattctact ttctgctgtt      37500
acatatagta attctgtgat taacatttttt gctgaaactg acattttttca ctgttgcata     37560 agatagcttc ccaggagtac taggtagacg tatataaaca tttaatacat gttcataaac      37620
ttgaaaaagt tttgtcagtt tatacaactg tcataatgta tgagtgttca tattataatt      37680
ttcttgatct ttatttgatg gttgaaaact gatatcttgt tttaacttga atttcttgat      37740
tactattgag gatagaaatt ttccacctgt cattactatt ctatgagtgt ctattcctgg     37800
ccttggttgt gccccatact gttaaagagg agacagctaa ggtacccaga ctgtgcagaa      37860
ctatgttgcc tagatggtta tttgcatgtt gaaaacatgc taattttgct aataaattag      37920
caaatagcta atttgtggct gatccagaat ttgatctcaa ttatctctac ttttaatatt      37980
tacaaaatga gagataaatg tataaagtag ggtggtgcac attcatgttt gacagaccta     38040
ggttttaact ccacacagac tccctctgat ggctgggggt tggggaggtg gtcctggacc      38100
atactttgag aaccagtgag ctaatacatg gtaaatgata aggtaatgc tgggaaagtt      38160 aggtagaggt ctttttgtga aggatcttac atctatgcta tacttagatt ttattctaca     38220
gaccgataat agcaattctg gacagtctgc attgtaactc ctagagacat ggagaaagta     38280
gggaggtgtt aagaaaatag acatgctggt ccactccagc gtcattcccc catctccacct    38340 tctccagcct gctccttgag ttgtactctg aaccttcact tacttagata ggttctggta     38400
gaaaaggtga gaatcattag tctgggtttc tggagcacta ctgagtcttt taagaaaggt    38460
aaacagtcat ttgtgtttta caaagttgaa tctgatagca gtatgaaggg tggcattttg    38520
gaagctgttg aaatataaga agtgagatgt gagggcctga agtgaactga gatggggaaa    38580
tagagtgtat acaacacatc tgataagaat taagaaagga gtctcaatga ttcattagat    38640
gtaggtagta aagaagaaaa gagtatagtg ttatgactcg caaaatatct agcttggtat    38700
ctgtcaccca agctagagaa taccatttgg tagagtaagg agtgagggag gagaaacaag    38760
tagaggagac caaacaacat tgtaggagga agtttcaggg ggagaagagg ataaatttaa    38820
ttttcaacat gttaaaactg cggtgcctct gagacatcca gtagaaatgt agagctcaag    38880
atttctgaca ggacggagtt aaagatgtag gcatcataat ataagcatgt aggagatagt    38940
cgacagcatg ggagtgaatg agcttattcc aacaaactta tagagtgacc agctttaggt   39000
tgaagaacat cagtcttaaa ataacagcca aagaaggat atactagtga ttgttcctga     39060
gaaggtgtgg tcaaggagga gggaggagaa ccagagatgt cagaaaagcc agggagagtt    39120
tcaagaaagg agttattacc agagtcaaat aatgctggga ggaccggtaa ggtgaggttg    39180
agaaagtacc tattccatttt ggcacatagg agtgctttgg tgactagaaa aaacagtttg    39240
ggttggggta tgggaagaag ctagattata gggtgaaggg tgggtttagt gtctttccat   39300
tttttttaac attttgaaag tagatggtag gagctagagg aagattggtt gaaggagagt    39360
gtgccccttc cactgccttt ttttttttttt tttaaagaga gaactagaga atattttttct   39420
```

-continued

```
tattatttct tgtctatgtg tatatcctct ttagcctggg aagatcttat gttgcagtct    39480
tgataaatat aaaaatttta atcatttgtt tattcagtgt tgtagcttat aggtttaaaa    39540
aaactaataa tagctttatt gagatataag tacctaccat aagatttatt catttaaagt    39600
ctatgattca ctagttttt attacattga tgaagttatg caacaataac cataatcaat    39660
tttaggacat tttcttcact ttctgtaccc attagcagtc actccccgcc ttcccataag    39720
ccccaggcaa ccacaaatct accttctgtt tccatagatt taagtattct ggacatttta    39780
tataaatgga atcatacaat atgtggtgtt ttgtgactga ctccacctaa catgatgatt    39840
tcaagtttca tccatgttat agtattgatc cgtagtactt ttggccttt tatggctgaa    39900 taatattcta ttgtatagat accacatttt gtttatccat tcatcgtgtt gatgggtatt    39960
tgaattgttt ccactttttg gctaatgtga ataatgcagc tatgaacatt tgtgtacaag    40020
tttctgtgtg gacacatttt caggtctctt gggtatatat ctaagtgtgg aattgctcag    40080
tcacgtggta acactatgtt taacattttg cggaactgcc agactgttat ccaaagctgc    40140
tgcacatatt acattccaat caggaatata tgagggttcc agttcctcta catcttcacc    40200
gatacttgtt gctgtctttt tgattatagg catcctactg ggtgtgaagt ggtatcttct    40260
tgtggttagc ttgtaagatt ttgtgtgtct taatttgtct ttcaaagcta gagtgatagg    40320
aaatattttc cagtccttgc atttgagcta atcttagtgc ttacccagtg ccactggttt    40380
agttatggtt ttcttatcca tcctttgatg agtattcacc taaacatatt tacatcaact    40440
aacttcagaa gtggaagtga acttttaagt aactctccag acatggttca ctgagacagt    40500
aaactaaaaa tttactttaa gcattctcaa gaatgtttta ctttatttac tttcaaaata    40560
tattaacttt tttccatcaa tatttgatat ttaacttgga aaaaggattt ttaaaggatg    40620
aaactgaaag taagacatta acatttaggt ggctgtaggt tttttgttca tatgttaaat    40680
acttctgtgt ttctgtagca ctgagttcat tagattcata aatatttaca tttctgtctt    40740
ccccagactg aacgcctccc aggctagaga ctgggactta attatccctg tatccccatt    40800
gcttaatata gtgcttggca tttaataggc actaatgtcc attgcatgtg cagacattgt    40860
agacaaactt aatgctgtaa gacagattta ttcttcaggt gaattcttca gtggtccaag    40920
ggtttgtctt ctagacgatc atgagaactg cttcttcccc tcctacacag atgtgctcac    40980
ataactcgtt gtattttcag tatccactga aaagaaaat acaagataag agctacattg    41040
aattcaaata ttttaaataa atatgatttt attagctgca gtttcttaag gtaacttctg    41100
tatttgtgca tcccacaccc aatggatcat actttgttga cattgtctta gagtattaat    41160
aaaatgtctt ttaaacttt ggctttggac ttaataaaat caagatatca tgtcatcggt    41220
atctcttcaa aaatagtgaa tttgtgggta tttagagagt gattacaagt gatatctgtt    41280
gttctctact tgcctctagt ttctttcctc atccagtcca ttcaacacat catactcact    41340
ttcaagtggc agcatctgta ggctaatgga aaccatactg gttgtacaat caggagatgt    41400
gggctgcact ggaagcatgg tttaatttt attattaaaa atataagtta aaaaaactca    41460 ttgctcccctt tgatgaccat tacaattatt ggaaatttta aatgtgtatt ttgaaagtca    41520
attcaaaaca tatgatccaa gtgctgctcc ttttcaaac tgtaattatg tctgtctctc    41580
tttccagaga gatttgattc cctgattttt cccttctcag ctccctccaa ttttaaatat    41640
atatatatag tttttttaa taattaaaaa aaatacttc acctggaagt tttcatccaa    41700
ttttgtaact ttggtcctag ttgagaatca caggcctata ggataaagtc tgtacttctt    41760
agcctggcat tccagaacct tcttaacata atgtcacagt acctttccag tgttaaactt    41820
```

-continued

```
ctatactctg gtatgtatcc tctcttcttt ttgaaggaag ctattcctgg tccttgagca     41880
tacctactaa atgaatgaaa tcttgcttat ctgtggttgt actgttgaac atactttttc     41940
cctcagaaag cttccctttt attttatttt attttatttt tttgagacaa agtcttgctt     42000
tgttgccagg ctggagtgca gtggcaccat ctcagctcac tgcaacctcc gcctcctggg     42060
ttcaagcaat tctgctgcct cggtctcctg agtagctggg attacgggcg cccgtgacca     42120
cacacagcta cttttttat ttttagtaga gatggggttt caccatgttg gccaggatgg      42180 tctcccctt tattttataa accagtactt ggaagatgag aaagctaaaa atttaaaatg      42240
acttcaccat gttcaccaaa aactcagaag caaaaatgtg attaattctc accttctaga     42300
ataaatattt tagcacagtt aatcttaaag cacttttct cctttgtaaa gtttgatctt      42360
taatatcaca agaaaaaaag cctttcatta gatttgagtt gaaaacttga taggtaaat      42420 caggtgatat gcaatttcta aaccactagt cttttccaaa tatgagttga actcctcttc     42480
cagcatttta tatttcctgt agtatttaag tttctttaga ttcatgcagt caaaccttga     42540
caattatctc cttccttctg aaatcacaca aaaatcttgt ttgcatttgt acagtattgt     42600
agggtctgta gctggcctat ggcagatata agaagcaaac agtagttgct ccctaaaagt     42660 ttttttttgga gaaagtggag tgtggactgt attagtccat tttcacactg ctatgaagaa    42720
ctgcccgaga ctgggtaatt tataaaggaa agaggtttaa ttgactcaca gttcagcatg     42780
gctggggagg cctcaggaaa cttacgattg tggtggaagg tgaagggaa gcaaggcacc      42840 ttcttcacaa ggtggcagga aggagaatga acatgggagg aactaccaaa catttgtaaa     42900
accatcagat cttgtgagaa ctcactatca ggagaatagc atgggggatt ataattacat     42960
agggattata attcaagatg agatttggtg gggacacaaa gcctagtcat atcgtggacc     43020
atgataatct cagaggcttt gggaagtgtg ctaatatcta catttcctgt ataactttt     43080 atatctaatc ggcattaaa aagctatttt aacaacattt gagtgactgt cctgataggc      43140
tctgaaggaa tgcaaagatt tgtctctgtc atccatccat ggtctctgtc atccatccat     43200
ggtctctatc atttatccat tcatacagaa ggtatttatg gagatacctg agtgcccact     43260
atgccctagg tactgtgttt ttgaattgac agttgaaaac atggcagtac tctgttcagg    43320
aagtttacta actgaacaga cctgtgagaa gcagcgggac ttttcctggg ggcagtgggt     43380
gggcttcagg ggaatctttg aacccttta aattatatat aatatttttt gtgtgtaagc     43440
ccattttagg gggaagaaag ttcatagctc ttagtttctc aaggagtttg ggtcccttag     43500
actagtggaa agataaggag tttaggagct atacagtcat taatttctat cctgccctg      43560 ctgtgattct gagcagatta tctagagaag ttggggctct aataccctacc tggaaagaac    43620 aagataatat atgtaaagtt tctaacatag tatatagaag gtagtcaaag gaatttgaga     43680
tgacatactg ctccagtgga agtatattcg gaatataagc cagagagaca ggagagccta     43740
aatctgtctg aatagatcat ggacagtttc cacaaagatg ctacatttga gctggttttt     43800
gaaggaagag tttgtcaggt gaactaggtg agtaaaaggc aacaacactt tcaaagactt     43860
ggagataaac agagatagaa ctgtgggttt tagatgggaa gaacagggtc agtgtgtata     43920
aaataagaaa atcttatgta cccaaataat aggatttcca aaggaatatc agcttaaatg     43980
ctattatgaa attggcctgt gttcctgagt gttttgatga ggagtgtttt gatgttccat     44040
tattatggca tagttgtttg atcttacagt aggacctttt aaaaattgag tccttgtcac     44100
atggtaaatg ttcttaaatc tggtaatttt actttatctc aggtatataa agtagtactc     44160
```

```
tctctgttta cacagttctt agatgactag attagtgttt ctcattggca tctatcagat  44220
atgtttaaag tgccctgtag aaagaaatta catttaaaaa gccttcagga ctaaggcagc  44280
ttatttataa tggtgggtct cttgcttagt ttggattcct cagcgaattg agttttccat  44340
aagatgactc tgaagaggtt ttgagactgc atttgtgacc agaaccaacg tgagaaagga  44400
agggagttct aggtcacatg ctacaaaacc atgaagaata acttctctag acaccttctt  44460
ccccattgtg tatgttggtt ttactcctga cgtcataaac tctttagtgt tagaaggaac  44520
ataaaaactg tttagaaatt aaggagcttg ttacaggtct tgccatagaa aggtggtgga  44580
actgggttag acccaagtta ggaaagcaga tgctttttat atgacatgat gctgcttagg  44640
ccaacatttt cagtcttagg gaaaaagtca ataaagcccc acttcctacc ccctagagt  44700 agagcataaa tatcctcaaa attacaaaaa aagttttctg tcagtataga ttttggttg  44760 cagcctactt ccaaaaagta gcttaagtga agaaagaatt tattgcaatg gaatactgcc  44820
cttgagcagg ttgaagcatc agaaccaaga aatagagagc ctgggtgact cctctctcca  44880
tgccagcctc tttgtctttc tatgttttc aagtttccat gtctctgggg ctgcttggat  44940
acttctcttt gcttctctgc acacctgctt tactattacc tctctctgca ttttgactt  45000 cactgttttg gcctgcatgt gctgaataaa gacatccctt atggtaatct aacctgtctc  45060
attcactttt atctcaaatt atggaaagag ctcagaatga ctagaattgc tacatcttgt  45120
tttcaatttc ctgaagaaaa taaccaactt gccagtgaga tgggtgttgt ataaggtggt  45180
gagcttattc atatgtgtat ggaaggaagg aacttttttt agagaaagga agggatggct  45240
tgataactag gcgggcagtc caagagtgt ctagtagaga atccttgaag caaaattgaa  45300
aaaaaattta ctattttaag gtttcagctc catatgaact ccacccacct tctttcagag  45360
atggaaaaag cacaaagagt ccttgtgact tgagagaaca atttgttggc tctggcagag  45420
cattatttca catttacagt tagacattaa acatcaggca aaattttaag gtttctgtgt  45480
agcaaactaa aattaagatt atctataagc tgcttattta tggtacctaa atttaaatta  45540 taattttca acattaaaat atggaacctt cttgcaagga aatcctgttt taagtttgg  45600 gttttgttt gtttgttttt tttttttta agagatagg tcctgctttg tcacacaggc  45660
tggagtgcag tggtgtaatc atagctcact gcagccctga cctcctggc tcaagtgatc  45720 ctctcacctc actcctgagt agctaggact acaagcatgt tgccaccatg tcctactaat  45780
ttttttacct tttttgtaga gacgaggtct tactatgttg cccagctggt ctcagactcc  45840
tggcctaaag caatccttcc atcttggctc cccaagtgct gggattatag gtgtgagcga  45900
ctgtgcctgg ccctaaggat cactttatc aaagtagtca ctatgattta ctccctgatc  45960
atatgtcaga aatatatcac tatctgaaaa actaacatat tttcttcaca ataggttttg  46020
cattgttaaa attatcctaa ctatagttct tttagttcat gaatcatcta aaatttatgt  46080
gttactatat tcattgtgtt tgcctggcta ttagtgtgcc tgtctttgtg cctgtgtgtc  46140
tgcctgcctg cctttgtgcc tcccttgaa attctatttg cctactcacc tttctctacc  46200
tactcagtca gttggttgtc tgtgcccaag atttattaat gtgtgttaac gtgtgggtag  46260
tagagataga ctggaaggta ctttgtagtt tagaaatgtc tgtaatttac acctagttgt  46320
ttgtaattca tctaatacgg taaatagatt atacaagggg acttcaaaaa gctcatggaa  46380
aaatggaatt aagtaaataa atgttattta ttaataaatt tataaataga ctaaaattaa  46440
aatataaagt taatttctga acataaactc catcagttta cttttataag tgatgataca  46500
ccaaccattt tgtttatccc taagaactga gggtcctaga aatttaacca tttcaatgca  46560
```

```
gttttttttac attattaact gaagagtaat gaatgccctt taaagatttt tttgagatta    46620
ggaaacaaaa cgaaggcaga aggagccaaa tcaggactgt aagtggatg cctaatggct     46680 tcccatctga actctcacaa aattgccctt gtttgatgag aggaatgagc aagaggcatt    46740
tttgtgggta gaaaggact  ctggtgacgc tttcttggat gttttctgc  taaagatttg   46800 gctgactttc tcgaaacact ctcataataa gcagatgttg tctttccttg gccctccaga   46860
aaaatcaaca tgcataatgc cttgagcatc cccagaaact gttgccatga gctttgctct   46920
tgactggtcc acttttgcct tgactggacc actgccacct cttggtagat tgctttgatt   46980
gactttgtct tcaggatcat actggtaaag ccatgtttca tctcctatta cagtcctttt   47040
aagaaatgct tcaggatctt gatcccactt gtttatttat ttatttattt attattttc    47100 attttgtttt tgagatggag tctcgctctg tcacccaggc tggggtgcag gggcatgatc   47160
tctgctcact gcagtctccg cctcctgggt tcaagcgatt ctccagcctc agcctcccaa   47220
gtagctggga ttacaggtgt gcgccaccac acccagctaa ttttttgtatt tttagtatag  47280 acaaggtttt gccatgttgt ccaggctggt cttggactcc ttacctcagg taatccaccc   47340
gccttggcct cccaaagtgc tgagattaca ggcatgacag tttaacatttt ccattgaaag  47400 ctctgctctt gtctgtagct atctgggtgc aatcattttg gcaccaactg agtggcaatt   47460
tgttcagctt taattttttca gtcagaattg tgtaagctga gcaacttaag atgtctgtgg  47520
tgttggctat tgtttatgct gttaattgca ggttctcttc agttagggca agtgacaaga   47580 tgaattttt  tctcaaaaat caatgtggat ggtctgctgc tacaggtttc ttcaacatca   47640
cgttgtcctt tcttaaaaag aggcatccat ttgtaagctg ctgatatttg gggcattgtc   47700
cccataaact ttgcttcacc attcttccat ccaagctttg ccataaattt gatgttttgt   47760
tcttgcttca gttttttagc agaattcatg ttgttctgat aggggctctt ttcaaactga   47820
tatcttatac ttcttagtgc ttcaaatgag atcctgttca tcagacatgt tataagaagt   47880
tagtatgagt ttattttggt gcaaaacaaa attgaaatcc atgcatagtt ttttccatgg   47940
tacatatttt ccatgaactt tctgaagacc ccttgtatga atgccaagga gaaacatagg   48000
gtgggtggtt attagtaata ggattttgca actgaaataa ttaaacatgt tcagatattt   48060
atctccacac ccattcactg acattattag atggtgcaca aaagtaaaaa gtttatttta   48120
aaattacttt ataatttaga tagaagatta ttaaaattca ttttttaagaa acagagtctg  48180 tctctgttgc tcaagcttga gtgcagtggc acaatcacag ctcactgtag cctcaaactc   48240
ctggactcaa cagatccgcc tgccttagcc tcctaagtag ataggactac aggcatgagc   48300
cactgctccc tggtggatta cttttaaagt atgttttttt tttttgaaa  atgcaactta   48360 aactagaagt acaggatgaa tatttaacca atacatttaa tttcttgtca ttgctttatt   48420
agatgctgtt tttgtattgt ttataaggtc tcagcatcat atgtatgata ttttcaaata   48480
tgttctaaaa tgacctcatc atttatttct ctagttgtta aagaaggtat agaggtttta   48540
tcatttttta aaataggatg taggttggat tagatctata aattattatt ttgcctttaa   48600
aacaggttat agataaaaga gggaaaggta atctggtgat actactgggc aggaatcttt   48660
aaattattta aagagggtgt aaacgaagga atgtacaaaa gtaaaaatag gcagggaaga   48720
aaagacctga tggaagtaac atatctttgt taggaatttg agtgtctagc attatagtgg   48780
acagtccaat gatatggttt acaacagtta tataggtatt agacctggcc attacttact   48840
atgtaatgtt gagtacatga tttgaaccac tctcaatctt agcttcttta tcgttaaaac   48900
```

```
agaaatagtt tgtaatgttt gaattagtaa gaataaagga cacagtgtca gatgtgtcag  48960
aaggaagcat gattagggca ttaagtgaga agttaaataa ataggagggg aaaaaggcca  49020 cccttgctc ttttctctt ttggaccttt ttggtgacag agacagaaag aatgtgtata  49080
gtatatttaa ttatctgaaa atacagagct gagcatccct aatctgaagt ttaaaatgcc  49140
cctacatcca aaattttttg agtgccatta tggtctgaga gcagacattg tgtatgattg  49200
ctgttttaaa tttgttgagg tgtgtttaat ggcccagaat ttggtctgtc ttgttgaatg  49260
tttcatgtaa acttgagaag aatgtgtatt ctgtagttgt tgtcttaggt agtctataga  49320
cgtgcattat atatccagtt gattgatgat gctgttaagt tcatctgtgt ccttactcat  49380
ttcctgcttg cttgatctgt ccatttctga tagaggagta cggaagtctt caactataat  49440
agtggattca aatatttctc cttgcagttc tatcagtttt ggctcacata tttttatgca  49500
caattgttag acacatatgg attaaggatt atgctgtctt cttggagaac tgacccttt  49560 atcatgatgt aaagccaccc tatccctgat aactttactt gccatgaaat ctgctttatc  49620
tgaaattaat aactagtctc atttatttt tgtgttagct gatatatttt tttccatcca  49680
tttgctttta atctgtgtgt gtttgtatat ttaaagtgga tctcttgtag acagcatata  49740
gttaggtctt ggttttaat ccactctgac aatcttttaa ttggtacatt tagaccattc  49800
acgttcagag tgattactga tagcattgga ttaatgtcta ccatatttgc cactattttc  49860
tgttgtcatt gttctttgtt cctattttt tttttgtctt ccactgtttt tctgcctttt  49920
gcagttttaa ttcaaaatat catatgactg tcctttctta gcatgtcagt tttacttctt  49980
ttttttttta cttttttgt ttttggtctt ttctaaagag acaaggtgtc gcttagttgc  50040
ttaggctgga atgcagtggc atgtcatagc tcactgtaac ctcaaacttc tgggctcacg  50100
tgatcctcct gcctcagcct cctgagtagc taggactaca agtgtgtgcc accaaccctc  50160
aagtaatgtt tttatttttt tgtagagaga aggtcttacc atgttgccca ggctgtcaaa  50220
ctcctggcct caagcaatcc tcctgccttg gcttcccaaa gtattgggat tataggcatg  50280
agccactgtg cccagctggg tgttttcact ttttaagtg gttgctctgg catttgcaat  50340
gtatatttcc agcaaatcca agtccatttt caggtaacac tgtaccactt tatggatggt  50400
gagattactt tataatgaca aagtaaccct aattctatcc cttgtatcat tgctggcatt  50460
atctcactta caaataaaca tacacacaca agcatatata accaaataca tgtttgctgc  50520
tattctgaat aaacgtatca gatcaattaa taagaaaat aaaagtttta attttacttt  50580
catttattct ttctctcatt tcttcttcct ttctttatgt agatgtgaat tccagactag  50640
ataaatttgt cttctctcta aaaatttat tttaacattt ctcacaaggt aggtctgtgg  50700
caacagattc tcttaatctt ttctgggga cagggtcttg ctctgtctgt catccaggct  50760
ataatgcggt ggcatgatca tggcacactg cagccttgac ctgctgggct caaccagtcc  50820
ttttgcccta gcctccggag tagcagagac tacaggcatg caccgccata ctcacttaag  50880 ttttttttg tttctgtttt tgtagaaacg aggtctcact gtgttgccca ggttggtctt  50940
gaactcctgg gctcaaacca tccacccacc tcagcctccc aaagcattag gactacaggc  51000
atgaaccacc ttgcccagcc ttaatttttg tttgttgaga agttttttat ttctctttgg  51060
tttttgaagg ataattttgc aaggttcagg attctaagtt ggtgggtttt ttcttctcaa  51120
tatgatattt tgtcactctc ttcttgcttt cctagtttct gaaacagagt cagatgtaat  51180
tcttattata cttgctcctc tttaggtaag atgatttttt ttcctctggc tttttaaacg  51240
atttgtttat cttttttttt ttttttgtagt ttgaaagtga tatgcctaca taagttattt  51300
```

```
ctggcattta ttctgatcag tgttctctga gctgcttgga tctgtggttt ggtttctgac    51360
attaatttgg ggaaattttc aatcattatt tcaaatattt cttctgttcc cttcttctct    51420
ttctgttatt acccttatgc atatttacat ctcttgtagt tgtccccaca gttttttgcat   51480 attccattct gttgtttcag ttttttttcta gtctttttaa tctcttttca gttttggaag   51540
cttttattga gatatcctca agttgagaga ttctttcctc agccatgtct agtctactag    51600
taagcccacc aacaacattc ttcatttttg ttacagtttt ttaaaaaaat ctctagcgtt    51660
tcttaggccg ggcacggtgg ctcacgcctg taatcccagg actttgggag cagaggtgg     51720 gtggatcgtg aggtcatgag atcgagacca tcctggctaa cacggtgaaa ccccatctct    51780
actaaaaata caaaaaatt agctgggcgt ggtggtgggc cctgtagtc ccagctactg      51840 gggaggctga ggcaggagaa tgtcgtgaac ccaggaggcg agcttgcag tgagccgaga     51900 tcacaccatt gcactccagc ctgggcgaca gggcgagact ccgtctcaaa aaaaaaaat    51960 ctctagtgtt tcttttttggt tatttctttg aatttctgtc tctttgctta tattgattgc  52020
ccatctattc tggcatactg tctactttat ctgttagagt tcttaggata ttaatcatag    52080
ggtgtttgtt tgtttgtttg tttgtttgtg tgaaacaggg ttttgctttg tctcccaggc   52140
tggagtgcag tgatacaatc atagctaact gcaacctccg cctcctgggc tcaagcaatc    52200
ctcccacctc agcctcccca gtagctggga tcacaggcat gtgtgaacat gcctggctaa    52260
gttttcatat ttttttgtag agaagggggtt tcgtcatgtt gcccaggctg gtctcgaact   52320
cctgggctga agagacctgc ctacctctgc ctcccaaagt gctgggatta caggcatgag    52380
ccacccagag ccaaggtctc agtctttttag tgagcttgtt tatggatttt gaactatatc   52440
ctgtttctca gcgcctcacc cccaggatgg cttgaatgac ctgtagttgg gtatttccct   52500
tacctcatgt aaataaggct ctgttaaaac cccagcaggt taggctcagg ttaaatcatt   52560
tctccgcagg gcagaccttg ttaagaagaa tggaatattc ggccaggcac agtggctcac   52620
acctgtaatc ccagcacttt gggaggctga ggctggtgga tcacaaggtc aagagataga    52680
gaccatcctg gccaacatgg tgaaaccccg tctctaataa aaattagctg agtgttcctg    52740
tagtcccagc tactcgggag gctgaggcag gagaatcact tgaacccggg aggtggaggt    52800
tgcagtgatc cgagaccgca ccactgcact ccagcctggt gacagagcaa gactccatct   52860
caaaaataaa aataaaaat acaaaaaaag ggattttctc taatacttac tatgagaacc    52920
tggtagagct cctggaggta aaacaaaat gtggggtccc ctttggattg ggtacaccag    52980 gagttttttgt ttgtttgttt gtttttgttt gttttttttt tagagcggtc tcgctgttgt   53040
ccaggctgga gtgcaacggc acagccttgg cacactgcag cctcaacctc gtggcctcat   53100
gtgatcctcc cacctcagcc tccctagtag ctgggactac agatgtatgc aaccacactt    53160 atctatttt aaatttttttg tagaggtggg gtctcactgt gtttgcctag gctggtctcg    53220 aaccctggg ctcaagaggt cctcccgctt ccacctccca gagtacttgg attacaagta   53280
tgagccactg catccagcct cccctggaga ttttaaccct catagttgtt cacactgagc    53340
ctctagcagt tcatcaatta cagttcaggt ttcttatgga agtttgctgt gtgagtgttt    53400
ctgctctgat tactcgtgat tctccgtatt caccttctgt ctctccagtt tgggggcagc    53460
tgtttgacct gtgacttaac ttctcttaca gatctaagaa aagttgttga tttttcagtt    53520
tgtttagctt tttacttgct cttaagattg agtgacagat ttttttttgc atttttttat    53580
tgtgataaaa tgtattaata caaaacattt atcatttaag tgtacagttc tgtggcatta    53640
```

```
gatacattca cactgtgcaa ttaggactct taaaaggaaa aagtcacata ctgttagaag    53700
ggtcatacaa ggctttatag aaaggatttt taagatgagc ttctatatat caattaaaag    53760
aacatttcag tagaaacatg ggcgtatggt atgataatta ccagaagaca aatgcaaata    53820
agtgctgaac acaggaaaaa aataatcaac ctctccaata atcagaaaaa ttgaagttaa    53880
tcatcattaa ctgttggggg agtagctacc aaatttgata aaaactcaaa aattcgtaat    53940
aattcagaaa ttgagaatag cggccgggcg tggtggctca cacctgtaat tctagcactt    54000
tgggaggctg aggcgggcag atcacgtgag ctcagaagtt cgagaccagc ctggccaaca    54060
tggcgaaacc ccatctctac taaaaataga aaaattagct gggcctggtg gtgggcgcgt    54120
gtaatcccag ctattcggga ggctgaggca ggagaatcgc ttgaacccat gaggtggagg    54180
ttgcagtcag ccaagatcac gccactgcac tccagcctgg gcaatagagc aagactccat    54240
ctcaaaaaaa aaaaaaaaa gaaaagaaa aagaaagaa aaagaaaatg gtaaggatat    54300
agaaaactag tgtttctagg tccattaagg ggagggtaaa ctggtgaagc ctgttttgga    54360
aggcagtttg gccacttcta atagaattga taaatgtaca tactctttga tccagcatgt    54420
caactttagg gatctttccg taaaaatact tgcatatgtg cataaaatag tatgtccaag    54480
tatgcaacaa ttttgtgaa acaacctaaa atagctatta gtaaggagac tttgcataac    54540
tggttaccta aaaggaaaca gatgtggagg ggagagagtt tggcttttc attttatacc    54600 tgtatgcaga aaagagtaac atagcaggcc taagactact atccttagaa aggcctgctt    54660
acaatgttat cccttggctg gtgtctggga acttagactt ttgggagaat ttccattatc    54720
ccctgataag agtggttcac tgtgcccaaa ctgtacaaac aatgtggttt atgagctggg    54780
cccagtggct caattgtgta atctcagtgc tttgggaggc cgaggcagga ggattccttg    54840
aggccagctt gggccacata gtaagacctc atctctacaa acatttttta aaaattagcc    54900
agatgtcatg gtgtgcacct gtgtagtctt agctactttg ggaagctgag gcaggcagat    54960
aacttgagtc cagtagttca aagttgcagt gagccttaat catgccactg cactccagca    55020
tgggtagcag aacaagactc tctctctgaa aaacaaaaat aaaaaataat atggtttatg    55080
ttgaacatct acttttttc tgggagtctg gaattttggt atattcttag gcagagtgcc    55140
tgtgtaacca gcctccaata aaagccttgg gcactttatt tctaatgcgc ttcccttgtg    55200
gacaacgttt cacacatgtt gtcacaactt atttctgcag gaattagagg atcgtgtgta    55260
atttcattag aagaggattt ttgaaagctt gtgcctagtt tcttctggac tttgcctctt    55320 gtgcctttt cttgctgct tttactttgt atcttttagc tgtgataaat tatagctctg    55380
agtatggtta tattcagtga tatgttggat cagttgatat gctgagtttt ttacatgtgt    55440
gtattatcta accccttat tgtgcacatt ttcccttgat ggtaaaacag tgaaagcttt    55500
ccttggtaac attgtaggtg atataataaa gaagtgaatc aaaaagtgag tgtctttagg    55560
tatgttattt aggacaagga gatactactt taggtaaatt attttaaatt acacttccag    55620
tttttattac cttcatatgt caataggatg ctaaaccaca gatgttaaat ttcaaatagc    55680
attttaagtt ttgctctcta gttttataaa tcatattaca taaacttact gaactaaatg    55740
tgaaaatagg gtgccaattc actgactatg tgatgttccg aatgggttat caatgtctat    55800
tacgtctagc agacttgccc tgctttgttg aatgtgtatt tggaagacac taggctctgt    55860
gggggaagaa aaagaaatag gttattatct gtgaggcagt gaattataat cttgggtgat    55920
ggcggcattg gtagtgatgg gataaaatgt gtaaacatga tggatattaa aggcaagaat    55980
gacaagtact atatgactag gacatgtttt tggaatatat gcctcattag agcagggatt    56040
```

```
ttgtcctgtt catctcttat cactagcacc taaaacagtc cctgggcata ggataggtta   56100
ggtggagtta atgtgaagcc agtcgtcgtc ataaaagtga taattgagtt tgaagaggaa   56160
gttcttttta ttataaatct ctgaatccag tatgtcagca aacttaaaaa tatttttggg   56220
gaatatcata acagttaatt catgaatagg tcagaacttt ctaatgttgt atgaatatta   56280
tgtgacctgg taatctgaga cactttaatg gcgcttgcct gcaactagct gttcttttg   56340
atactggata ggacatttaa ttctgtacaa acaactacta agggtttctt tcccttaaaa   56400
aatttttttt aattgtggta aaatacatgt aacatgaaaa cctatcatct aagccatttt   56460
taaatgtaca gttcaatagc gttaagtaca ttcacattgt tgtataacca atctctagaa   56520
ctcttctcat cttagaaagc taaaactctg ttcccattaa accaccctct ttattccaaa   56580
ctcattctcc tccttcctcc aacctgtagc accattctat tacactttct gtctgtatgg   56640
atttgacaat tctaggtgcc tcatataatt aggattataa aatattgtct ttttgtgact   56700
ggtgtatttc agttagcata atgtcctcag ggttcatcca tgttgtagta tgtgtcaaaa   56760
tcttcctttt taaagggttg aaaaatactg cattgtatgt atatactaca ttttgtttat   56820
ctatttgccc atagcatgac acttaggttg cttccacctt ttggctattg tgaatgctcc   56880
tgctgtgaac atggttgtac aaatatctgt tcgagaccct gctttccgtt ctttggggta   56940
tacccaaaa aatggaattg ctgaatgata tgataattct acttttactt tttgaggaac   57000
caccgtactg tttcctatag taactgtatc attttacatt tcacaacaga gcacaagggt   57060
tccagtttct ccatatcctt gccaatacct gttattctgg cttgttttgt tttgttttt    57120
gttttttgtt tttatagag ttgaggtttt gctgtgttgc ccagactggt cttgaactcc   57180
tcaagtggca caagcgatcc tcctgccttg gcctcccaaa gtgcttgggt tatagttatg   57240
agccactgtg cccagcctat tttggttttt tgatagtagc catcacaatg gttcgagtgg   57300
attgctaagt catacaggga tgtaaaattg tgtctgttga atcatctata tgaaatactt   57360
cataggaatt gaagctatta agattttgat gcctgttgga gattattggt gacttgctaa   57420
aagtaatttt agtagggtaa taaagggaaa aatgaaattt tcagagggtg taggagttag   57480
tggttcacca ggaagtgtag tttctcttta gaaagtttgg tcagctgacc acagcactgt   57540
ggcagtctcc ggccttgcaa aaataacttt tttccatata gcggtcaata agtattgagg   57600
tctcttaaac tacacaagtg actcttcctg tgctatattt gttttgcag agagaagtgt   57660
gaattctgaa tctctgctac taatttggga gtctttgttt tatatttgta atcggaggta   57720
aagagaattg atgtaattgt ggcttaatat gttaatacta gaacttaata ttctcaattt   57780
tactgtatgt ttttaattaa ttaattaatt aattaatttt atttatttat ttatttattt   57840
ttgagacaga gtcttgctct gtcgcccagg ctggaatgca gtggcacgat ctcggctcac   57900
tgcaagctcc gcctcctggg ttcatgccat tctcctgcct cagcctccca gtagctggg    57960
actacaagtg cccatcacca cgcccaacta attttgtat ttttagtaga cgggggttt    58020
caccgtgtta gccaggatgg tctcggtctc ctgacctcat gatctgcccg cctcggccta   58080
ccaaagtgta tttatttatt ttttgagaca gagtctcact ctgttgccca ggctggagtg   58140
cagtggtgca gtctcggctc actgcaacct ctgcctcctg ggttcaagcg attctcctgc   58200
cccagcctcc cgagtagctg gcattacagg cgcatgccac cacgcccagc taattttgt    58260
attttttagt agagatgggg tttcaccacc ttggccaagc tggtctcaaa ctcccaacct   58320
caggtgatcc acccacctcg gccccaaagt gctgggatta caggagtgag ccactgcttc   58380
```

```
cggcctgctg tatgttttta ttatatacta tgagataatg agattagtga tggattgctt    58440
tgtaatactt tgggagtctg ggtttggcag agtgtgcccc tatgaagact aagtgggact    58500
ataatgattg tgttttctta aatcagaatc aggatgcata accagatgaa ggaagacata    58560
gtcgggagcc atagttttaa tatctagatt ttggaatttt agggtgattt actataggga    58620
caaagtattt gaaattggga ttggcggaac atcagtggaa ccagcgattg ctaagttaaa    58680
tatatacagg gacattagat aatggatgat gaggaaatgg gtaaagaaa gtgagggcct    58740 tgtgagttga aacaaaaata atcaaacctg gaacactttc catttattgt attagatatc    58800
ttcatttcaa taaaattaat gtatatgaca aaattttatt gtcctcctag ttcaagtggt    58860
attctacttt tatttccata aaaatatact ttcaggatag ggaaagggta aacttgcatt    58920
ataagtttgt attttctcac gaagggacag gagagaagaa aaaaatcatt tgcttattgt    58980
ctaggctatg caaaaaaaaa aaaagaacag ccttgttttt ttattacatt ttttcattta    59040
gtttatgatt tgccatattt attattttaa aacatgaagt ctgtagtaca aggttttatt    59100
taaaaacatt ctcaaaatca aggactatta ctacatgcat tcagggaaga ttatctagct    59160
atattggaga gatctccttc gctagtaatt gatgaaacct aggaattgaa ccccagcttc    59220
tctgacttaa agctgcccta ttgtgaagta gaaatgaagt gtaagcaata tattcttaag    59280
tatactggtc aattctgatt tacatagaag acctaacagt ttatttactc cctactattt    59340
gttatgggat tatgctgata gtagctatta ctaatagaag atacggtcta aatcagggaa    59400
ttcgtgttct atcagggatg gcatatgtgc atatctaaat aattactgta cactgggata    59460
tgttctagat aagaggtgta tataaagtag atagagatga ggaagtggat gatgggcctg    59520
tatgccagta ctactatcag gaaaaatttc atgaagatga tttctgtatt gggctagtaa    59580
aaagcaggga gtttcttggc agacaattag gggaataagt gaagcataca ttttgacatg    59640
agcaaagcac agaatcattt tattactcca agactcataa gactggccct gtttacttca    59700
aagttacttt ctttattatc aatcctgagt tggcttcaaa tgaggaggca tagccatgca    59760
tttctgaaaa aaaagggaga gaattagtct gttaggcagc agtgggtgaa cagtgagcaa    59820
agataggaag atgaattttg ataggcagag ttgcatattt tgcaactaaa ggtagacatt    59880
gcagttgtat agttgaaaga ccctttggtt attttagctg cttataacca ttatcgttag    59940
tgatgtgcat ttttctttt tttttgagat ggagctctgt cgcccaggct ggagtgcagt    60000
ggtgtgatct cggctcactg caacctcagc ctcctgagta gctgggacta cgggcacaca    60060
ccacgaggct tggctaattt ttgtattttt tggtagagat tgggtttcac catgttggcc    60120
aggctggtct tgagctcctg acctcaagtg atctgcccac cttggcctcc taaagtgctg    60180
ggattacagg cacaagccac cgtgcccagc ccatatacat atttttatgt aagtatgttt    60240
gtaaagttag agataaaata gtgataatac agtgttactt tgagatagta tagtgttact    60300
ttggctggta ctctaatttt actgtatgct gctattaatt tatatttggg gttttaagaa    60360
attttggttt ggttatcatg cagtttgtag ggttaaatta atactattaa gatggtgtgg    60420
tttttcttac tgaggacagt taaaattttc aaatataaag ccagatgaat ttatttattt    60480
aacaatggtt attgaatgtg aactatgtcc caaacctgct accgtttaaa attcagatga    60540
attctccagt aattgcctca gaaattttcc ggagcaatta ggtaaaagga gtatgatttt    60600
atgggttagg tagccttaat attttgccac agtataactc ttaagcttaa agtaattttcc   60660 attttttattt actatacaaa gtatagtttt aatatttgta tattcttata tgcatattta   60720
ctaaaagttg tgccttatga aactcatact gtgttttgtt ttgtttttt gttgtcgtgt     60780
```

-continued

```
tttttttttt tttttttttt tttttttttg agacggaatc tcgcccttgt gccaggctgg    60840
agtgcagtgg cacgatctca gctcactgca acctccgcct tactggttta agtgattctc    60900
ctacctcagc cttccgagta gcttggatta caggcatgcg ccaccatgcc cagctaattt    60960
ttgtattttt agtagagatg gggtttcacc atgttggcca ggatggtctc gatctcctga    61020
cttcgtgatc taccagcctt ggcctcccaa agtgctggga ttagaggcat gagccaccgc    61080
acccagctga aactcgtact gtgttttaag tgttataaca ttgaggaatt tgaggcagtg    61140
gtgtgtggtc taataacaga gcatgagaga gcttcagctt tgatacttaa tttctatata    61200
tcccatctta ttccgaaagg aatttcagtt agcttaattt ccattttagt gctgtttctt    61260
tttgtgttaa tttattgttt tcttaattgt gctgatttaa aatccagcca acaaattaat    61320
ttaacgcttg tctgtctaaa tgtattttca cttcaaagtc tcttcagtga atatgaagac    61380
aattagctat attttttgcta acaagatttg ctgatgggga gaagagcgag ataaaggaac    61440
aaatcaagga tgagtgttag gttttttggct tgaactactg ttgaatggtg gtggtttttg    61500
gcttgaactg ctgttgaatg gtggtgctat ttgggcatgt ttgtgatgcc cattacacat    61560
ccagtggaca ggccaataga cagctcttttg actctggaga gatttaacaa actttaaaca    61620
ttctcaggag cttagatgaa caatgaactg ttccactctt ttaagaactt gaatcttgac    61680
acacaagtgg gtatcttaaa gtcacattgc atgtgatttt ggaggctttt gagaatccat    61740
ttattgattt aggattaggg gaatacaaat ttagtgtttt aggaaattgt ttaaagcaaa    61800
gtgaatatta aactcgaatt ttgtttgtat caaaaattct aagtattaaa aatgtttctc    61860
tgacttgtct gagaaggctc agtaaataat tcttcaattt gtaatgagag ttttgctttg    61920
cattagctat tggtctataa agtccagtaa gatagtctaa tctctgcctt cagttttata    61980
gattagtgga cgagacagac aagtactgaa atacttaaga aatacttttc acaagtggca    62040
atagaacaat gtgttatgga ctcattgcag aaggctgagg agcagtaaag gagggaaggt    62100
tcaagaaagc cttcaaaaag gaaataacac tttagccaga gccctactca ccagtaagag    62160
caaaaattgt gcaactttga tatttaagaa atggagggtt actgctagtc atagtggtgg    62220
tgagtaattc tatatgacta aagcatcaaa ctctaataag agcattataa aaagaggcta    62280
gaaaattgga caggcaacat tcaacatatc ttataattaa agatttggta gtttatgtta    62340
gaggtgatag acacatagga gagttttttaa atgtgggagt aaaatggtca gacttgactt    62400
tttagaacag taataaagga gtgcagttat ttttggaatt catttatgtg actttttaaa    62460
gacttctggg gtaggctggt gcagtggctt atgctgtaa tcccatcact ttgggaggct    62520
aaggtgggca gatggcttca gtccaggagt tcgagaccag cctggacaac gtggcgaaac    62580
cccatctcta caaaaaatac aattagccag gcgtggcggt gcgtgcctat agtcccagct    62640
actcgctaag ggacgctgag gtgggagaat cacctgagcc caggagttta agactgcagt    62700
gagctgtgat tgcaccactg cattccagcc tgggcaacag agtgagtccc tgtctcaata    62760
aagatcttta gggtagactt aattgcaaat gctttcttaa aggatttgtt tgttttctta    62820
gctttttttt aaaagtcac acgataaagg gtgtggtggg tacctataac ttaatacgga    62880
catcatttag ctatattttt gcccagttaa tacagtaaat gattaaaaat tctttcttgc    62940
tttaggatta tatgaaataa ttaaattata taataaatga attattttat taatgtttag    63000
tgctattctc atacagtcta tgaataaggt ttccttagtat attatgtttc tcaataatac    63060
agaatttttt tgtttctttc ttagtaatag cttcatcaga gacaatagaa tagtggtcgg    63120
```

```
gaagttaaaa tgaaattata tgtgtagata attctgtttc atagagttta aatgaacttt    63180
ggtgctactt ctattcagga actatttaga cattaatgtt gatgtgttaa aaaaaaaaaa    63240
aaacctgctc taggccaaat cagatcttaa tctggtggta attttgtacc cacagagttt    63300
attgtttaac agggcaaatt agatgtattc tctttatata tttatcataa gagtaagaaa    63360
tgtaagtgtt ctaaaagtac atataaaggt aaaacaattc agaggggaag attatgtctg    63420
gaggaagggc atcagaaact ctgtaggagc tagggcttaa aattaaaaga taagtaagct    63480
ttggaggtgt gcaagtgggg agaccaccaa caagcaaaga aaaagcatac acaaagacac    63540
agaaaaatga ttatcatggg attttttta aagtagaatc ttagcaactt ttaaaaagac    63600
aaattatcag gcaattacca cctcagacct actgaatcag aaactactgg gatgaggccc    63660
agcaatgtgg ccctccaggt gattctgaag cacactcaaa tttgacaaac tgctttgcaa    63720
tttcaggcag ataaattgac ctggaatatg caactctttc tgatctttga tctaggaaag    63780
gttttaaaga aataaatctg aagtaacaac atttaaagag ttccagtaat tagttcaata    63840
ataatagtta acatttattg agccatttta tgtactagac ctttgctga gtaaaggtta    63900 ttatctcagt tttatagatg agacacagag aggttaaata tgttaattgt cacacagcta    63960
agaaagtacc agatccagaa ttttaattta tgtagcttac tataaagctg acatttttg    64020 gtgggaaata agttccaact tgtagatacc tttttaaagt acaaaacaaa gttttactt    64080 gttttatgga ccacttttgt atctctgatg ggcatgaaaa ttgctaagaa cactattgta    64140
gatttttatt ttaatagagc attctccatt ttaaacttta attatagaaa gcattttaag    64200
aaatggcatg ctaggcttta agaaaactgg ataaatgaaa atccaaactt aaataagata    64260
aatatttgga cgcaaaagtt ctcaaggttc attatgagaa atgtagtcat ttcacataaa    64320
agctttgttt tgcacatttc tcaataatgt aatttgtcat gtaaaagaag aaaagtctgg    64380
agtgggccag gcatggtggc ttacacttgt attccccagc actttggaat gttgaggcag    64440
gaggattgct ggagcccagg agttcgagac cagcctccgc aacatacatg gggagacccc    64500
agccctacaa aaaatagtaa taataattag ctgggcatgg tgacatgagc ctgtggttcc    64560
agccactttg gaggctgagg caggaggatc atttgaacat gggagtttga agctatggtg    64620
agccatgatc atgccactgc attccagttt agacaacaga gtgagactcc gtctgtgaat    64680
gagtgaatga atgaatgaaa agaaaaagc ttagagtgat tgtaccaggc attcctgagg    64740
tacattcaca ttttataatt aaactcaacc actctttgta ctaaattttt tctcgctgac    64800
attgacctaa gatatattcc tttcccctct gtgtttctgc aactatttaa gttgatatcc    64860
ttctctaagt cagattcaaa ataatatttt gaaatgcact gatactataa gtatctaaaa    64920
atacatcttt tcagatgctt aatctttgag cagagaaaat acaaacattc taattaaatg    64980
tgcaagatgc gtatataagt aaccatgagg atctttgtta atatggagta acgacatcat    65040
aaacaatctt ttctactgtc ctttttttatt tacgttcaat tttttgaaca ggcaatacag    65100
tcatacaatc caaagatat gaaaagacat aatagtaatg tctcattctc atccgttttcc    65160 cttaggtacc catttccctt ccccacagac acatactttg ttaatagttt ttcttccaga    65220
gatgatatat gcatgtgtac aagcaaatgc aaatgttttt atttctttt aacaccagta    65280 gtaatatatt acatatatac atactgcact gtgtatataa tgtacactat tgtttcctgc    65340
tttttacatt tatacttaat atgtattttt cagatactgt catcttacta tatataaaaa    65400
gctaactcat ttgttttttca gctctctcat atttgatggt atgaataaaa caaatttagc    65460
cagttttgta ttaagaggtt tctttgattg tagttttttg ctgttactaa caatgctgca    65520
```

```
gtggttgggc gcgtggctca cacctgtaat ctcagcactt tggaaggctg aggcgggtgg   65580
atcacctaag gtcaggagtt caagaccagc ctggataaca tagtgaaacg ctgtctctac   65640
taaaaatatg aaaattagct ggacctggtg gcacgcatct gtaattccag ctactcagga   65700
ggctgaggca caagaattgc ttgaacctgg gaagccgagg ttgcagtggg ccgagatcgc   65760
accactgcac tccagcctgg gcaacagagt gagatcctgt ctcaaaacaa acaaacaaag   65820
tgctgtggta tgtaactttg aatataaatc atttcatgtg tgtcccattt ttatctggag   65880
gacaaagttg tagaagtaca attcagagac agggtcttgc attgttaagc aggctggtct   65940
tgaactcctg gcttcaagca gtcctcccaa agtgctagga ttacaagtgt gagccaccat   66000
gctcggcccc cacttgcttt tgaatacagt ttttcctctg acacatgtat atatttggag   66060
aactctatta ccacaggaaa tcacaagaaa tagcatcata aatgtgggga attttacttt   66120
gacattgtgc cagtgcagaa taagattcta gtaaatcttt atcataaaga aaaaaatgta   66180
ttcctgttgt aggtctctag tattgtgatg ataaaattta gtcgttttc aagaaaaag    66240 aaaggtttat aggcagtttt agttccttaa atatcagtat cacaagtagc aaaaattaat   66300
gagaaagtta aattttatca gatttatttt tcattttatt tgtatttaat aatttgttga   66360
atggtaaaac cagaatgctt ttaatatgtc ttgaggcctg aaagaaagtt cctttgaaat   66420
taaatttcag caatgtagtt gtgtagaatt tgaacaattc acaatactga ctttcagtgc   66480
ttctgaaagc aggaagtgta ttactgacac gcagaaatat tccagcccaa gaacatccc    66540 tactgccata tgtggtaaga atttgtcact aacccacaaa ctagttctgt aatgcagtga   66600
ataagcagaa ttggtctttg ttggacattt ccaattcaat atgaaagaac tttgttttgc   66660
agtgtcttgt aagtaattat tagcttatgc cttgggagaa agcctggcac atcatgggtg   66720
cgtgctcatg gtttattgag agaagaaaat tcttttaggc atgttttta aacttggtta    66780 ttgtgaccct tagttaaaac actgaaatta ctcgaatatg ttaaagactg agttaaatat   66840
tctgactcag cttattaatg atatctttaa attatattac ttttattctg ttttcctct   66900 ttgctgctca tgtgaaataa atatgaatct tatgtttgca cttatgctat aaaagaaatt   66960
atccttgggg ttaattatta agggatgggg aaattaagag ctaagagaca ggaaaatgag   67020
ttgtgaggaa ttggggtcac cagatttcat taaaaatttg aaaatatcac tgtttctcta   67080
aactttaatt tttatttgtt gtattttaag cggttaagaa gattgtctac caaatataga   67140
acagaaaaga tatatcccac agccactgga gaaaaagaag aaaatgttaa aaagaacaga   67200
tacaaggaca tactgccatg taagttggaa atgcccttga taaaatacat agaaatgcta   67260
attagccttt tgtaacctaa ctagttttat tcttcctgag tttcactgtt aaggaagtag   67320 taattaaccct atcttttcaaa gtacatggaa agataataat tcataattgt gcttttttgtt 67380 tttccttctg atcctaattt ttgtttaatt tttttcctgt aagtatcaca gttgctctaa   67440
tactaaatta cttttaaata ctgtaaatcc aagtgaaaat atcttctgtc aactctctgt   67500
tcaaagatgt tatttcatta aaataataga caactgaata catttataa aatgctaaca   67560 atgttgattt ttcatatatc tatacataag aaccttaatt gattaattat gcatgagaaa   67620
atgaagcata ggatgactca acatctgtg tgtctactat tctcagcagt ctgaatatgt    67680
gcctctaagt atatgtctta gactgattgc attacattct aatgatattt tatttattta   67740
tttatttatt tatttgtttg tttgtttgtt tagaggtggg ggttctcact gtgttcccca   67800
ggctggtctc aaactcctga gctcatacga tcctcccacc tcagcctccc caagtgttgt   67860
```

```
gattacaggt gtgagccact gcgccctgtc tgtattctta aatagcacag ttttctggca    67920
agataacttt aactctgaaa gtatacttaa ggtgtgccat cactttatcc agtaaaagct    67980
atacgtcata cttgctatct tttaaagctg ccgtcgtttt tctttcttca taagtatttt    68040
gaaatatcta cattccatca catcatttcc tcaattctta ttcagtctta aaggttgttc    68100
tctctaaaat gcctttaaag ttcttggtga cttttttttt tttttttgtg acagtcttgc    68160
tctgtagccc aggctggagt gcggtggtgg gatcttggct cactgcaacc tctgcctccc    68220
aggttcaagc gactcttgta ccttagcctc ctgagagctg ggacagctct aatacaggtg    68280
cctgccacca tacccagcta attttttgta ttttagtaga cagggtttt caccatgttg    68340 cccagggccc agtggctttt taattgccag atttggtggt ctttttttac tgtttattct    68400
aacaggaaga atattgatta ttcaagaatg ttgaactatt ttgatgccat tgatcaatcc    68460 ctattttga aattttcttc ttccatgata actcttttaa aacacctctt ccctctcatc    68520
tctttccctc ttttctccac taacttcttt gcctcaattt aatccttcat cctttgttg    68580 ttctacatta ttatcagctg tgggatatgt ggatagcctg tgttggcaga attaacaagt    68640
ggcaacataa cataatggta tagtgttctg attctggaag ttgaaatcct gactccacca    68700
gttgctagct atatgacctt ggactgatcc tctctgtgcc ttggttttgt catccttaaa    68760
atggagatta taataatact ttttaggatt atttgcacaa taggttaata ttaaatgctt    68820
aaaagtgtac ccagtggcca ggcgcggtgg ctcacgccta taatcccagc actttgggag    68880
gccgagactg gtggatcacg aggtcaggag ttcgcgacca gcctgaccaa catggtgaaa    68940
ccccatctct atcaaaaata caaaaattag ccagatgtgg tggcacgtgc ctgtaattcc    69000
agctactcag gaggctgagg caggagaatt gcctgaaccc aggaggtgga ggttgccatg    69060
agccgagatt gcgccattgc attccagcct gggcgacaga gtaagactct atctcaaaaa    69120 aaaaaaaac aaaaaaacaa aaaaaccag tgtacctagc acatagtaac caatcattaa    69180
gcttttgcaa aataaccagt ataccctagca catagtaacc aatcattaag cttttgcaaa    69240
atacactcca cttttctcac ctgttgtctt agtctgttca ggctattaca gaaataccat    69300
aaacagggtt gcttattaat aacagacatt tgtatcttca aattctagag actgggaagt    69360
ccaagatgaa ggcaccagca gatatgctgt ctagtgaagg gtcactctgg ctcatagatg    69420
gtgccttctc actgcacttc acatggtgga aggggcaaac aagctctctc gggcctcttt    69480
agtaaaagct ggtaatccca ttcacaaggc ataatctaat catctcctaa aggccctacc    69540
acttaatact gttgcattgg aatttatgtt ttaacttatg aatttgggaa ggacacaaat    69600
attcagacca tagcaccagt ctgcctcaga ataggggatg acatggcttt ctggatactt    69660
cgtattaagc aagataattt taaggtgatc ctacattgct ctggaattat tcatgcacac    69720
attcaaagag ttagcctgtc cactttcttt ttctgtcgtc tagccgtagg tttctctttt    69780
catatgatgt ttcatttct tctttgtttt tgaaacggtg tcttgctctg ttgcccaggc    69840
tggagtgcag tggtgcgatc tccgcacact ataacctctg cctaccagct tcaagctatt    69900
ttcctgcctc agcctcccaa gtagctggga ttacaggcac ccgctgccac atccggctaa    69960
tttttgtatt gttagtagag acgtggtttc accatgttgg ccaggctgct ctcgaactcc    70020
taacgtcagg tcatccgcct cccttggcat ttactcattt tacagaaagc ttctgagggt    70080
gtactgtatg ctgggaatgc aacaaaaaac aaactggcaa aaatccctgc ccttgtggag    70140
cttatatgtt agtcaaggtg atggacgata catattaaca tatatggtct gtcatgtggt    70200
ggtaattagt gttattgaga gtgtggttcg aatgagggat agggagaaag cagagaatag    70260
```

```
aagggtaagt ttacagtttt ggctggggta gtgggaaagg ttagtggtgt agtgttaaac    70320
tggtcctctg aaagttctga tttgtattgt ttgctgattt ctgtgataaa tggattattt    70380
accataatca tcacagcaaa actctgaggt aagtactgtt atgtgccatt ttgcaaacag    70440
gaaactgaga cagagaggtt aaaaagcttg tcacacagtt aaatattgtg gggtaagaat    70500
ttaaacacag gcggttttaa agccttcact agggtgattt tgcctctcaa gggacactta    70560
gcaatgtctg gagagatttg gttgtcacaa ctggggtatg ggagtggaca ggctgctaat    70620
ggcatctaac aagtagaggc taggaatact gctacacatc ctgcagtgca taggatgcag    70680 ccccctttccc caaacaaaga cttctcgcca aaatatatga gtgtcagcgt tgagagacct    70740
tgtccaagag cttgagttct taattactgt gcagtaatca gattgacagt gccttttttc    70800
ctttaagtta tttaaagttt gataagtagg tctccagtaa atttctagtt attttgactt    70860
gggatttttt tttcttttttt ttgagacaga atctcactct tgtcgccctg gctggagtgc    70920
agtgtgggat ctcggctcac tgcaacctct atctcccggg tttaagcaat tctcgtgcct    70980
cagcctccca gtagctggg attacaagca cctgccacca tgcccagcta attttttggt    71040 attttttagta gagacagggt ttcaccatgt cggccaggct ggtctcaaac tcctgacctc    71100
aggtgatcca cccgcttcag cctcccaaag tactaggatt actggtgtga gccactgcac    71160
ctggcctgga aatttatatt gaaagtaatt gtactgagag atatgtgctt atttactgtt    71220
agataactat ttaattcatt gcccgggcac agtggctcat gcatgtaatc ccagcacttt    71280
aggaggccaa gctgggcaga ttatttgagc tcaggagttc aagaccagcc tgggcaacat    71340
agcaaaactc aacacacaca cgcacgcacg cacgcacaca cacatactct ctctttctct    71400
ctctcgtgtg tacacttgtg gtcccagcta ctcagtaggc tgatgtggga ggatcacttg    71460
agaccaggag gtcaaggctg cagtgaacta tgattgcacc actgcactcc agcctgggta    71520
acagagcgag actgtctcaa aaaataagat ggagaagaat ttaattcact aacttccttt    71580
gcatgtttta acatgtgcag tgcttgcaga aatagaattt ttaaaacagg tttgaggtat    71640
aatttacata cccatgaaat ttatccattt taattgtgca attcaatgat tttttttaaag    71700 taaatttata gagttttgca acaattaata caatctagtt ttaggacatt tccatcaccc    71760
ctaaaagatc tgagtcttca gccctgggca gctgttaatc agctttctgt ctgtatagat    71820
tttccttttc tgtgaattta atataaatgt aatcatacaa tatatagtct tttgtgtcta    71880
gctcttttaa cagttttttt ttgagatgaa gtctcattct gttgcccagg ctggagtgca    71940
gtggcatgat ctcggctcac tgcgacctcc gcctcccagg ttcatgagat tctcctgtct    72000
cagcctcctg agtagctggg attataggcg cacatcacca tgcctggcta attttttgtg    72060
ttatttttag tagatacagg gtttcactat gttggccaga ctggtctcga actcctgacc    72120
tcgtgatccg cctgcctcgg cctcccaaag tgctgggatt acaggcttga gccactgtgc    72180
ccagcctctt gttaacacat tttaaagatt cattcacgat gtagcatgca tcgatagttc    72240
attccttttt gttgttgaat aatattccat tgtatgaatg atgaacatat tgaataatgc    72300
tgctatgaac atgtcataca actctctgtg tggacctatg gttttgtttc tcttggttgg    72360
atagctagca aaaccatgga gaggaataat tgttttcatt tttttgatat ttagattatt    72420
tctaaatatg cttaataaga gcaccaatct ggcagggcga ggtgactcat gtctgtaatc    72480
ccaggacttt ggaggccgaa gcgggcaga tcacttgaga tcagatcaag accagcctgg    72540
ccaatacggt gaaaccccgc ctctactaaa aatacaaaaa ttagctaggc atgatggcac    72600
```

```
gtgcctgtag tcccagctac ttgagaggct gaggcacgag aatcacttga acctgggagg    72660
cagaggttgc agtgagccaa gatggtgcca ctgcactcca acctgggtga cagagccaga    72720
cactgtctca aaaaaaaaag agcaccaatg aagaatatta aaacagccac ccaagttctt    72780
tctcgctact tctagttccc ggcgctttgc cgggtgttaa tggtggccca aaatcatggg    72840
tgctgtggct ttctccctaa ggtgtcacag gagctaaggg tgccacttaa caaactgcag    72900
aagatgcagg caggtgaagg acacccagtc tgctgtggca gtggaatgtg gcagaaaagc    72960
cagctgggag ggcggggagc aatcctggaa ggcctggctg accccacaat tgaacagggt    73020
ttggtgtgtc attgctttta ggccttttca gtggacagaa ctgggtggga tatacactca    73080
tttatttgaa atcatgcatt tgttccatac tccaattcca gcccaccct tctttgctct    73140 atggtcaagt gagtgagaac aggcggctac atttttcagcc ttgttgctca ccgcttcctt    73200
ccagtagtcc catgttgctt catatctctt cagtacatgt attatttaga cccagagcct    73260
tggcttttaa atcaggcagc cccagtttca aatgtgtcac tgccatctca gttttgtgat    73320
ttgggcatac ctctgtctgt gcatagcgat attaacttct atctccatgg gtgtgtggtg    73380
aggataaaat tatgtgctta gaggaaacgt tcattccatg gtagctattt tttattaatt    73440 ctatacttt gaacctatta tgctacctat aatgccctat ttttttttc tttttaatca    73500 ttggcaaact tctcattccc tgagacccag cttgtcacac ctctgaagac tgctgatatc    73560
ctcaagatgt tccttactcc ctttccttgc tactacttta ctatggatat atgaacaaca    73620
ttattgtgct tattacatgc aataaatatt tattggatga atgatactaa aattcacatt    73680
taaaatgcca aaatcaaaat acacatgata tgctgtataa gtagcataat gttgattttt    73740
aaatctaatg tgctgtgggt acatagtaga aagcagtgac taccaaattt gcctgtgttt    73800
tagaatttaa atggggagtt ttaaaaaggg tatttctgtg ccccatttt aatttactga    73860 attgaactta ctacaagatg tagtactcca gaaatcttgg atttttaattt gctttccca    73920 gctgttgaat gattgggat agatgaaata agattggcaa aatgttgata atgaagctgg    73980
gtaatggata tacaaagatt cattatactg ttctattttg gtgtatgctt aaaattttcc    74040
atcttagaaa attttttaaa aaagaaatt accagcctgc atgtagccag cctggcacca    74100
gtcctaacta tcatttggga gccactattc tcatttggat ttacagtcac cagaaacttt    74160
actgaggacc cagtggtaaa ccagctattg tattctgcct ttgagatact ttgaatagag    74220
gctaatatgt catatgaata agggtaatta actgagaccc cttattactg gcaaacatgg    74280
taagaggaag cttcctgtag ttattcagcc atcattatcc taaccactga atattctatt    74340
ctcattttcc agagtcatag ctttttttg tatgtgtatt tcctatccca aatggcatat    74400
aaaaaggggg atgggacatg tagggtggcg tgaaataaat gacagagcat tgacaaacat    74460 atttttaaaca ttctgtttct tagaatacag tgaggagatg aataattttc accagaagca    74520
agtatatctt ccttatatgt gtcttctaca aatttctaaa gaagactttt ttaaaagtaa    74580
atttatcaat taaattagca gaactgggcc tttagtgcta tgtataaaat ttgagccaat    74640
gaaaaataaa ttagttacta ttagttgttc tttaatactt tgctaagaag tttattcatg    74700
tctgttaaca tttccgtatt tccttttgta tttttactgc ctttgatact cattcatgga    74760
ttagaaggga ttataatttg ataataataa tggcatttta catgttatat gttatggtcc    74820
cttctaatcc agaaacaatg aatactaggc aattctactt taggatttca taatctgaaa    74880
gcgtctaacc tcaaatactt actaactata aagggaaag gcagtaactt tcccttttgg    74940
taaccaagca ataccatatt aaccaagtga ccaaggttaa catcacaagt actaaagcat    75000
```

```
atgtatatca tgtatcctct gatgtgttgt gctgagaagg acacaatatc gttctgtggt    75060
attaccaaaa attcataact tcgttccagt catttaaaaa aaatcaatca gagaaacttt    75120
tttagattga aggagactaa ggagaaataa aaattattat tattattatc ttgagatgga    75180
gtcccactct gtcacccagg ctggagtgca gtggcgcgat ctcggcttac cacaacctcc    75240
gcttcctggg ttcaagtgat tctcctgcct cagcctcccg agtagctgag attacaggca    75300
tgcgccacga tgccctgcca attttttttg tattttttagt agagatgggg tttcgccatg    75360
tgggccaggc tggtctcaaa ctcttaacct catgtgatcc gcccaccttg gcctcccaaa    75420
atgctgggat tacaggggtg agccactatg cctggccact aaaaattaaa tttaatatga    75480
gatcctcgaa agagaaaaaa gattagaaaa cactgacttg tatagtcttg tttaattaat    75540
agttttataa gtgttaattt tgtggtatta ttgatcattg tcttatggtt atataagatg    75600
ttactattag aggaagttca gtgagaggca tgggaattct ctgtactatt tttacagttt    75660
ttctataaat ctaaaattag ttctaaataa aaagttttaa acatcagcac aaactggaaa    75720
aaactatttg cacttcctgt gacagagggc tgatttttc tttttacata gatctcataa    75780
aaatcagtag gacaaaacag acgtggaaaa atgggcaaag gatataaaca agtggtttat    75840
ggaaaaagaa gtacacagaa ccaataaata gattaaaaca tacaatcctt tgcataattc    75900
aagaaatgga aattaaaaca agatatttt acttttggt ttgtcagtga tgaaaagttt    75960
ggtaataccc agtcaccctt attacataac cctgtataaa ttgtttcata ccttttagaa    76020
ggcaagtagc aattcctctg ttaggaattt accctacagc aatgctggta acagctatat    76080
atacattagt gttcattgta gtaatgtttt taataggaaa aaaatggccc atcagtagag    76140
tagctaaata aagaatgaaa cattcacatg atggaattct ctgttacact aaaaagagtg    76200
agatagccta gtgcaagctg agtgcaatgg ttcacacctg taatccaaac acttgggagc    76260
ctgagccagg aagatctgta gtccaggagt tttaggttcg aatgagctat gattgcagca    76320
ctgcacttca gcctgagtga cagagtgaga ccttgtctct gtattttaaa ataatagtaa    76380
aaataataaa gtaaatcttt ctgtgctttg ggaagagttc caggatatac tataaactga    76440
aaagtaatga tacagaacag catgtatagg atgcttgcat ttgtgtagta gttttttcaaa    76500 gtatataact atatgtgtaa taagtacact tggaatggga aaagtaactt taatatagta    76560
tcttgatggg agagagccct ggaattgaag ggcaggggag gcttactttt cactttatac    76620 cttttctttaa ggtctaattt ttaaaaatta tatacatatt cctttaaaag aaatcaataa    76680
aaacttaaaa gaaaaatata cttcataaaa ttttttaaag attttttttac tctattacct    76740 aataataact attattagcc aagagcagtg ttgaacactt tttatatata atctcaattc    76800
attaatttgt tataatttgc tttttatagt ttcttgtgaa atatgaaagt tacatttttt    76860
aaataagaat tttagcatat gggcttgtgt atcactggtt agtattcatc agccacttgg    76920
tatgtttgtt aaaagctgca gaggctgaaa ccctagactc tgctctagta aatcagagat    76980
aatgtcctgg aatttgaatt ttaaaagagt tccagagatg attcttattg caactttaat    77040
acactgcttt acgtcactgg tggtggtgtt tttttgtttt gttttgtttt gttttgtttt    77100
tttgctgttg ttgttttgtt ttaagacaga atcttcactc tgtcgcccag gctagagtgc    77160
agtggcgcaa tcttggctca ctgcaacctc tgcctcccag ccagtttcaa gtggttctcc    77220
tgccacagcc tcccgagtag ctgggattac aggtgcctgc caggtggtgg ttgtctgaaa    77280
atttatttca tttcctttca gtttaatgtt agaaattacc ctgctggtac ctagagtcca    77340
```

-continued

| | | | | | |
|---|---|---|---|---|---|
| ttttcatcca | ttgtttttta | aaataaatgt | tcttaagctg | tctatttaac | cttacttacg | 77400 |
| cttcattaga | aaatacctgt | gtgtcaacca | tacatatttt | atgaattttt | ttctcgtagt | 77460 |
| tgatcacagc | cgagttaaat | tgacattaaa | gactccttca | caagattcag | actatatcaa | 77520 |
| tgcaaatttt | ataaaggtat | gtactaactt | taaatggtgt | ttctctgcca | tattaatgtc | 77580 |
| tttctacata | ctagttttgt | aaaaactttt | tgaattgctc | aaacatgata | ccaacagcaa | 77640 |
| aagaaataaa | aataaagcca | ctgccctggc | acaatgtttt | tatatgcttt | ccttctagcc | 77700 |
| ttcttattca | tatagataaa | tagtttctac | ttagttttgt | gatagcagag | ataacatttt | 77760 |
| cttttttatt | tcttctttcc | catggaagtc | ttacctatta | ctaaattatt | ttctcagtta | 77820 |
| tccctttgga | cacaaatgaa | catcatcaat | ccccgttgtt | gacccatata | ggttgtttcc | 77880 |
| aaatttttaa | aatgataata | ttgcagtaaa | catctttgtt | gttttgaata | atttcttagg | 77940 |
| ataaattact | aggggtggga | ttactggata | atactgatt | aaaattctag | aacatagctt | 78000 |
| taaatgtaaa | acttttggca | gttgtcactg | tttcaggtgg | caacccaaaa | tccaagatta | 78060 |
| aatagtctct | tttataacct | tgtttggat | acccttgat | gaaaagcagt | caagttcttt | 78120 |
| tttttttttt | tttttttttt | ttttgagac | ggagtctcgc | tctgtctccc | agtctggagt | 78180 |
| gcagtggcgc | tatctcggct | cactgcaagc | tctgcttccc | gggttcacgc | cattctcctg | 78240 |
| ccttggtctc | gatctcctga | cctgtgatcc | acccgcctct | gcctcccaaa | gtgctaggat | 78300 |
| tataggcgtg | agccactgcg | cccagcgtca | agttctttat | ggtagcagta | gagatagatg | 78360 |
| caaagtgcta | cttgattcag | tttaaataaa | aggcttttt | tccatcagct | aatctgtgat | 78420 |
| ttttaatctt | tcaagtgata | tgatagtata | attttcattt | attttatata | tggtgtttat | 78480 |
| acatattttc | atgttttgt | tgataaaaat | gttaactgat | aaaagtttat | gccaggccgg | 78540 |
| gcacggtggc | tcatgtccgt | aatcccagca | ctttgggaga | cctaggcggg | tggatcacct | 78600 |
| gagatcagga | gttcgagacc | agcctggcca | acatggggaa | acccagtctc | tactaaaaat | 78660 |
| acaaaaatta | gccggtcatg | gtggtgcatg | cctgtaatac | cagcttctcg | ggagactgag | 78720 |
| gcaggagaat | cgcctgaacc | caggaggtgg | aagttcagt | aagccgagat | cgtgccaatg | 78780 |
| cactccagtc | tgggtgacag | agcaagactc | cgtctcaaaa | aaaaaaaaa | aagtttatgt | 78840 |
| ggtaaaatta | ttatctatgt | caatattcag | cagtcatggt | tttaaataaa | aatttctttt | 78900 |
| tttaacaaag | ttaaaaacca | aaatgaatac | attaaataaa | aactaataaa | ttgatagttt | 78960 |
| gctatttcag | atgttgtcaa | tgttcatatt | cttttttaa | ggctgtttgt | taaaagttat | 79020 |
| agttttact | tatgcttaat | gacactgatt | cattgtatga | gtcagttatg | taccagttta | 79080 |
| gtatttagt | cagtgacatt | gtttggttta | tattctcatg | ttcattatta | aaaacctgta | 79140 |
| tagtagatgc | ttgataaact | tttgagttga | atagataatg | gaaggtagct | atggaagaaa | 79200 |
| ctaagaaaga | gctcttcact | agttttagta | ttgttttaga | atcagagcat | gctctgtatt | 79260 |
| tctgccagtt | agctttgttg | agtaggtatt | agggcttttg | ttattaatgc | ctagataagt | 79320 |
| aataatttt | aattagcata | aggcggttct | taaatacccta | ttctgtgcac | catatccagt | 79380 |
| aaacacaaag | taatagcagt | catcaaaagc | ttaagtgaat | tgaatatatt | ttgccatgct | 79440 |
| ttaatatact | atgaaagaca | cattatttgg | aaatggttta | agttaaaaca | acaatattac | 79500 |
| taatacaatt | tgaaaccta | tattttgggt | aatgaaatat | ttttggtaat | caaaataaat | 79560 |
| gtgaaatttg | cttttaacca | tttttagggc | gtctatgggc | caaaagcata | tgtagcaact | 79620 |
| caaggaccttt | tagcaaatac | agtaatagat | ttttggagga | tgatatggga | gtataatgtt | 79680 |
| gtggtaagta | atttactttt | cacaataaat | tttgagaaat | acttatgtaa | taacataggc | 79740 |

```
tattttactg aataaggaat gagggattt ttaaaaaatc cataattatg tttacttatt    79800
gctgatgttt actaaaaaga tggacccatt tttaggatgt ctcattaaat ttttacaaac    79860
taggctaaat attttaagaa ggtgtgataa taatttaaat cttgtcctaa gtcagtaagt    79920
aatgatacag ctatcaaaca acttataaaa agcagaaaag gattagtgct ctaataggtc    79980
agtaaaatac ttgatagtac agttatactc atttgagtcc ctcttctcag gaaaatatat    80040
ataaacacat aactataaat agactataaa tatgcagtat aagagaattt catctatccc    80100
tggagttcat tcagtgccct cttgttcttt tggatgaagg gaaataatat gcccttagat    80160
ttagaagcag agaaattaga atactgcgaa gagctaccct atactgctct gtagtattct    80220
tgaaacctaa ccatgtgcat tgatactttt cattgtgtgg atgtgaaaaa tcagtaatgt    80280
gaaactttca tttttgtctt acggcttttt aatggaattg taatgattct aaagcattga    80340
catgctctgg tctttgaaag attaataaaa gggggaaat tttccagtta tttatatttg    80400
ctgtacttca ctttaaaaac tagatgtgct tggggattga gaaagagcat gaagaaactt    80460
tctggatgat gggaacatcc tgtatcttga taagatttgt gttgcacaga tgtgtgtatt    80520
tgtccaaact cggagaatgt tcactttagg atttgtgcat ttcattatat gtaaaatttg    80580
cctcaaggga aaaatactgg aaacaatata aaaattatgt tctagattgg ccgcgtgggg    80640
tggctcatgc ctgtaatccc agcactttgg gaggccgagg tgggcagatc acgaggtcag    80700
gagatcgaga ccatcctggc taacacggtg aaaccctgtc tctactaaaa atacaaaaaa    80760
ttagctggac gtggtggcgg gcgcctgtag tcccagctac tcagcaggct aaggcaggag    80820
aatggcgtga acccgggagg cagcgcttgc agtgagctga gatagcgcca ctgcactcca    80880
gcctgggcga cagagcgaga ctccgtctca aaaaaaaaa aaaaaattta ttgtgttcta    80940
gataataata tgcatgctga agtattttgg ggagagtgta ctgatgttca caacttactt    81000
tgaaatgcat ttttaaaata agatggattg atagagggat agctatgtga taaaacatgg    81060
tgaaatgtta atgatagaat ataggtgatg gctatacaat gtttactgta aaattctcaa    81120
ctatgctgtg tgttggaaag tttacattat aaaatgggaa aaagcaggtg tgatcaactt    81180
ttaaaatggt gttaaacgca ttcaatattt aaataattat aaatatattt ttaattaata    81240 gtgctatta taattaggta aatatcctaa aagtgatatt ttaatataat ttcagaagtc    81300
acaaagtaaa tctgtaagat ttacatgatt taattcaaac caaaaacatc atgttaattg    81360
gaaccaattt aatttgttgc tgtatagtta gcccttgttt ggaaagtcta attttgataa    81420
tttctttaac ttacacattt aatattgaaa ctactttttt aggcaagcca attatacttc    81480
tcggtgcaaa attcttgaaa tctgtatttt attaaaaagt aaaattgtgt ttaactgata    81540
cgttctttat ctcactcccc accatcactt tttagatcat tgtaatggcc tgccgagaat    81600
ttgagatggg aagggtatgt ataatctatt cctcttacta tttcatttt acggataaat    81660 attcttagtc ttttattatt atagtcttaa cataagcggt taatgtagat acttctttta    81720
ttttggggta ctgctgttgc ttttatttca tacaagggac aaaataatct ctcaagcatg    81780
ttgttttctt ttatattttg taagtatgtt ttatcacaca caggcatacc tcagagatat    81840
tataggttca gttccagacc accacaatag cgcaattcaa acaaatttt tgttttctta    81900 gtgcatataa aagtcatatt tatactgtat tatagtctgt taaatgttca gtagcattat    81960
acctataaaa cacttcatgc cttattttat ttttttattt tttctagaca gagtctcgct    82020
ctgttgccca ggctggagtg cagtggtaca atcttggctc actgcaacct ccgcctccca    82080
```

```
ggttcaagcg actctcctgc cttagccttc tgagtagctg ggattatagg catgtgccac    82140
cacaactggc taattttttgt agttttagta aagatggggt ttcaccatgt tggccaggct    82200
ggtttcgaac tcctgacctc aggtgttctg cccacctcgg cctcccaaag tgctaggatt    82260
atagacgtga gccactgcgc ctggccttcc atgccttaat ttaaaaataa tttattgcta    82320
aaaaatgtta atgatcatct gagccttcag ctagttgtaa tctttatgct ggtaaagggt    82380
tttgttgacg ttgatggctg ccgactgatc aagttggtat ttgctaaagg ttggggtagc    82440
tgtggcaatt tttgataaaa tacaagacag gaccaggaac ggtagttcac atttgaatcc    82500
cagcactttg ggaggtggag gtgggaggat cacttgagcc cagaaggttg aggctgcggt    82560
gagctatgat tatgctactg tactccagcc tgggcagagg gagactccac ctataaaaac    82620
ataaaataag aaacagtgaa gtttgccaca ttgattgtct cttcctttca tgaaagattg    82680
ctctgtagca tgccatgctg tttgatagca acagcagttg ctgttctacc cacagtagaa    82740
ctacttggca aattggagtc agtcctttca aacccttcca ctgctttatc aactaagttg    82800
atttaatgtc ctaaatcctt tgttgtcatt tcaagtgctc acagcatctt caccaaaagt    82860
atattccatc tcaagaaagt agattccatc tcaagaaacc actttatttt cttatccgta    82920
agaagcaact cctcatccat tccaggtttt atcatgagat tgtggcaatt catttccatc    82980
ttcaagctcc acttctgatt ctctttgttg tttccaccac atttgcagtt acttcctcta    83040
ctgaagtctt gaacctctca aagttatcac gagggttgga attaactttt tccaaactcg    83100
tgttaatctt gatatttcga cctcctccca cgaatcatga atgtaattaa ttgcatctag    83160
aatgctgaat cctttccaga aggttttcag ttcactttcc ctagacccat cagagtaatc    83220
atgatttatg gcagctttag ctttacaaaa tatgtttctt aaataataag acttgaaact    83280
caaaattact ccttgatcca tgggctgcag aatggatgtt gtattagcag gcatgaaaac    83340
atattaatct ccttgtacat gtccatcaga gcttttgggt gaccaggtgc gttgtaaacg    83400
gaaatatttt gaaaggaatt ttttttttcca accagtagtc cccagtagtg agcttaaaat    83460
attcattaaa ccatgcaata gggatgggct ggggtggggg ttgaaaaaac aaaaacatgc    83520
tgtaaacaga tgtgctgaca tccaggcctt actccattta tagaggacag acagagtaca    83580
tttggcatga tttttagagc ccttaggatt ttcagaatgg taaatgagca ttggcttcaa    83640
cttaatgtca ccagctgcat taacccctaa caagagagtc agcatgtcct ttgaagcttt    83700
gaagctagac gttgacttct tttctctagt tctgaaaatc ctagatggca tcttcttcca    83760
atataaggat gtttcatcca tactgaaaat atgtcattta gtatagcttg tttcatcagt    83820
gctcttagct tagatctttg gataacttgc tgcagcctct aaatcagaat ttggtgcttc    83880
atctcgcact tttatgttat ggggacagct tctttcctta aacttcgtga accagccttt    83940
gctagcttct aactttcctt ctgcagcttc ctcacacttt atagaaatga agggagttag    84000
tgccttgctc tggattaggc tttggcttgt agaaatgttg cagctggttt gatcttctat    84060
ctagaccact aaaactttct ccatgtaagc aataaggctg tttgacctac ttaattttg    84120 tgtgtttcct ggagtagctc ttttaatgtc ctccaaaaac ttttcctttt tgttctaaac    84180
ttggctgatt agtacaagag gcctaccttt ctgcctatct cagttttcaa catgccttct    84240
ttactaagct taatcatttt tagctttttt atttaaagtg aaaagtttgt gacccttttc    84300
acttgaatac tttgaggcca ttgtagggtt attagttagt ctaatttcaa tattgtgtct    84360
caggaaatag gaaagcccaa ggagaggaag agagactgta caaaaacttg tcaatggaac    84420
agtgagaatg ctcacaacat ctgttgatta agtttgccat tttatatggg agcagtttgt    84480
```

```
agcaccccaa aacagagtag taacttcaaa catcactgat cagattacaa taacagatat   84540
catcataatg aaaaagtttg gaatactgca agagtttcca aaatgtgaca cagacctgaa   84600
gtgagcatat gctgttgaaa aaatgatacc gatatacttg cttggtgcag ggttgccaca   84660
aaacttcaat ttgtaaaata tgcagtgtct gagaaacaca gtaaaatgag gtatgcctgt   84720
acttaacaat aattaattag gtattgttac ttagtaaact tcaaatattc agtggtgttg   84780
taactagaat gctatctatg gactgaaata gagaggtatt tttaaatagg aataaaattg   84840
aacaagtgga aatacatttt aaaaatctgg ttatcattaa tatatggttt gaattttttgt  84900 ttgtttgttt gttttgagac tgtgagacag aatcctgctg tgtcagtcag gctggagtgc   84960
agtggcgcga tctcggctca ctgcaacctc catctcccgg gttcaggtat atttcctgtc   85020
tcagcctccc gagtagctgg gactacaggc gcctaccacc atggctcagc tcattttttgt  85080 attttttagta gagatggggt ttcactgtgt tggccaggct ggtctcgaac tcctgacctc   85140
aggtgatccg accgcctttg tctcccaaag tgctgggatt acaggcatat aatcccatgt   85200
aatccaccgc accaggcctg aatatcttga ttagtctgtt tgttaatacc acagtatgtt   85260
ttgtttgttt cctatcttca aaactgagag aagataattt cttaccctga ttttctaaca   85320
ttggtatttt tatgctatgt cgaagtaaaa tttatttcaa agctattctg gtatcctaca   85380
gcatcatatt ctgtcctcac tgtaggaggt aatgatatat ttacagataa ttcatattta   85440
aataaaactt ataagtgtg gtcttctata aatatggcat acaaatcaaa cttacaaatt    85500
acatagtgat tttatttgaa gttttttaat actaatgtag ttaatatatt taaaattatc   85560
tttagtttgt aaatatgtta attttttcag taagcaatat attgcaaaag atacatcttt   85620
cagttatatt acataaataa ttgggaagcc ttaatttatt ccattactcc caactatttc   85680
ctatgtcagt attaagtaat gttggacaga aagtgaataa aatgagaaaa tataaaaact   85740
gagaaattat taagtaatca agttatctat ttaagggttg tcaatatata cattaatatt   85800
attaatcaat tgtctaagag aatttaaatg tcattctcct aatgttttaa gttactgtta   85860
aggtttagga tgtatttctc ttttcattat attagtaagc tcatagtatg tatcaagtta   85920
ttgatgaaaa atcaagtagc attgagtaca taatttttttg aagcgaaagg ttttttgtgat  85980 tcactgtgtc ttattagtaa tagattatga gcaagttagg aactatgaaa ttatctgata   86040
accttgactt tgatcttgac tttgaatgtg acctggtgga aaaagcatag ataattaaat   86100
cagacaaacc taccttttac aagcattttg accatggtgc agtacagttc actctgagct   86160
tcagtttcct cacatttgaa aggaaataat acccaccttg cagtgttaga gattatgtat   86220
gtatgatatt taacacatag ttttttgatat cattattagt tttataccag gaatataagt    86280
accaatataa tcttattact gctcatctga atgaggggca ttgttagtca caccgctttc   86340
tattcttaac taaattaatc tcttacaact tgttttctat ctgtttcaaa gtattaaagt   86400
tttgtcaggt aaaagattaa aaaaatgttt tttaaactct caaaaataat ttaaggtcca   86460
agtgtaagta tagtggctca cacctgtaat cccagctact gggaggcta gggtgggaga    86520 attgcttgag cccaggagtt tgagaccagc tttggcaaca tggcaagacc ccatctctat   86580 ttttttttaaa tcttttttttt tttttgtgg ggagagacag tctcgctctg tcgcccaggc   86640
ttgagtgcag tggcacaatc tcagctcttt gcaacctgca tctcccaggt tcaaacgatt   86700
ctcatgtctc agcctcctga gtagctggga ttaaaggcat gtgccaccat gcctggctaa   86760 ttttttttgta ttttttgagta gagacaaggt tttgccatgt tggccagtct ggtcttgaac   86820
```

```
tccttgcctt aagtcatcca cccacgttgg ccttccaaag tgctgggatt ataggcatga  86880
gccaccacgc ccggcctcca tctattaaaa aaaaaaaaaa ttagccggtt gtggtggcac  86940
acgcctgtgg tcccagctac tcaggaggct gaggtgggaa gatcacttga gcccagaagg  87000
tagaggctgc agtgagccgt gattgcacca ctgcacactc cagcctgggt gacaaagtga  87060
gaccctatct aaaaaagag agaatttaat ttaatcattt tctgtaaaca tctcttggaa   87120
aatgagattt ggaagttacc tgtgttttta agcctctaaa atgttagcta acccaacata  87180
ccagacagtt ctactttgtt tctctgtgag cattactgtc aacttatagt tcattcagcc  87240
tataggtaat aactccattt actgtatttg gaactgtgaa gatttaatta ggaattcatt  87300
aaccaatgca tttcccactg cttaaaaggt ttatttaagc tagatggtca cttagagact  87360
ttgattttat tgggccttga tacaaattgc atcatttctt aatacctgaa tcattctatt  87420
ttccataaag ttaggctttt cattcactta actgattttc taaaatgatg aggtgcttga  87480
tattagaaac tgatgaaaat ttatcattct ttttctatac ctgtttaaaa taggaaggta  87540
agaggagaaa ttatttgact acactttctg taatctctaa taaaattgaa tagttaatac  87600
atcatgtttg tgtagggctt ttaccatctg tggtacattt gaaatacact gttatttaac  87660
aaacatgcaa caactctgta agataaggat tattattcct attttacag ataaagaaac   87720 taaggtcaa taaaggagta gaattagtac ttgcaaaatt cttctgattc caagtagaat   87780
attctttcca cttcatcaca tattttacat ttaatgagaa ttcagccaga tatttgtaga  87840
gattgtcatg ttacaagcaa tacaacttac ctagcaacct ttataccaaa tacctccttg  87900
taccagacac tttttttaaaa ttagtttttc ttgtctagag gaggatctttt ggtctactct  87960 gtagacctgg cagatagcaa tgaacagtta tgcacttaag tcagtaaggt tcttatgact  88020
attcttggag aagacacagt agcctatttt ttaaaacaac tgggtaaatc taagctctct  88080
cagctccatg cctgctaatg tgggttttttc tgttttgggg aagtagaagt aagcagaacc  88140
tcaggacaca aaatatttat aacagtttaa gaaaaactta catgaattac ttactaattt  88200
ttttttttgg atgacagaaa aaatgtgagc gctattggcc tttgtatgga gaagacccca  88260
taacgtttgc accatttaaa atttcttgtg taagtatcca tttttgtaaa cacttttttc  88320
agaaaattgg catgctatac tgatgaataa ttaaattata atgtggtatg aacccaggct  88380
tatagacgcc aaggactcac aaacctatgc ttacatttaa aaaaattttg tttatatact  88440
gcttttaaat ttggaagctt ttgggttgac ttcataaatg catattttcc ttgtatctta  88500
ctatattgat tgtgtgttag tctttgtata tcaattgata gtaggtgttt acatgtaaat  88560
gaagtaactg tgcttttaat atttggaaat cgtgtattca tttcaaattg attaaatggg  88620
aaagacttgg taactggagt acagtgtatc atattaaccc ttcatatcta attgtgctct  88680
caaaaattgt tataattata tataaagata agtttaagac ctaccatact ggaagtaaag  88740
attggtcctg tctggcagat tatttgatat gaaacttaaa atgttttctt aatatgtaat  88800
gacctctgga aatgaattaa attcaagctc aaaagctaac acagcaaaaa tctgagaaaa  88860
tgaataaaaa aatgaaaaca gtgaaggaaa taggagtagg aaaaagaaag gcatggacaa  88920
aaagaaggaa aatataagtg aattttaaaa tagaaccaag ttttctttag gtgccataaa  88980
aagactgtaa ttgaacataa cctaaaaatc aattaattta ggccaggcac agtagctcat  89040
gcctgtatcc taccactttg agaggccaag gcgagtggat cacttgaggt caggagttcg  89100
agaccagcct ggacaacatg gcaaaactcc ttttctacta aaaatacaaa aattagctgg  89160
gtatggtggt gggcacctgt aatcccagct acttgggagg ctgaggcacg agaattgctt  89220
```

-continued

```
gaatctggga ggtggaggtt gcagtgagct gaaattgcac cactgcactc cagtctgggc  89280
gacaagggtg aaactccatc tcaaaaaaaa aaaaaaaatt aatgaatttg cctatattag  89340
ggttctccag agaagcagaa ccaatagaat aagagtgtgt gtgcatgcgt ctgtgtgcat  89400
gtgtatacat ttaaggagat ttattacgag gaattggctc aggcagttat ggaggctggc  89460
cagtccaaaa tctgcagggt aggctggaga tcctggagag ccaatgctgc agtttcagtc  89520
tgaatgctga taagctggag acccaggaga gctgatgttc agttctagtt ggaaaagtct  89580
gttgtagaat caggatgagc caatgttgca gatgaaggca gcctgctgga gaattctgtc  89640
ttgcttcagg aggctggtcc ttttgttgta ttcaggcctt caacagattg gatgaggccc  89700
aacaacatta tggaggacag tttgcttttac tcagagacta ccagtttaaa tgttaatctt  89760
ctccaaaaac agtgtcacag aaataactag aataatgttt gaccaaatat tctgggcaca  89820
ctgtggccca gccaagttga cagataaaat taaatatcac attccttatt cagagtttct  89880 tgttttgac tttgttttcc atgattaaac gaaatataat ttctgtggtt ttacttgtca  89940
ttgctgagtt cttgaactcc ataatttat gacttagtta tactcatgac ttctgaattc  90000
ctctcataca tacccaaagt ttagtgcttt ctaggttgac ataaaaagg acaggactgt  90060 atctgtatta tgctgtctac tttataaatc aatgttgttt ttataatgtt aactataact  90120
caccattgaa ctttttggat gtagtattta gtcaatattc ttaaggtgct gattagaatt  90180
aactatttgt ggggtaaatg taaaaatttt aggccaggtg cagtggctca cacctgtcat  90240
cccagcactt tgggaggctg aggtggggag gattgcttga gcccaggagt ttgagacaag  90300
cccgggcaaa atagtgagac attattaaca tttttaaaaa cgttaaaaat cccactgcat  90360
ttccttttat ttggcttgaa taatacccaa tacacaccac actgtctact tcagtgggga  90420
aataccaacc ctccttcacc aatccagaaa gaaatctgta atattagatt cctcgacagt  90480
gtagaaacct agttctgtgt agtatggttg ttttggacat ttgtaaattt attttaaag  90540 ttttatttgt atatatcttt ttgagacagg attttgccct gtcagccagg ttggagtgca  90600
gtggtctgat catggcccac tgcagcctca atccccagg ctcaagtgat tctctcacct  90660
cagcttccca agtagtcggg gctgctggca tgggccacta ctaattttg tcttttgta  90720 gagacgaggt ctccctgtgt tgcccaggct gattttaaac tcctgagctc aagcagtttg  90780
cccgccttgg cctcccaaag tactaggact acaggccacc acaccggccc aaacatttgt  90840
aaatttagat gtaataagat aactatagtg aatattataa ttcaagagaa aatacagtgc  90900
ttaacatcaa caacaaacca acttgaaatt tttgaacatt tgagagtcag gaatagtaaa  90960
caatttacaa taatggatat aaggcagaat gcaatagttt ataatgtaga aaatgaattg  91020
attcttgggg gatggttttt caattaaact aaaaggtata tctctataaa tggttcacaa  91080
agaaaaaaca aaacatggag aaagatttat taaaagaaaa acagataact tgaaaggtct  91140
ctagataagt ggtttggttt gattttgatta gtaacgactt ggtttaattt gtcagcgtca  91200
ggattgatcc atgctgaaga aatatttctt ttgataattt taaaatggaa ggtaatttgt  91260
ttgtcttata attggttcag acaactcggg atttgttatc attgacttaa ctgcaaagaa  91320
aaatcaaatt tataaatagc atgttggtaa aaatattcgt agtaagtcat ttgactactt  91380
ggcagtcaga gtttgagact gagaaatgac tgtcttttct agagctctct ctcgatgtgg  91440
gatgaggaca agggtaaagt ggtggtgaaa gggtgaagac tggttagcag gagctcaatc  91500
acatgttgcc acatgtaagc acttagactg gatgtcagca cactacccat ggctcagatc  91560
```

```
tagcccactg cctgtttcgt aaataaagtt ttgttagaac acatctatat gcattaattt    91620
atgaatttgt ctatcacaat agcaagttg tgtagacaaa gactttgtgg cccaaaaagc    91680
caaaaatatt tactatctgg tcctttacag aaatatttga aaaagttcaa atattatttg    91740
aaaagttcaa agtaaattac tgtaatttta aaaattaaag caggtataat agtattattt    91800
ttattaataa aacaacatac actgttgttc ttcataatcc ttgttctaaa ctatctgtag    91860
ttttaaccaa taaggcaaaa agaataattt gcttagtgat agactgatgt agattaacac    91920
tttgactaaa tcacagtaag agcctttaa agtggttatg ttatcaacaa ccacaataat    91980
aataataatt tggggtgttc ttccctcttc cttcttcagt tgctatccag ttaattgaaa    92040
cttgaatgtt agggaaaatc atgtgttatg gaaggtaaa atggttgaag ataggatatg    92100
gtggttggta ctgaggaatg acattctatg tatatttaca tgattctggg ggtggttact    92160
actttgcaga tattttattg ggtggtagat gcttaagtaa ttcgtttaga cacttttttt    92220
taggtataag taaaacttac aaaagcaaat tgatgttttt ttctttactg tctatacaaa    92280
tttttttaat gaattttttt tcttcaagtt cttagtttta gtaggtaact tgattcccaa    92340
attcacttct cttatttgta catattgttt gggtctatct gttaggagac tttatctgat    92400
aggagacttc atttttaaggt ttttaaaaaa atttttttt tagtgttttt tgttttgaga    92460
cagggtctca ctgtgtcacc cagactggaa tgcagcgacg tgatcgcagc tcactatata    92520
gccttggcct cactgctggg cttagtgatc cacctacctc agcctcccaa gtagctgaga    92580
gcacaggctt acgcctcaat gtccagctag ttttttgtatt tttttgtaga gacagggttc    92640
tgctatattg ttcaggctgg tcttgaaccc ctaggctaaa gcgatccgtc cacctcagcc    92700
tctcaaacta ctggcattac aggtgtgagc cactgcctaa ctttttcaag actatttttt    92760
ttagagcagt tttaggttta cagcaaaatt gagaggaagg tacagagatt cttatatac    92820 accctgtccc cacacatgta gccctcatta tcaacattcc ctaccagagc agtctctttg    92880
ttacaattca caaacctaca ttgacaagtc attatcacca agagttcaca ttttacatta    92940
gggttcattc ttggtgctat acattctgtg ggtttgaaga aatatatgat gacgtgtatc    93000
caccattgtg gtatcataca gaatagtgtc attgctctaa aagtcctgtg ctccacctat    93060
tcattcatct cacccccttc ccaaccctag gtagtcatta ttttactgt ctccatagtt    93120 ttgccttttt cagaagtcat atagtttgtt tttgtttgtt tgtttgtttg ttttgagacg    93180
gagtcttgct ctgtcgccca ggctggagtg cggtggcact atctcagctc actataacct    93240
ctgcctcctg ggttcaagca attctactgc ctcaacctcc tgagtagctg ggattacagg    93300
tgcgcgccac cacacacagc taagttttgt attttcgtag agatgggtt ttaccatgtt    93360 ggccaggctg gtctcgaact cctgacctca agtgatccac ctgcctcagc ctcctgaagt    93420
gctggaatta caggcatgag ccactgctcc cagctcagaa gtcatatagt ttgaatcata    93480
cagtatgtag ccttttcaga ttggcttatt tcacttagta atgtgcattt agggttcatc    93540
catgtctttt catggcttac tagctctttt tttccttttta ttatttttaa ttgacacata    93600
gtatctatac ttattaatgg ggtacatgtg attttggtac atgtatgtgt aatttaaaat    93660
gtggagtgac taaatcagga taattagcat gtctatcact tcaaacattt caaatgtttg    93720
atgactttta gaatttttt ataattatca ggtacatctg gaatttttaaa gattaatttt    93780 atattgtgga ctttgataca agtattttat ttgttttgat gtgtcttttt gttttaacgt    93840
tttcactgac ttagaaatgt ttctctttat ttaggaggat gaacaagcaa gaacagacta    93900
cttcatcagg acactcttac ttgaatttca aaatgtaggt acttaccatt tatagactat    93960
```

```
ctgtaagaat agttttcagg ctgggtgcag tggctcatgc ctgtaatccc aacactttgg   94020
gaggctgaag tgggagggtg acttgagtcc aggggttcaa gactagcctg ggcaacatag   94080
tgagatcttg tgtctacaaa aagaaaaaag ttagccgggc atggtggcat gtgcccatag   94140
tcccactcac tcagaaggct gagcccggga ggttgaggct gcagtgagcc atgattgtgc   94200
cactgcactc cagcctgggc aacagaggga gactctcaaa aatggttttg agaatagaga   94260
atagttttca aagagaagac atagagaggg aggggagcgt gggctgaaaa accacctatt   94320
gggtagtatg ctcactcctt tggtaaggat catttgtatt ccagacctca gcattataca   94380
atacacccat gtaagctgca catgtacccc ttaatccaaa ataaaagttg aggccaggta   94440
tggtggctca ctcctgtaat ccccaacact tgggtggct gaggtgggtt ggtcacttga   94500
ggccaggagt tcaagaccag cctggccaac acggcgaagc cccatctcta ctaaaaata   94560 ctaaaattag ctgggcatgg tggtgcacac ctataatccc agctactcag gaggctgagg   94620
cacttgaatt gcttgagcct gggagacaga ggttgcaata agccgagatg gtgccactgc   94680
actctagcct gggcaacaga gcaagactct gtctcaaaaa ataaaataaa aataaaata   94740 aatgttttaa aaatagaaaa tataatacta ctacctaaat gttttatttg gtaaatggg   94800 tttgctagaa aattattttg ctttatatct gcaaaatgca aataatatat ataatatata   94860
ttattatttt gctttatatc tgctttatag ttttttgtaa gtaaaaaaag taacagcaat   94920
ttttattttt aaagcatgtg aagttagttt ttgtctttgc aaactaatca acttttagct   94980
actaaaaaaa taaaacaagc tatataaata gtatactatg ttatttaaca taattaatga   95040
aatttggtaa tttttagtt acgaagatga aatgagagtg taatatttag tcttgacatt   95100
tatgcttatc acattacata aaaagtaata ttaattataa catacctaa atttgttaaa   95160 tttgaatag ttataccttc tttgcagcaa atattttat tctattgcag taagcaggtt   95220
attgcattgt ttatataatt attaccctgt tttactggtt tacaattttgt taaagaaaag   95280 tcactatcaa agctaagtct tcattagat atatattgtt tttagttgaa acccccaca   95340 gcgcccgac ttttttttt ttttttttgg caacagggtc tcactatata ttgcccaggc   95400
tggactcaaa ctcctgagct caagcagtcc tcccatctcc accttcctag tatctgagac   95460
tatagggatg agccaccaaa cccagctaaa ttttttatag tttatagaga tgaagtcttg   95520
ccatgttgct caggctgctg tcaaattcct ggccttgagt gatcttgcct tttgcattgg   95580
ccacccaaag tgttgggatt acagatgtga gccactgaat ctggactggt tgctaattt   95640 ttaatctacg gtaataataa taagtacctt aatgaattc tgtggtagat caggcatctt   95700
aattctgcta actgcatcat atccagatac tgttacgtct gttgcacata gatgaagata   95760
cagaagcttt aagaagttaa atagcttacc tgaagttatt taggaaatgg ccaaagtagg   95820
aatttgagta tggtttgctt agattccgag tattgctctt tctgttaaac acctgcaata   95880
accattctca aaacatttga catcagtact cctttacatt cttcaaagtt attgaggatc   95940
ccaaagtttt tgtttctggg ggttgtatct ttcagtatat actatatttg aaattaaaac   96000
tgagaaattt ttaaaaaca tgaatacata agcatatatt gtattggctg ttaaagaata   96060
aggcacgtaa catttagta ttattctgag aattatttaa agctcataga ctccctcaaa   96120
agggttgagg ggaggggta cccagaccgt atattgagaa ccactaatct gtaagaagac   96180
tagtgagttt ggcattggac aaattcatct ctccattctt tttcagttta atgttctgtt   96240
agtcttctga ttacaatgaa tactactcta acctactcta acatggtgct tacggtatat   96300
```

-continued

```
tgctcatcca tttaatagtg tagattagtt aaatagtata tatagtgtta tgtttacagt    96360
acatgctctg gaagtagaac tgcctggttt agagcccaca cttgtcactt cttaggaaag    96420
tttgggcaag ttattttatc tgtatatctc agttataaaa tgaggatggt attaacagta    96480
ctttcctcat ggaaattaaa ttgttacatg tgaagcccttt aggtatttgg catgtgttta   96540
acagtcaata agtgttggct attatttatt tgggtttttt taaaagcagt gctaaatgcc    96600
acacaaattt cttagaaatg gcagtttaaa tgagctgtgc aactttaaac tttgcaaagt    96660
attttcataa ttgttgactt tctgttttc ttgaaggaat ctcgtaggct gtatcagttt     96720
cattatgtga actggccaga ccatgatgtt ccttcatcat ttgattctat tctggacatg    96780
ataagcttaa tgaggaaata tcaagaacat gaagatgttc ctatttgtat tcattgcagg    96840
tacaaaagaa tttcccaagt ttataaatac attatttaag tttgatgtta cacaaggttt    96900
tatttctgca ttaatatgtt agtaatcttg aatttctcct agccttgata caatgtttgg    96960
gactagggcc ttgtaagttg atgtggtctc atttggttga cagaccgttt agagtattgt    97020
tgcattaaaa cacaggatca tctatttgaa aatagtattc acatggtggg aagctataga    97080
acatactctt tttactgttc actgattaga gcatataatc tcagatcctc atcatactct    97140
actttctaaa gtcagtatgg tagtattttc ttttaatcaa tttccctgaa acaatgacca    97200
agcaattttc attcctgata aacactgaca tgagattttt aaaaacagga tattgctctg    97260
atgcccaggt tggagtgcag tggcacaatc atagcttact gtaaactcaa actcctggcc    97320
tgacgtgatc cttctgcctc agcttcccaa gtagctagga ctacaggcat gtgctaccac    97380
actgaactaa ttttttttaa ttaaaaaaaa tttttttaa gagaccaagt cttgctctgt    97440
tgcccaggct gatccgaact cctgtcctca agtgattctc ccactttgct ctcccagagt    97500
cttgggctta caggcgtgag ccactacgcc tggcaacatg actttctttt tttaatatat    97560
gtaagatgta catacgtagg tcttattgat ctaagatatc atcaattcta agacacacca    97620
ttattatata tattaacagt aaaaaaatca ctgccaatta taagggaca atgtcatttg     97680 taagaagcca ttggtggtaa gatacatacc aatctcagag ctgttacatt gagatgaaaa    97740 agtgtgttttt agtttgatga aaaactaaat gctgttttta ttcttgggga acatcagttt    97800
ccacgtttgc accacttcct gtcatatcat gaaattttat aatttatagc tactgaaaaa    97860
tttaaagccg gaagcaagca ttcttgtagt aaagtaataa aaactattga tacacattta    97920
ctagacattt ttattatgtt ttatagtaga ttacttcatt ataaggatta cataaaattc    97980
aatgattact gacctagtta agctacctct gaatgtgaaa ggacaagtat aggtgcacct    98040
actttaaatt gcacaatata aatcttttca tttattcaaa taatatttga agttcagtta    98100
ggttttgcaa aattactcgt ttggatgtgt taagaaatca tgtaaactct tcctttgact    98160
ttgggggaat gaacatgaga tttgtttatt cttgggggggc agttaatttt gtattctaga    98220
aggggggtta atgtataata tattttagct aagagaaatc agtttaagat aaccaacttt    98280
tcttaatcta acattttggc ttatttctgt catctggtca ttctcataca aataatacaa    98340
agctaaatat acataataca tatgcacata tatgtatatg tatacattat atgtaataca    98400
taaaacaaag ctaaatttgt attatggatt taggagtgta atggaaaata ccccttttaag   98460 aggaaaagca caaaactgaa ttagtcaaga aaataataaa tgtttgcaat aagtgtcatg    98520
accgggtata gtggctcagt gctttgggag gccgaggcag gatgattgct tgagcccaga    98580
actttgaggc tgcagtagac accaattaca ctactgcact ccagcctggg tgacatagta    98640
gaccctatct tttaaaaaaa aaaaagaat ataggtatca ttataatatg ggtgatacag     98700
```

```
gatattttga aacctaattt ttggaatttc attatatagg tatgggtttc tacatagtag    98760
aagctacttg aatccttaga cagtttttct actctgaatt tttagtttac attagattct    98820
tctaaaggcc ttacagtcat agtacttact tcataagact gctatcaatt tattcctcta    98880
agggacttgt tatctgcatt cacatttgtt ataaaaagta aatgagattt ttcaaactta    98940
agagatttat tttttattat ttacatagtt aaaatatttt ttcagtggag ttgaagcatt    99000
gaagatagtt ttcttattca cttggtttga ccgtaatgct cataattaac gaagtaaaag    99060
ggctactttt tattcatggg ccaggaaagt aacttgctgg tggagatgtg ggaatcagtt    99120
aacaacttgg ttcattaaaa ctattttttt ctgtggttaa ttcagtggtt agttgaccat    99180
ttaattaagt aggattgacc agttaaaaat aaacaatatg tttaattata gaattaaaag    99240
ataaagaaat tgctttcact ttgacttctt ataagttagt taaaataatt tcctgttcaa    99300
tcataaatcc atttgtatag gaaggctttt catcaaaaac taaattgacc gttaaatatt    99360
tttagacaat caaaacagta cgttaactgt aaggacttag aaaacacatc cataaaagca    99420
agaaaattct tttgctttcc actagttcca ctggagataa ccattgttaa aactcgagaa    99480
tgtgtccttt cagtgtgtgt atgtgtacat acagtattgt tttgttttat tttgtttgac    99540
ggagttttgc tcttgttgcc caggctggag tgcagtggca caatctcggc tcactgcaac    99600
ctccgcctca actattttaa acagcagttt aaatgcttag tggccactct gttttttttgt    99660 ttttaattta ctttaatggc catcttattg ttaaatcttt gagcacatct gcagttatta    99720
ggacaaagtt attattggat aaatatccag aagtgagatt tgttggtcaa ggacataaac    99780
ttttaaagta ttttaatgag tattttttaa tgtgttatcc agaaaattga tgctacttaa    99840
ttctgccact ggcagtatgt gagagtacct atttccctat accttcccca atactgtgtg    99900
ttatcttttt gtttgctttt tttttttttt ttttttttttg agacagagtc ttgcactgtc    99960
gcccgggctg gagtgcaatg gcacgatctc agctcactgc aacctctgcc tcctgggttc   100020
atgcgattct cctgcctcag cctcccgagt actgggatta caggcacaca ccactacacc   100080
cagctaattt tgggtatttt ttagtagaga cggggtttca ctatgttggc cagactggtc   100140
ttgaactcct gacctcatga tctgcccgcc tccacctccc aaagtgctgg gattacaggt   100200
gtgagccacg gttcccagcc tttgtttgca tttttttctt ccttttttttt ttttttttt   100260 tttttgaga cggagtcttg gctgtcgcc tgggctggag tgcaatggtg cgatcttggc   100320
ttgctgcaac ctctgcctcc tgggttcaag tgattctcct gcctcagcct cccgagtagc   100380
tgggattata ggcatgcacc accacacccg gttaattta tatttttagt agagttgggg   100440
attctccatg tttgtcaggc tggtcttgaa ctcctgacct caggtgatca cctgcctcgg   100500
cctcccaaag tgctgggatt acaggcgtga accactgcgc ccagcctcat cttttaatag   100560
ttatacaagt gctttatata ttgaggacat taacttttat tcatgttgta agtaccatgg   100620
tttttcctgt cttctgcctg tttgcaatac ataagtttca ttttgtcatg tcagatttt    100680 gaatggtttt tgtccattga gatatttgta catagaaagt ctttccctaa cacaatagtg   100740
tatatatttt gcatatattt ttagtacttt catagattta cttttttaaca tttatcattg   100800 gataaatatc caatatgttt atatcatata tatatatata ttttttatcca cctggatttt   100860 ttatggttaa ggtatgtgat cagaatttaa ttttttgctc ttcattgata gctaacttct   100920
cctttgccac ttactgaacg gtctgatctc tggagaattc actgttatgt aagaaatgtt   100980
acatgtactc agatctgttc ctgaactttc tattgtgttt cattgatctg gttatctgta   101040
```

-continued

```
tctttatgtt atacttttaa ctatcaaatt ttagatatat ataatttatc ccagtaactc 101100
aactaaaatt ctataaatgt tttgatgcac agaattcaca aatgtatcaa ctaaaaatta 101160 ataataattga ttatgtttat taagagtttt aaaaaatctt tctaggttgt ttatagtgta 101220
cttttatcag gaattttagg ttacatgttt aacaaactgc tgataggtat acatttcaaa 101280
atatgcatta aaatgttaca caactttgtg ggggttttg ccaaagatta ttctggtgat 101340
gtcagtaaca tcttataatt actcatagtg attttcaatt ctaagatgca taagcctttc 101400
tctagttgag aagcagttac tttaaaatac ttttgtcatg agtttttttt tttttttttt 101460
tttttttttt gagacggagt ctcgctctgt cgcccaagct ggagtgcaat ggcgtgatct 101520
cagctcactg caacctccgc ctcccaggtt caagtgattc tcctgcctca gcctcccaag 101580
tagctgggat tacaggcgcc cactaccacg cccggctaat ttttttttttt tgtatttgca 101640 gtagagacgg ggtttcacca cgttggccag gcttgtctcc tgacctcagg tgatccgccc 101700
tccttggcct cccattgtgt tgggattaca ggcgtgagcc actgagccca gcctgtcatg 101760
ttttaaaata aaaaaaaccta tggtatgtta ctctaaagtc cccagctccc attagttttt 101820
tgggatatga gagcatatca ttgtcttgtt cttttgtgga aatcactgct gttgctcaat 101880 ccgtttttcta gggcttatag cattcttcac ctttcctata ccttctatag attgaaatga 101940
tgtaccattt cctcctgtac tctaaaacaa gagccatctt tttttttttt tttttttttt 102000
ttttgagttg gagttttact cttgctgccc aagctggagt gcaatggcac gatcttgggt 102060
cactgcaacc tccacttccc cggttcaagt gattctcctg cctcagcctc ctgaatagct 102120
gggattgcgt gtgtctgcca gcacgcccag ctaattatgt gttttcagta gagatggggt 102180
ttcaccgtgt tggccagggt ggtctcaaac tcctgacctc aagtgatcca ccggcctcag 102240
gctcccaaag tgctgagatt acaggcatga gccctgcgc ccagccacaa gagccatctt 102300
gaacatagaa taaatgtctc tgtaagacgt tgttagctag tcacattttc tgatgtagca 102360
ttagacttcc agagtgacaa cttagtagct attctctgtg tcacttactc ttggaagttc 102420
cttaaattaa ttttttgtttt tcttttttgag atgaagtcac actctgttac ccaggctgga 102480
atgcattggt gccatcatgg cttactgcag cctcgacctc ccaggctcaa gcaatccttc 102540
tgccttggcc tccaaagtg ctgggacaac aggcatgagc cactgcgccc aaccccttaa 102600
aaatgaaatg tttaaaagat agaagacaat aggccttcct tattcaagac ttcactgtcc 102660
tcagtttcag ttactcatag ttcaaaaata tcaaatggaa aatttcagaa gtaaacactt 102720 tgtaagttttt aaatgctgca ccattctgag aagcatgggg aagtatgtcc tgcttgcaag 102780
ataaatcatc ccatggtcca gtgtgtacac actgtagact ctaccagccc attagtcaca 102840
tagtagatac tgcagttacc agatggactg tcatggtgtc ccagtggtta tgttcacatg 102900
acccttattt tacttataat ggcccaaacc tcaacagtag tgaggtagtg actagtgata 102960
gattgttata attgttctaa tgtattatta gttattgttg ttaatctctt gttgtgcctg 103020
atttataaat taaactttat cataggtatg tacatatagg aaaaatcata gtgtatatgt 103080
atatgtattc tgtgtaacag atgttgccat gaacacactg taagttgtat tttgtttatt 103140
actaagtaga attttgtcaa acttcttaaa tgatttttttg tttctgaata ttaacatgtc 103200
tatccacatt tattttatag ttgttttatc acaaaaatca attgttttttc aaactttata 103260 tccttagtgc aggctgtgga agaacaggtg ccatttgtgc catagattat acgtggaatt 103320
tactaaaagc tgggtaagaa ataatttttt gtagcattat gttcaattga tctattatga 103380
ttttcaaact taattataat tgcagtaaat tatagtgtat atttttattat acatgttatt 103440
```

-continued

```
ttttccaaag tagttttatt aagtaagaaa taaaggtagt gaaggccggg cacagtggct 103500
tacgcctgta atcctagcac tttgggaggc caaggtggga ggatcgcttg agccctgggg 103560
ctcgagacca gcctggggaa catagggaga cccccgtctc taaaaataat taaaaaataa 103620
aatgattata aaaaataaag gtggagaaaa ggtataattg ctgcatattg cctttgatag 103680
gatgcattgg ggaacaatgt gacagtgttc taggtgagtg aatacttgca ttaggatata 103740
aactgttact gacttttcca atactaaatt ttcattgcct ttttttttt ttcttttttt 103800 tccgagatag agtttcactc ttgttgccca ggctggagtc gatggtgcg atctcagctc 103860 actgcaacct ccacctcctg ggttgaagcc attctcctgc ttcagcctcc ctagcagctg 103920
ggattacagg tgcctgccat cacgcccagc taatgtttta tattttggt acagacaggg 103980 tttcaccatg ttggccaggc tggtctcgaa cttctgacct caggtgatcc actcatctcg 104040
gccttccaaa gtgccgggat tgtaggcgtg agctacggtg cctggcccat tgccttttat 104100
gtttactcta ggtataagtg tatttcactc agtatgtatt tatgcctgct ggagacatta 104160
tagtattgta gtctatgaat gctgactcga gccaaattgc ccagattata attctggctt 104220
tctcatttac tagctgtggg atcttggtca aaatactaat cccatagtgc ctctatttct 104280
ttatcagaaa atagggtca tagtagtagt aatgcataag aattaaataa cttttgtgaa 104340
gttcttcaga actatgtggt aaattgtaag tactcagttt attgttagtg ttgattactg 104400
ttgctgttgt gattgttgtt cctactactg cttttccaa gaaatagtgt ttgatactgt 104460
ggatgataca gagataaata agatacagcc ttcattatag atttgaaaaa caagtctctt 104520
cattatgtat acatttgatt cttttgctgg ttccataatg tgttcatttc tagagaggcg 104580
cctttaatcc ttcatagctt tatagtttcc atgaattgtt catctttgtc ttgtacagag 104640
tagaattaat aaaatgttta ttttttcttt ttcttccttc ttcccttat ttctcttttt 104700 tccctgccat ctctccattt tttattgttg caaggaaata tttacatgtt aaacagttcc 104760
ttaaaaagcc ctctgggtt aaatatttt ttcctcaaaa actataatca tctaattctc 104820
aaatgaaaat gcttaagtga acaaaattta actggaattc gatcacattt taacataaaa 104880
gtcaaagatt aaaattggaa tgagaaggga cacataaatg aatgctagca aacaaaacaa 104940
acatttggtc atttttaaaag ttgtgtattt tggataggtg ccatggctta tgccataatt 105000
ccagcacttt tgaaggctga ggtgggcgga tcacctgagg tcaggagttt gagaccaacc 105060
tggccaacat ggtgaaaccc catttctact aaaaatacaa aaattagcca ggcgtggtgg 105120
ccggcgcctg taatcccagt tacttgtcag gctgaggcag gagaattgct tgaacctgga 105180
aggcagaggt tgcagtgagc cgagattgtg ccattgcact gcaaactggg tgacagagca 105240
agactccgtc tcaaaaaata aaataaaata aagttgtgt attttgaaca tagttctctc 105300
tctctctttt ttttttttt ttgagatgga gtctcactct gttgcctagg ctggagggca 105360
gtggtgtaat ctcggctcac tgcaacctct gactctcagg ttcaagcgat tctcctgcct 105420
tagtctcccg agtagctggg attacatgca cgcggcacca tgcctggcta atttttgtat 105480
ttttagtaga gatgggggttt caccgtgttt cgggctggtc tcaaactcct gacctcaggt 105540
gatccgcctg ccttggcctc tcaaagtgct gggattacag acatgagcca ctgcacccgg 105600
cctagttgtt aagtcttcat gtaaaaatct tggctgggcg cggtggctca cgcctgtaat 105660
cccagcactt cgggaagccg aggcgggcgg atcacgaggt cagcagattg agaccaccct 105720
ggctaacacg gtgaaaccct gtctctacta aaaatataaa aaaatcgcc aggcgtagtg 105780
```

```
gcggggcct gtagtcccag ctactccgga ggctgaggca ggagaatggc gtgaacccgg   105840
gaggcggagc ttgcagtgag cggatatcac gccaccgtac tccagcctgg gcgacagagc   105900
gagactccgt ctcaaaaaaa aaacaacaaa aaaaaaccc aaaatctta tgatgtatat     105960 aaggacttcc aagcagcaaa cctggaaatc atttttaacc cttccatctt aatcactcca   106020
aaatattctt gttgataaca gttatgatat ttctgcttct gtaaacctcc gccagtttct   106080
cactctttca gactgtcctc ttccttgata caaaaattgt gtgaatatca gatcttctca   106140
tgtcaacatt gcctattgca gtagtcgcaa ttccatatac acaaagaat tgtctaggtc    106200 gtttcataat tagttcccca acttggagcc aaaggatcta tatttttacc taggtctttt   106260
agctggtcct tatatagcca atccaggaga tactggccaa tagaataaat tcagtctctt   106320
tattatgttc acagtctgat cctaaatatc cttatcttct ctcctccttt gagtaccttc   106380
tccttctttt agtcttaggc tttgtttaca tcaaacttct caattcccca catagattat   106440
acattgaatc tgctgtgctt atgtatattt ccttcactt ttatgggata accttcttt    106500 gatatccaac tatgttgtag ctgcacacac tcaacagtta gccatagcct ctttattccc   106560
tgtatactgc agtcatactt tggctggaca taactgtctc cccatcttga atgctgaggg   106620
tcaagaacag ttttgtttcc acagtgccaa gcacagtgtc tgagatgcat taagtggtgt   106680
tcaataaatg tttgcagtaa accagcaggt atttaagttt tatgtgaaaa gctgaagaag   106740
attttactat tttctgaata gatacacaaa gttgatgtat taaatttct gttttagaaa    106800 ataccagagg aatttaatgt atttaattta atacaagaaa tgagaacaca aaggcattct   106860
gcagtacaaa caaaggtata gttgtttgtt tcccttata aactgctatt ttataaatgc    106920
tttcttcttt tttaaaatgt tgttttcatt ttgttttta atcattttc tccttcatag     106980 gagcaatatg aacttgttca tagagctatt gcccaactgt ttgaaaaaca gctacaacta   107040
tatgaaattc atggagctca gaaaattgct gatggagtgg taggtgttct tggtctatta   107100 atttaggaa acttttactc tttgttaaga tgtaatattt agcctttttt tgttgtctt    107160 gtgttttgtc taacatgaga agaatatcca ggacacttaa cattttact taaactcatt    107220 tccttcttat tcgtatctgt attatgatgg ctatttaatg actccgatat aaggtaaatt   107280
atgttctaaa tgaaataaag ttaggaaaga tctcatgtca aaaatcatat aattcgttaa   107340
tgttttactt ttttaaaaaa taattgcatt gttctcttta ctcttccctt ccacccccac   107400
ccaagtaatt ctgcattgat tctacttgaa tttcattttg tataaagtgt tttagttatt   107460
tgtgtatatg cttttctttt cttttctttt ttttgagaca gagtttcact cttgttgccc   107520
aggctggagt gcaatggcac agtctcagct cactgcaacc tctacctccc aagttcaagt   107580
gattttcctg cctcagcctc ctgagtagct gggattacag gcgcacgcca ctgtgcccag   107640
ctagtttttg tatttttagt agagacggag tttcgccatg ttgaccaggc tggtctcgaa   107700
ctcctgacct caggtggtct gcccgccttg gcctcccagt gtgcaatgtg ctgggattac   107760
aggcatgagc caacactcct ggccttgtgt atatgctttt cagttaagca gaattaaaga   107820
gccacagtta actcccttt gttgtgttat aattcagtgt tattttagcc ttgtaacatc    107880
ttactggata ttcaacttct agacctgaca aaaacactgt attctcttag tattctcatt   107940
tctgcctttg ttttctaacc aattgtcttg cttcaattct atatataacc accttgtccc   108000
tgaaggtgct gagattttt ttttttttt gtagaatttg tttacatctt tgtcattgag     108060
tctatgataa ctattacatt gttaaaccaa gtatgagaaa ataagttgca aaatttataa   108120
ccttcatttt ccttttctcc ctttaaatgg ttttgtcagt tcccagaata tttgtttgaa   108180
```

```
ttttcttggt tttccaaatg acagatttat taccaaatgc tgatctcagt ttgttaggat    108240
aatctaatat cggtccatga gttttaggaa atatgcattt cttttattag ccaagtgaca    108300
atttcacgtt tttaagtttt atgtgacatc gttcttattc ctttattaac ataggaatta    108360
ttgtgcaagg aaatcctcct acaatgcctt tagcttaatt aaatcctatt atgcacatgct   108420 ctgaatctag ccaaatattt tataatgtag aatcaaatgt gttttttgttt tgttttattt   108480 tgttttttga aatggagttt cactattgtt gcccaggctg gagtgcaatg gtgcaatctt    108540
ggctcaccgt aacctccgcc tcccaggttc aagcgattct cctgcctcag cctccctagt    108600
agctgggatc acaagcatgt gccaccacac ctggctaatt ttgtatttt aatagagacg     108660 gagtttgtcc atgttggtca ggctggtctc gaactcccaa cctcaggtga tccgcctgcc    108720
tcagcctccc aagtgctagg attacaggca tgagccaccg cgcccggcct cgaatgtgtt    108780
ttttgtttgt tttgtttgat tggttttttt tgttttttgg ttttttggttt tttttttgat   108840 gacgaagtct cactctgtca cttaggctgg agtgcagtgg cgcaacctct gcctcccggg    108900
ttcaagcgat tctcctgcct cagcctcctg aatagctggg attacaggca tgtatcacca    108960
catccagcta atttttgtat ttttagtaga gatgggggttt tgcatgttgg ccaggctagt   109020
ctcaaactcc tgacctcagg cgatccccct gcctcagcct cccaaagtgc taggattata    109080
ggtgtgagcc actgcacccg gccaaacatt tgtattattt tgtataattt aatctaagtt    109140
gagatattta atatttcgaa aagctgagta ggctataaac agttttcttt aattttttggg   109200 tttttttttt tttttttttt tttttgagat ggagtctcgc tctgttgccc agaatggagt    109260
gcagtagcac agtctcggct cactgcaacc tctgcctccc gggttcatgt gattttcctg    109320
cctcagcctc ccaagtagct gagattacag gcgcccacca ccatgctcag ctaattttttg  109380 tatttttagt agagacaggg tttcaccatg ttggccaggc tggtcttaaa ctcctgacct    109440
caagtgatcc acccacctca gcctcccaaa gtgccaggat tacaggcata agctactgca    109500
cccagcatct ttaaaccttta attgaaaagc atttctgttt tattccatga attcaagatt   109560
aatttcaaag ctaaagttttt tatatctgga aatacaggtt tttaggctgg atgcagtggc   109620
tcatgcctgg aatcccagca ctttgggagg ccgaagcagg caggatcacc tgaggccaag    109680
agttgaagac cagcctgggc aacatggcaa acccccgtct ctaccaaaaa tacaaaaaag    109740
attagcctcc cagactcacg ggtacatcac cttgccgagt ttattttttt tatagagatg    109800
aggttttact gtgttgccca gcctggtctc aaatccttgg actcaagcaa tccatccgcc    109860
tcagcctccc aaagtgcagg aattataggc taaagttctt ttattgcaat attcagtgtt    109920
tgggttttgt tttgttttgt ttgagacgag gtcttgctat ttcacccagg ccagagtgca    109980
gtggaacaat cagggctcac tgcgccctca acctcccgga ctcaagcttt cctcctgcct    110040
cagcctccca agtagctgag actataggca catataccac acctagctaa ttaaaaaaaa   110100 atttttttt gtagagatgt tgccaggttg gtcttgagct cctgggctcc aacagtcctc    110160
ccccacctca gcctcccaaa gcactgagat tacaggcatg agccattgtg cccagctatt    110220
gttgtatttt ttaaaactttt taactatatt taaataatct ccagaaaata tgtgataaat   110280
accgcatcac cttttcatct ttttctaatt agatcaaagt ctgatctttg taaggtttta    110340
ttccattgaa tcaatccttt tttaatatcc tgaaatctat actaggatta taattctatc    110400
ataggctctt tctgtctaat aggtcagagc tttacgggaa tataataaaa aagtcatact    110460
ttgtaggaga tgagatgaaa taatacccat agcagataag tagttaactt caaacctact   110520
```

```
ttcgtacctc attgcatggt acatagtaga cataaactaa atgtttgaga gaaatctctc  110580
catagatgaa tggataaata gtaaaaaaaa acagaagaaa agatggatta tcattccaga  110640
taacttttta gtattttctt cttaagaaat catgttttct gtaaacttgt aaatataggt  110700
gactcttttt ataggatggc tgtctgtggt tgcagaccat aaatcttaaa gaaaatgtgg  110760
aatctgaaaa attgagaaaa atcatcttag aactgtgtgg ttgaatgaaa tgacttgaaa  110820
ggtgtattaa ctatttagaa gctatgctgt gagaagtaaa aataagtccc cacttactac  110880
ttttctgaca atttaatcgg taaaagtttt gtttaaatgt tctgtgttcc agtattattt  110940
ctgtagaaat tttagtttga tatactagtt ggttgtttaa gactttaaaa tgaatagtgt  111000
tttttagaga tatttataac tacagtgact tcctggagtg agagatctaa agagaaaatt  111060
tattctgtaa gcctgtatca tattgactga ggatttagag gtaccttaat aagcaaacat  111120
ctgttaagtt gtgcagtgtg cctttttatc ttgtgtgtaa aggacaccgt tacaagtact  111180
gtcaacacca gtatttcagt tctagaatga ttaagtaata gcaataacag tttgtattat  111240
cgtccttttg ttgtgtttgt atagtacatt ttagatgtga taatgaattc tggatttttt  111300
ttcctaaaat ataatttttt tattttaaa gcaccctgat ttataattta ttttcttctg  111360
cagctgataa tattcttaaa tattagataa tttgtttctt aatgttttg tagcatttca  111420 taaagctgtt atatggaaaa taacagtacg caagataact ttagaaagtt ctgtttaaaa  111480
caagagaaca caggctaggc gccgtggctc atttcatgcc tataatccca gctctttggg  111540
atgccagggc aggagaattg cttgagacca ggagtttgag acctgccagg gcgacaaagc  111600 gagacccat ctatacaaaa caattttttt ttaattacct gggtatggta gcacgtgcct  111660
gtagtcctag ctacttggga ggctgagatg gaaggattgt tgagcccag gagttcaagg  111720 ctgcagaggt atgatcatgc cactgcatta gattatttaa ttcctaaaat tctttccat  111780 ttcaaaagtt ggtgattgct tcagcaagtt gtatacatga caaatgtgga ctcaaaaatt  111840
ataggtaata aaagagagtc agaagatgtg ggtgtgtagg agacattaac taggaaatcc  111900
aagaacattg tgaagtccag tgaccaggag gttttgtaca tgctgtttag gtagtggctc  111960
tttatcgaat tgcagttctg cattgtcaca ttgattcctt tcatcagagg aaactcagta  112020
tgttctgaaa gctaatctct cccagaagct ctcttttggt tcttcctgtt aatggcttca  112080
tcctgctctt actcacccag aatgaggaat ccttcatgaa acctttactt tctcacatgt  112140
agtgtttgcc taaaatgtcc ttactatctc ttctctttac ccttccacct gttttccttc  112200
ttccaatcct cattcatttt ttgtcaaaat cttaccaatc cctcaatgcc attctgcatt  112260
ttaccttaat attgtcaact tacttttct caattatatt cttaatattc tcaactatag  112320 ctttttttc tgatttcata gcttcatagt actgattatg ccactttggg gctgtagtat  112380 taccccttcta cttttttct ggggattta ccagactaca ttttgaagtt aaagataata  112440
ccatgtcctt cttacatttt agtatcctct gctttgctga ctttattcag tgcatttcac  112500
tagatgtcca cattgcctta cctgcagttc caaaatccaa agaaaacata gttttgtttt  112560
gtttttgtga attcaatatt acactcactt ggcaacaaaa tatttcattg acatgacatg  112620
agtttatgtg tgctacaaaa gaaaatgct gttttgtatg ttagaaacag ttcaaaagga  112680
gtttcatatg gtttgccttt aattttatt taacctactt aatgcacatt ttggtacaaa  112740
atatcaagtg ttacagaatt atggttatat cattaatgga aataataagc agatgatcaa  112800
taatatgttg ggggtacttt tttgtttttt tttgagacgg agtcttgctc tgtcgcccac  112860
actggagtgc agagacacga tctcagctta ctgcaacctc tgcctctcag gttcaagtga  112920
```

```
ttctcctgcc tcagcctccc aagtaactgg aattacagac gtgcaccacc acgcctggct  112980 aattttttgta ttgtagtaga gacagggttt cactatgttg gccaaggctg gtctcgaact  113040
ctagacctca agtgatccac cagtctcagc ctcccaaagt tctgggatta caggtgtgag  113100
ccactgcgcc cagcctaggg ggtacctttt tgatgcagag tctctaaatt ctggtggtac  113160
ctgaggatct gaaactttgg cgaccaaaag tcctgatttg cgtgaggcac accagttcac  113220
actagttgtc taggtttaat aattaataat gcttcttttt cattctcaaa agagccctga  113280
tttagacaat aaattatatg gtcaccctac ctatagccag atatttctgc accaaatgcc  113340
tcgattttgg tgggtggctt taattaagga agaatgcttt aagtttttatg acataactct  113400 gttgttcttg tcaggaagtg atatgtataa aactattaat tcatcagatt atatataagg  113460
agatagggtg cacttaaaat tgctaggaag ttgagatctc tagttgttta gttggaagta  113520
attgaagtaa cagttggaca agctgtcatg atggacatag tagaagtgcc ttttaattaa  113580
aaacaatgat aacaaaacaa aatgcagcta cggtttcaga gttccttagt tgatagtatg  113640
tgtaacgatg gctgttgtct aaaattatct gagatgttgg caagggtgaa atcattcct  113700 ctcttctgga cataacatac cctagaatta aaatacccta gctagataaa tatgagatat  113760
gttgacagtg aaactaattc aaggccgtat tttcatttca ccgctcccct attcacagtc  113820
ctaaacctaa ggttcttata cctgtattga ctctgaaaca tcaatgttaa tgatgttatt  113880
ggtccttgtg accagcaaga accaaggata ttctggggat gggctctgtc tgcctttttg  113940
aggtccattt gggtagccag tgatatagga gctatattcc ctaatggatt agagcactcc  114000
acatagtgac agagtgagag tgaggcaaga aatggttaaa atgaatccta ggaccaccag  114060
tttaaaagta ctaggtagta atggggagtc ataaaaagat actccattac ttggtaaatg  114120
gtataagcct tatttgttgg ctttttttt gtctctgcat atattaagtt cctagtggta  114180
gtgatggcgg ggcgggggga tactacgttc tttaatccac attatcttgg ggaatctgtt  114240
tttttacggt agcatttgag atgtgttgaa atgctgctgt acaccttgat cttttccagta  114300 actgtgatgc gctgtttttt tgatacaatc tctccattga agtctggtcc ttcaggctaa  114360
aatatagagc cagaatataa gactttttt ttttaacttg gcaaaattgg cattgtttaa  114420
ggattgaaaa gcacagaaac aatttagttg aaacatgaag aggaaaaatt atttttctct  114480
taaccttagt gaagtatttt ttcccttggc agaatgaaat taacactgaa acatggtca  114540 gctccataga gcctgaaaaa caagattctc ctcctccaaa accaccaagg acccgcaggt  114600
attgtatgtc ttcgaacatt ttctttaaaa gcatacttgt ttctactcac tgttaattaa  114660
aatgacaaat tctgaatatt tctaaattac ttttataact tttattatta ttttgttagg  114720
atgtaacata cgtatgacaa ctgatttgtt actggtttat taaaaatttg gtttcatttt  114780
ggataaaatt tcaataatat actgtagcag aatgtggata ctaccatgaa ttgactatgg  114840
tttatgtttt gatatgtgat ataactaaaa ttttagttat tctaaagatt cccatttttt  114900
tcctgatgac taaatatgct tgccaaaaat tgcatgcatg ttgaagtgtg aggatatta  114960 ataacgttac tagcaaagat gagtttattt ctttaatttt tcttgctttt ctaccaagct  115020
catttataat agttaaaatc atatatattc atatctttct tttccttccc ttcttgttca  115080
gggtagctgc ttagtcagta acatggtagt atggagagaa tacagaggca gaagaagata  115140
gtttcaactc ctttttagcc atttagctct gggatctagg attaatttac ttaatcctgg  115200
ggagaaggag ttgtttaaat attgtcctaa ggattaaata aaaaactatt agaatatttt  115260
```

-continued

```
atagtgtctt tcttgcacat agatctgcca aaactgatcg acttcccatc aaataaatt  115320
cttttataca ggatacacca attgtttcca tcttaaaact ttggggaaag ttgggtcaga  115380
cggccagggt catgtcttag cattgagttg ctaattccaa gagatcattc taacgaaatc  115440
atctctctga acaaaagaaa aagcctgcag cttccctcag taactgaagg tttggttaga  115500
atccctgcac accacaggaa taatttattc tcattttgac catgcaagat tctaactgcc  115560
tgggaaggaa gctgctgagt acagaaagag gcagtgtact ctggtataaa gaggcttttt  115620
acataaatag gtcccattcc aaattttaac tttagcattt gccactgaat gaactttgac  115680
aagccacttc tctgaaaata ctttacttca ttgtagtgag agtactcgta ttctccgttt  115740
ttaaaaatta gtgataatgt atataaagca tgtagttaca tgcccggcct atagtaacag  115800
atttttttaag tgtggtggta gttatagtct ctagaatacc tttgcatact tctcttagga  115860
acctcaggaa gcctatatat agatgaggtt aggtctcaac atttaaatgt tcgagatgtt  115920
aactgtgtgc tatcagaact tttagtagtt cttttcctgtt cgatttccac tttggtatcc  115980
accaaaactg gttggcattt tagccgtctg tggaaggtaa ccagttgaaa cctataaaat  116040
attaagttct ctaacttctc tgttccatat aggagcccta gaatcctaaa agaaactact  116100
ggccctaaaa aaattaagga acattttttgc tgccctgtgt tttaatttgg tttttgagat  116160
tgagccaata tagaggtttt caaagtctac actgatattt atgatttgta tgttcttcta  116220
cctctaacta catgtagcag cagtctcttc ttaattttac aggaaaaaag aatagaatat  116280
ctgaatttaa agccttttc ctatacctgt tgaaaagttt tacttctgtt actctctaat  116340
aaacaaaaag ataataaaga aaaagcaaa tgcatattaa gaaaaaatat tcaactcaag  116400
acagattttt attaggcata cattctaaaa gttctttgtg tgtgattta taatacatgc  116460
ataggtcacc ttttttcttc ttcatgtaat ggagtcaaat gccagaatgt cattattttt  116520
gacaaagaga accttgtgac ttctaagttg ggatgatttt tagaactatt ataaattgtt  116580
ccaacataac tgaaaataaa atcacaaaat cataagattg ataacaagta aatagtata  116640
ttttgttttt cagtatggct acagtaaaca cattaattgt ttgtttaaag tacatgatgg  116700
ggccaggcgt ggtggctcac gcctgtaatc ccagcacttt ggtaggccaa ggcaggcgga  116760
tcacaaggtc aggagtttaa gaccagcctg atcaatatgg tgaaacccg tctctactaa  116820
aaatagaaaa attagccagg cgtggtggca cgcgcctgca gttccagcta cttgggagac  116880
tgaggcagga gaatcgcttg aacccaggaa gcgaaggtgc cagtgagcca agttcatgcc  116940
actgcactcc agcctgggtg aaaaagcgag actttgtctc aaaaataaaa aaacaaaaat  117000
aaagtacatg ttggctgggc atagtggctc acgcctgtag tcccaacatt tgggaggct  117060
aaggtgggcg gattgcttga atccatatat atatatatat ataaaaatat gtgttgtgtg  117120
tatatttcat ttttatttat ttatttattt atttactttt taaacgtttt tgttaaaaat  117180
aagacacaca cacacagtag cctaagcata cacagggtca ggatcatcaa tatcactgcc  117240
ttctgcctcc atatcttgtc ctgctggaag gtatcgggca gaaacacaca tggagctgtc  117300
atcccctatg ataacagtgc cctcttctag aatacctcct gaagaacctg cctgaagctg  117360
tttaacagtt aactaatttt ttaacaatta gaaggaatac actcaaaatt aacaacaaaa  117420
agtaagtacg tggccaggcg cctgtaatcc cagcattttg ggaggccaag gtgggtggat  117480
cacctgaggt tgggagttcg agaccagcct ggccaccata gcgaaccct gtgtctccta  117540
aaaatacaaa aattagctgg gcgttgtggc gggcacctgt agtctcagct acttgggagg  117600
ctaaggcaaa agaattgctt gaacccggga agtggaggtt gcagtgagcc aagattgcac  117660
```

```
cactggactc cagcctgggt gtgacagagc gagactccat ctcaaaaaaa aaagtacata   117720
agccaataac tattttcttt atcattatta tcaaggattg tgtcctgtac gtaattacat   117780
gtgctgtgct tttatatgac tgacagcata gtagctttgt ttataccagc atcacaacaa   117840
acgtgaatga cgcattttgc tacaaattca tgggaattt tcagctccat tataactttg    117900
tggggccacc atgttatgtg tggcccatca ttgactgaaa cgtcacatga ctgtacatgt   117960 cttcagtaa tttaatat tccaattctt tctgtttat tttgttttgt tttcagacag       118020
agccttgctc ttttgcgcag gctggagtgc agtggtgtga ttatggctca ctgcagcctc   118080
gacctcaatt gaacctccca ccctagactc ccaactagct ggaactatag acacacacca   118140
ccatgcctgg ctaatttccg tatttttgt agagatgggt tttctccttg ttgcctaggc    118200
cagttttaaa ctcttgggct caagggatcc acccattttg gcctcccaaa gtgctgggat   118260
tgcaggcgtg agccaccatg tcccaccagt attccagttc ttccagttct aaaagtgaa    118320 cagaactagg aatgactggg catttgacag aagcctctaa tatgaaaaaa cagaggaaat   118380
ggagacaata cagagtaaaa tgaaaaagat ggggaaaaa agaaacaaca gtccacttt     118440 ctcagtcatt gggaaatgct gcaaccacga ataagaact gtgggtaata agtaagaagc    118500
tcttagaaat taagaatata ggccaggcgc agtggctcat gcctgtaatc ccagcacttt   118560
gggaggctga ggcgggcaga tcacaaggtc aggagtttga ccagcctg acaatatgg      118620 tgaaacccag tctctactaa aaatacaaaa aaaattagct gggcgtggtg gtgtgtgcct   118680
gtagtcccag ctactcagga ggctgaggca ggagaatcgc ttgaacccgg gaggcggaag   118740
ttacagtgag tcgagatcgc gccactgctc tccagcctgg gcaacagaat gagactcttg   118800
tctcaaaaaa aagaaagaa agaaattaaa atactataaa tttaaaaatt aagcagaagt    118860
ttggaaaata aggaactcca ttttccaata aaatttccaa aataaagaaa ttcattcatt   118920
tcaagaaaat gaatggataa agaaaagta ggagagaaaa gataaggaaa ttagaaagca    118980
aaactagaag atctgtcact gaactaataa tagtctaaaa ggagagtagg gaagaagaaa   119040
ttagcaaaaa aaaaaagaa gaaaaaatgt gttagaatta aagggcataa attttttatat   119100 agagcgtata caccaagctt gatatacacc accaaatgtg atggataaaa ataaaattgt   119160 taaaaatat agttttttaa gttacattat gaaattatag aacatccaac ataagaacct    119220
tgcttaggtt tagagtaaga taaaaataat gctgaaattt ggagtaagtt ttttaaatt    119280 aaaaactttg aaaatactcg attaacaaac ccatatatca tactcgatat ctgtcaagca   119340
ctgttctaat tgttgttcag atgttaactc atttaattct cctaactacc ctgtgaaaaa   119400
ggtactgtta aggatatatg gggtttgtta atcaagtaaa tctgtaaaat actggtcatg   119460
aggccgggca tggtgtttca cacctgtaat cccagcattt gggagcctg aggagggcgg    119520 atcacttgac gttagaagtt taagaccagc ctggccaaca tggcgaaacc ctgtctctac   119580
taaaaataca acattagcc gggcgtcatg gcgcgtgcct ataatcccag ctacttgtga    119640
ggctgaggca ggagattcgc ttgaacctgg gaggcggcgg aggttgcagt aagctgagat   119700
tgcaccactg tactccagcc tgagtaacag aatgagactc tgtctcaata aaaatatgt    119760 aaataaaata ctgattatgg aaagtggtc tcaccatgta cacgtaggga aaataataca    119820
cctcaattta tatcaaaatt ttatctcatc cttttaaaac tcatatttc tatttgtatt    119880 ataatatgtt cttaggataa cctattggtc tttgcatatg ctttataaat tgtaggaggt   119940
gtctgcaatt attttgttt tagatcgcaa aaatttgaca gccactcttt cagattaaga   120000
```

-continued

```
accaacttgt aggccaggta caatgcctca cacctgtaat cccagctctt tgggaggaca 120060
tggcaggtga attgcttaag tttaggagtt tgagatcagt ctgggcaaca tgaacatggc 120120
aaaaccacat ctctacaaaa aatacaaaac ttagccaggt gtggtagtgc acacctgtag 120180
tcccagctgc ttgggaggct aaactgggag gatggcttga gccctgaagg cagaggttgc 120240
agtgagccaa gatagtgcaa ctgtactcca gccaggtgg cagagcagga ccctgtctca 120300
aaaaaaaaaa aaagaatcta cttgtaaaac ttgaacagat ataggaatat cttatgagag 120360
tattgctgtc attttaatat gatcagtatt ctggagatat tcatttatct tctcatgtcc 120420
taggaatgtg ggaatgtgtc tagagaatct gaacttcaca gagtctttat ttatttattt 120480
tatttatttt gagacagagt cttgctctgt cacctaggct ggagtgcagt ggcgtgatct 120540
cagctcactg caacctctgc ctcccgaatt caagtgattc tcctgactca gcttcctgag 120600
tagctgggat tacaggcgca cgctaccatg cctgactagg gttttgtgtt tttagtagag 120660
acggggtttt gccatgttgg ttaggctggt ctcaaactcc tgatcttgtg atccgcctgc 120720
cttggcctcc caaagtgcta ggattacagg cgtgagccac catgcctggc ccacagagtc 120780
tcttttaagg ggaaacctgg tgtaccatgt gattactgcc agttatctgg ttggataaaa 120840
aaaggttgat cacctggggg gagaaaaaaa agcaaaaact ctgaggtggg gtccagtggc 120900
tcacccctgt aatcccagca ctttgcgggg gccgaggcag gcaaatcact tgaggccagg 120960
agttggagac cagcctggcc aacatggcaa aaccccatct ctactaaaaa tacaaaaatt 121020
agccaggtgt ggtggcatgt gcctgtagtc ccagctactc aggaggttga agcacaagaa 121080
ttgctggaac ccaggaggta gaggttccaa tgagccaaga tggtgccact gcactccagc 121140
ctgggtgaca gaacaagact ctatctcaaa agaaaaacag aacacaaaaa cttaaatata 121200
caagccctca agaagtttgc ttcatataaa gttcttaaaa agcaacaaag cctgggcaac 121260
atagtaaacc ctatcttctt ctttggtttt ttttttttt tgagacagga tctcattctt 121320
tcacccaggc tggagtgcag tggcatgatc agagctccct gcagccttga cctccccagg 121380
ctcaggtgat cctcctacct cagccttcct agtagctggg actacaagca tgcattgcca 121440
catccagtta attttttttgt atttgttaaa gacacagggt tttgccatat tgcccaggct 121500
gctcgctctc tctctctctc tctctctctc tctctctctc tctcactc 121560 tcactctcac tcgcgctctc tctctcgctc tctctctctt tttttttttt tttttttttt 121620
tggagacagt cttgctctgt cgcccagact ggagtgcagt ggcgtgatct caactcactg 121680
ccatctccac ctcctgggct caagcaattc tcctgcctca gcctcccaag tatctgggac 121740
tgcaggtgtg tgccaccaca cctggcaaat ttttgtatta ttagtagaga tggggttta 121800 ctgtgttgct caggctggtc tcaaactcct gagctcaatt gatccaccca ccttggcctc 121860
ccaaagtgct gggattacag gcgtgagcca ccatgcctgg cccctatttc tttaaggaaa 121920
aaaataaagg caactagagg gtataaccca cccgaacaaa ggagtatacc cagaaagagg 121980
aaaatgagac ctgggaaaca ggagaatctg aaaccagaga gaacattagc tctgtgatga 122040
actagggaac cagtagtcca cactggagca ggaggccaaa agttactaac aaggatgtct 122100
gtggtattga tacttactat gtgtgcttgt cattattgag aggaggtata ccaatctgca 122160
agaaagttag aagaaaagct gagtaactga tgatgcatag agagctaagc catcagaaat 122220
ccaaggcagt cattagggga aaacaagaca ctatagaaga aaagatacga aatcatggtg 122280
tcatagatgg gaatactatc tgcagtcata cgactgaggt aatgaaaaat tacaatataa 122340
cagtattgga aagatagaga aggacacttc cacagtagga agtcagtaga aaatgtgtga 122400
```

```
aacaaagatc aagaaataac tttttgaaata gtctgaaata cagaggtgta aattttagaa   122460
gcagctataa aaaaatgttg aaagttgatg cctctggcta acaggagggc tgcggggcag   122520
agactatgtt tttcattcaa agtcttgtat ttgactttt aaacagtata tgtgtattac   122580
cttgatgaac attaaatttt cttagtctga aaaactgcag tttttattcg caaccagatt   122640
gtaatggctc ttaatatgct actcttagct acataattct caggtatcaa cttgtttaac   122700
agtcttaaaa tgcccttttt aaatgtttgt ttttcagttg ccttgttgaa ggggatgcta   122760
aagaagaaat actgcagcca ccggaacctc atccagtgcc acccatcttg acccttctc   122820 cccttcagc ttttccaaca gtcactactg tgtggcagga caatgataga taccatccaa   122880
agccagtgtt gcatatggtt tcatcagaac aacattcagc agacctcaac agaaactata   122940
gtaaatcaac agaacttcca gggaaaaatg aatcaacaat tgaacagata gataaaaaat   123000
tggaacgaaa tttaagtttt gagattaaga aggtccctct ccaagaggga ccaaaaagtt   123060
ttgatgggaa cacactttg aatagggac atgcaattaa aattaaatct gcttcacctt   123120
gtatagctga taaaatctct aagccacagg aattaagttc agatctaaat gtcggtgata   123180
cttcccagaa ttcttgtgtg gactgcagtg taacacaatc aaacaaagtt tcagttactc   123240
caccagaaga atcccagaat tcagacacac ctccaaggcc agaccgcttg cctcttgatg   123300
agaaaggaca tgtaacgtgg tcatttcatg gacctgaaaa tgccataccc atacctgatt   123360
tatctgaagg caattcctca gatatcaact atcaaactag gaaaactgtg agtttaacac   123420
caagtcctac aacacaagtt gaaacacctg atcttgtgga tcatgataac acttcaccac   123480
tcttcagaac acccctcagt tttactaatc cacttcactc tgatgactca gactcagatg   123540
aaagaaactc tgatggtgct gtgacccaga ataaaactaa tatttcaaca gcaagtgcca   123600
cagtttctgc tgccactagt actgaaagca tttctactag gaaagtattg ccaatgtcca   123660
ttgctagaca taatatagca ggaacaacac attcaggtgc tgaaaaaggt aataatatag   123720
tgtcaaatac ttaaatgtct ttcctatgtg ctagtcactg ttttaagcac tttagctgta   123780
ttgatttatt atgtttatt ccacactcta ccatagaacc tacagcaaaa tctgtcttag   123840
atactaattt tttaatataa gcttttaatg tattgttaac aatttggtca cattatatta   123900
ctgggttttg tgtttctaaa ttattttagt agttataact ggataactta ttttctttt   123960 cttctgtatt atagatctta gtgttttgt atcggtcaaa aatttatctg actgaataat   124020
tagaaataat ttagggaaga atcacttaaa ataacagtgg caaaaatact gtagaatgtc   124080
ttgattggcc atataatgtt actcgttttt cctaaatgtt tagtcatttt ttactgttcc   124140
tttaactaca gattacattt ttttgttgt ttgtttac tgtcttcaca aatgcttcca   124200
aatatggctg cttccaaccc tgagtttaac ccaggaacaa tactgcaaac tgctcaattc   124260
agtagtgagt gggctatatg cataccact catcaaagct attatttaaa gaattattat   124320
ttttttagca ctcttagcat ttcaagataa tgcatgcact cagttcccaa agtgtattat   124380
tgcttcttga aactcctctt tgatctgctg aaagtaatga tggctaccat cttaaacaga   124440
ccctaaggtt gagagtaaac atataaattt gaaagctgtt tattgatata ttgattatca   124500
gtggtcactt acctatcagt gaactttggt agtgacacat acagactggt atttataacg   124560
tgcaggcaaa ataagtactg tgaccttgaa agattttttt tttttttga gacttgcact   124620 caaaagattt ttttttgag tcttgcactg tcacccaggc tagagtgcag tggcaagatc   124680
tcggctcagc ctcccaagta gctgggatta caggcaccca ctaccacacc cagctaattt   124740
```

-continued

```
ttatgttttt agtagagaca gggtttcgat atgtttgcca ggctggtctc aaattcctgg    124800
cctcaagtga tctgcccacc taggcctccc aaagtgctgg gattacagac gtgagctacc    124860
acacctggcc ttgaaagatt attttctatt tctgacccat tatataccac ccatactgta    124920
gtgcttgtat tttctctcac acatactgta tttttttaact tgagagagtg tatttggtag   124980
actagatgac agtcttttg agacagagtt ttgctcttgt tgcccaggct gaagtgcagt     125040
ggcgcaatct tggctcactg caacctccgc ctcctgggtt caaggaattc tcctgcctca    125100
tcctccctag tagttgggaa tacaggcatg cgccaccatg cctggctaat ttttgtatt    125160 tttagtagag acagggtttc actgtgttag ccaggatggt ctggatctcc tgacctcgtg    125220
atccgcccac ctcggcctcc caagggctg gattacagg cgtgagccac cacgcccagc     125280
caggtgacag tcttaaacta tttgcttaaa ttacagaatt atcttttctt gatttatctt   125340
tgttttattt gaaggatctt tagaagataa tgaatagtat aatattactt taccagttta   125400
ccataatttt aaattgctaa tgtcttttgt tcctcagctt cagaatttga aatataactg    125460
cccagctgta actatataag aaaatatgta gataagaaat tttcattttg agttttagt     125520 atatcaagca tgtggtattg tacctaggaa gttttattgt tttttgttg ttgttttgtt    125580 cttttgcttt tttttttaaa aaaaccaaa aaaccattac tggaaatagg atttggtgag    125640
ggccagaaag atgtatgatg tgatatgctt attaaaagtt actactacat gacgagtctg    125700
ttggtggctc atgcctgtaa tcccagcatt ttgggaggct gaggcaggaa gttcacttga    125760
gcccaggagt tcataaccag tctgggtgac atagtgcaca ccaatctcta caaagataa    125820 aaaactagcc gggcatggtg gtgcacactt gtggtcccag ctactctgga ggctgaggta    125880
ggaagatcac ttgagcctag gagctcaagg ctgcagtgag ccataattgc gtcccggcac    125940
tctgcctggg caacagaggg agaccctgtc tcaaaaaaaa aaaaaaaaaa agagtaagat    126000
atagctaaaa gcaccctact atgtgccagc tcatttctgt ttgtttggtt ttgtatttca    126060
aagcaaaaat cactatacat gtgatttctg gtttcttttt actcaaccctt aactatgtta   126120 ttggtttgat tttaaccgaa gattttcctg tgtgtaaatg ttctttgttg cagcataact    126180
acaagtagtc tcattttaa tgtgttgcca aatatttacc atatggatta tttactttat    126240
agattgttta tttaccttat agattattat ttcctttgta gatcattatc ttatagagcc    126300
attggcacca gaattagagt tttgggggt ttttggtcc tagaacttgt tagtgaatta     126360
cagtcacaca tttcttaatg gcagggatat gttctaagaa aaatatgtca ttaggcagtt    126420
ttgccattgt gtgaatgtca tagaatgtat ttacacaaac ctagatggta tagtatatac   126480
tacacatctg ggcctacaa tgtaacctct tgctcctagg ctacaaactt gtatagcata    126540
ttaccatact caacaattgt aacacaatgg taagtatttg tgtatctaaa catagaaaag    126600
gtacagtaaa aatatggtat cataatctta caggaccgct gttgtttatg cggtcttgtt    126660
gatgaaaaca tcattatgta gtgcatgact ataatggaat acttttgtat tgatacctaa    126720
aaaaaacttt tgcataagtt actgcctgac aaaaattctt agctatcaat tctaatttca    126780
gtcttgactt aggcctcctg aaagatttct cagattcaac tacagaaggc cccatacagt    126840
gtatgatttg caaagccta tataaaatac gcaatatctg gttggataac ctctaaaaca    126900 aagttttta acaggaaagg cagcccaaag ttccagggag aaacatgcat ttgcaaagca    126960
agggccacgc ttagaaaata aaagttttta agggtgagaa ctgccatgag agaaaaagca    127020
cagagtttct ggaagataac tgatagaaaa agggctgaac tgccctttttt gttttgttca    127080 tttaattaa gaaatggtac cagaatgcca agattatgtg tcccttcctt ccaacagcca    127140
```

```
tctcttcact gtgcgctgtt agtagcaaga gggcaaggag acatatggtg atgactcaga    127200
ctaccactac tggataaggt agatagttct ttagtggcaa gagagagttc tggtactctt    127260
ggtagatgta tcaagtattg gactggaact cctctttcag gaggacccag aagctgtatt    127320
ttcttgcgtc tccagctaaa taaatgtagg tggggcaaaa gcaatcatac tcacctcatg    127380
cgtgttgaaa attgacaaga cctatgcata gccatcaggt gtggtaaaat agcagagtat    127440
catggcagaa ctgtgtgttc atttaagaac aatgggcaag gctcaagaca aaataataca    127500
ggaccgtcgc atttcttttt ctttatccca ccctccccaa cctgagagtt cacacacagg    127560
attgtattct tatattttct ttctattcct ccagtgaaaa ctcaaagatc aaatacactc    127620
atttaccttg agccataata aagctaacca atgaggctta cttaatgcac tctctttccc    127680
aagagctaat tttgttttta ctagtgaaaa acctgtatat agcttcagtc agcattctca    127740
aagtacagcc atgtgccact gtacacaaaa tcttttagcaa taaataaatg aagatttttt    127800
aaaaaacttt aatagctata tctttatctg ttttggaaaa ataactagta tttccaatgt    127860
tatttcagtt attgctgttt aagacatgac tgaggtacac agttaagttt aaaatgagtc    127920
agatttaaaa agtgaatagg acacatgtta catagtatgg caaaaatcat gaaaggtgtt    127980
aagcaattga atcctgtttg ggaaacactg gcttaggcgt tcataacgc aaatgaccaa    128040
agctttcctt tttggacaca aacatcatc agtaagctca gtagagaagt cacttgccag    128100
ctgacttctc tactgaagat tcccttcagg cttggagaac tgaatgatgt ctgtagagtg    128160
acaggaaagt catgggagag agtcatttct gtatacatta tctttgctca ataagcatca    128220
taattcttga taatgagtgg aaaaggtttc ttgcattttt ttgcattttt aaaaactgat    128280
ctagatattt gtgacaggaa tttttagaat gtcaagaaag ctctctgatt ttgtttagat    128340
gacatgttaa tttgtctaaa tttttatgtg tttaatttag atgttgatgt tagtgaagat    128400
tcacctcctc ccctacctga aagaactcct gaatcgtttg tgttagcaag tgaacatagt    128460
gagtgtctct tttgctttta catttacttc atattctaat aataaactcc gaaaaacata    128520
cctgatttta atctattagc tattgtgcta cataattaaa ttcaaaaaca agtaaattga    128580
tgttgacatg cttttaattc tttgtttgaa aaatgctttt aaattatatt ttttacttgc    128640
taagatcgat agaaattact gcatttatgt tagatatcag aattcaattc atttaaatgt    128700
aattataggc tgggcatggt ggttcaagcc tgtgatccta gcactttggg aggcctaggc    128760
aggtggatca cctgaggtca ggagttggag accagcctgg ccaacatggt gaaactccat    128820
ctctactaaa aatataaaaa ttagctgggc atggtggtgg acacctataa tctcagctac    128880
ttgagaggct gaggcaggaa aatgacttga acccgggagt tggaggttgc agtgagccga    128940
gattgcgcca ttgcattcca gcctgggcga agagcaagat tcgtctcaa aaagtaaata    129000
aataaataaa tgcaattaca aagccaggtg cagtggctca tacctgtaat cccagccct    129060
tgggaggctg agatgcactg atcacctgag gtcaggagtt caagaccagc gtgaccaaca    129120
tggagaaacc ccgtctctac taaaaataca aaattagcca ggcgtggtgg cgcatgcctg    129180
taatcccacc tacttgggag actgaggcag gagaattgct tgaacctggg aggtggatat    129240
tgcagtgagc cgagatcaca ctattgcact ccaacctggg caacaagagc gaaactccat    129300
cttaaaaaaa aaatgcaatt ataagtgtat ttgcaatctg gtgtattttc attcattaaa    129360
aatagcactt attgactcat gcctgtaatc ctgccacttt gggagaccaa ggcgggcaga    129420
tcacgaggtc aggacatcaa gaccatcctg gctaacacac tgaaaccctg tctctactag    129480
```

```
aaatacaaaa aattagctgt gtgtggtggc atgcaccagt agtcccagct gctcgggagg   129540
ctgaggcagg agaatcgctt gaaccccgga ggcagaggtt ggagtgagcc gagaccatgc   129600
cactgcactc cagcctgggc aacagagcaa gactccatct caaaaaaaaa aaaagtagca   129660
cttatttatg aaaacattaa ttgctttcct tagatttagg tcagtaaaca tttctgttgg   129720
gtgggcgtca ctggattggt gttaactgaa agacatttaa caccactgga gtagactgag   129780
cacattggct catacctgta atcgcagcac tttgggagtc caaggcgcga ggattgcttg   129840
agcctaagag tttgagacca gcctgggcaa cacagtgata cctcctctct tctaaaaata   129900
aaataactgt ccagttgtgg tggtgggcgc ctgtaatccc agctgcttgg gaggctgagg   129960
caggagaatt gcttgaaccc aggatgcaga ggttgcagcg agctgagacc acgccattgc   130020
attccagcct gggcaacaag agcaaaaaac tttgtctcaa aaataataa taacaacaaa   130080 aaattagcca ggtgtggtgg catgtgcctg tagtccttgc tactcaggag gctgaagaag   130140
aaggattgct tgatccctgt agttggaggc tgcagtgagc catgatcgca ccactgtact   130200
ccagtttggt aacagtgaga ccccgtctgt ggaagaaaaa aaaagacca ctggagtatc   130260 agaactggga gaaagtgatg atactttaaa acattgataa tatacttctc cctattaatc   130320
ctctaaaaaa gagtgcagaa acagcttgat tgtatttaca gtgtctcatg ctcagtggag   130380
gtgctcactt gtctaagtac attttaccaa tatattaatt ttgactgatt tttgttttgt   130440
ttcatttggt tttcttttta ttttatttatt ttttatttat tcatttttt gagatggagt   130500 ctcattctgt cgccccggct ggagtgcagt ggcacgatct cggctcactg caagctccac   130560
ctcttgggtt catgccattc tcctgcctca gcctcccatg tagctgggac tacaggtgcc   130620
tgccaccaca cccggcttat tttttgtat ttttttagt agagacaggg tttcaccgtg   130680
ttagccagga tggtccatct cctgacctca tgatccgccc acctcagcct ctcaaagtgc   130740
tgggattaca ggcatgagcc accacgcccg gctaattttt ttgtattttt ttagtagaga   130800
cagggtttca ccatgttagc caggatggtc tccatctcct gacctcgtga tcgcccgcct   130860
cagcctccca aagtgctggg attacaggcg ggagccacca cgcccggcct tgttttgttt   130920
tatttcgagt tggagttcca ctctgtcact caggctggag tgcagtggca cgatctgggc   130980
tcaagctgtt ctcctgcctc agcctcctga gtagctgcga ttagaggcat acaccgtcac   131040
tcccaactaa ttttttatt agagataggg tctcaccatg ttggccaggc tggtcttgaa   131100
ctcctgacct caagtgatct gcctgcctca gcctcccaaa gtgaattttg actgatttta   131160
agataaatgt taaagagcca agcacaatgg cttatgcctg tgatcccagc actttgggag   131220
accaaggcag gtggatctct gttccatttg ccctaggagt ttgagaccag cctgggcaac   131280
atggcaaaac cctgtctgta taaatcaaa aattagccag gcgaggtggc atgcacctat   131340
agtcccagct actcaagaag ctgagatggg aagattgcct gagcctggga ggttgaggct   131400
ccagtgagcc gagatcgcgc ctggtcaaca gagtgagacc ctgtctcaac aacaattaaa   131460
aagaatgttg aaagcaatga aacggtatac ttcagttgtc taagtctgtc acgttgtctg   131520
tagattaagc agtatacttc acttgtctgt cacattatct atagactgta atacactgat   131580
gactgaattt atttacttag gttttgaagg aaggaaacag aatgttctcg aattaataga   131640
aactacaatt tttttttttt agaaacttca gaaatatgct tacccagaaa ctacaaaatt   131700
tttgtggaag cgatagtttc taaaatcttt aggatctgtt ttttgtatta ctttaatgca   131760
aagaaatttc agaaattcaa ggtgttaata acaataagat ttcattttc tcagatacac   131820 ctgtaagatc ggaatggagt gaacttcaaa gtcaggaacg atctgaacaa aaaagtctg   131880
```

```
aagtaagtcc ttttggaatt ggaacagtta tagcttaaca tttctactct tttgttaact    131940
aatcttgcag ttgttgaaat agctgtcatc ttaagatcgt taaatatagt ttgtaatttt    132000
tgatcggcat ttcttatact aagatttcag atgaaaagcc catataaaag gtaggttctg    132060
aaatttttta aaagggtaac ctgatctaca tacaactatc actttaaagt attgttttct    132120
caagctgttt ttgaaatatg taaattatgc ttcaaataat tttgaaggta tgaatgaaat    132180
aggagttact attttcaggg tcctaattct ttcttacatt tctagatgct tcccattata    132240
acactaggca catagtcgct tcttttgttt ttttctggct acctggcatt tctttgacat    132300
tcgagaaatg ttttggcaat taaatatttt gagggcgtgg catggtggct catgtctgta    132360
atcacagcac tttgggaggc caagcagaag gatcacttga gcccaggagt tcaagaccat    132420
cctgggcaac atgggagac cttatctcta caaaaatttt taaaattagc caggcgtggt    132480
ggcgcatgtc tatggtccca gctttttggg aggctgagat gggaggattg cttgggcccc    132540
agaggtcaag gctgcagtga gccatgatca caccactgca ctccagcctg agtgacagag    132600
tgagaccctg tctcagcaac aacacatttg tccataggag ataacatttt ttattaacat    132660
taatactttt tgtattttct cccatacttt aatatctctg aaatttagct acatcttata    132720
tttgatttta agacatgatg tagtttaatt gacatataaa atacaataat gatataatta    132780
gtaatagtgg ctggcaaaac acagctgtat gttccttcat gcagtagccc atgcttttca    132840
gtgctcatcc agaaacattt actccaagga gaaatagcat aacatttaa aattttaagc    132900 ctaattaaaa aacaattgtt tgcttttcct ctgatgctga aaatgatagg ccttgatttc    132960
ttgggatata tacccataac agacccagct ttctattatt tgtatataaa atgaatgtat    133020
tgtaataggt attaaatgtc ttcctcgtag ggcttgataa cctctgaaaa tgagaaatgt    133080
ggtaagttgt tagatttttt ttttccttt tactgtagat tttattgatt aatttctaca    133140
aaataacatg cttcatagtt catgctatat agttatttct gtatgtgaaa atgtctagga    133200
caactcttgt agaagcttaa tattgtacta taattcttcc aaattaatta ttaccaccag    133260
atagtagtat tgatctggaa aatcatggga gcatttacta tcaataatta caggctaatg    133320
ggaaagagat tttttaaaaa tattttttctg ttttttattt tctgttttta aaaacaccta    133380
gaagttagat cccgacttaa ataaatgatg gaattgcttc tgtagaaacc tattgtttta    133440
gaaatcttcc ttttagtact ttttcattta tttgtgaaga ccaataaaat tgtgaaagaa    133500
tgaatgaatt ttagtagtta acatcttttg ttactaatct taaacactgg taattaaaga    133560
gtaaactaca atctaaacaa cataaaactt taaaagtgga gttattaggc ctggcgtggt    133620
ggctcacacc tataatccca gcactttggg agacccaggc aggcaatcac ctgaggtcag    133680
gagttcgaaa ccagccttga gcaacatggt gaaacccgt ctctactaaa aataaaaaaa    133740
atagctaggc gtcatgccat ctgcctgtaa tcccagctac tagggagact gaggcaggag    133800
aatcccttga acccggagg cagaggttgc agtgcgccga gattgcgcca ttgcactcca    133860
acccgggcaa caagagggaa actccgtctc aaaaaaaaaa aaaaaaaaac aagtagagtt    133920
attatttcaa ggtgcaaata gtgcattaat taaccctgac cttgttgatt tcttaaaatt    133980
tttttttttt tttttttttt ttttttttgag acagaggtct tgctctgtcg cccaggctgg    134040
agtgcagtgg cgcgatctcg gctcactgca agctccacct cctgggttca acacattctc    134100
ctgcctcagc ctcctgagta gctgggacta caggcgcccg ccaccacgcc tggctaattt    134160
ttttgtattt ttagtagaga cggggtttca ccatgttagc caggatgatc tcgatatcct    134220
```

-continued

```
gacctcatga tcggctcgcc tcggcctccc aaagtgctgg gattacaggc atgagccacc   134280
gcgcctggcc tgaccttgtt gatttctata caaagacatt tcagttgcaa ctattccctt   134340
agaacatagg catatagtat agctaccttta agggaatgta atatgtcaag acctagattt   134400
atgaagtaag aataacgaga atcctcacat tgcagaagta ctcactgcag atttctgtgt   134460
gaccacaata atacctgaca tgattttctg tgcacactac acttgtattt atattgttct   134520
tgacctgtaa aattatggtg cccaggagag aaagttttct ctttttcatgc ttgccaacat   134580 ttaaaaaatt aaagagttat atatatatga tgctacaaag gatggtgatt aacaaaggct   134640
ttgtgttgct acttagatca tccagcggga ggtattcact atgaaatgtg catagaatgt   134700
ccacctactt tcagtgacaa gagagaacaa atatcagaaa atccaacaga agccacagat   134760
attggtaatt tgtttaataa ataatttttta gtaagtagtt aacactggca ggaatgagaa   134820
aagctcattt gccattgtga aatgacactt gccaagaata aaacatgatt ttccaaagtt   134880
gcttggacta gtcatgaaat aaatgaaata cttaattcta tttcacattg agattaaaaa   134940
ctaaaataga aaactgcagt ataaaaaatc ttttgtgttg gaaagactaa attatcatgg   135000 atattttttct tacattgtga taaaattggt tttatttcca gcataagatt tttaaaagaa   135060
gcaatcattt tcagttattc caaataaatt tacaattgtt ttgcatttac caagttttgt   135120
ttggcttaaa ttctaaattc ccttgtggaa atttatttgt tccagaaaat gagaatgtct   135180
gtggacatgg ttttttagtag tttgaaagta tttctgaaca ctgactagtt attgtggtgt   135240
tttcactgta ggttttggta atcgatgtgg aaaacccaaa ggaccaagag atccaccttc   135300
agaatggaca tgattcaggg agctagaaga cactttaagt tatactggaa aattcaggtg   135360
ccactgaaag ccagatttat agtattccat ctttaatatg tgggactaac agcagtgtag   135420
attgttacct taatatttttt tgctgggacc atctacctgc cttatactac acttaggaaa   135480
aagtattaca tatggtttat tttgaaactt caagtattat tgccttaatg tctcttaacc   135540
ctgttacacg ctgcttgtag acatgttaat atagtaatac ctttatgata tattgagttt   135600
aaggactact cttttttctgt tttatcatgt atgcattatt ttgtatatgt acagggcaag   135660
taggtatata atttgataaa gttgcaattg aaatattatt aacagaagat gtaagaaatt   135720
tctgcatggt ctaaatcttt gtgtacttta tttgtaaatt atttgccctg gagttttaga   135780
aaatagtttc tgaattttaa acttgctgga ttcatgcagc cagctttgca ggttatcaga   135840
gatcaaagat tgtaataata attttgtaaa ttgtaagcaa aaagttattt ttatattata   135900
tacagtctaa ttgttcatcc taattgttcc tgttttcatc tagtcagaga ttcagtaagt   135960
gccttggaac aatattgaat tctcttagct tgtgtgtgtt tctttaatat ttgaactcaa   136020
gtgggattag aagactatca aaatacatgt atgtttcagg atatttgacc tgtcattaaa   136080 aaaacaaac agttttacag tgcctacttg ttgccttggc ttttcatttc tcattcctag   136140
gatattggac ttaactatca gcctttttgc tggctcagtc ttggtatgaa atgaatgtga   136200 atgggggttta atttctttttt ttttttcttt ttttagacag agtattgctc tgtcacccag   136260
gctggagtac agtggtacca tcttggctca ctgtaacctc cacttctgag gttcaagtga   136320
ttctcctgtc tcagcctccc aagtagcctg ccacgacgcc cggctaattt ttgtattttc   136380
agtagagatg gtttcaccat gttggcgagg ctggtctcaa actcctgaac tcaggtggtc   136440
cacctacctt ggcctctcca aatgctggga ttacaggcat gagtcaccat gccaggccta   136500
atctcttaat taaggaatag agagtacctt ctgcaaaaaa catggttctg cggattctaa   136560
atacttattg ccccctaggca ttcctcatcc ttatcattat tagcctacca aagtcctagt   136620
```

```
agaaaaccca acagaggggg ccagaccggg tggctcacgc ctgtaattcc agccctttgg    136680
gaggccaagg caggcagatc acttgaggtc aggagttcaa gaccagtctg gccaacatgg    136740
tgaaacccca tctctactaa aattacaaaa aaattagctg ggcatggtgg cacatgcctg    136800
gaatcccagg tattcaggag gctgaggcag gagaattgct tgaaccaagg agatggaggt    136860
tgcagtgagc tgagatcgca ccactgcact ccagcctggg caacagagca agactacatc    136920
tcaaaaaaaa aaaaaagaaa gaaaaccaaa ccaaggggat gttgagaacg ggaactggtt    136980
tcttgtcatc ccatgactgg                                                137000

<210> SEQ ID NO 12
<211> LENGTH: 519
<212> TYPE: DNA
<213> ORGANISM: H. sapiens
<220> FEATURE:

<400> SEQUENCE: 12
catctgtcta cttggaaagg ctaaagatcc tccgacagcg atgtggtctg gacaacacaa     60
agcaagatga ccgacctcct ttgacctctt tgctctccaa accagcagtt cctactgtcg    120
cctcttccac agacatgctc cacagcaaac tctctcagct ccgggagtca cgggagcagc    180
accagcattc agacctggat ctaaccaga ctcactcttc aggagggagc cgcggggctt     240
ggcggggtcg ggagggaggg acgtgctggg ggaacgagct ggggaagacg gagcgggctc    300
tgtgccgggc gggcgggcgg cggggggggcc agcgaccgca gccggggggga cgcgggagga    360 tggagcaagt ggagatcctg aggaaattca tccagaggat ccaggccatg aagagtcctg    420
accacaatgg ggaggacaac ttcgcccggg acttcatgcg gttaagaaga ttgtctacca    480
aatatagaac agaaaagata tatcccacag ccactggag                            519

<210> SEQ ID NO 13
<211> LENGTH: 649
<212> TYPE: DNA
<213> ORGANISM: H. sapiens
<220> FEATURE:

<400> SEQUENCE: 13
gggagcaagt ggagatcctg aggaaattca tccagagggt ccaggccatg aagagtcctg     60
accacaatgg ggaggacaac ttcgcccggg acttcatgct ggacctggtg gcacgcatct    120
gtaattccag ctactcagga ggctgaggca caagaattgc ttgaacctgg gaagccgagg    180
ttgcagtggg ccgagatcgc accactgcac tccagcctgg gcaacagagt gagatcctgt    240
ctcaaaacaa acaaacaaag tgctgtgcgg ttaagaagat tgtctaccaa atatagaaca    300
gaaaagatat atcccacagc cactggagaa aagaagaaa atgttaaaaa gaacagatac    360
aaggacatac tgccatatca ttgtaatggc ctgccgagaa tttgagatgg gaaggaacaa    420
atgtgagcgc tattggcctt tgtatggaga agaccccata acgtttgcac catttaaaat    480
gccttgtgag gatgaacaag caagaacaga ctacttcatc aggacactct tacttgaatt    540
tcaaaatgaa tctcgtaggc tgtatcagtt tcattatgtg aactggccag accatgatgt    600
tccttcatca tttgattcta ttctggacat gataagctta atgaggaaa                 649

<210> SEQ ID NO 14
<211> LENGTH: 368
<212> TYPE: DNA
<213> ORGANISM: H. sapiens
<220> FEATURE:
```

<400> SEQUENCE: 14

| cccataacgt | ttgcaccatt | taaaatttct | tgtgaggatg | aacaagcaag | aacagactac | 60 |
| ttcatcagga | cactcttact | tgaatttcaa | aatgaatctc | gtaggctgta | tcagtttcat | 120 |
| tatgtgaact | ggccagacca | tgatgttcct | tcatcatttg | attctattct | ggacatgata | 180 |
| agcttaatga | ggaaatatca | agaacatgaa | gatgttccta | tttgtattca | ttgcaggtac | 240 |
| aaaagaattt | cccaagttta | taaatacatt | atttaagttt | gatgttacac | aggttttatt | 300 |
| tctgcattaa | tatgttagta | atcgtgattt | ctcctagcct | tgatacaatg | ttgggaccac | 360 |
| ggccttgt | | | | | | 368 |

<210> SEQ ID NO 15
<211> LENGTH: 985
<212> TYPE: DNA
<213> ORGANISM: H. sapiens
<220> FEATURE:
<220> FEATURE:
<221> NAME/KEY: CDS
<222> LOCATION: (443)...(585)

<400> SEQUENCE: 15

| aatggatact | actctaacct | actctaacat | ggtgcttacg | gtatattgct | catccattta | 60 |
| atagtgtaga | ttagttaaat | agtatatata | gtgttatgtt | tacagtacat | gctctggaag | 120 |
| tagaactgcc | tggtttagag | cccacacttg | tcacttctta | ggaaagtttg | ggcaagttat | 180 |
| tttatctgta | tatctcagtt | ataaaatgag | gatggtatta | acagtacttt | cctcatggaa | 240 |
| attaaattgt | tacatgtgaa | gcccttaggt | attttggcatg | tgtttaacag | tcaataagtg | 300 |
| ttggctatta | tttatttggg | tttttttaaa | agcagtgcta | aatgccacac | aaatttctta | 360 |
| gaaatggcag | tttaaatgag | ctgtgcaact | ttaaactttg | caaagtattt | tcataattgt | 420 |
| tgactttctg | ttttttcttga | ag gaa tct cgt agg ctg tat cag ttt cat tat | 472 |
|  |  | Glu Ser Arg Arg Leu Tyr Gln Phe His Tyr |  |
|  |  | 1 5 10 |  | gtg aac tgg cca gac cat gat gtt cct tca tca ttt gat tct att ctg    520
Val Asn Trp Pro Asp His Asp Val Pro Ser Ser Phe Asp Ser Ile Leu
            15                  20                  25 gac atg ata agc tta atg agg aaa tat caa gaa cat gaa gat gtt cct    568
Asp Met Ile Ser Leu Met Arg Lys Tyr Gln Glu His Glu Asp Val Pro
        30                  35                  40 att tgt att cat tgc ag  gtacaaaaga atttcccaag tttataaata cattatttaa    625
Ile Cys Ile His Cys
        45

| gtttgatgtt | acacaaggtt | ttatttctgc | attaatatgt | tagtaatctt | gaatttctcc | 685 |
| tagccttgat | acaatgtttg | ggactagggc | cttgtaagtt | gatgtggtct | catttggttg | 745 |
| acagaccgtt | tagagtattg | ttgcattaaa | acacaggatc | atctatttga | aaatagtatt | 805 |
| cacatggtgg | gaagctatag | aacatactct | ttttactgtt | cactgattag | agcatataat | 865 |
| ctcagatcct | catcatactc | tactttctaa | agtcagtatg | gtagtatttt | cttttaatca | 925 |
| atttccctga | aacaatgacc | aagcaatttt | cattcctgat | aaacactgac | atgagatttt | 985 |

<210> SEQ ID NO 16
<211> LENGTH: 20
<212> TYPE: DNA
<213> ORGANISM: Artificial Sequence
<220> FEATURE:
<223> OTHER INFORMATION: Antisense Oligonucleotide

```
<400> SEQUENCE: 16
ggccattaca atgatcacaa                                                   20

<210> SEQ ID NO 17
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 17
aatacttgaa gtttcaaaat                                                   20

<210> SEQ ID NO 18
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 18
agtgttatca tgatccacaa                                                   20

<210> SEQ ID NO 19
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 19
tccattctga aggtggatct                                                   20

<210> SEQ ID NO 20
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 20
cctacgagat tcattttgaa                                                   20

<210> SEQ ID NO 21
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 21
atcttcttaa ccgcatgaag                                                   20

<210> SEQ ID NO 22
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 22
tggagctgat catgttttca                                                   20

<210> SEQ ID NO 23
<211> LENGTH: 20
```

```
<212> TYPE: DNA
<213> ORGANISM: Artificial Sequence
<220> FEATURE:
<223> OTHER INFORMATION: Antisense Oligonucleotide

<400> SEQUENCE: 23
aatctctgac tagatgaaaa                                         20

<210> SEQ ID NO 24
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 24
gtgtcaagat gggtggcact                                         20

<210> SEQ ID NO 25
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 25
agcctacgag attcattttg                                         20

<210> SEQ ID NO 26
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 26
ttaaactcac agttttccta                                         20

<210> SEQ ID NO 27
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 27
ttttccagta taacttaaag                                         20

<210> SEQ ID NO 28
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 28
tcaacaaggc aactgcgggt                                         20

<210> SEQ ID NO 29
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 29
```
ttttggtccc tcttggagag 20

<210> SEQ ID NO 30
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 30
tatggagctg atcatgtttt 20

<210> SEQ ID NO 31
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 31
acattaaggc aataatactt 20

<210> SEQ ID NO 32
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 32
caagaattct gggaagtatc 20

<210> SEQ ID NO 33
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 33
ttaagcttat catgtccaga 20

<210> SEQ ID NO 34
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 34
aagttcactc cattccgatc 20

<210> SEQ ID NO 35
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 35
tacatatgct tttggcccat 20

<210> SEQ ID NO 36
<211> LENGTH: 20
<212> TYPE: DNA
<213> ORGANISM: Artificial Sequence

```
<220> FEATURE:
<223> OTHER INFORMATION: Antisense Oligonucleotide

<400> SEQUENCE: 36
tcaccgacat ttagatctga                                               20

<210> SEQ ID NO 37
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 37
tcaggctcta tggagctgat                                               20

<210> SEQ ID NO 38
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 38
gaagtcccgg gcgaagttgt                                               20

<210> SEQ ID NO 39
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 39
agtagtcctt aaactcaata                                               20

<210> SEQ ID NO 40
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 40
ctggctttgg atggtatcta                                               20

<210> SEQ ID NO 41
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 41
gggttttcca catcgattac                                               20

<210> SEQ ID NO 42
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 42
tcaaatgatg aaggaacatc                                               20
```

<210> SEQ ID NO 43
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 43
caacatcttt ttcagcacct                                           20

<210> SEQ ID NO 44
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 44
agatcgttcc tgactttgaa                                           20

<210> SEQ ID NO 45
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 45
tggctgcatg aatccagcaa                                           20

<210> SEQ ID NO 46
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 46
tgcagaaatt tcttacatct                                           20

<210> SEQ ID NO 47
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 47
cacagcacca tcagagtttc                                           20

<210> SEQ ID NO 48
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 48
ttcacataat gaaactgata                                           20

<210> SEQ ID NO 49
<211> LENGTH: 20
<212> TYPE: DNA
<213> ORGANISM: Artificial Sequence
<220> FEATURE:
<223> OTHER INFORMATION: Antisense Oligonucleotide

```
<400> SEQUENCE: 49
ctgaagagtg gtgaagtgtt                                               20

<210> SEQ ID NO 50
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 50
gctgttagtc ccacatatta                                               20

<210> SEQ ID NO 51
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 51
ctcctttgtt tgtactgcag                                               20

<210> SEQ ID NO 52
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 52
tgcagtccac acaagaattc                                               20

<210> SEQ ID NO 53
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 53
atctccactt gctccatcct                                               20

<210> SEQ ID NO 54
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 54
cagtggctgt gggatatatc                                               20

<210> SEQ ID NO 55
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 55
ctgtgatcaa atggcagtat                                               20

<210> SEQ ID NO 56
```

```
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 56
cattgatata gtctgaatct                                              20

<210> SEQ ID NO 57
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 57
gttcatcctc acaagaaatt                                              20

<210> SEQ ID NO 58
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 58
ctccatgaat ttcatatagt                                              20

<210> SEQ ID NO 59
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 59
ctgatgaaac catatgcaac                                              20

<210> SEQ ID NO 60
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 60
agattttatc agctatacaa                                              20

<210> SEQ ID NO 61
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 61
ttgatatctg aggaattgcc                                              20

<210> SEQ ID NO 62
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 62
```
gtctgagtca tcagagtgaa                                              20

<210> SEQ ID NO 63
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 63
gtagaaatgc tttcagtact                                              20

<210> SEQ ID NO 64
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 64
aatacctccc gctggatgat                                              20

<210> SEQ ID NO 65
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 65
tccctgaatc atgtccattc                                              20

<210> SEQ ID NO 66
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 66
tttctaaaac tccagggcaa                                              20

<210> SEQ ID NO 67
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 67
agagactcac catgaagtcc                                              20

<210> SEQ ID NO 68
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 68
ttagcctaca gatgctgcca                                              20

<210> SEQ ID NO 69
<211> LENGTH: 20
<212> TYPE: DNA

```
<213> ORGANISM: Artificial Sequence
<220> FEATURE:
<223> OTHER INFORMATION: Antisense Oligonucleotide

<400> SEQUENCE: 69
aaataattta aagattcctg                                              20

<210> SEQ ID NO 70
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 70
acattattga gaaatgtgca                                              20

<210> SEQ ID NO 71
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 71
tccaacttac atggcagtat                                              20

<210> SEQ ID NO 72
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 72
ctggtatttt ctaaaacaga                                              20

<210> SEQ ID NO 73
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 73
taatgacaag cacacatagt                                              20

<210> SEQ ID NO 74
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 74
agacactcac tatgttcact                                              20

<210> SEQ ID NO 75
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 75
gtcggtcatc ttgctttgtg                                              20
```

```
<210> SEQ ID NO 76
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 76
ggagcatgtc tgtggaagag                                              20

<210> SEQ ID NO 77
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 77
gctccctcct gaagagtgag                                              20

<210> SEQ ID NO 78
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 78
ccaggtccag catgaagtcc                                              20

<210> SEQ ID NO 79
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 79
ggttcaagca attcttgtgc                                              20

<210> SEQ ID NO 80
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 80
tgcccaggct ggagtgcagt                                              20

<210> SEQ ID NO 81
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 81
ttcttaaccg cacagcactt                                              20

<210> SEQ ID NO 82
<211> LENGTH: 20
<212> TYPE: DNA
<213> ORGANISM: Artificial Sequence
<220> FEATURE:
```

<223> OTHER INFORMATION: Antisense Oligonucleotide

<400> SEQUENCE: 82
taaaacctgt gtaacatcaa                                              20

<210> SEQ ID NO 83
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 83
ttactaacat attaatgcag                                              20

<210> SEQ ID NO 84
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 84
acatgccaaa tacctaaggg                                              20

<210> SEQ ID NO 85
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 85
gccaacactt attgactgtt                                              20

<210> SEQ ID NO 86
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 86
cacatcaact tacaaggccc                                              20

<210> SEQ ID NO 87
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 87
actattttca aatagatgat                                              20

<210> SEQ ID NO 88
<211> LENGTH: 20
<212> TYPE: DNA
<213> ORGANISM: H. sapiens
<220> FEATURE:

<400> SEQUENCE: 88
ttgtgatcat tgtaatggcc                                              20

<210> SEQ ID NO 89

```
<211> LENGTH: 20
<212> TYPE: DNA
<213> ORGANISM: H. sapiens
<220> FEATURE:

<400> SEQUENCE: 89
ttgtggatca tgataacact                                                    20

<210> SEQ ID NO 90
<211> LENGTH: 20
<212> TYPE: DNA
<213> ORGANISM: H. sapiens
<220> FEATURE:

<400> SEQUENCE: 90
agatccacct tcagaatgga                                                    20

<210> SEQ ID NO 91
<211> LENGTH: 20
<212> TYPE: DNA
<213> ORGANISM: H. sapiens
<220> FEATURE:

<400> SEQUENCE: 91
agtgccaccc atcttgacac                                                    20

<210> SEQ ID NO 92
<211> LENGTH: 20
<212> TYPE: DNA
<213> ORGANISM: H. sapiens
<220> FEATURE:

<400> SEQUENCE: 92
caaaatgaat ctcgtaggct                                                    20

<210> SEQ ID NO 93
<211> LENGTH: 20
<212> TYPE: DNA
<213> ORGANISM: H. sapiens
<220> FEATURE:

<400> SEQUENCE: 93
taggaaaact gtgagtttaa                                                    20

<210> SEQ ID NO 94
<211> LENGTH: 20
<212> TYPE: DNA
<213> ORGANISM: H. sapiens
<220> FEATURE:

<400> SEQUENCE: 94
acccgcagtt gccttgttga                                                    20

<210> SEQ ID NO 95
<211> LENGTH: 20
<212> TYPE: DNA
<213> ORGANISM: H. sapiens
<220> FEATURE:

<400> SEQUENCE: 95
tctggacatg ataagcttaa                                                    20

<210> SEQ ID NO 96
<211> LENGTH: 20
<212> TYPE: DNA
```

<213> ORGANISM: H. sapiens
<220> FEATURE:

<400> SEQUENCE: 96
tcagatctaa atgtcggtga                                              20

<210> SEQ ID NO 97
<211> LENGTH: 20
<212> TYPE: DNA
<213> ORGANISM: H. sapiens
<220> FEATURE:

<400> SEQUENCE: 97
atcagctcca tagagcctga                                              20

<210> SEQ ID NO 98
<211> LENGTH: 20
<212> TYPE: DNA
<213> ORGANISM: H. sapiens
<220> FEATURE:

<400> SEQUENCE: 98
tattgagttt aaggactact                                              20

<210> SEQ ID NO 99
<211> LENGTH: 20
<212> TYPE: DNA
<213> ORGANISM: H. sapiens
<220> FEATURE:

<400> SEQUENCE: 99
tagataccat ccaaagccag                                              20

<210> SEQ ID NO 100
<211> LENGTH: 20
<212> TYPE: DNA
<213> ORGANISM: H. sapiens
<220> FEATURE:

<400> SEQUENCE: 100
gtaatcgatg tggaaaaccc                                              20

<210> SEQ ID NO 101
<211> LENGTH: 20
<212> TYPE: DNA
<213> ORGANISM: H. sapiens
<220> FEATURE:

<400> SEQUENCE: 101
ttcaaagtca ggaacgatct                                              20

<210> SEQ ID NO 102
<211> LENGTH: 20
<212> TYPE: DNA
<213> ORGANISM: H. sapiens
<220> FEATURE:

<400> SEQUENCE: 102
ttgctggatt catgcagcca                                              20

<210> SEQ ID NO 103
<211> LENGTH: 20
<212> TYPE: DNA
<213> ORGANISM: H. sapiens
<220> FEATURE:

-continued

```
<400> SEQUENCE: 103
agatgtaaga aatttctgca                                              20

<210> SEQ ID NO 104
<211> LENGTH: 20
<212> TYPE: DNA
<213> ORGANISM: H. sapiens
<220> FEATURE:

<400> SEQUENCE: 104
gaaactctga tggtgctgtg                                              20

<210> SEQ ID NO 105
<211> LENGTH: 20
<212> TYPE: DNA
<213> ORGANISM: H. sapiens
<220> FEATURE:

<400> SEQUENCE: 105
tatcagtttc attatgtgaa                                              20

<210> SEQ ID NO 106
<211> LENGTH: 20
<212> TYPE: DNA
<213> ORGANISM: H. sapiens
<220> FEATURE:

<400> SEQUENCE: 106
taatatgtgg gactaacagc                                              20

<210> SEQ ID NO 107
<211> LENGTH: 20
<212> TYPE: DNA
<213> ORGANISM: H. sapiens
<220> FEATURE:

<400> SEQUENCE: 107
gaattcttgt gtggactgca                                              20

<210> SEQ ID NO 108
<211> LENGTH: 20
<212> TYPE: DNA
<213> ORGANISM: H. sapiens
<220> FEATURE:

<400> SEQUENCE: 108
gatatatccc acagccactg                                              20

<210> SEQ ID NO 109
<211> LENGTH: 20
<212> TYPE: DNA
<213> ORGANISM: H. sapiens
<220> FEATURE:

<400> SEQUENCE: 109
agattcagac tatatcaatg                                              20

<210> SEQ ID NO 110
<211> LENGTH: 20
<212> TYPE: DNA
<213> ORGANISM: H. sapiens
<220> FEATURE:

<400> SEQUENCE: 110
```
aatttcttgt gaggatgaac                    20

<210> SEQ ID NO 111
<211> LENGTH: 20
<212> TYPE: DNA
<213> ORGANISM: H. sapiens
<220> FEATURE:

<400> SEQUENCE: 111
gttgcatatg gtttcatcag                    20

<210> SEQ ID NO 112
<211> LENGTH: 20
<212> TYPE: DNA
<213> ORGANISM: H. sapiens
<220> FEATURE:

<400> SEQUENCE: 112
ttgtatagct gataaaatct                    20

<210> SEQ ID NO 113
<211> LENGTH: 20
<212> TYPE: DNA
<213> ORGANISM: H. sapiens
<220> FEATURE:

<400> SEQUENCE: 113
ggcaattcct cagatatcaa                    20

<210> SEQ ID NO 114
<211> LENGTH: 20
<212> TYPE: DNA
<213> ORGANISM: H. sapiens
<220> FEATURE:

<400> SEQUENCE: 114
ttcactctga tgactcagac                    20

<210> SEQ ID NO 115
<211> LENGTH: 20
<212> TYPE: DNA
<213> ORGANISM: H. sapiens
<220> FEATURE:

<400> SEQUENCE: 115
agtactgaaa gcatttctac                    20

<210> SEQ ID NO 116
<211> LENGTH: 20
<212> TYPE: DNA
<213> ORGANISM: H. sapiens
<220> FEATURE:

<400> SEQUENCE: 116
gaatggacat gattcaggga                    20

<210> SEQ ID NO 117
<211> LENGTH: 20
<212> TYPE: DNA
<213> ORGANISM: H. sapiens
<220> FEATURE:

<400> SEQUENCE: 117
ttgccctgga gttttagaaa                    20

```
<210> SEQ ID NO 118
<211> LENGTH: 20
<212> TYPE: DNA
<213> ORGANISM: H. sapiens
<220> FEATURE:

<400> SEQUENCE: 118
tggcagcatc tgtaggctaa                                             20

<210> SEQ ID NO 119
<211> LENGTH: 20
<212> TYPE: DNA
<213> ORGANISM: H. sapiens
<220> FEATURE:

<400> SEQUENCE: 119
tctgttttag aaaataccag                                             20

<210> SEQ ID NO 120
<211> LENGTH: 20
<212> TYPE: DNA
<213> ORGANISM: H. sapiens
<220> FEATURE:

<400> SEQUENCE: 120
agtgaacata gtgagtgtct                                             20

<210> SEQ ID NO 121
<211> LENGTH: 20
<212> TYPE: DNA
<213> ORGANISM: H. sapiens
<220> FEATURE:

<400> SEQUENCE: 121
ctgcattaat atgttagtaa                                             20

<210> SEQ ID NO 122
<211> LENGTH: 20
<212> TYPE: DNA
<213> ORGANISM: H. sapiens
<220> FEATURE:

<400> SEQUENCE: 122
cccttaggta tttggcatgt                                             20

<210> SEQ ID NO 123
<211> LENGTH: 20
<212> TYPE: DNA
<213> ORGANISM: H. sapiens
<220> FEATURE:

<400> SEQUENCE: 123
gggccttgta agttgatgtg                                             20
```

ANTISENSE MODULATION OF PTPN12 EXPRESSION

FIELD OF THE INVENTION

The present invention provides compositions and methods for modulating the expression of PTPN12. In particular, this invention relates to compounds, particularly oligonucleotides, specifically hybridizable with nucleic acids encoding PTPN12. Such compounds have been shown to modulate the expression of PTPN12.

BACKGROUND OF THE INVENTION

The process of phosphorylation, defined as the attachment of a phosphate moiety to a biological molecule through the action of enzymes called kinases, represents one course by which intracellular signals are propagated resulting finally in a cellular response. Within the cell, proteins can be phosphorylated on serine, threonine or tyrosine residues and the extent of phosphorylation is regulated by the opposing action of phosphatases, which remove the phosphate moieties. While the majority of protein phosphorylation within the cell is on serine and threonine residues, tyrosine phosphorylation is modulated to the greatest extent during oncogenic transformation and growth factor stimulation (Zhang, Critical Review in Biochemistry and Molecular Biology, 1998, 33, 1–52).

Because phosphorylation is such a ubiquitous process within cells and because cellular phenotypes are largely influenced by the activity of these pathways, it is currently believed that a number of disease states and/or disorders are a result of either aberrant activation of, or functional mutations in, kinases and phosphatases. Consequently, considerable attention has been devoted recently to the characterization of tyrosine kinases and tyrosine phosphatases.

PTPN12 (also known as protein tyrosine phosphatase, non-receptor type 12, PTP-PEST and protein tyrosine phosphatase G1; PTPG1) was first cloned from human colon tissue (Takekawa et al., Biochem. Biophys. Res. Commun., 1992, 189, 1223–1230) and human skeletal muscle and (Yang et al., J. Biol. Chem., 1993, 268, 6622–6628) and subsequently found in a variety of human cell lines (Yang et al., J. Biol. Chem., 1993, 268, 6622–6628). It shares 36% identity with the placental PTP1B enzyme (Cool et al., Proc. Natl. Acad. Sci. USA, 1989, 86, 5257–5261; Yang et al., J. Biol. Chem., 1993, 268, 6622–6628) which has an essential regulatory role in signaling mediated by the insulin receptor (Goldstein et al., Mol. Cell. Biochem., 1998, 182, 91–99). The major distinguishing feature of PTPN12 is a hydrophilic C-terminal segment rich in proline, glutamate, aspartate, serine and threonine amino acid residues arranged in motifs known as PEST sequences which are thought to cause rapid turnover of PEST-containing proteins in vivo (Yang et al., J. Biol. Chem., 1993, 268, 6622–6628).

In 1994 the PTPN12 gene was mapped to chromosome 7q11.23, a region with frequent abnormalities implicated in malignant melanoma, and residing near recurrent breakpoints of chromosomal rearrangements found in tumor cells. In addition, allelic deletions of 7q have been reported in solid tumors including colorectal carcinomas. Abnormalities of this locus may be associated with these disorders are a result of alterations in the PTPN12 gene (Takekawa et al., FEBS Lett., 1994, 339, 222–228). Three aberrant mRNA transcripts of PTPN12 have been identified in colon carcinoma cells, including two mRNA transcripts which are predicted to encode PTPN12 proteins prematurely truncated in the phosphatase domain (Takekawa et al., FEBS Lett., 1994, 339, 222–228).

PTPN12 has been implicated in signaling events influencing the execution phase of apoptosis via association with the cytoskeletal proteins paxillin (Song et al., Free Radical Biol. Med., 2000, 29, 61–70), and p130cas (Garton et al., Mol. Cell. Biol., 1996, 16, 6408–6418), focal adhesion phosphoproteins responsible for the recruitment of structural and signaling molecules to focal adhesions (Song et al., Free Radical Biol. Med., 2000, 29, 61–70). Hic-5, a homologue of paxillin has also been found to act as a regulator of PTPN12 in mouse fibroblasts (Nishiya et al., J. Biol. Chem., 1999, 274, 9847–9853).

It was subsequently found that PTPN12's proline-rich sequences constitute specific binding sites for the src homology 3 (SH3) domains of p130cas (Garton et al., Oncogene, 1997, 15, 877–885). Additionally, investigations of murine PTPN12 have indicated that the proline-rich domains provide the basis for interactions involved in recruitment of PTPN12 to activated epidermal growth factor (EGF) receptors, thus implicating PTPN12 in EGF receptor-mediated signal transduction events (Charest et al., Oncogene, 1997, 14, 1643–1651).

The involvement of PTPN12 in cell signaling events and proliferation make it a potentially useful therapeutic target for intervention in hyperproliferative disorders and disorders arising from aberrant apoptosis.

Disclosed and claimed in U.S. Pat. No. 6,087,109 are conjugated compounds comprised of an ST receptor-binding moiety and an antisense molecule for the purpose of targeting PTPN12 and other genes involved in colorectal cancer (Waldman, 2000).

Currently, there are no known therapeutic agents which effectively inhibit the synthesis of PTPN12.

To date, investigative strategies aimed at modulating PTPN12 function have involved the use of ST receptor-binding moieties conjugated to antisense molecules and the protein Hic-5. However, they have yet to be tested as therapeutic protocols.

Consequently, there remains a long felt need for agents capable of effectively inhibiting PTPN12 function.

Antisense technology is emerging as an effective means for reducing the expression of specific gene products and may therefore prove to be uniquely useful in a number of therapeutic, diagnostic, and research applications for the modulation of PTPN12 expression.

The present invention provides compositions and methods for modulating PTPN12 expression, including modulation of truncated forms of PTPN12.

SUMMARY OF THE INVENTION

The present invention is directed to compounds, particularly antisense oligonucleotides, which are targeted to a nucleic acid encoding PTPN12, and which modulate the expression of PTPN12. Pharmaceutical and other compositions comprising the compounds of the invention are also provided. Further provided are methods of modulating the expression of PTPN12 in cells or tissues comprising contacting said cells or tissues with one or more of the antisense compounds or compositions of the invention. Further provided are methods of treating an animal, particularly a human, suspected of having or being prone to a disease or condition associated with expression of PTPN12 by administering a therapeutically or prophylactically effective amount of one or more of the antisense compounds or compositions of the invention.

DETAILED DESCRIPTION OF THE INVENTION

The present invention employs oligomeric compounds, particularly antisense oligonucleotides, for use in modulating the function of nucleic acid molecules encoding PTPN12, ultimately modulating the amount of PTPN12 produced. This is accomplished by providing antisense compounds which specifically hybridize with one or more nucleic acids encoding PTPN12. As used herein, the terms "target nucleic acid" and "nucleic acid encoding PTPN12" encompass DNA encoding PTPN12, RNA (including pre-mRNA and mRNA) transcribed from such DNA, and also cDNA derived from such RNA. The specific hybridization of an oligomeric compound with its target nucleic acid interferes with the normal function of the nucleic acid. This modulation of function of a target nucleic acid by compounds which specifically hybridize to it is generally referred to as "antisense". The functions of DNA to be interfered with include replication and transcription. The functions of RNA to be interfered with include all vital functions such as, for example, translocation of the RNA to the site of protein translation, translocation of the RNA to sites within the cell which are distant from the site of RNA synthesis, translation of protein from the RNA, splicing of the RNA to yield one or more mRNA species, and catalytic activity which may be engaged in or facilitated by the RNA. The overall effect of such interference with target nucleic acid function is modulation of the expression of PTPN12. In the context of the present invention, "modulation" means either an increase (stimulation) or a decrease (inhibition) in the expression of a gene. In the context of the present invention, inhibition is the preferred form of modulation of gene expression and mRNA is a preferred target.

It is preferred to target specific nucleic acids for antisense. "Targeting" an antisense compound to a particular nucleic acid, in the context of this invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. In the present invention, the target is a nucleic acid molecule encoding PTPN12. The targeting process also includes determination of a site or sites within this gene for the antisense interaction to occur such that the desired effect, e.g., detection or modulation of expression of the protein, will result. Within the context of the present invention, a preferred intragenic site is the region encompassing the translation initiation or termination codon of the open reading frame (ORF) of the gene. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding PTPN12, regardless of the sequence(s) of such codons.

It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which is known in the art to refer to the region between the translation initiation codon and the translation termination codon, is also a region which may be targeted effectively. Other target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene, and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'—5' triphosphate linkage. The 5' cap region of an mRNA is considered to include the 5' cap structure itself as well as the first 50 nucleotides adjacent to the cap. The 5' cap region may also be a preferred target region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. mRNA splice sites, i.e., intron-exon junctions, may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. mRNA transcripts produced via the process of splicing of two (or more) mRNAs from different gene sources are known as "fusion transcripts". It has also been found that introns can be effective, and therefore preferred, target regions for antisense compounds targeted, for example, to DNA or pre-mRNA.

It is also known in the art that alternative RNA transcripts can be produced from the same genomic region of DNA. These alternative transcripts are generally known as "variants". More specifically, "pre-mRNA variants" are transcripts produced from the same genomic DNA that differ from other transcripts produced from the same genomic DNA in either their start or stop position and contain both intronic and extronic regions.

Upon excision of one or more exon or intron regions or portions thereof during splicing, pre-mRNA variants produce smaller "mRNA variants". Consequently, mRNA variants are processed pre-mRNA variants and each unique pre-mRNA variant must always produce a unique mRNA variant as a result of splicing. These mRNA variants are also known as "alternative splice variants". If no splicing of the pre-mRNA variant occurs then the pre-mRNA variant is identical to the mRNA variant.

It is also known in the art that variants can be produced through the use of alternative signals to start or stop transcription and that pre-mRNAs and mRNAs can possess more that one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites.

Once one or more target sites have been identified, oligonucleotides are chosen which are sufficiently complementary to the target, i.e., hybridize sufficiently well and with sufficient specificity, to give the desired effect.

In the context of this invention, "hybridization" means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that the sequence of an antisense compound need not be 100% complementary to that of its target nucleic acid to be specifically hybridizable.

An antisense compound is specifically hybridizable when binding of the compound to the target DNA or RNA molecule interferes with the normal function of the target DNA or RNA to cause a loss of activity, and there is a sufficient degree of complementarity to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed. It is preferred that the antisense compounds of the present invention comprise at least 80% sequence complementarity to a target region within the target nucleic acid, moreover that they comprise 90% sequence complementarity and even more comprise 95% sequence complementarity to the target region within the target nucleic acid sequence to which they are targeted. For example, an antisense compound in which 18 of 20 nucleobases of the antisense compound are complementary, and would therefore specifically hybridize, to a target region would represent 90 percent complementarity. Percent complementarity of an antisense compound with a region of a target nucleic acid can be determined routinely using basic local alignment search tools (BLAST programs) (Altschul et al., *J. Mol. Biol.,* 1990, 215, 403–410; Zhang and Madden, *Genome Res.,* 1997, 7, 649–656).

Antisense and other compounds of the invention, which hybridize to the target and inhibit expression of the target, are identified through experimentation, and representative sequences of these compounds are hereinbelow identified as preferred embodiments of the invention. The sites to which these preferred antisense compounds are specifically hybridizable are hereinbelow referred to as "preferred target regions" and are therefore preferred sites for targeting. As used herein the term "preferred target region" is defined as at least an 8-nucleobase portion of a target region to which an active antisense compound is targeted. While not wishing to be bound by theory, it is presently believed that these target regions represent regions of the target nucleic acid which are accessible for hybridization.

While the specific sequences of particular preferred target regions are set forth below, one of skill in the art will recognize that these serve to illustrate and describe particular embodiments within the scope of the present invention. Additional preferred target regions may be identified by one having ordinary skill.

Target regions 8–80 nucleobases in length comprising a stretch of at least eight (8) consecutive nucleobases selected from within the illustrative preferred target regions are considered to be suitable preferred target regions as well.

Exemplary good preferred target regions include DNA or RNA sequences that comprise at least the 8 consecutive nucleobases from the 5'-terminus of one of the illustrative preferred target regions (the remaining nucleobases being a consecutive stretch of the same DNA or RNA beginning immediately upstream of the 5'-terminus of the target region and continuing until the DNA or RNA contains about 8 to about 80 nucleobases). Similarly good preferred target regions are represented by DNA or RNA sequences that comprise at least the 8 consecutive nucleobases from the 3'-terminus of one of the illustrative preferred target regions (the remaining nucleobases being a consecutive stretch of the same DNA or RNA beginning immediately downstream of the 3'-terminus of the target region and continuing until the DNA or RNA contains about 8 to about 80 nucleobases). One having skill in the art, once armed with the empirically-derived preferred target regions illustrated herein will be able, without undue experimentation, to identify further preferred target regions. In addition, one having ordinary skill in the art will also be able to identify additional compounds, including oligonucleotide probes and primers, that specifically hybridize to these preferred target regions using techniques available to the ordinary practitioner in the art.

Antisense compounds are commonly used as research reagents and diagnostics. For example, antisense oligonucleotides, which are able to inhibit gene expression with exquisite specificity, are often used by those of ordinary skill to elucidate the function of particular genes. Antisense compounds are also used, for example, to distinguish between functions of various members of a biological pathway. Antisense modulation has, therefore, been harnessed for research use.

For use in kits and diagnostics, the antisense compounds of the present invention, either alone or in combination with other antisense compounds or therapeutics, can be used as tools in differential and/or combinatorial analyses to elucidate expression patterns of a portion or the entire complement of genes expressed within cells and tissues.

Expression patterns within cells or tissues treated with one or more antisense compounds are compared to control cells or tissues not treated with antisense compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds which affect expression patterns.

Examples of methods of gene expression analysis known in the art include DNA arrays or microarrays (Brazma and Vilo, *FEBS Lett.*, 2000, 480, 17–24; Celis, et al., *FEBS Lett.*, 2000, 480, 2–16), SAGE (serial analysis of gene expression) (Madden, et al., *Drug Discov. Today,* 2000, 5, 415–425), READS (restriction enzyme amplification of digested cDNAs) (Prashar and Weissman, *Methods Enzymol.,* 1999, 303, 258–72), TOGA (total gene expression analysis) (Sutcliffe, et al., *Proc. Natl. Acad. Sci. U.S.A.,* 2000, 97, 1976–81), protein arrays and proteomics (Celis, et al., *FEBS Lett.,* 2000, 480, 2–16; Jungblut, et al., *Electrophoresis,* 1999, 20, 2100–10), expressed sequence tag (EST) sequencing (Celis, et al., *FEBS Lett.,* 2000, 480, 2–16; Larsson, et al., *J. Biotechnol.,* 2000, 80, 143–57), subtractive RNA fingerprinting (SuRF) (Fuchs, et al., *Anal. Biochem.,* 2000, 286, 91–98; Larson, et al., *Cytometry,* 2000, 41, 203–208), subtractive cloning, differential display (DD) (Jurecic and Belmont, *Curr. Opin. Microbiol.,* 2000, 3, 316–21), comparative genomic hybridization (Carulli, et al., *J. Cell Biochem. Suppl.,* 1998, 31, 286–96), FISH (fluorescent in situ hybridization) techniques (Going and Gusterson, *Eur. J. Cancer,* 1999, 35, 1895–904) and mass spectrometry methods (reviewed in To, *Comb. Chem. High Throughput Screen,* 2000, 3, 235–41).

The specificity and sensitivity of antisense is also harnessed by those of skill in the art for therapeutic uses. Antisense oligonucleotides have been employed as therapeutic moieties in the treatment of disease states in animals and man. Antisense oligonucleotide drugs, including ribozymes, have been safely and effectively administered to humans and numerous clinical trials are presently underway. It is thus established that oligonucleotides can be useful therapeutic modalities that can be configured to be useful in treatment regimes for treatment of cells, tissues and animals, especially humans.

In the context of this invention, the term "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

While antisense oligonucleotides are a preferred form of antisense compound, the present invention comprehends other oligomeric antisense compounds, including but not limited to oligonucleotide mimetics such as are described below. The antisense compounds in accordance with this invention preferably comprise from about 8 to about 80 nucleobases (i.e. from about 8 to about 80 linked nucleosides). Particularly preferred antisense compounds are antisense oligonucleotides from about 8 to about 50 nucleobases, even more preferably those comprising from about 12 to about 30 nucleobases. Antisense compounds include ribozymes, external guide sequence (EGS) oligonucleotides (oligozymes), and other short catalytic RNAs or catalytic oligonucleotides which hybridize to the target nucleic acid and modulate its expression.

Antisense compounds 8–80 nucleobases in length comprising a stretch of at least eight (8) consecutive nucleobases selected from within the illustrative antisense compounds are considered to be suitable antisense compounds as well.

Exemplary preferred antisense compounds include DNA or RNA sequences that comprise at least the 8 consecutive nucleobases from the 5'-terminus of one of the illustrative preferred antisense compounds (the remaining nucleobases being a consecutive stretch of the same DNA or RNA beginning immediately upstream of the 5'-terminus of the antisense compound which is specifically hybridizable to the target nucleic acid and continuing until the DNA or RNA contains about 8 to about 80 nucleobases). Similarly preferred antisense compounds are represented by DNA or RNA sequences that comprise at least the 8 consecutive nucleobases from the 3'-terminus of one of the illustrative preferred antisense compounds (the remaining nucleobases being a consecutive stretch of the same DNA or RNA beginning immediately downstream of the 3'-terminus of the antisense compound which is specifically hybridizable to the target nucleic acid and continuing until the DNA or RNA contains about 8 to about 80 nucleobases). One having skill in the art, once armed with the empirically-derived preferred antisense compounds illustrated herein will be able, without undue experimentation, to identify further preferred antisense compounds.

Antisense and other compounds of the invention, which hybridize to the target and inhibit expression of the target, are identified through experimentation, and representative sequences of these compounds are herein identified as preferred embodiments of the invention. While specific sequences of the antisense compounds are set forth herein, one of skill in the art will recognize that these serve to illustrate and describe particular embodiments within the scope of the present invention. Additional preferred antisense compounds may be identified by one having ordinary skill.

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn, the respective ends of this linear polymeric structure can be further joined to form a circular structure, however, open linear structures are generally preferred. In addition, linear structures may also have internal nucleobase complementarity and may therefore fold in a manner as to produce a double stranded structure. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, certain of which are commonly owned with this application, and each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., *Science,* 1991, 254, 1497–1500.

Most preferred embodiments of the invention are oligonucleotides with phosphorothioate backbones and oligonucleosides with heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O[($CH_2$)$_n$O]$_m$$CH_3$, O($CH_2$)$_n$O$CH_3$, O($CH_2$)$_n$$NH_2$, O($CH_2$)$_n$$CH_3$, O($CH_2$)$_n$ON$H_2$, and O($CH_2$)$_n$ON[($CH_2$)$_n$$CH_3$]$_2$, where n and m are from 1 to about 10. Other preferred oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2CH_2OCH_3$, also known as 2'-O-(2-methoxyethyl) or 2'-MOE) (Martin et al., *Helv. Chim. Acta,* 1995, 78, 486–504) i.e., an alkoxyalkoxy group. A further preferred modification includes 2'-dimethylaminooxyethoxy, i.e., a O($CH_2$)$_2$ON($CH_3$)$_2$ group, also known as 2'-DMAOE, as described in examples hereinbelow, and 2'-dimethylaminoethoxyethoxy (also known in the art as 2'-O-dimethyl-amino-ethoxy-ethyl or 2'-DMAEOE), i.e., 2'-O—$CH_2$—O—$CH_2$—N($CH_3$)$_2$, also described in examples hereinbelow.

Other preferred modifications include 2'-methoxy (2'-O—$CH_3$), 2'-aminopropoxy (2'-O$CH_2CH_2CH_2NH_2$), 2'-allyl (2'-$CH_2$—CH=$CH_2$), 2'-O-allyl (2'-O—$CH_2$—CH=$CH_2$) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'–5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, certain of which are commonly owned with the instant application, and each of which is herein incorporated by reference in its entirety.

A further preferred modification includes Locked Nucleic Acids (LNAs) in which the 2'-hydroxyl group is linked to the 3' or 4' carbon atom of the sugar ring thereby forming a bicyclic sugar moiety. The linkage is preferably a methelyne (—CH$_2$—)$_n$ group bridging the 2' oxygen atom and the 4' carbon atom wherein n is 1 or 2. LNAs and preparation thereof are described in WO 98/39352 and WO 99/14226.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2 (3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687, 808, those disclosed in *The Concise Encyclopedia Of Polymer Science And Engineering*, pages 858–859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289–302, Crooke, S. T. and Lebleu, B., ed., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2° C. (Sanghvi, Y. S., Crooke, S. T. and Lebleu, B., eds., *Antisense Research and Applications*, CRC Press, Boca Raton, 1993, pp. 276–278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175, 273; 5,367,066; 5,432,272; 5,457,187; 5,459,255; 5,484, 908; 5,502,177; 5,525,711; 5,552,540; 5,587,469; 5,594, 121, 5,596,091; 5,614,617; 5,645,985; 5,830,653; 5,763, 588; 6,005,096; and 5,681,941, certain of which are commonly owned with the instant application, and each of which is herein incorporated by reference, and U.S. Pat. No. 5,750,692, which is commonly owned with the instant application and also herein incorporated by reference.

Another modification of the oligonucleotides of the invention involves chemically linking to the oligonucleotide one or more moieties or conjugates which enhance the activity, cellular distribution or cellular uptake of the oligonucleotide. The compounds of the invention can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Representative conjugate groups are disclosed in International Patent Application PCT/US92/09196, filed Oct. 23, 1992 the entire disclosure of which is incorporated herein by reference. Conjugate moieties include but are not limited to lipid moieties such as a cholesterol moiety (Letsinger et al., *Proc. Natl. Acad. Sci. USA*, 1989, 86, 6553–6556), cholic acid (Manoharan et al., *Bioorg. Med. Chem. Let.*, 1994, 4, 1053–1060), a thioether, e.g., hexyl-S-tritylthiol (Manoharan et al.,*Ann. N.Y. Acad. Sci.*, 1992, 660, 306–309; Manoharan et al., *Bioorg. Med. Chem. Let.*, 1993, 3, 2765–2770), a thiocholesterol (Oberhauser et al., *Nucl. Acids Res.*, 1992, 20, 533–538), an aliphatic chain, e.g., dodecandiol or undecyl residues (Saison-Behmoaras et al., *EMBO J.*, 1991, 10, 1111–1118; Kabanov et al., *FEBS Lett.*, 1990, 259, 327–330; Svinarchuk et al., *Biochimie*, 1993, 75, 49–54), a phospholipid, e.g., di-hexadecyl-rac-glycerol or triethyl-ammonium 1,2-di-O-hexadecyl-rac-glycero-3-H-phosphonate (Manoharan et al., *Tetrahedron Lett.*, 1995, 36, 3651–3654; Shea et al., *Nucl. Acids Res.*, 1990, 18, 3777–3783), a polyamine or a polyethylene glycol chain (Manoharan et al., *Nucleosides & Nucleotides*, 1995, 14, 969–973), or adamantane acetic acid (Manoharan et al., Tetrahedron Lett., 1995, 36, 3651–3654), a palmityl moiety (Mishra et al., Biochim. Biophys. Acta, 1995, 1264, 229–237), or an octadecylamine or hexylamino-carbonyl-oxycholesterol moiety (Crooke et al., J. Pharmacol. Exp. Ther., 1996, 277, 923–937). Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999) which is incorporated herein by reference in its entirety.

Representative United States patents that teach the preparation of such oligonucleotide conjugates include, but are not limited to, U.S. Pat. Nos. 4,828,979; 4,948,882; 5,218, 105; 5,525,465; 5,541,313; 5,545,730; 5,552,538; 5,578, 717, 5,580,731; 5,580,731; 5,591,584; 5,109,124; 5,118, 802; 5,138,045; 5,414,077; 5,486,603; 5,512,439; 5,578, 718; 5,608,046; 4,587,044; 4,605,735; 4,667,025; 4,762, 779; 4,789,737; 4,824,941; 4,835,263; 4,876,335; 4,904, 582; 4,958,013; 5,082,830; 5,112,963; 5,214,136; 5,082, 830; 5,112,963; 5,214,136; 5,245,022; 5,254,469; 5,258, 506; 5,262,536; 5,272,250; 5,292,873; 5,317,098; 5,371, 241, 5,391,723; 5,416,203, 5,451,463; 5,510,475; 5,512, 667; 5,514,785; 5,565,552; 5,567,810; 5,574,142; 5,585, 481; 5,587,371; 5,595,726; 5,597,696; 5,599,923; 5,599,928 and 5,688,941, certain of which are commonly owned with the instant application, and each of which is herein incorporated by reference.

It is not necessary for all positions in a given compound to be uniformly modified, and in fact more than one of the aforementioned modifications may be incorporated in a single compound or even at a single nucleoside within an oligonucleotide. The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, increased stability and/or increased binding affinity for the target nucleic acid. An additional region of the oligonucleotide may serve as a substrate for enzymes capable of cleaving RNA:DNA or RNA:RNA hybrids. By way of example, RNAse H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. The cleavage of RNA:RNA hybrids can, in like fashion, be accomplished through the actions of endoribonucleases, such as interferon-induced RNAseL which cleaves both cellular and viral RNA. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

The compounds of the invention may also be admixed, encapsulated, conjugated or otherwise associated with other molecules, molecule structures or mixtures of compounds, as for example, liposomes, receptor-targeted molecules, oral, rectal, topical or other formulations, for assisting in uptake, distribution and/or absorption. Representative United States patents that teach the preparation of such uptake, distribution and/or absorption-assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The antisense compounds of the invention encompass any pharmaceutically acceptable salts, esters, or salts of such esters, or any other compound which, upon administration to an animal, including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl)phosphate] derivatives according to the methods disclosed in WO 93/24510 to Gosselin et al., published Dec. 9, 1993 or in WO 94/26764 and U.S. Pat. No. 5,770,713 to Imbach et al.

The term "pharmaceutically acceptable salts" refers to physiologically and pharmaceutically acceptable salts of the compounds of the invention: i.e., salts that retain the desired biological activity of the parent compound and do not impart undesired toxicological effects thereto.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge et al., "Pharmaceutical Salts," *J. of Pharma Sci.,* 1977, 66, 1–19). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid form of one of the components of the compositions of the invention. These include organic or inorganic acid salts of the amines. Preferred acid salts are the hydrochlorides, acetates, salicylates, nitrates and phosphates. Other suitable pharmaceutically acceptable salts are well known to those skilled in the art and include basic salts of a variety of inorganic and organic acids, such as, for example, with inorganic acids, such as for example hydrochloric acid, hydrobromic acid, sulfuric acid or phosphoric acid; with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha-amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acid organic compounds, such as ascorbic acid. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible.

For oligonucleotides, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalene-disulfonic acid, polygalacturonic acid, and the like; and (d) salts formed from elemental anions such as chlorine, bromine, and iodine.

The antisense compounds of the present invention can be utilized for diagnostics, therapeutics, prophylaxis and as research reagents and kits. For therapeutics, an animal, preferably a human, suspected of having a disease or disorder which can be treated by modulating the expression of PTPN12 is treated by administering antisense compounds in accordance with this invention. The compounds of the invention can be utilized in pharmaceutical compositions by adding an effective amount of an antisense compound to a suitable pharmaceutically acceptable diluent or carrier. Use of the antisense compounds and methods of the invention may also be useful prophylactically, e.g., to prevent or delay infection, inflammation or tumor formation, for example.

The antisense compounds of the invention are useful for research and diagnostics, because these compounds hybridize to nucleic acids encoding PTPN12, enabling sandwich and other assays to easily be constructed to exploit this fact. Hybridization of the antisense oligonucleotides of the invention with a nucleic acid encoding PTPN12 can be detected by means known in the art. Such means may include conjugation of an enzyme to the oligonucleotide, radiolabelling of the oligonucleotide or any other suitable detection means. Kits using such detection means for detecting the level of PTPN12 in a sample may also be prepared.

The present invention also includes pharmaceutical compositions and formulations which include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful. Preferred topical formulations include those in which the oligonucleotides of the invention are in admixture with a topical delivery agent such as lipids, liposomes, fatty acids, fatty acid esters, steroids, chelating agents and surfactants. Preferred lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA). Oligonucleotides of the invention may be encapsulated within liposomes or may form complexes thereto, in particular to cationic liposomes. Alternatively, oligonucleotides may be complexed to lipids, in particular to cationic lipids. Preferred fatty acids and esters include but are not limited arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan- 2-one, an acylcarnitine, an acylcholine, or a $C_{1-10}$ alkyl ester (e.g. isopropylmyristate IPM), monoglyceride, diglyceride or pharmaceutically acceptable salt thereof. Topical formulations are described in detail in U.S. patent application Ser. No. 09/315,298 filed on May 20, 1999 which is incorporated herein by reference in its entirety.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which oligonucleotides of the invention are administered in conjunction with one or more penetration enhancers surfactants and chelators. Preferred surfactants include fatty acids and/or esters or salts thereof, bile acids and/or salts thereof. Preferred bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24,25-dihydro-fusidate and sodium glycodihydrofusidate. Preferred fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a monoglyceride, a diglyceride or a pharmaceutically acceptable salt thereof (e.g. sodium). Also preferred are combinations of penetration enhancers, for example, fatty acids/salts in combination with bile acids/salts. A particularly preferred combination is the sodium salt of lauric acid, capric acid and UDCA. Further penetration enhancers include polyoxyethylene-9-lauryl ether, polyoxyethylene-20-cetyl ether. Oligonucleotides of the invention may be delivered orally, in granular form including sprayed dried particles, or complexed to form micro or nanoparticles. Oligonucleotide complexing agents include poly-amino acids; polyimines; polyacrylates; polyalkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. Particularly preferred complexing agents include chitosan, N-trimethylchitosan, poly-L-lysine, polyhistidine, polyornithine, polyspermines, protamine, polyvinylpyridine, polythiodiethylamino-methylethylene P(TDAE), polyaminostyrene (e.g. p-amino), poly(methylcyanoacrylate), poly(ethylcyanoacrylate), poly(butylcyanoacrylate), poly(isobutylcyanoacrylate), poly(isohexylcyanoacrylate), DEAE-methacrylate, DEAE-hexylacrylate, DEAE-acrylamide, DEAE-albumin and DEAE-dextran, polymethylacrylate, polyhexylacrylate, poly(D,L-lactic acid), poly(DL-lactic-co-glycolic acid (PLGA), alginate, and polyethyleneglycol (PEG). Oral formulations for oligonucleotides and their preparation are described in detail in U.S. application Ser. No. 08/886,829 (filed Jul. 1, 1997), Ser. No. 09/108,673 (filed Jul. 1, 1998), Ser. No. 09/256,515 (filed Feb. 23, 1999), Ser. No. 09/082,624 (filed May 21, 1998) and Ser. No. 09/315,298 (filed May 20, 1999), each of which is incorporated herein by reference in their entirety.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. The preparation of such compositions and formulations is generally known to those skilled in the pharmaceutical and formulation arts and may be applied to the formulation of the compositions of the present invention.

Emulsions

The compositions of the present invention may be prepared and formulated as emulsions. Emulsions are typically heterogenous systems of one liquid dispersed in another in the form of droplets usually exceeding 0.1 μm in diameter (Idson, in *Pharmaceutical Dosage Forms*, Lieberman, Rieger and Banker (Eds.), 1988, Marcel Dekker, Inc., New York, N.Y., volume 1, p. 199; Rosoff, in *Pharmaceutical Dosage Forms*, Lieberman, Rieger and Banker (Eds.), 1988, Marcel Dekker, Inc., New York, N.Y., Volume 1, p. 245; Block in *Pharmaceutical Dosage Forms*, Lieberman, Rieger and Banker (Eds.), 1988, Marcel Dekker, Inc., New York, N.Y., volume 2, p. 335; Higuchi et al., in *Remington's Pharmaceutical Sciences*, Mack Publishing Co., Easton, Pa., 1985, p. 301). Emulsions are often biphasic systems comprising two immiscible liquid phases intimately mixed and dispersed with each other. In general, emulsions may be of either the water-in-oil (w/o) or the oil-in-water (o/w) variety. When an aqueous phase is finely divided into and dispersed as minute droplets into a bulk oily phase, the resulting composition is called a water-in-oil (w/o) emulsion. Alternatively, when an oily phase is finely divided into and dispersed as minute droplets into a bulk aqueous phase, the resulting composition is called an oil-in-water (o/w) emulsion. Emulsions may contain additional components in addition to the dispersed phases, and the active drug which may be present as a solution in either the aqueous phase, oily phase or itself as a separate phase. Pharmaceutical excipients such as emulsifiers, stabilizers, dyes, and anti-oxidants may also be present in emulsions as needed. Pharmaceutical emulsions may also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous phase provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion may be a semisolid or a solid, as is the case of emulsion-style ointment bases and creams. Other means of stabilizing emulsions entail the use of emulsifiers that may be incorporated into either phase of the emulsion. Emulsifiers may broadly be classified into four categories: synthetic surfactants, naturally occurring emulsifiers, absorption bases, and finely dispersed solids (Idson, in *Pharmaceutical Dosage Forms*, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (Rieger, in *Pharmaceutical Dosage Forms*, Lieberman, Rieger and Banker (Eds.), 1988, Marcel Dekker, Inc., New York, N.Y., volume 1, p. 285; Idson, in *Pharmaceutical Dosage Forms*, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants may be classified into different classes based on the nature of the hydrophilic group: nonionic, anionic, cationic and amphoteric (Rieger, in *Pharmaceutical Dosage Forms*, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in *Pharmaceutical Dosage Forms*, Lieberman, Rieger and Banker (Eds.), 1988, Marcel Dekker, Inc., New York, N.Y., volume 1, p. 335; Idson, in *Pharmaceutical Dosage Forms*, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that may readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used may be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (Idson, in *Pharmaceutical Dosage Forms*, Lieberman, Rieger and Banker (Eds.), 1988, Marcel Dekker, Inc., New York, N.Y., volume 1, p. 199). Emulsion formulations for oral delivery have been very widely used because of ease of formulation, as well as efficacy from an absorption and bioavailability standpoint (Rosoff, in *Pharmaceutical Dosage Forms*, Lieberman, Rieger and Banker (Eds.), 1988, Marcel Dekker, Inc., New York, N.Y., volume 1, p. 245; Idson, in *Pharmaceutical Dosage Forms*, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

In one embodiment of the present invention, the compositions of oligonucleotides and nucleic acids are formulated as microemulsions. A microemulsion may be defined as a system of water, oil and amphiphile which is a single optically isotropic and thermodynamically stable liquid solution (Rosoff, in *Pharmaceutical Dosage Forms*, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: *Controlled Release of Drugs: Polymers and Aggregate Systems*, Rosoff, M., Ed., 1989, VCH Publishers, New York, pages 185–215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in *Remington's Pharmaceutical Sciences*, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (Rosoff, in *Pharmaceutical Dosage Forms*, Lieberman, Rieger and Banker (Eds.), 1988, Marcel Dekker, Inc., New York, N.Y., volume 1, p. 245; Block, in *Pharmaceutical Dosage Forms*, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain (C8–C12) mono, di, and tri-glycerides, polyoxyethylated glyceryl fatty acid esters, fatty alcohols, polyglycolized glycerides, saturated polyglycolized C8–C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (Constantinides et al., *Pharmaceutical Research*, 1994, 11, 1385–1390; Ritschel, *Meth. Find. Exp. Clin. Pharmacol.*, 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., *Pharmaceutical Research*, 1994, 11, 1385; Ho et al., *J. Pharm. Sci.*, 1996, 85, 138–143). Often microemulsions may form spontaneously when their components are brought together at ambient temperature. This may be particularly advantageous when formulating thermolabile drugs, peptides or oligonucleotides. Microemulsions have also been effective in the transdermal delivery of active components in both cosmetic and pharmaceutical applications. It is expected that the microemulsion compositions and formulations of the present invention will facilitate the increased systemic absorption of oligonucleotides and nucleic acids from the gastrointestinal tract, as well as improve the local cellular uptake of oligonucleotides and nucleic acids within the gastrointestinal tract, vagina, buccal cavity and other areas of administration.

Microemulsions of the present invention may also contain additional components and additives such as sorbitan monostearate (Grill 3), Labrasol, and penetration enhancers to improve the properties of the formulation and to enhance the absorption of the oligonucleotides and nucleic acids of the present invention. Penetration enhancers used in the microemulsions of the present invention may be classified as belonging to one of five broad categories—surfactants, fatty acids, bile salts, chelating agents, and non-chelating non-surfactants (Lee et al., *Critical Reviews in Therapeutic Drug Carrier Systems*, 1991, p. 92). Each of these classes has been discussed above.

Liposomes

There are many organized surfactant structures besides microemulsions that have been studied and used for the formulation of drugs. These include monolayers, micelles, bilayers and vesicles. Vesicles, such as liposomes, have attracted great interest because of their specificity and the duration of action they offer from the standpoint of drug delivery. As used in the present invention, the term "liposome" means a vesicle composed of amphiphilic lipids arranged in a spherical bilayer or bilayers.

Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo.

In order to cross intact mammalian skin, lipid vesicles must pass through a series of fine pores, each with a diameter less than 50 nm, under the influence of a suitable transdermal gradient. Therefore, it is desirable to use a liposome which is highly deformable and able to pass through such fine pores.

Further advantages of liposomes include; liposomes obtained from natural phospholipids are biocompatible and biodegradable; liposomes can incorporate a wide range of water and lipid soluble drugs; liposomes can protect encapsulated drugs in their internal compartments from metabolism and degradation (Rosoff, in *Pharmaceutical Dosage Forms*, Lieberman, Rieger and Banker (Eds.), 1988, Marcel Dekker, Inc., New York, N.Y., volume 1, p. 245). Important considerations in the preparation of liposome formulations are the lipid surface charge, vesicle size and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes and as the merging of the liposome and cell progresses, the liposomal contents are emptied into the cell where the active agent may act.

Liposomal formulations have been the focus of extensive investigation as the mode of delivery for many drugs. There is growing evidence that for topical administration, liposomes present several advantages over other formulations. Such advantages include reduced side-effects related to high systemic absorption of the administered drug, increased accumulation of the administered drug at the desired target, and the ability to administer a wide variety of drugs, both hydrophilic and hydrophobic, into the skin.

Several reports have detailed the ability of liposomes to deliver agents including high-molecular weight DNA into the skin. Compounds including analgesics, antibodies, hormones and high-molecular weight DNAs have been administered to the skin. The majority of applications resulted in the targeting of the upper epidermis.

Liposomes fall into two broad classes. Cationic liposomes are positively charged liposomes which interact with the negatively charged DNA molecules to form a stable complex. The positively charged DNA/liposome complex binds to the negatively charged cell surface and is internalized in an endosome. Due to the acidic pH within the endosome, the liposomes are ruptured, releasing their contents into the cell cytoplasm (Wang et al., *Biochem. Biophys. Res. Commun.*, 1987, 147, 980–985).

Liposomes which are pH-sensitive or negatively-charged, entrap DNA rather than complex with it. Since both the DNA and the lipid are similarly charged, repulsion rather than complex formation occurs. Nevertheless, some DNA is entrapped within the aqueous interior of these liposomes. pH-sensitive liposomes have been used to deliver DNA encoding the thymidine kinase gene to cell monolayers in culture. Expression of the exogenous gene was detected in the target cells (Zhou et al., *Journal of Controlled Release*, 1992, 19, 269–274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Several studies have assessed the topical delivery of liposomal drug formulations to the skin. Application of liposomes containing interferon to guinea pig skin resulted in a reduction of skin herpes sores while delivery of interferon via other means (e.g. as a solution or as an emulsion) were ineffective (Weiner et al., *Journal of Drug Targeting*, 1992, 2, 405–410). Further, an additional study tested the efficacy of interferon administered as part of a liposomal formulation to the administration of interferon using an aqueous system, and concluded that the liposomal formulation was superior to aqueous administration (du Plessis et al., *Antiviral Research*, 1992, 18, 259–265).

Non-ionic liposomal systems have also been examined to determine their utility in the delivery of drugs to the skin, in particular systems comprising non-ionic surfactant and cholesterol. Non-ionic liposomal formulations comprising Novasome™ I (glyceryl dilaurate/cholesterol/polyoxyethylene-10-stearyl ether) and Novasome™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporin-A into different layers of the skin (Hu et al. *S.T.P.Pharma. Sci.*, 1994, 4, 6, 466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., *FEBS Letters*, 1987, 223, 42; Wu et al., *Cancer Research*, 1993, 53, 3765).

Various liposomes comprising one or more glycolipids are known in the art. Papahadjopoulos et al. (*Ann. N.Y. Acad. Sci.*, 1987, 507, 64) reported the ability of monosialoganglioside $G_{M1}$, galactocerebroside sulfate and phosphatidylinositol to improve blood half-lives of liposomes. These findings were expounded upon by Gabizon et al. (*Proc. Natl. Acad. Sci. U.S.A.*, 1988, 85, 6949). U.S. Pat. No. 4,837,028 and WO 88/04924, both to Allen et al., disclose liposomes comprising (1) sphingomyelin and (2) the ganglioside $G_{M1}$ or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al.).

Many liposomes comprising lipids derivatized with one or more hydrophilic polymers, and methods of preparation thereof, are known in the art. Sunamoto et al. (*Bull. Chem. Soc. Jpn.*, 1980, 53, 2778) described liposomes comprising a nonionic detergent, $2C_{12}15G$, that contains a PEG moiety. Illum et al. (*FEBS Lett.*, 1984, 167, 79) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534,899). Klibanov et al. (*FEBS Lett.*, 1990, 268, 235) described experiments demonstrating that liposomes comprising phosphatidylethanolamine (PE) derivatized with PEG or PEG stearate have significant increases in blood circulation half-lives. Blume et al. (*Biochimica et Biophysica Acta*, 1990, 1029, 91) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent No. EP 0 445 131 B1 and WO 90/04384 to Fisher. Liposome compositions containing 1–20 mole percent of PE derivatized with PEG, and methods of use thereof, are described by Woodle et al. (U.S. Pat. Nos. 5,013,556 and 5,356,633) and Martin et al. (U.S. Pat. No. 5,213,804 and European Patent No. EP 0 496 813 B1). Liposomes comprising a number of other lipid-polymer conjugates are disclosed in WO 91/05545 and U.S. Pat. No. 5,225,212 (both to Martin et al.) and in WO 94/20073 (Zalipsky et al.) Liposomes comprising PEG-modified ceramide lipids are described in WO 96/10391 (Choi et al.). U.S. Pat. No. 5,540,935 (Miyazaki et al.) and U.S. Pat. No. 5,556,948 (Tagawa et al.) describe PEG-containing liposomes that can be further derivatized with functional moieties on their surfaces.

A limited number of liposomes comprising nucleic acids are known in the art. WO 96/40062 to Thierry et al. discloses methods for encapsulating high molecular weight nucleic acids in liposomes. U.S. Pat. No. 5,264,221 to Tagawa et al. discloses protein-bonded liposomes and asserts that the contents of such liposomes may include an antisense RNA. U.S. Pat. No. 5,665,710 to Rahman et al. describes certain methods of encapsulating oligodeoxynucleotides in liposomes. WO 97/04787 to Love et al. discloses liposomes comprising antisense oligonucleotides targeted to the raf gene.

Transfersomes are yet another type of liposomes, and are highly deformable lipid aggregates which are attractive candidates for drug delivery vehicles. Transfersomes may be described as lipid droplets which are so highly deformable that they are easily able to penetrate through pores which are smaller than the droplet. Transfersomes are adaptable to the environment in which they are used, e.g. they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in *Pharmaceutical Dosage Forms*, Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in *Pharmaceutical Dosage Forms*, Marcel Dekker, Inc., New York, N.Y., 1988, p. 285).

Penetration Enhancers

In one embodiment, the present invention employs various penetration enhancers to effect the efficient delivery of nucleic acids, particularly oligonucleotides, to the skin of animals. Most drugs are present in solution in both ionized and nonionized forms. However, usually only lipid soluble or lipophilic drugs readily cross cell membranes. It has been discovered that even non-lipophilic drugs may cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers may be classified as belonging to one of five broad categories, i.e., surfactants, fatty acids, bile salts, chelating agents, and non-chelating non-surfactants (Lee et al., *Critical Reviews in Therapeutic Drug Carrier Systems*, 1991, p.92). Each of the above mentioned classes of penetration enhancers are described below in greater detail.

Surfactants: In connection with the present invention, surfactants (or "surface-active agents") are chemical entities which, when dissolved in an aqueous solution, reduce the surface tension of the solution or the interfacial tension between the aqueous solution and another liquid, with the result that absorption of oligonucleotides through the mucosa is enhanced. In addition to bile salts and fatty acids, these penetration enhancers include, for example, sodium lauryl sulfate, polyoxyethylene-9-lauryl ether and polyoxyethylene-20-cetyl ether) (Lee et al., *Critical Reviews in Therapeutic Drug Carrier Systems*, 1991, p.92); and perfluorochemical emulsions, such as FC-43. Takahashi et al., *J. Pharm. Pharmacol.*, 1988, 40, 252).

Fatty acids: Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, $C_{10}$ alkyl esters thereof (e.g., methyl, isopropyl and t-butyl), and mono- and di-glycerides thereof (i.e., oleate, laurate, caprate, myristate, palmitate, stearate, linoleate, etc.) (Lee et al., *Critical Reviews in Therapeutic Drug Carrier Systems*, 1991, p.92; Muranishi, *Critical Reviews in Therapeutic Drug Carrier Systems*, 1990, 7, 1–33; El Hariri et al., *J. Pharm. Pharmacol.*, 1992, 44, 651–654).

Bile salts: The physiological role of bile includes the facilitation of dispersion and absorption of lipids and fat-soluble vitamins (Brunton, Chapter 38 in: Goodman & Gilman's *The Pharmacological Basis of Therapeutics*, 9th Ed., Hardman et al. Eds., McGraw-Hill, New York, 1996, pp. 934–935). Various natural bile salts, and their synthetic derivatives, act as penetration enhancers. Thus the term "bile salts" includes any of the naturally occurring components of bile as well as any of their synthetic derivatives. The bile salts of the invention include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (Lee et al., *Critical Reviews in Therapeutic Drug Carrier Systems*, 1991, page 92; Swinyard, Chapter 39 In: *Remington's Pharmaceutical Sciences*, 18th Ed., Gennaro, ed., Mack Publishing Co., Easton, Pa., 1990, pages 782–783; Muranishi, *Critical Reviews in Therapeutic Drug Carrier Systems,* 1990, 7, 1–33; Yamamoto et al., *J. Pharm. Exp. Ther.,* 1992, 263, 25; Yamashita et al., *J. Pharm. Sci.,* 1990, 79, 579–583).

Chelating Agents: Chelating agents, as used in connection with the present invention, can be defined as compounds that remove metallic ions from solution by forming complexes therewith, with the result that absorption of oligonucleotides through the mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, *J. Chromatogr.,* 1993, 618, 315–339). Chelating agents of the invention include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines) (Lee et al., *Critical Reviews in Therapeutic Drug Carrier Systems,* 1991, page 92; Muranishi, *Critical Reviews in Therapeutic Drug Carrier Systems,* 1990, 7, 1–33; Buur et al., *J. Control Rel.,* 1990, 14, 43–51).

Non-chelating non-surfactants: As used herein, non-chelating non-surfactant penetration enhancing compounds can be defined as compounds that demonstrate insignificant activity as chelating agents or as surfactants but that nonetheless enhance absorption of oligonucleotides through the alimentary mucosa (Muranishi, *Critical Reviews in Therapeutic Drug Carrier Systems,* 1990, 7, 1–33). This class of penetration enhancers include, for example, unsaturated cyclic ureas, 1-alkyl- and 1-alkenylazacyclo-alkanone derivatives (Lee et al., *Critical Reviews in Therapeutic Drug Carrier Systems,* 1991, page 92); and non-steroidal anti-inflammatory agents such as diclofenac sodium, indomethacin and phenylbutazone (Yamashita et al., *J. Pharm. Pharmacol.,* 1987, 39, 621–626).

Agents that enhance uptake of oligonucleotides at the cellular level may also be added to the pharmaceutical and other compositions of the present invention. For example, cationic lipids, such as lipofectin (Junichi et al, U.S. Pat. No. 5,705,188), cationic glycerol derivatives, and polycationic molecules, such as polylysine (Lollo et al., PCT Application WO 97/30731), are also known to enhance the cellular uptake of oligonucleotides.

Other agents may be utilized to enhance the penetration of the administered nucleic acids, including glycols such as ethylene glycol and propylene glycol, pyrrols such as 2-pyrrol, azones, and terpenes such as limonene and menthone.

Carriers

Certain compositions of the present invention also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate oligonucleotide in hepatic tissue can be reduced when it is coadministered with polyinosinic acid, dextran sulfate, polycytidic acid or 4-acetamido-4'isothiocyano-stilbene-2,2'-disulfonic acid (Miyao et al., *Antisense Res. Dev.,* 1995, 5, 115–121; Takakura et al., *Antisense & Nucl. Acid Drug Dev.,* 1996, 6, 177–183).

Excipients

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient may be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc.).

Pharmaceutically acceptable organic or inorganic excipient suitable for non-parenteral administration which do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids may include sterile and non-sterile aqueous solutions, non-aqueous solutions in common solvents such as alcohols, or solutions of the nucleic acids in liquid or solid oil bases. The solutions may also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

Other Components

The compositions of the present invention may additionally contain other adjunct components conventionally found in pharmaceutical compositions, at their art-established usage levels. Thus, for example, the compositions may contain additional, compatible, pharmaceutically-active materials such as, for example, antipuritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions may contain substances which increase the viscosity of the suspension including, for example, sodium carboxymethylcellulose, sorbitol and/or dextran. The suspension may also contain stabilizers.

Certain embodiments of the invention provide pharmaceutical compositions containing (a) one or more antisense compounds and (b) one or more other chemotherapeutic agents which function by a non-antisense mechanism. Examples of such chemotherapeutic agents include but are not limited to daunorubicin, daunomycin, dactinomycin, doxorubicin, epirubicin, idarubicin, esorubicin, bleomycin, mafosfamide, ifosfamide, cytosine arabinoside, bischloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). See, generally, *The Merck Manual of Diagnosis and Therapy,* 15th Ed. 1987, pp. 1206–1228, Berkow et al., eds., Rahway, N.J. When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. See, generally, *The Merck Manual of Diagnosis and Therapy,* 15th Ed., Berkow et al., eds., 1987, Rahway, N.J., pages 2499–2506 and 46–49, respectively). Other non-antisense chemotherapeutic agents are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. Numerous examples of antisense compounds are known in the art. Two or more combined compounds may be used together or sequentially.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 ug to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 ug to 100 g per kg of body weight, once or more daily, to once every 20 years.

While the present invention has been described with specificity in accordance with certain of its preferred embodiments, the following examples serve only to illustrate the invention and are not intended to limit the same.

EXAMPLES

Example 1

Nucleoside Phosphoramidites for Oligonucleotide Synthesis Deoxy and 2'-Alkoxy Amidites 2'-Deoxy and 2'-methoxy beta-cyanoethyldiisopropyl phosphoramidites were purchased from commercial sources (e.g. Chemgenes, Needham, Mass. or Glen Research, Inc Sterling, Va.). Other 2'-O-alkoxy substituted nucleoside amidites are prepared as described in U.S. Pat. No. 5,506, 351, herein incorporated by reference. For oligonucleotides synthesized using 2'-alkoxy amidites, optimized synthesis cycles were developed that incorporate multiple steps coupling longer wait times relative to standard synthesis cycles.

The following abbreviations are used in the text: thin layer chromatography (TLC), melting point (MP), high pressure liquid chromatography (HPLC), Nuclear Magnetic Resonance (NMR), argon (Ar), methanol (MeOH), dichloromethane ($CH_2Cl_2$), triethylamine (TEA), dimethyl formamide (DMF), ethyl acetate (EtOAc), dimethyl sulfoxide (DMSO), tetrahydrofuran (THF).

Oligonucleotides containing 5-methyl-2'-deoxycytidine (5-Me-dC) nucleotides were synthesized according to published methods (Sanghvi, et. al., *Nucleic Acids Research,* 1993, 21, 3197–3203) using commercially available phosphoramidites (Glen Research, Sterling, Va. or ChemGenes, Needham, Mass.) or prepared as follows:

Preparation of 5'-O-Dimethoxytrityl-thymidine Intermediate for 5-Methyl dC Amidite To a 50 L glass reactor equipped with air stirrer and Ar gas line was added thymidine (1.00 kg, 4.13 mol) in anhydrous pyridine (6 L) at ambient temperature. Dimethoxytrityl (DMT) chloride (1.47 kg, 4.34 mol, 1.05 eq) was added as a solid in four portions over 1 h. After 30 min, TLC indicated approx. 95% product, 2% thymidine, 5% DMT reagent and by-products and 2% 3',5'-bis DMT product ($R_f$ in EtOAc 0.45, 0.05, 0.98, 0.95 respectively). Saturated sodium bicarbonate (4 L) and $CH_2Cl_2$ were added with stirring (pH of the aqueous layer 7.5). An additional 18 L of water was added, the mixture was stirred, the phases were separated, and the organic layer was transferred to a second 50 L vessel. The aqueous layer was extracted with additional $CH_2Cl_2$ (2×2 L). The combined organic layer was washed with water (10 L) and then concentrated in a rotary evaporator to approx. 3.6 kg total weight. This was redissolved in $CH_2Cl_2$ (3.5 L), added to the reactor followed by water (6 L) and hexanes (13 L). The mixture was vigorously stirred and seeded to give a fine white suspended solid starting at the interface. After stirring for 1 h, the suspension was removed by suction through a ½" diameter teflon tube into a 20 L suction flask, poured onto a 25 cm Coors Buchner funnel, washed with water (2×3 L) and a mixture of hexanes—$CH_2Cl_2$ (4:1, 2×3 L) and allowed to air dry overnight in pans (1" deep). This was further dried in a vacuum oven (75° C., 0.1 mm Hg, 48 h) to a constant weight of 2072 g (93%) of a white solid, (mp 122–124° C.). TLC indicated a trace contamination of the bis DMT product. NMR spectroscopy also indicated that 1–2 mole percent pyridine and about 5 mole percent of hexanes was still present.

Preparation of 5'-O-Dimethoxytrityl-2'-deoxy-5-methylcytidine Intermediate for 5-Methyl-dC Amidite To a 50 L Schott glass-lined steel reactor equipped with an electric stirrer, reagent addition pump (connected to an addition funnel), heating/cooling system, internal thermometer and an Ar gas line was added 5'-O-dimethoxytrityl-thymidine (3.00 kg, 5.51 mol), anhydrous acetonitrile (25 L) and TEA (12.3 L, 88.4 mol, 16 eq). The mixture was chilled with stirring to −10° C. internal temperature (external −20° C.). Trimethylsilylchloride (2.1 L, 16.5 mol, 3.0 eq) was added over 30 minutes while maintaining the internal temperature below −5° C., followed by a wash of anhydrous acetonitrile (1 L). Note: the reaction is mildly exothermic and copious hydrochloric acid fumes form over the course of the addition. The reaction was allowed to warm to 0° C. and the reaction progress was confirmed by TLC (EtOAc-hexanes 4:1; $R_f$ 0.43 to 0.84 of starting material and silyl product, respectively). Upon completion, triazole (3.05 kg, 44 mol, 8.0 eq) was added the reaction was cooled to −20° C. internal temperature (external −30° C.). Phosphorous oxychloride (1035 mL, 11.1 mol, 2.01 eq) was added over 60 min so as to maintain the temperature between −20° C. and −10° C. during the strongly exothermic process, followed by a wash of anhydrous acetonitrile (1 L). The reaction was warmed to 0° C. and stirred for 1 h. TLC indicated a complete conversion to the triazole product ($R_f$ 0.83 to 0.34 with the product spot glowing in long wavelength UV light). The reaction mixture was a peach-colored thick suspension, which turned darker red upon warming without apparent decomposition. The reaction was cooled to −15° C. internal temperature and water (5 L) was slowly added at a rate to maintain the temperature below +10° C. in order to quench the reaction and to form a homogenous solution. (Caution: this reaction is initially very strongly exothermic). Approximately one-half of the reaction volume (22 L) was transferred by air pump to another vessel, diluted with EtOAc (12 L) and extracted with water (2×8 L). The combined water layers were back-extracted with EtOAc (6 L). The water layer was discarded and the organic layers were concentrated in a 20 L rotary evaporator to an oily foam. The foam was coevaporated with anhydrous acetonitrile (4 L) to remove EtOAc. (note: dioxane may be used instead of anhydrous acetonitrile if dried to a hard foam). The second half of the reaction was treated in the same way. Each residue was dissolved in dioxane (3 L) and concentrated ammonium hydroxide (750 mL) was added. A homogenous solution formed in a few minutes and the reaction was allowed to stand overnight (although the reaction is complete within 1 h).

TLC indicated a complete reaction (product $R_f$ 0.35 in EtOAc-MeOH 4:1). The reaction solution was concentrated on a rotary evaporator to a dense foam. Each foam was slowly redissolved in warm EtOAc (4 L; 50° C.), combined in a 50 L glass reactor vessel, and extracted with water (2×4 L) to remove the triazole by-product. The water was back-extracted with EtOAc (2 L). The organic layers were combined and concentrated to about 8 kg total weight, cooled to 0° C. and seeded with crystalline product. After 24 hours, the first crop was collected on a 25 cm Coors Buchner funnel and washed repeatedly with EtOAc (3×3 L) until a white powder was left and then washed with ethyl ether (2×3 L). The solid was put in pans (1" deep) and allowed to air dry overnight. The filtrate was concentrated to an oil, then redissolved in EtOAc (2 L), cooled and seeded as before. The second crop was collected and washed as before (with proportional solvents) and the filtrate was first extracted with water (2×1 L) and then concentrated to an oil. The residue was dissolved in EtOAc (1 L) and yielded a third crop which was treated as above except that more washing was required to remove a yellow oily layer.

After air-drying, the three crops were dried in a vacuum oven (50° C., 0.1 mm Hg, 24 h) to a constant weight (1750, 600 and 200 g, respectively) and combined to afford 2550 g (85%) of a white crystalline product (MP 215–217° C.) when TLC and NMR spectroscopy indicated purity. The mother liquor still contained mostly product (as determined by TLC) and a small amount of triazole (as determined by NMR spectroscopy), bis DMT product and unidentified minor impurities. If desired, the mother liquor can be purified by silica gel chromatography using a gradient of MeOH (0–25%) in EtOAc to further increase the yield.

Preparation of 5'-O-Dimethoxytrityl-2'-deoxy-N4-benzoyl-5-methylcytidine Penultimate Intermediate for 5-Methyl dC Amidite Crystalline 5'-O-dimethoxytrityl-5-methyl-2'-deoxycytidine (2000 g, 3.68 mol) was dissolved in anhydrous DMF (6.0 kg) at ambient temperature in a 50 L glass reactor vessel equipped with an air stirrer and argon line. Benzoic anhydride (Chem Impex not Aldrich, 874 g, 3.86 mol, 1.05 eq) was added and the reaction was stirred at ambient temperature for 8 h. TLC ($CH_2Cl_2$-EtOAc; $CH_2Cl_2$-EtOAc 4:1; $R_f$ 0.25) indicated approx. 92% complete reaction. An additional amount of benzoic anhydride (44 g, 0.19 mol) was added. After a total of 18 h, TLC indicated approx. 96% reaction completion. The solution was diluted with EtOAc (20 L), TEA (1020 mL, 7.36 mol, ca 2.0 eq) was added with stirring, and the mixture was extracted with water (15 L, then 2×10 L). The aqueous layer was removed (no back-extraction was needed) and the organic layer was concentrated in 2×20 L rotary evaporator flasks until a foam began to form. The residues were coevaporated with acetonitrile (1.5 L each) and dried (0.1 mm Hg, 25° C., 24 h) to 2520 g of a dense foam. High pressure liquid chromatography (HPLC) revealed a contamination of 6.3% of N4, 3'-O-dibenzoyl product, but very little other impurities.

THe product was purified by Biotage column chromatography (5 kg Biotage) prepared with 65:35:1 hexanes-EtOAc-TEA (4 L). The crude product (800 g), dissolved in $CH_2Cl_2$ (2 L), was applied to the column. The column was washed with the 65:35:1 solvent mixture (20 kg), then 20:80:1 solvent mixture (10 kg), then 99:1 EtOAc:TEA (17 kg). The fractions containing the product were collected, and any fractions containing the product and impurities were retained to be resubjected to column chromatography. The column was re-equilibrated with the original 65:35:1 solvent mixture (17 kg). A second batch of crude product (840 g) was applied to the column as before. The column was washed with the following solvent gradients: 65:35:1 (9 kg), 55:45:1 (20 kg), 20:80:1 (10 kg), and 99:1 EtOAc:TEA (15 kg). The column was reequilibrated as above, and a third batch of the crude product (850 g) plus impure fractions recycled from the two previous columns (28 g) was purified following the procedure for the second batch. The fractions containing pure product combined and concentrated on a 20 L rotary evaporator, co-evaporated with acetonitrile (3 L) and dried (0.1 mm Hg, 48 h, 25° C.) to a constant weight of 2023 g (85%) of white foam and 20 g of slightly contaminated product from the third run. HPLC indicated a purity of 99.8% with the balance as the diBenzoyl product.

[5'-O-(4,4'-Dimethoxytriphenylmethyl)-2'-deoxy-$N^4$-benzoyl-5-methylcytidin-3'-O-yl]-2-cyanoethyl-N,N-diisopropylphosphoramidite (5-Methyl dC Amidite)

5'-O-(4,4'-Dimethoxytriphenylmethyl)-2'-deoxy-$N^4$-benzoyl-5-methylcytidine (998 g, 1.5 mol) was dissolved in anhydrous DMF (2 L). The solution was co-evaporated with toluene (300 ml) at 50° C. under reduced pressure, then cooled to room temperature and 2-cyanoethyl tetraisopropylphosphorodiamidite (680 g, 2.26 mol) and tetrazole (52.5 g, 0.75 mol) were added. The mixture was shaken until all tetrazole was dissolved, N-methylimidazole (15 ml) was added and the mixture was left at room temperature for 5 hours. TEA (300 ml) was added, the mixture was diluted with DMF (2.5 L) and water (600 ml), and extracted with hexane (3×3 L). The mixture was diluted with water (1.2 L) and extracted with a mixture of toluene (7.5 L) and hexane (6 L). The two layers were separated, the upper layer was washed with DMF-water (7:3 v/v, 3×2 L) and water (3×2 L), and the phases were separated. The organic layer was dried ($Na_2SO_4$), filtered and rotary evaporated. The residue was co-evaporated with acetonitrile (2×2 L) under reduced pressure and dried to a constant weight (25° C., 0.1 mm Hg, 40 h) to afford 1250 g an off-white foam solid (96%).

2'-Fluoro Amidites

2'-Fluorodeoxyadenosine Amidites

2'-fluoro oligonucleotides were synthesized as described previously [Kawasaki, et. al., *J. Med. Chem.*, 1993, 36, 831–841] and U.S. Pat. No. 5,670,633, herein incorporated by reference. The preparation of 2'-fluoropyrimidines containing a 5-methyl substitution are described in U.S. Pat. No. 5,861,493. Briefly, the protected nucleoside N6-benzoyl-2'-deoxy-2'-fluoroadenosine was synthesized utilizing, commercially available 9-beta-D-arabinofuranosyladenine as starting material and whereby the 2'-alpha-fluoro atom is introduced by a $S_N2$-displacement of a 2'-beta-triflate group. Thus N6-benzoyl-9-beta-D-arabinofuranosyladenine was selectively protected in moderate yield as the 3',5'-ditetrahydropyranyl (THP) intermediate. Deprotection of the THP and N6-benzoyl groups was accomplished using standard methodologies to obtain the 5'-dimethoxytrityl-(DMT) and 5'-DMT-3'-phosphoramidite intermediates.

2'-Fluorodeoxyguanosine

The synthesis of 2'-deoxy-2'-fluoroguanosine was accomplished using tetraisopropyldisiloxanyl (TPDS) protected 9-beta-D-arabinofuranosylguanine as starting material, and conversion to the intermediate isobutyryl-arabinofuranosylguanosine. Alternatively, isobutyryl-arabinofuranosylguanosine was prepared as described by Ross et al., (Nucleosides & Nucleosides, 16, 1645, 1997). Deprotection of the TPDS group was followed by protection of the hydroxyl group with THP to give isobutyryl di-THP protected arabinofuranosylguanine. Selective O-deacylation and triflation was followed by treatment of the crude product with fluoride, then deprotection of the THP groups. Standard methodologies were used to obtain the 5'-DMT- and 5'-DMT-3'-phosphoramidites.

2'-Fluorouridine

Synthesis of 2'-deoxy-2'-fluorouridine was accomplished by the modification of a literature procedure in which 2,2'-anhydro-1-beta-D-arabinofuranosyluracil was treated with 70% hydrogen fluoride-pyridine. Standard procedures were used to obtain the 5'-DMT and 5'-DMT-3'phosphoramidites.

2'-Fluorodeoxycytidine

2'-deoxy-2'-fluorocytidine was synthesized via amination of 2'-deoxy-2'-fluorouridine, followed by selective protection to give N4-benzoyl-2'-deoxy-2'-fluorocytidine. Standard procedures were used to obtain the 5'-DMT and 5'-DMT-3'phosphoramidites.

2'-O-(2-Methoxyethyl) Modified Amidites

2'-O-Methoxyethyl-substituted nucleoside amidites (otherwise known as MOE amidites) are prepared as follows, or alternatively, as per the methods of Martin, P., (Helvetica Chimica Acta, 1995, 78, 486–504).

Preparation of 2'-O-(2-methoxyethyl)-5-methyluridine Intermediate 2,2'-Anhydro-5-methyl-uridine (2000 g, 8.32 mol), tris(2-methoxyethyl)borate (2504 g, 10.60 mol), sodium bicarbonate (60 g, 0.70 mol) and anhydrous 2-methoxyethanol (5 L) were combined in a 12 L three necked flask and heated to 130° C. (internal temp) at atmospheric pressure, under an argon atmosphere with stirring for 21 h. TLC indicated a complete reaction. The solvent was removed under reduced pressure until a sticky gum formed (50–85° C. bath temp and 100–11 mm Hg) and the residue was redissolved in water (3 L) and heated to boiling for 30 min in order the hydrolyze the borate esters. The water was removed under reduced pressure until a foam began to form and then the process was repeated. HPLC indicated about 77% product, 15% dimer (5' of product attached to 2' of starting material) and unknown derivatives, and the balance was a single unresolved early eluting peak.

The gum was redissolved in brine (3 L), and the flask was rinsed with additional brine (3 L). The combined aqueous solutions were extracted with chloroform (20 L) in a heavier-than continuous extractor for 70 h. The chloroform layer was concentrated by rotary evaporation in a 20 L flask to a sticky foam (2400 g). This was coevaporated with MeOH (400 mL) and EtOAc (8 L) at 75° C. and 0.65 atm until the foam dissolved at which point the vacuum was lowered to about 0.5 atm. After 2.5 L of distillate was collected a precipitate began to form and the flask was removed from the rotary evaporator and stirred until the suspension reached ambient temperature. EtOAc (2 L) was added and the slurry was filtered on a 25 cm table top Buchner funnel and the product was washed with EtOAc (3×2 L). The bright white solid was air dried in pans for 24 h then further dried in a vacuum oven (50° C., 0.1 mm Hg, 24 h) to afford 1649 g of a white crystalline solid (mp 115.5–116.5° C.).

The brine layer in the 20 L continuous extractor was further extracted for 72 h with recycled chloroform. The chloroform was concentrated to 120 g of oil and this was combined with the mother liquor from the above filtration (225 g), dissolved in brine (250 mL) and extracted once with chloroform (250 mL). The brine solution was continuously extracted and the product was crystallized as described above to afford an additional 178 g of crystalline product containing about 2% of thymine. The combined yield was 1827 g (69.4%). HPLC indicated about 99.5% purity with the balance being the dimer.

Preparation of 5'-O-DMT-2'-O-(2-methoxyethyl)-5-methyluridine Penultimate Intermediate In a 50 L glass-lined steel reactor, 2'-O-(2-methoxyethyl)-5-methyl-uridine (MOE-T, 1500 g, 4.738 mol), lutidine (1015 g, 9.476 mol) were dissolved in anhydrous acetonitrile (15 L). The solution was stirred rapidly and chilled to −10° C. (internal temperature). Dimethoxytriphenylmethyl chloride (1765.7 g, 5.21 mol) was added as a solid in one portion. The reaction was allowed to warm to −2° C. over 1 h. (Note: The reaction was monitored closely by TLC (EtOAc) to determine when to stop the reaction so as to not generate the undesired bis-DMT substituted side product). The reaction was allowed to warm from −2 to 3° C. over 25 min. then quenched by adding MeOH (300 mL) followed after 10 min by toluene (16 L) and water (16 L). The solution was transferred to a clear 50 L vessel with a bottom outlet, vigorously stirred for 1 minute, and the layers separated. The aqueous layer was removed and the organic layer was washed successively with 10% aqueous citric acid (8 L) and water (12 L). The product was then extracted into the aqueous phase by washing the toluene solution with aqueous sodium hydroxide (0.5N, 16 L and 8 L). The combined aqueous layer was overlayed with toluene (12 L) and solid citric acid (8 moles, 1270 g) was added with vigorous stirring to lower the pH of the aqueous layer to 5.5 and extract the product into the toluene. The organic layer was washed with water (10 L) and TLC of the organic layer indicated a trace of DMT-O-Me, bis DMT and dimer DMT.

The toluene solution was applied to a silica gel column (6 L sintered glass funnel containing approx. 2 kg of silica gel slurried with toluene (2 L) and TEA(25 mL)) and the fractions were eluted with toluene (12 L) and EtOAc (3×4 L) using vacuum applied to a filter flask placed below the column. The first EtOAc fraction containing both the desired product and impurities were resubjected to column chromatography as above. The clean fractions were combined, rotary evaporated to a foam, coevaporated with acetonitrile (6 L) and dried in a vacuum oven (0.1 mm Hg, 40 h, 40° C.) to afford 2850 g of a white crisp foam. NMR spectroscopy indicated a 0.25 mole % remainder of acetonitrile (calculates to be approx. 47 g) to give a true dry weight of 2803 g (96%). HPLC indicated that the product was 99.41% pure, with the remainder being 0.06 DMT-O-Me, 0.10 unknown, 0.44 bis DMT, and no detectable dimer DMT or 3'-O-DMT. Preparation of [5'-O-(4,4'-Dimethoxytriphenylmethyl)-2'-O-(2-methoxyethyl)-5-methyluridin-3'-O-yl]-2-cyanoethyl-N,N-diisopropylphosphoramidite (MOE T Amidite)

5'-O-(4,4'-Dimethoxytriphenylmethyl)-2'-O-(2-methoxyethyl)-5-methyluridine (1237 g, 2.0 mol) was dissolved in anhydrous DMF (2.5 L). The solution was co-evaporated with toluene (200 ml) at 50° C. under reduced pressure, then cooled to room temperature and 2-cyanoethyl tetraisopropylphosphorodiamidite (900 g, 3.0 mol) and tetrazole (70 g, 1.0 mol) were added. The mixture was shaken until all tetrazole was dissolved, N-methylimidazole (20 ml) was added and the solution was left at room temperature for 5 hours. TEA (300 ml) was added, the mixture was diluted with DMF (3.5 L) and water (600 ml) and extracted with hexane (3×3 L). The mixture was diluted with water (1.6 L) and extracted with the mixture of toluene (12 L) and hexanes (9 L). The upper layer was washed with DMF-water (7:3 v/v, 3×3 L) and water (3×3 L). The organic layer was dried (Na$_2$SO$_4$), filtered and evaporated. The residue was co-evaporated with acetonitrile (2×2 L) under reduced pressure and dried in a vacuum oven (25° C., 0.1 mm Hg, 40 h) to afford 1526 g of an off-white foamy solid (95%).
Preparation of 5'-O-Dimethoxytrityl-2'-O-(2-methoxyethyl)-5-methylcytidine Intermediate To a 50 L Schott glass-lined steel reactor equipped with an electric stirrer, reagent addition pump (connected to an addition funnel), heating/cooling system, internal thermometer and argon gas line was added 5'-O-dimethoxytrityl-2'-O-(2-methoxyethyl)-5-methyl-uridine (2.616 kg, 4.23 mol, purified by base extraction only and no scrub column), anhydrous acetonitrile (20 L), and TEA (9.5 L, 67.7 mol, 16 eq). The mixture was chilled with stirring to −10° C. internal temperature (external −20° C.). Trimethylsilylchloride (1.60 L, 12.7 mol, 3.0 eq) was added over 30 min. while maintaining the internal temperature below −5° C., followed by a wash of anhydrous acetonitrile (1 L). (Note: the reaction is mildly exothermic and copious hydrochloric acid fumes form over the course of the addition). The reaction was allowed to warm to 0° C. and the reaction progress was confirmed by TLC (EtOAc, R$_f$ 0.68 and 0.87 for starting material and silyl product, respectively). Upon completion, triazole (2.34 kg, 33.8 mol, 8.0 eq) was added the reaction was cooled to −20° C. internal temperature (external −30° C.). Phosphorous oxychloride (793 mL, 8.51 mol, 2.01 eq) was added slowly over 60 min so as to maintain the temperature between −20° C. and −10° C. (note: strongly exothermic), followed by a wash of anhydrous acetonitrile (1 L). The reaction was warmed to 0° C. and stirred for 1 h, at which point it was an off-white thick suspension. TLC indicated a complete conversion to the triazole product (EtOAc, R$_f$ 0.87 to 0.75 with the product spot glowing in long wavelength UV light). The reaction was cooled to −15° C. and water (5 L) was slowly added at a rate to maintain the temperature below +10° C. in order to quench the reaction and to form a homogenous solution. (Caution: this reaction is initially very strongly exothermic). Approximately one-half of the reaction volume (22 L) was transferred by air pump to another vessel, diluted with EtOAc (12 L) and extracted with water (2×8 L). The second half of the reaction was treated in the same way. The combined aqueous layers were back-extracted with EtOAc (8 L) The organic layers were combined and concentrated in a 20 L rotary evaporator to an oily foam. The foam was coevaporated with anhydrous acetonitrile (4 L) to remove EtOAc. (note: dioxane may be used instead of anhydrous acetonitrile if dried to a hard foam). The residue was dissolved in dioxane (2 L) and concentrated ammonium hydroxide (750 mL) was added. A homogenous solution formed in a few minutes and the reaction was allowed to stand overnight.

TLC indicated a complete reaction (CH$_2$Cl$_2$-acetone-MeOH, 20:5:3, R$_f$ 0.51). The reaction solution was concentrated on a rotary evaporator to a dense foam and slowly redissolved in warm CH$_2$Cl$_2$ (4 L, 40° C.) and transferred to a 20 L glass extraction vessel equipped with a air-powered stirrer. The organic layer was extracted with water (2×6 L) to remove the triazole by-product. (Note: In the first extraction an emulsion formed which took about 2 h to resolve). The water layer was back-extracted with CH$_2$Cl$_2$ (2×2 L), which in turn was washed with water (3 L). The combined organic layer was concentrated in 2×20 L flasks to a gum and then recrystallized from EtOAc seeded with crystalline product. After sitting overnight, the first crop was collected on a 25 cm Coors Buchner funnel and washed repeatedly with EtOAc until a white free-flowing powder was left (about 3×3 L). The filtrate was concentrated to an oil recrystallized from EtOAc, and collected as above. The solid was air-dried in pans for 48 h, then further dried in a vacuum oven (50° C., 0.1 mm Hg, 17 h) to afford 2248 g of a bright white, dense solid (86%). An HPLC analysis indicated both crops to be 99.4% pure and NMR spectroscopy indicated only a faint trace of EtOAc remained.
Preparation of 5'-O-Dimethoxytrityl-2'-O-(2-methoxyethyl)-N4-benzoyl-5-methyl-cytidine Penultimate Intermediate:

Crystalline 5'-O-dimethoxytrityl-2'-O-(2-methoxyethyl)-5-methyl-cytidine (1000 g, 1.62 mol) was suspended in anhydrous DMF (3 kg) at ambient temperature and stirred under an Ar atmosphere. Benzoic anhydride (439.3 g, 1.94 mol) was added in one portion. The solution clarified after 5 hours and was stirred for 16 h. HPLC indicated 0.45% starting material remained (as well as 0.32% N4, 3'-O-bis Benzoyl). An additional amount of benzoic anhydride (6.0 g, 0.0265 mol) was added and after 17 h, HPLC indicated no starting material was present. TEA (450 mL, 3.24 mol) and toluene (6 L) were added with stirring for 1 minute. The solution was washed with water (4×4 L), and brine (2×4 L). The organic layer was partially evaporated on a 20 L rotary evaporator to remove 4 L of toluene and traces of water. HPLC indicated that the bis benzoyl side product was present as a 6% impurity. The residue was diluted with toluene (7 L) and anhydrous DMSO (200 mL, 2.82 mol) and sodium hydride (60% in oil, 70 g, 1.75 mol) was added in one portion with stirring at ambient temperature over 1 h. The reaction was quenched by slowly adding then washing with aqueous citric acid (10%, 100 mL over 10 min, then 2×4 L), followed by aqueous sodium bicarbonate (2%, 2 L), water (2×4 L) and brine (4 L). The organic layer was concentrated on a 20 L rotary evaporator to about 2 L total volume. The residue was purified by silica gel column chromatography (6 L Buchner funnel containing 1.5 kg of silica gel wetted with a solution of EtOAc-hexanes-TEA (70:29:1)). The product was eluted with the same solvent (30 L) followed by straight EtOAc (6 L). The fractions containing the product were combined, concentrated on a rotary evaporator to a foam and then dried in a vacuum oven (50° C., 0.2 mm Hg, 8 h) to afford 1155 g of a crisp, white foam (98%). HPLC indicated a purity of >99.7%.

Preparation of [5'-O-(4,4'-Dimethoxytriphenylmethyl)-2'-O-(2-methoxyethyl)-$N^4$-benzoyl-5-methylcytidin-3'-O-yl]-2-cyanoethyl-N,N-diisopropylphosphoramidite (MOE 5-Me-C Amidite)

5'-O-(4,4'-Dimethoxytriphenylmethyl)-2'-O-(2-methoxyethyl)-$N^4$-benzoyl-5-methylcytidine (1082 g, 1.5 mol) was dissolved in anhydrous DMF (2 L) and co-evaporated with toluene (300 ml) at 50° C. under reduced pressure. The mixture was cooled to room temperature and 2-cyanoethyl tetraisopropylphosphorodiamidite (680 g, 2.26 mol) and tetrazole (52.5 g, 0.75 mol) were added. The mixture was shaken until all tetrazole was dissolved, N-methylimidazole (30 ml) was added, and the mixture was left at room temperature for 5 hours. TEA (300 ml) was added, the mixture was diluted with DMF (1 L) and water (400 ml) and extracted with hexane (3×3 L). The mixture was diluted with water (1.2 L) and extracted with a mixture of toluene (9 L) and hexanes (6 L). The two layers were separated and the upper layer was washed with DMF-water (60:40 v/v, 3×3 L) and water (3×2 L). The organic layer was dried (Na$_2$SO$_4$), filtered and evaporated. The residue was co-evaporated with acetonitrile (2×2 L) under reduced pressure and dried in a vacuum oven (25° C., 0.1 mm Hg, 40 h) to afford 1336 g of an off-white foam (97%).

Preparation of [5'-O-(4,4'-Dimethoxytriphenylmethyl)-2'-O-(2-methoxyethyl)-$N^6$-benzoyladenosin-3'-O-yl]-2-cyanoethyl-N,N-diisopropylphosphoramidite (MOE A Amidite)

5'-O-(4,4'-Dimethoxytriphenylmethyl)-2'-O-(2-methoxyethyl)-$N^6$-benzoyladenosine (purchased from Reliable Biopharmaceutical, St. Lois, Mo.), 1098 g, 1.5 mol) was dissolved in anhydrous DMF (3 L) and co-evaporated with toluene (300 ml) at 50° C. The mixture was cooled to room temperature and 2-cyanoethyl tetraisopropylphosphorodiamidite (680 g, 2.26 mol) and tetrazole (78.8 g, 1.24 mol) were added. The mixture was shaken until all tetrazole was dissolved, N-methylimidazole (30 ml) was added, and the mixture was left at room temperature for 5 hours. TEA (300 ml) was added, the mixture was diluted with DMF (1 L) and water (400 ml) and extracted with hexanes (3×3 L). The mixture was diluted with water (1.4 L) and extracted with the mixture of toluene (9 L) and hexanes (6 L). The two layers were separated and the upper layer was washed with DMF-water (60:40, v/v, 3×3 L) and water (3×2 L). The organic layer was dried (Na$_2$SO$_4$), filtered and evaporated to a sticky foam. The residue was co-evaporated with acetonitrile (2.5 L) under reduced pressure and dried in a vacuum oven (25° C., 0.1 mm Hg, 40 h) to afford 1350 g of an off-white foam solid (96%).

Preparation of [5'-O-(4,4'-Dimethoxytriphenylmethyl)-2'-O-(2-methoxyethyl)-$N^4$-isobutyrylguanosin-3'-O-yl]-2-cyanoethyl-N,N-diisopropylphosphoramidite (MOE G Amidite)

5'-O-(4,4'-Dimethoxytriphenylmethyl)-2'-O-(2-methoxyethyl)-$N^4$-isobutyrylguanosin (purchased from Reliable Biopharmaceutical, St. Louis, Mo., 1426 g, 2.0 mol) was dissolved in anhydrous DMF (2 L). The solution was co-evaporated with toluene (200 ml) at 50° C., cooled to room temperature and 2-cyanoethyl tetraisopropylphosphorodiamidite (900 g, 3.0 mol) and tetrazole (68 g, 0.97 mol) were added. The mixture was shaken until all tetrazole was dissolved, N-methylimidazole (30 ml) was added, and the mixture was left at room temperature for 5 hours. TEA (300 ml) was added, the mixture was diluted with DMF (2 L) and water (600 ml) and extracted with hexanes (3×3 L). The mixture was diluted with water (2 L) and extracted with a mixture of toluene (10 L) and hexanes (5 L). The two layers were separated and the upper layer was washed with DMF-water (60:40, v/v, 3×3 L). EtOAc (4 L) was added and the solution was washed with water (3×4 L). The organic layer was dried (Na$_2$SO$_4$), filtered and evaporated to approx. 4 kg. Hexane (4 L) was added, the mixture was shaken for 10 min, and the supernatant liquid was decanted. The residue was co-evaporated with acetonitrile (2×2 L) under reduced pressure and dried in a vacuum oven (25° C., 0.1 mm Hg, 40 h) to afford 1660 g of an off-white foamy solid (91%).

2'-O-(Aminooxyethyl) Nucleoside Amidites and 2'-O-(Dimethylaminooxyethyl) Nucleoside Amidites 2'-(Dimethylaminooxyethoxy) Nucleoside Amidites 2'-(Dimethylaminooxyethoxy) nucleoside amidites (also known in the art as 2'-O-(dimethylaminooxyethyl) nucleoside amidites) are prepared as described in the following paragraphs. Adenosine, cytidine and guanosine nucleoside amidites are prepared similarly to the thymidine (5-methyluridine) except the exocyclic amines are protected with a benzoyl moiety in the case of adenosine and cytidine and with isobutyryl in the case of guanosine.

5'-O-tert-Butyldiphenylsilyl-$O^2$-2'-anhydro-5-methyluridine $O^2$-2'-anhydro-5-methyluridine (Pro. Bio. Sint., Varese, Italy, 100.0 g, 0.416 mmol), dimethylaminopyridine (0.66 g, 0.013 eq, 0.0054 mmol) were dissolved in dry pyridine (500 ml) at ambient temperature under an argon atmosphere and with mechanical stirring. tert-Butyldiphenylchlorosilane (125.8 g, 119.0 mL, 1.1 eq, 0.458 mmol) was added in one portion. The reaction was stirred for 16 h at ambient temperature. TLC ($R_f$ 0.22, EtOAc) indicated a complete reaction. The solution was concentrated under reduced pressure to a thick oil. This was partitioned between CH$_2$Cl$_2$ (1 L) and saturated sodium bicarbonate (2×1 L) and brine (1 L). The organic layer was dried over sodium sulfate, filtered, and concentrated under reduced pressure to a thick oil. The oil was dissolved in a 1:1 mixture of EtOAc and ethyl ether (600 mL) and cooling the solution to −10° C. afforded a white crystalline solid which was collected by filtration, washed with ethyl ether (3×200 mL) and dried (40° C., 1 mm Hg, 24 h) to afford 149 g of white solid (74.8%). TLC and NMR spectroscopy were consistent with pure product.

5'-O-tert-Butyldiphenylsilyl-2'-O-(2-hydroxyethyl)-5-methyluridine

In the fume hood, ethylene glycol (350 mL, excess) was added cautiously with manual stirring to a 2 L stainless steel pressure reactor containing borane in tetrahydrofuran (1.0 M, 2.0 eq, 622 mL). (Caution: evolves hydrogen gas). 5'-O-tert-Butyldiphenylsilyl-$O^2$-2'-anhydro-5-methyluridine (149 g, 0.311 mol) and sodium bicarbonate (0.074 g, 0.003 eq) were added with manual stirring. The reactor was sealed and heated in an oil bath until an internal temperature of 160° C. was reached and then maintained for 16 h (pressure<100 psig). The reaction vessel was cooled to ambient temperature and opened. TLC (EtOAc, $R_f$ 0.67 for desired product and $R_f$ 0.82 for ara-T side product) indicated about 70% conversion to the product. The solution was concentrated under reduced pressure (10 to 1 mm Hg) in a warm water bath (40–100° C.) with the more extreme conditions used to remove the ethylene glycol. (Alternatively, once the THF has evaporated the solution can be diluted with water and the product extracted into EtOAc). The residue was purified by column chromatography (2 kg silica gel, EtOAc-hexanes gradient 1:1 to 4:1). The appropriate fractions were combined, evaporated and dried to afford 84 g of a white crisp foam (50%), contaminated starting material (17.4 g, 12% recovery) and pure reusable starting material (20 g, 13% recovery). TLC and NMR spectroscopy were consistent with 99% pure product.

2'-O-([2-Phthalimidoxy)ethyl]-5'-t-butyldiphenylsilyl-5-methyluridine

5'-O-tert-Butyldiphenylsilyl-2'-O-(2-hydroxyethyl)-5-methyluridine (20 g, 36.98 mmol) was mixed with triphenylphosphine (11.63 g, 44.36 mmol) and N-hydroxyphthalimide (7.24 g, 44.36 mmol) and dried over $P_2O_5$ under high vacuum for two days at 40° C. The reaction mixture was flushed with argon and dissolved in dry THF (369.8 mL, Aldrich, sure seal bottle). Diethylazodicarboxylate (6.98 mL, 44.36 mmol) was added dropwise to the reaction mixture with the rate of addition maintained such that the resulting deep red coloration is just discharged before adding the next drop. The reaction mixture was stirred for 4 hrs., after which time TLC (EtOAc:hexane, 60:40) indicated that the reaction was complete. The solvent was evaporated in vacuo and the residue purified by flash column chromatography (eluted with 60:40 EtOAc:hexane), to yield 2'-O-([2-phthalimidoxy)ethyl]-5'-t-butyldiphenylsilyl-5-methyluridine as white foam (21.819 g, 86%) upon rotary evaporation.

5'-O-tert-butyldiphenylsilyl-2'-O-[(2-formadoximinooxy)ethyl]-5-methyluridine

2'-O-([2-phthalimidoxy)ethyl]-5'-t-butyldiphenylsilyl-5-methyluridine (3.1 g, 4.5 mmol) was dissolved in dry $CH_2Cl_2$ (4.5 mL) and methylhydrazine (300 mL, 4.64 mmol) was added dropwise at −10° C. to 0° C. After 1 h the mixture was filtered, the filtrate washed with ice cold $CH_2Cl_2$, and the combined organic phase was washed with water and brine and dried (anhydrous $Na_2SO_4$). The solution was filtered and evaporated to afford 2'-O-(aminooxyethyl) thymidine, which was then dissolved in MeOH (67.5 mL). Formaldehyde (20% aqueous solution, w/w, 1.1 eq.) was added and the resulting mixture was stirred for 1 h. The solvent was removed under vacuum and the residue was purified by column chromatography to yield 5'-O-tert-butyldiphenylsilyl-2'-O-[(2-formadoximinooxy)ethyl]-5-methyluridine as white foam (1.95 g, 78%) upon rotary evaporation.

5'-O-tert-Butyldiphenylsilyl-2'-O-[N,N dimethylaminooxyethyl]-5-methyluridine

5'-O-tert-butyldiphenylsilyl-2'-O-[(2-formadoximinooxy) ethyl]-5-methyluridine (1.77 g, 3.12 mmol) was dissolved in a solution of 1M pyridinium p-toluenesulfonate (PPTS) in dry MeOH (30.6 mL) and cooled to 10° C. under inert atmosphere. Sodium cyanoborohydride (0.39 g, 6.13 mmol) was added and the reaction mixture was stirred. After 10 minutes the reaction was warmed to room temperature and stirred for 2 h. while the progress of the reaction was monitored by TLC (5% MeOH in $CH_2Cl_2$). Aqueous $NaHCO_3$ solution (5%, 10 mL) was added and the product was extracted with EtOAc (2×20 mL). The organic phase was dried over anhydrous $Na_2SO_4$, filtered, and evaporated to dryness. This entire procedure was repeated with the resulting residue, with the exception that formaldehyde (20% w/w, 30 mL, 3.37 mol) was added upon dissolution of the residue in the PPTS/MeOH solution. After the extraction and evaporation, the residue was purified by flash column chromatography and (eluted with 5% MeOH in $CH_2Cl_2$) to afford 5'-O-tert-butyldiphenylsilyl-2'-O-[N,N-dimethylaminooxyethyl]-5-methyluridine as a white foam (14.6 g, 80%) upon rotary evaporation.

2'-O-(Dimethylaminooxyethyl)-5-methyluridine

Triethylamine trihydrofluoride (3.91 mL, 24.0 mmol) was dissolved in dry THF and TEA (1.67 mL, 12 mmol, dry, stored over KOH) and added to 5'-O-tert-butyldiphenylsilyl-2'-O-[N,N-dimethylaminooxyethyl]-5-methyluridine (1.40 g, 2.4 mmol). The reaction was stirred at room temperature for 24 hrs and monitored by TLC (5% MeOH in $CH_2Cl_2$). The solvent was removed under vacuum and the residue purified by flash column chromatography (eluted with 10% MeOH in $CH_2Cl_2$) to afford 2'-O-(dimethylaminooxyethyl)-5-methyluridine (766 mg, 92.5%) upon rotary evaporation of the solvent.

5'-O-DMT-2'-O-(dimethylaminooxyethyl)-5-methyluridine

2'-O-(dimethylaminooxyethyl)-5-methyluridine (750 mg, 2.17 mmol) was dried over $P_2O_5$ under high vacuum overnight at 40° C., co-evaporated with anhydrous pyridine (20 mL), and dissolved in pyridine (11 mL) under argon atmosphere. 4-dimethylaminopyridine (26.5 mg, 2.60 mmol) and 4,4'-dimethoxytrityl chloride (880 mg, 2.60 mmol) were added to the pyridine solution and the reaction mixture was stirred at room temperature until all of the starting material had reacted. Pyridine was removed under vacuum and the residue was purified by column chromatography (eluted with 10% MeOH in $CH_2Cl_2$ containing a few drops of pyridine) to yield 5'-O-DMT-2'-O-(dimethylaminooxyethyl)-5-methyluridine (1.13 g, 80%) upon rotary evaporation.

5'-O-DMT-2'-O-(2-N,N-dimethylaminooxyethyl)-5-methyluridine-3'-[(2-cyanoethyl)-N,N-diisopropylphosphoramidite]

5'-O-DMT-2'-O-(dimethylaminooxyethyl)-5-methyluridine (1.08 g, 1.67 mmol) was co-evaporated with toluene (20 mL), N,N-diisopropylamine tetrazonide (0.29 g, 1.67 mmol) was added and the mixture was dried over $P_2O_5$ under high vacuum overnight at 40° C. This was dissolved in anhydrous acetonitrile (8.4 mL) and 2-cyanoethyl-N,N, $N^1,N^1$-tetraisopropylphosphoramidite (2.12 mL, 6.08 mmol) was added. The reaction mixture was stirred at ambient temperature for 4 h under inert atmosphere. The progress of the reaction was monitored by TLC (hexane:EtOAc 1:1). The solvent was evaporated, then the residue was dissolved in EtOAc (70 mL) and washed with 5% aqueous $NaHCO_3$ (40 mL). The EtOAc layer was dried over anhydrous $Na_2SO_4$, filtered, and concentrated. The residue obtained was purified by column chromatography (EtOAc as eluent) to afford 5'-O-DMT-2'-O-(2-N,N-dimethylaminooxyethyl)-5-methyluridine-3'-[(2-cyanoethyl)-N,N-diisopropylphosphoramidite] as a foam (1.04 g, 74.9%) upon rotary evaporation.

2'-(Aminooxyethoxy) Nucleoside Amidites

2'-(Aminooxyethoxy) nucleoside amidites (also known in the art as 2'-O-(aminooxyethyl) nucleoside amidites) are prepared as described in the following paragraphs. Adenosine, cytidine and thymidine nucleoside amidites are prepared similarly.

N2-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite]

The 2'-O-aminooxyethyl guanosine analog may be obtained by selective 2'-O-alkylation of diaminopurine riboside. Multigram quantities of diaminopurine riboside may be purchased from Schering AG (Berlin) to provide 2'-O-(2-ethylacetyl)diaminopurine riboside along with a minor amount of the 3'-O-isomer. 2'-O-(2-ethylacetyl) diaminopurine riboside may be resolved and converted to 2'-O-(2-ethylacetyl)guanosine by treatment with adenosine deaminase. (McGee, D. P. C., Cook, P. D., Guinosso, C. J., WO 94/02501 A1 940203.) Standard protection procedures should afford 2'-O-(2-ethylacetyl)-5'-O-(4,4'-dimethoxytrityl)guanosine and 2-N-isobutyryl-6-O-diphenylcarbamoyl-2'-O-(2-ethylacetyl)-5'-O-(4,4'-dimethoxytrityl)guanosine which may be reduced to provide 2-N-isobutyryl-6-O-diphenylcarbamoyl-2'-O-(2-hydroxyethyl)-5'-O-(4,4'-dimethoxytrityl)guanosine. As before the hydroxyl group may be displaced by N-hydroxyphthalimide via a Mitsunobu reaction, and the protected nucleoside may be phosphitylated as usual to yield 2-N-isobutyryl-6-O-diphenylcarbamoyl-2'-O-([2-phthalimidoxy]ethyl)-5'-O-(4,4'-dimethoxytrityl)guanosine-3'-[(2-cyanoethyl)-N,N-diisopropylphosphoramidite].

2'-Dimethylaminoethoxyethoxy (2'-DMAEOE) Nucleoside Amidites

2'-dimethylaminoethoxyethoxy nucleoside amidites (also known in the art as 2'-O-dimethylaminoethoxyethyl, i.e., 2'-O—CH$_2$—O—CH$_2$—N(CH$_2$)$_2$, or 2'-DMAEOE nucleoside amidites) are prepared as follows. Other nucleoside amidites are prepared similarly.

2'-O-[2(2-N,N-dimethylaminoethoxy)ethyl]-5-methyl Uridine

2[2-(Dimethylamino)ethoxy]ethanol (Aldrich, 6.66 g, 50 mmol) was slowly added to a solution of borane in tetrahydrofuran (1 M, 10 mL, 10 mmol) with stirring in a 100 mL bomb. (Caution: Hydrogen gas evolves as the solid dissolves). O$^2$-,2'-anhydro-5-methyluridine (1.2 g, 5 mmol), and sodium bicarbonate (2.5 mg) were added and the bomb was sealed, placed in an oil bath and heated to 155° C. for 26 h. then cooled to room temperature. The crude solution was concentrated, the residue was diluted with water (200 mL) and extracted with hexanes (200 mL). The product was extracted from the aqueous layer with EtOAc (3×200 mL) and the combined organic layers were washed once with water, dried over anhydrous sodium sulfate, filtered and concentrated. The residue was purified by silica gel column chromatography (eluted with 5:100:2 MeOH/CH$_2$Cl$_2$/TEA) as the eluent. The appropriate fractions were combined and evaporated to afford the product as a white solid.

5'-O-Dimethoxytrityl-2'-O-[2(2-N,N-dimethylaminoethoxy) ethyl)]-5-methyl Uridine To 0.5 g (1.3 mmol) of 2'-O-[2(2-N,N-dimethylaminoethoxy)ethyl)]-5-methyl uridine in anhydrous pyridine (8 mL), was added TEA (0.36 mL) and dimethoxytrityl chloride (DMT-Cl, 0.87 g, 2 eq.) and the reaction was stirred for 1 h. The reaction mixture was poured into water (200 mL) and extracted with CH$_2$Cl$_2$ (2×200 mL). The combined CH$_2$Cl$_2$ layers were washed with saturated NaHCO$_3$ solution, followed by saturated NaCl solution, dried over anhydrous sodium sulfate, filtered and evaporated. The residue was purified by silica gel column chromatography (eluted with 5:100:1 MeOH/CH$_2$Cl$_2$/TEA) to afford the product.

5'-O-Dimethoxytrityl-2'-O-[2(2-N,N-dimethylaminoethoxy)-ethyl)]-5-methyl Uridine-3'-O-(cyanoethyl-N,N-diisopropyl)phosphoramidite Diisopropylaminotetrazolide (0.6 g) and 2-cyanoethoxy-N,N-diisopropyl phosphoramidite (1.1 mL, 2 eq.) were added to a solution of 5'-O-dimethoxytrityl-2'-O-[2(2-N,N-dimethylaminoethoxy)ethyl)]-5-methyluridine (2.17 g, 3 mmol) dissolved in CH$_2$Cl$_2$ (20 mL) under an atmosphere of argon. The reaction mixture was stirred overnight and the solvent evaporated. The resulting residue was purified by silica gel column chromatography with EtOAc as the eluent to afford the title compound.

Example 2

Oligonucleotide Synthesis

Unsubstituted and substituted phosphodiester (P=O) oligonucleotides are synthesized on an automated DNA synthesizer (Applied Biosystems model 394) using standard phosphoramidite chemistry with oxidation by iodine.

Phosphorothioates (P=S) are synthesized similar to phosphodiester oligonucleotides with the following exceptions: thiation was effected by utilizing a 10% w/v solution of 3H-1,2-benzodithiole-3-one 1,1-dioxide in acetonitrile for the oxidation of the phosphite linkages. The thiation reaction step time was increased to 180 sec and preceded by the normal capping step. After cleavage from the CPG column and deblocking in concentrated ammonium hydroxide at 55° C. (12–16 hr), the oligonucleotides were recovered by precipitating with >3 volumes of ethanol from a 1 M NH$_4$OAc solution. Phosphinate oligonucleotides are prepared as described in U.S. Pat. No. 5,508,270, herein incorporated by reference.

Alkyl phosphonate oligonucleotides are prepared as described in U.S. Pat. No. 4,469,863, herein incorporated by reference.

3'-Deoxy-3'-methylene phosphonate oligonucleotides are prepared as described in U.S. Pat. Nos. 5,610,289 or 5,625,050, herein incorporated by reference.

Phosphoramidite oligonucleotides are prepared as described in U.S. Pat. No. 5,256,775 or U.S. Pat. No. 5,366,878, herein incorporated by reference.

Alkylphosphonothioate oligonucleotides are prepared as described in published PCT applications PCT/US94/00902 and PCT/US93/06976 (published as WO 94/17093 and WO 94/02499, respectively), herein incorporated by reference.

3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Borano phosphate oligonucleotides are prepared as described in U.S. Pat. Nos. 5,130,302 and 5,177,198, both herein incorporated by reference.

Example 3

Oligonucleoside Synthesis

Methylenemethylimino linked oligonucleosides, also identified as MMI linked oligonucleosides, methylenedimethyl-hydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and P=O or P=S linkages are prepared as described in U.S. Pat. Nos. 5,378,825, 5,386,023, 5,489,677, 5,602,240 and 5,610,289, all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

Example 4
PNA Synthesis

Peptide nucleic acids (PNAs) are prepared in accordance with any of the various procedures referred to in Peptide Nucleic Acids (PNA): Synthesis, Properties and Potential Applications, *Bioorganic & Medicinal Chemistry*, 1996, 4, 5–23. They may also be prepared in accordance with U.S. Pat. Nos. 5,539,082, 5,700,922, and 5,719,262, herein incorporated by reference.

Example 5
Synthesis of Chimeric Oligonucleotides

Chimeric oligonucleotides, oligonucleosides or mixed oligonucleotides/oligonucleosides of the invention can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers".

[2'-O-Me]-[2'-deoxy]-[2'-O-Me] Chimeric Phosphorothioate Oligonucleotides

Chimeric oligonucleotides having 2'-O-alkyl phosphorothioate and 2'-deoxy phosphorothioate oligonucleotide segments are synthesized using an Applied Biosystems automated DNA synthesizer Model 394, as above. Oligonucleotides are synthesized using the automated synthesizer and 2'-deoxy-5'-dimethoxytrityl-3'-O-phosphoramidite for the DNA portion and 5'-dimethoxytrityl-2'-O-methyl-3'-O-phosphoramidite for 5' and 3' wings. The standard synthesis cycle is modified by incorporating coupling steps with increased reaction times for the 5'-dimethoxytrityl-2'-O-methyl-3'-O-phosphoramidite. The fully protected oligonucleotide is cleaved from the support and deprotected in concentrated ammonia (NH$_4$OH) for 12–16 hr at 55° C. The deprotected oligo is then recovered by an appropriate method (precipitation, column chromatography, volume reduced in vacuo and analyzed spetrophotometrically for yield and for purity by capillary electrophoresis and by mass spectrometry.

[2'-O-(2-Methoxyethyl)]-[2'-deoxy]-[2'-O-(Methoxyethyl)] Chimeric Phosphorothioate Oligonucleotides

[2'-O-(2-methoxyethyl)]-[2'-deoxy]-[-2'-O-(methoxyethyl)] chimeric phosphorothioate oligonucleotides were prepared as per the procedure above for the 2'-O-methyl chimeric oligonucleotide, with the substitution of 2'-O-(methoxyethyl) amidites for the 2'-O-methyl amidites.

[2'-O-(2-Methoxyethyl)Phosphodiester]-[2'-deoxy Phosphorothioate]-[2'-O-(2-Methoxyethyl) Phosphodiester] Chimeric Oligonucleotides

[2'-O-(2-methoxyethyl phosphodiester]-[2'-deoxy phosphorothioate]-[2'-O-(methoxyethyl) phosphodiester] chimeric oligonucleotides are prepared as per the above procedure for the 2'-O-methyl chimeric oligonucleotide with the substitution of 2'-O-(methoxyethyl) amidites for the 2'-O-methyl amidites, oxidation with iodine to generate the phosphodiester internucleotide linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides are synthesized according to U.S. Pat. No. 5,623,065, herein incorporated by reference.

Example 6
Oligonucleotide Isolation

After cleavage from the controlled pore glass solid support and deblocking in concentrated ammonium hydroxide at 55° C. for 12–16 hours, the oligonucleotides or oligonucleosides are recovered by precipitation out of 1 M NH$_4$OAc with >3 volumes of ethanol. Synthesized oligonucleotides were analyzed by electrospray mass spectroscopy (molecular weight determination) and by capillary gel electrophoresis and judged to be at least 70% full length material. The relative amounts of phosphorothioate and phosphodiester linkages obtained in the synthesis was determined by the ratio of correct molecular weight relative to the −16 amu product (±32±48). For some studies oligonucleotides were purified by HPLC, as described by Chiang et al., *J. Biol. Chem.* 1991, 266, 18162–18171. Results obtained with HPLC-purified material were similar to those obtained with non-HPLC purified material.

Example 7
Oligonucleotide Synthesis—96 Well Plate Format

Oligonucleotides were synthesized via solid phase P(III) phosphoramidite chemistry on an automated synthesizer capable of assembling 96 sequences simultaneously in a 96-well format. Phosphodiester internucleotide linkages were afforded by oxidation with aqueous iodine. Phosphorothioate internucleotide linkages were generated by sulfurization utilizing 3,H-1,2 benzodithiole-3-one 1,1 dioxide (Beaucage Reagent) in anhydrous acetonitrile. Standard base-protected beta-cyanoethyl-diiso-propyl phosphoramidites were purchased from commercial vendors (e.g. PE-Applied Biosystems, Foster City, Calif., or Pharmacia, Piscataway, N.J.). Non-standard nucleosides are synthesized as per standard or patented methods. They are utilized as base protected beta-cyanoethyldiisopropyl phosphoramidites.

Oligonucleotides were cleaved from support and deprotected with concentrated NH$_4$OH at elevated temperature (55–60° C.) for 12–16 hours and the released product then dried in vacuo. The dried product was then re-suspended in sterile water to afford a master plate from which all analytical and test plate samples are then diluted utilizing robotic pipettors.

Example 8
Oligonucleotide Analysis—96-Well Plate Format

The concentration of oligonucleotide in each well was assessed by dilution of samples and UV absorption spectroscopy. The full-length integrity of the individual products was evaluated by capillary electrophoresis (CE) in either the 96-well format (Beckman P/ACE™ MDQ) or, for individually prepared samples, on a commercial CE apparatus (e.g., Beckman P/ACE™ 5000, ABI 270). Base and backbone composition was confirmed by mass analysis of the compounds utilizing electrospray-mass spectroscopy. All assay test plates were diluted from the master plate using single and multi-channel robotic pipettors. Plates were judged to be acceptable if at least 85% of the compounds on the plate were at least 85% full length.

Example 9
Cell Culture and Oligonucleotide Treatment

The effect of antisense compounds on target nucleic acid expression can be tested in any of a variety of cell types provided that the target nucleic acid is present at measurable levels. This can be routinely determined using, for example, PCR or Northern blot analysis. The following cell types are provided for illustrative purposes, but other cell types can be routinely used, provided that the target is expressed in the cell type chosen. This can be readily determined by methods routine in the art, for example Northern blot analysis, ribonuclease protection assays, or RT-PCR.

T-24 Cells:

The human transitional cell bladder carcinoma cell line T-24 was obtained from the American Type Culture Collection (ATCC) (Manassas, Va.). T-24 cells were routinely cultured in complete McCoy's 5A basal media (Invitrogen Corporation, Carlsbad, Calif.) supplemented with 10% fetal calf serum (Invitrogen Corporation, Carlsbad, Calif.), penicillin 100 units per mL, and streptomycin 100 micrograms per mL (Invitrogen Corporation, Carlsbad, Calif.). Cells were routinely passaged by trypsinization and dilution when they reached 90% confluence. Cells were seeded into 96-well plates (Falcon-Primaria #3872) at a density of 7000 cells/well for use in RT-PCR analysis.

For Northern blotting or other analysis, cells may be seeded onto 100 mm or other standard tissue culture plates and treated similarly, using appropriate volumes of medium and oligonucleotide.

A549 Cells:

The human lung carcinoma cell line A549 was obtained from the American Type Culture Collection (ATCC) (Manassas, Va.). A549 cells were routinely cultured in DMEM basal media (Invitrogen Corporation, Carlsbad, Calif.) supplemented with 10% fetal calf serum (Invitrogen Corporation, Carlsbad, Calif.), penicillin 100 units per mL, and streptomycin 100 micrograms per mL (Invitrogen Corporation, Carlsbad, Calif.). Cells were routinely passaged by trypsinization and dilution when they reached 90% confluence.

NHDF Cells:

Human neonatal dermal fibroblast (NHDF) were obtained from the Clonetics Corporation (Walkersville, Md.). NHDFs were routinely maintained in Fibroblast Growth Medium (Clonetics Corporation, Walkersville, Md.) supplemented as recommended by the supplier. Cells were maintained for up to 10 passages as recommended by the supplier.

HEK Cells:

Human embryonic keratinocytes (HEK) were obtained from the Clonetics Corporation (Walkersville, Md.). HEKs were routinely maintained in Keratinocyte Growth Medium (Clonetics Corporation, Walkersville, Md.) formulated as recommended by the supplier. Cells were routinely maintained for up to 10 passages as recommended by the supplier.

Treatment with Antisense Compounds:

When cells reached 70% confluency, they were treated with oligonucleotide. For cells grown in 96-well plates, wells were washed once with 100 μL OPTI-MEM™-1 reduced-serum medium (Invitrogen Corporation, Carlsbad, Calif.) and then treated with 130 μL of OPTI-MEM™-1 containing 3.75 μg/mL LIPOFECTIN™ (Invitrogen Corporation, Carlsbad, Calif.) and the desired concentration of oligonucleotide. After 4–7 hours of treatment, the medium was replaced with fresh medium. Cells were harvested 16–24 hours after oligonucleotide treatment.

The concentration of oligonucleotide used varies from cell line to cell line. To determine the optimal oligonucleotide concentration for a particular cell line, the cells are treated with a positive control oligonucleotide at a range of concentrations. For human cells the positive control oligonucleotide is selected from either ISIS 13920 (TCCGTCATCGCTCCTCAGGG, SEQ ID NO: 1) which is targeted to human H-ras, or ISIS 18078, (GTGCGCGCGAGCCCGAAATC, SEQ ID NO: 2) which is targeted to human Jun-N-terminal kinase-2 (JNK2). Both controls are 2'-O-methoxyethyl gapmers (2'-O-methoxyethyls shown in bold) with a phosphorothioate backbone. For mouse or rat cells the positive control oligonucleotide is ISIS 15770, ATGCATTCTGCCCCCAAGGA, SEQ ID NO: 3, a 2'-O-methoxyethyl gapmer (2'-O-methoxyethyls shown in bold) with a phosphorothioate backbone which is targeted to both mouse and rat c-raf. The concentration of positive control oligonucleotide that results in 80% inhibition of c-Ha-ras (for ISIS 13920) or c-raf (for ISIS 15770) mRNA is then utilized as the screening concentration for new oligonucleotides in subsequent experiments for that cell line. If 80% inhibition is not achieved, the lowest concentration of positive control oligonucleotide that results in 60% inhibition of H-ras or c-raf mRNA is then utilized as the oligonucleotide screening concentration in subsequent experiments for that cell line. If 60% inhibition is not achieved, that particular cell line is deemed as unsuitable for oligonucleotide transfection experiments. The concentrations of antisense oligonucleotides used herein are from 50 nM to 300 nM.

Example 10
Analysis of Oligonucleotide Inhibition of PTPN12 Expression

Antisense modulation of PTPN12 expression can be assayed in a variety of ways known in the art. For example, PTPN12 mRNA levels can be quantitated by, e.g., Northern blot analysis, competitive polymerase chain reaction (PCR), or real-time PCR (RT-PCR). Real-time quantitative PCR is presently preferred. RNA analysis can be performed on total cellular RNA or poly(A)+ mRNA. The preferred method of RNA analysis of the present invention is the use of total cellular RNA as described in other examples herein. Methods of RNA isolation are taught in, for example, Ausubel, F. M. et al., *Current Protocols in Molecular Biology*, Volume 1, pp. 4.1.1–4.2.9 and 4.5.1–4.5.3, John Wiley & Sons, Inc., 1993. Northern blot analysis is routine in the art and is taught in, for example, Ausubel, F. M. et al., *Current Protocols in Molecular Biology*, Volume 1, pp. 4.2.1–4.2.9, John Wiley & Sons, Inc., 1996. Real-time quantitative (PCR) can be conveniently accomplished using the commercially available ABI PRISM™ 7700 Sequence Detection System, available from PE-Applied Biosystems, Foster City, Calif. and used according to manufacturer's instructions.

Protein levels of PTPN12 can be quantitated in a variety of ways well known in the art, such as immunoprecipitation, Western blot analysis (immunoblotting), ELISA or fluorescence-activated cell sorting (FACS). Antibodies directed to PTPN12 can be identified and obtained from a variety of sources, such as the MSRS catalog of antibodies (Aerie Corporation, Birmingham, Mich.), or can be prepared via conventional antibody generation methods. Methods for preparation of polyclonal antisera are taught in, for example, Ausubel, F. M. et al., (*Current Protocols in Molecular Biology*, Volume 2, pp. 11.12.1–11.12.9, John Wiley & Sons, Inc., 1997). Preparation of monoclonal antibodies is taught in, for example, Ausubel, F. M. et al., (*Current Protocols in Molecular Biology*, Volume 2, pp. 11.4.1–11.11.5, John Wiley & Sons, Inc., 1997).

Immunoprecipitation methods are standard in the art and can be found at, for example, Ausubel, F. M. et al., (*Current Protocols in Molecular Biology*, Volume 2, pp. 10.16.1–10.16.11, John Wiley & Sons, Inc., 1998). Western blot (immunoblot) analysis is standard in the art and can be found at, for example, Ausubel, F. M. et al., (*Current Protocols in Molecular Biology*, Volume 2, pp. 10.8.1–10.8.21, John Wiley & Sons, Inc., 1997). Enzyme-linked immunosorbent assays (ELISA) are standard in the art and can be found at, for example, Ausubel, F. M. et al., (*Current Protocols in Molecular Biology*, Volume 2, pp. 11.2.1–11.2.22, John Wiley & Sons, Inc., 1991).

Example 11
Poly(A)+ mRNA Isolation

Poly(A)+ mRNA was isolated according to Miura et al., (*Clin. Chem.*, 1996, 42, 1758–1764). Other methods for poly(A)+ mRNA isolation are taught in, for example, Ausubel, F. M. et al., (*Current Protocols in Molecular Biology*, Volume 1, pp. 4.5.1–4.5.3, John Wiley & Sons, Inc., 1993). Briefly, for cells grown on 96-well plates, growth medium was removed from the cells and each well was washed with 200 µL cold PBS. 60 µL lysis buffer (10 mM Tris-HCl, pH 7.6, 1 mM EDTA, 0.5 M NaCl, 0.5% NP-40, 20 mM vanadyl-ribonucleoside complex) was added to each well, the plate was gently agitated and then incubated at room temperature for five minutes. 55 µL of lysate was transferred to Oligo d(T) coated 96-well plates (AGCT Inc., Irvine Calif.). Plates were incubated for 60 minutes at room temperature, washed 3 times with 200 µL of wash buffer (10 mM Tris-HCl pH 7.6, 1 mM EDTA, 0.3 M NaCl). After the final wash, the plate was blotted on paper towels to remove excess wash buffer and then air-dried for 5 minutes. 60 µL of elution buffer (5 mM Tris-HCl pH 7.6), preheated to 70° C., was added to each well, the plate was incubated on a 90° C. hot plate for 5 minutes, and the eluate was then transferred to a fresh 96-well plate.

Cells grown on 100 mm or other standard plates may be treated similarly, using appropriate volumes of all solutions.

Example 12
Total RNA Isolation

Total RNA was isolated using an RNEASY 96™ kit and buffers purchased from Qiagen Inc. (Valencia, Calif.) following the manufacturer's recommended procedures. Briefly, for cells grown on 96-well plates, growth medium was removed from the cells and each well was washed with 200 µL cold PBS. 150 µL Buffer RLT was added to each well and the plate vigorously agitated for 20 seconds. 150 µL of 70% ethanol was then added to each well and the contents mixed by pipetting three times up and down. The samples were then transferred to the RNEASY 96™ well plate attached to a QIAVAC™ manifold fitted with a waste collection tray and attached to a vacuum source. Vacuum was applied for 1 minute. 500 µL of Buffer RW1 was added to each well of the RNEASY 96™ plate and incubated for 15 minutes and the vacuum was again applied for 1 minute. An additional 500 µL of Buffer RW1 was added to each well of the RNEASY 96™ plate and the vacuum was applied for 2 minutes. 1 mL of Buffer RPE was then added to each well of the RNEASY 96™ plate and the vacuum applied for a period of 90 seconds. The Buffer RPE wash was then repeated and the vacuum was applied for an additional 3 minutes. The plate was then removed from the QIAVAC™ manifold and blotted dry on paper towels. The plate was then re-attached to the QIAVAC™ manifold fitted with a collection tube rack containing 1.2 mL collection tubes. RNA was then eluted by pipetting 170 µL water into each well, incubating 1 minute, and then applying the vacuum for 3 minutes.

The repetitive pipetting and elution steps may be automated using a QIAGEN Bio-Robot 9604 (Qiagen, Inc., Valencia, Calif.). Essentially, after lysing of the cells on the culture plate, the plate is transferred to the robot deck where the pipetting, DNase treatment and elution steps are carried out.

Example 13
Real-Time Quantitative PCR Analysis of PTPN12 mRNA Levels

Quantitation of PTPN12 mRNA levels was determined by real-time quantitative PCR using the ABI PRISM™ 7700 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., FAM or JOE, obtained from either PE-Applied Biosystems, Foster City, Calif., Operon Technologies Inc., Alameda, Calif. or Integrated DNA Technologies Inc., Coralville, Iowa) is attached to the 5' end of the probe and a quencher dye (e.g., TAMRA, obtained from either PE-Applied Biosystems, Foster City, Calif., Operon Technologies Inc., Alameda, Calif. or Integrated DNA Technologies Inc., Coralville, Iowa) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ 7700 Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

PCR reagents were obtained from Invitrogen Corporation, (Carlsbad, Calif.). RT-PCR reactions were carried out by adding 20 μL PCR cocktail (2.5× PCR buffer (—MgCl2), 6.6 mM MgCl2, 375 μM each of dATP, dCTP, dCTP and dGTP, 375 nM each of forward primer and reverse primer, 125 nM of probe, 4 Units RNAse inhibitor, 1.25 Units PLATINUM® Taq, 5 Units MuLV reverse transcriptase, and 2.5× ROX dye) to 96-well plates containing 30 μL total RNA solution. The RT reaction was carried out by incubation for 30 minutes at 48° C. Following a 10 minute incubation at 95° C. to activate the PLATINUM® Taq, 40 cycles of a two-step PCR protocol were carried out: 95° C. for 15 seconds (denaturation) followed by 60° C. for 1.5 minutes (annealing/extension).

Gene target quantities obtained by real time RT-PCR are normalized using either the expression level of GAPDH, a gene whose expression is constant, or by quantifying total RNA using RiboGreen™ (Molecular Probes, Inc. Eugene, Oreg.). GAPDH expression is quantified by real time RT-PCR, by being run simultaneously with the target, multiplexing, or separately. Total RNA is quantified using RiboGreen™ RNA quantification reagent from Molecular Probes. Methods of RNA quantification by RiboGreen™ are taught in Jones, L. J., et al, (Analytical Biochemistry, 1998, 265, 368–374).

In this assay, 170 μL of RiboGreen™ working reagent (RiboGreen™ reagent diluted 1:350 in 10 mM Tris-HCl, 1 mM EDTA, pH 7.5) is pipetted into a 96-well plate containing 30 μL purified, cellular RNA. The plate is read in a CytoFluor 4000 (PE Applied Biosystems) with excitation at 480 nm and emission at 520 nm.

Probes and primers to human PTPN12 were designed to hybridize to a human PTPN12 sequence, using published sequence information (GenBank accession number M93425.1, incorporated herein as SEQ ID NO: 4). For human PTPN12 the PCR primers were:

forward primer: TGCAGCCACCGGAACCT (SEQ ID NO: 5)
reverse primer: AGTAGTGACTGTTGGAAAAGCT-GAAG (SEQ ID NO: 6) and
the PCR probe was: FAM-ATCCAGTGCCACCCATCTTGACACCTT-TAMRA (SEQ ID NO: 7) where FAM is the fluorescent dye and TAMRA is the quencher dye. For human GAPDH the PCR primers were:

forward primer: GAAGGTGAAGGTCGGAGTC (SEQ ID NO: 8)
reverse primer: GAAGATGGTGATGGGATTTC (SEQ ID NO: 9) and the
PCR probe was: 5' JOE-CAAGCTTCCCGTTCTCAGCC-TAMRA 3' (SEQ ID NO: 10) where JOE is the fluorescent reporter dye and TAMRA is the quencher dye.

Example 14
Northern Blot Analysis of PTPN12 mRNA Levels

Eighteen hours after antisense treatment, cell monolayers were washed twice with cold PBS and lysed in 1 mL RNAZOL™ (TEL-TEST "B" Inc., Friendswood, Tex.). Total RNA was prepared following manufacturer's recommended protocols. Twenty micrograms of total RNA was fractionated by electrophoresis through 1.2% agarose gels containing 1.1% formaldehyde using a MOPS buffer system (AMRESCO, Inc. Solon, Ohio). RNA was transferred from the gel to HYBOND™-N+ nylon membranes (Amersham Pharmacia Biotech, Piscataway, N.J.) by overnight capillary transfer using a Northern/Southern Transfer buffer system (TEL-TEST "B" Inc., Friendswood, Tex.). RNA transfer was confirmed by UV visualization. Membranes were fixed by UV cross-linking using a STRATALINKER™ UV Crosslinker 2400 (Stratagene, Inc, La Jolla, Calif.) and then probed using QUICKHYB™ hybridization solution (Stratagene, La Jolla, Calif.) using manufacturer's recommendations for stringent conditions.

To detect human PTPN12, a human PTPN12 specific probe was prepared by PCR using the forward primer TGCAGCCACCGGAACCT (SEQ ID NO: 5) and the reverse primer AGTAGTGACTGTTGGAAAAGCTGAAG (SEQ ID NO: 6). To normalize for variations in loading and transfer efficiency membranes were stripped and probed for human glyceraldehyde-3-phosphate dehydrogenase (GAPDH) RNA (Clontech, Palo Alto, Calif.).

Hybridized membranes were visualized and quantitated using a PHOSPHORIMAGER™ and IMAGEQUANT™ Software V3.3 (Molecular Dynamics, Sunnyvale, Calif.). Data was normalized to GAPDH levels in untreated controls.

Example 15
Antisense Inhibition of Human PTPN12 Expression by Chimeric Phosphorothioate Oligonucleotides Having 2'-MOE Wings and a Deoxy Gap In accordance with the present invention, a series of oligonucleotides were designed to target different regions of the human PTPN12 RNA, using published sequences (GenBank accession number M93425.1, incorporated herein as SEQ ID NO: 4; residues 1–137000 of GenBank accession number AC006451.5, incorporated herein as SEQ ID NO: 11; GenBank accession number AI341063.1, the complement of which is incorporated herein as SEQ ID NO: 12, GenBank accession number BG829296.1, incorporated herein as SEQ ID NO: 13, GenBank accession number BF735405.1, the complement of which is incorporated herein as SEQ ID NO: 14, and GenBank accession number AL119248.1, incorporated herein as SEQ ID NO: 15). The oligonucleotides are shown in Table 1. "Target site" indicates the first (5'-most) nucleotide number on the particular target sequence to which the oligonucleotide binds. All compounds in Table 1 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE) nucleotides. The internucleoside (backbone) linkages are phosphorothioate (P=S) throughout the oligonucleotide. All cytidine residues are 5-methylcytidines. The compounds were analyzed for their effect on human PTPN12 mRNA levels by quantitative real-time PCR as described in other examples herein. Data are averages from two experiments in which T-24 cells were treated with the oligonucleotides of the present invention. The positive control for each datapoint is identified in the table by sequence ID number. If present, "N.D." indicates "no data".

TABLE 1

Inhibition of human PTPN12 mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO | CONTROL SEQ ID NO |
|---|---|---|---|---|---|---|---|
| 154857 | Coding | 4 | 406 | ggccattacaatgatcacaa | 57 | 16 | 2 |
| 154858 | 3'UTR | 4 | 2558 | aatacttgaagtttcaaaat | 0 | 17 | 2 |
| 154859 | Coding | 4 | 1771 | agtgttatcatgatccacaa | 79 | 18 | 2 |
| 154860 | Coding | 4 | 2348 | tccattctgaaggtggatct | 56 | 19 | 2 |
| 154861 | Coding | 4 | 574 | cctacgagattcattttgaa | 21 | 20 | 2 |
| 154862 | Coding | 4 | 122 | atcttcttaaccgcatgaag | 36 | 21 | 2 |
| 154863 | Coding | 4 | 983 | tggagctgatcatgttttca | 8 | 22 | 2 |
| 154864 | 3'UTR | 4 | 2992 | aatctctgactagatgaaaa | 33 | 23 | 2 |
| 154865 | Coding | 4 | 1112 | gtgtcaagatgggtggcact | 72 | 24 | 2 |
| 154866 | Coding | 4 | 576 | agcctacgagattcattttg | 65 | 25 | 2 |
| 154867 | Coding | 4 | 1715 | ttaaactcacagttttccta | 55 | 26 | 2 |
| 154868 | 3'UTR | 4 | 2392 | ttttccagtataacttaaag | 0 | 27 | 2 |
| 154869 | Coding | 4 | 1047 | tcaacaaggcaactgcgggt | 40 | 28 | 2 |
| 154870 | Coding | 4 | 1354 | ttttggtccctcttggagag | 2 | 29 | 2 |
| 154871 | Coding | 4 | 985 | tatggagctgatcatgtttt | 14 | 30 | 2 |
| 154872 | 3'UTR | 4 | 2571 | acattaaggcaataatactt | 0 | 31 | 2 |
| 154873 | Coding | 4 | 1494 | caagaattctgggaagtatc | 39 | 32 | 2 |
| 154874 | Coding | 4 | 656 | ttaagcttatcatgtccaga | 50 | 33 | 2 |
| 154875 | Coding | 4 | 2116 | aagttcactccattccgatc | 0 | 34 | 2 |
| 154876 | Coding | 4 | 322 | tacatatgcttttggcccat | 34 | 35 | 2 |
| 154877 | Coding | 4 | 1476 | tcaccgacatttagatctga | 67 | 36 | 2 |
| 154878 | Coding | 4 | 993 | tcaggctctatggagctgat | 68 | 37 | 2 |
| 154879 | Coding | 4 | 106 | gaagtcccgggcgaagttgt | 29 | 38 | 2 |
| 154880 | 3'UTR | 4 | 2650 | agtagtccttaaactcaata | 42 | 39 | 2 |
| 154881 | Coding | 4 | 1184 | ctggctttggatggtatcta | 74 | 40 | 2 |
| 154882 | Coding | 4 | 2317 | gggttttccacatcgattac | 52 | 41 | 2 |
| 154883 | Coding | 4 | 630 | tcaaatgatgaaggaacatc | 31 | 42 | 2 |
| 154884 | Coding | 4 | 2012 | caacatcttttcagcacct | 21 | 43 | 2 |
| 154885 | Coding | 4 | 2134 | agatcgttcctgactttgaa | 46 | 44 | 2 |
| 154886 | 3'UTR | 4 | 2862 | tggctgcatgaatccagcaa | 60 | 45 | 2 |
| 154887 | 3'UTR | 4 | 2766 | tgcagaaatttcttacatct | 66 | 46 | 2 |
| 154888 | Coding | 4 | 1861 | cacagcaccatcagagtttc | 43 | 47 | 2 |
| 154889 | Coding | 4 | 597 | ttcacataatgaaactgata | 53 | 48 | 2 |
| 154890 | Coding | 4 | 1785 | ctgaagagtggtgaagtgtt | 0 | 49 | 2 |
| 154891 | 3'UTR | 4 | 2453 | gctgttagtcccacatatta | 65 | 50 | 2 |
| 154892 | Coding | 4 | 853 | ctcctttgtttgtactgcag | 0 | 51 | 2 |

TABLE 1-continued

Inhibition of human PTPN12 mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO | CONTROL SEQ ID NO |
|---|---|---|---|---|---|---|---|
| 154893 | Coding | 4 | 1505 | tgcagtccacacaagaattc | 63 | 52 | 2 |
| 195303 | Start Codon | 4 | 27 | atctccacttgctccatcct | 31 | 53 | 2 |
| 195304 | Coding | 4 | 167 | cagtggctgtgggatatatc | 72 | 54 | 2 |
| 195305 | Coding | 4 | 228 | ctgtgatcaaatggcagtat | 20 | 55 | 2 |
| 195306 | Coding | 4 | 281 | cattgatatagtctgaatct | 51 | 56 | 2 |
| 195307 | Coding | 4 | 512 | gttcatcctcacaagaaatt | 47 | 57 | 2 |
| 195308 | Coding | 4 | 926 | ctccatgaatttcatatagt | 36 | 58 | 2 |
| 195309 | Coding | 4 | 1205 | ctgatgaaaccatatgcaac | 58 | 59 | 2 |
| 195310 | Coding | 4 | 1436 | agattttatcagctatacaa | 69 | 60 | 2 |
| 195311 | Coding | 4 | 1686 | ttgatatctgaggaattgcc | 56 | 61 | 2 |
| 195312 | Coding | 4 | 1831 | gtctgagtcatcagagtgaa | 79 | 62 | 2 |
| 195313 | Coding | 4 | 1935 | gtagaaatgctttcagtact | 71 | 63 | 2 |
| 195314 | Coding | 4 | 2203 | aatacctcccgctggatgat | 21 | 64 | 2 |
| 195315 | Stop Codon | 4 | 2361 | tccctgaatcatgtccattc | 58 | 65 | 2 |
| 195316 | 3'UTR | 4 | 2822 | tttctaaaactccagggcaa | 58 | 66 | 2 |
| 195317 | Exon: Intron Junction | 11 | 33669 | agagactcaccatgaagtcc | 11 | 67 | 2 |
| 195318 | Intron | 11 | 41347 | ttagcctacagatgctgcca | 81 | 68 | 2 |
| 195319 | Intron | 11 | 48650 | aaataatttaaagattcctg | 0 | 69 | 2 |
| 195320 | Intron | 11 | 64331 | acattattgagaaatgtgca | 30 | 70 | 2 |
| 195321 | Exon: Intron Junction | 11 | 67210 | tccaacttacatggcagtat | 23 | 71 | 2 |
| 195322 | Intron: Exon Junction | 11 | 106788 | ctggtattttctaaaacaga | 45 | 72 | 2 |
| 195323 | Intron | 11 | 122116 | taatgacaagcacacatagt | 14 | 73 | 2 |
| 195324 | Exon: Intron | 11 | 128449 | agacactcactatgttcact | 49 | 74 | 2 |
| 195325 | Genomic | 12 | 56 | gtcggtcatcttgctttgtg | 0 | 75 | 2 |
| 195326 | Genomic | 12 | 122 | ggagcatgtctgtggaagag | 0 | 76 | 2 |
| 195327 | Exon: Exon Junction | 12 | 211 | gctccctcctgaagagtgag | 0 | 77 | 2 |
| 195328 | Exon: Exon Junction | 13 | 89 | ccaggtccagcatgaagtcc | 6 | 78 | 2 |
| 195329 | Coding | 13 | 148 | ggttcaagcaattcttgtgc | 19 | 79 | 2 |
| 195330 | Coding | 13 | 204 | tgcccaggctggagtgcagt | 32 | 80 | 2 |

TABLE 1-continued

Inhibition of human PTPN12 mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO | CONTROL SEQ ID NO |
|---|---|---|---|---|---|---|---|
| 195331 | Exon: Exon Junction | 13 | 258 | ttcttaaccgcacagcactt | 0 | 81 | 2 |
| 195332 | Intron | 14 | 279 | taaaacctgtgtaacatcaa | 11 | 82 | 2 |
| 195333 | Intron | 14 | 302 | ttactaacatattaatgcag | 48 | 83 | 2 |
| 195334 | 5'UTR | 15 | 262 | acatgccaaatacctaaggg | 57 | 84 | 2 |
| 195335 | 5'UTR | 15 | 286 | gccaacacttattgactgtt | 39 | 85 | 2 |
| 195336 | 3'UTR | 15 | 712 | cacatcaacttacaaggccc | 75 | 86 | 2 |
| 195337 | 3'UTR | 15 | 783 | actattttcaaatagatgat | 10 | 87 | 2 |

As shown in Table 1, SEQ ID NOs 16, 18, 19, 24, 25, 26, 28, 33, 36, 37, 39, 40, 41, 44, 45, 46, 47, 48, 50, 52, 54, 56, 57, 59, 60, 61, 62, 63, 65, 66, 68, 72, 74, 83, 84 and 86 demonstrated at least 40% inhibition of human PTPN12 expression in this assay and are therefore preferred. The target sites to which these preferred sequences are complementary are herein referred to as "preferred target regions" and are therefore preferred sites for targeting by compounds of the present invention. These preferred target regions are shown in Table 2. The sequences represent the reverse complement of the preferred antisense compounds shown in Table 1. "Target site" indicates the first (5'-most) nucleotide number of the corresponding target nucleic acid. Also shown in Table 2 is the species in which each of the preferred target regions was found.

TABLE 2

Sequence and position of preferred target regions identified in PTPN12.

| SITEID | TARGET SEQ ID NO | TARGET SITE | SEQUENCE | REV COMP OF SEQ ID | ACTIVE IN | SEQ ID NO |
|---|---|---|---|---|---|---|
| 70358 | 4 | 406 | ttgtgatcattgtaatggcc | 16 | H. sapiens | 88 |
| 70360 | 4 | 1771 | ttgtggatcatgataacact | 18 | H. sapiens | 89 |
| 70361 | 4 | 2348 | agatccaccttcagaatgga | 19 | H. sapiens | 90 |
| 70366 | 4 | 1112 | agtgccacccatcttgacac | 24 | H. sapiens | 91 |
| 70367 | 4 | 576 | caaaatgaatctcgtaggct | 25 | H. sapiens | 92 |
| 70368 | 4 | 1715 | taggaaaactgtgagtttaa | 26 | H. sapiens | 93 |
| 70370 | 4 | 1047 | acccgcagttgccttgttga | 28 | H. sapiens | 94 |
| 70375 | 4 | 656 | tctggacatgataagcttaa | 33 | H. sapiens | 95 |
| 70378 | 4 | 1476 | tcagatctaaatgtcggtga | 36 | H. sapiens | 96 |
| 70379 | 4 | 993 | atcagctccatagagcctga | 37 | H. sapiens | 97 |
| 70381 | 4 | 2650 | tattgagtttaaggactact | 39 | H. sapiens | 98 |
| 70382 | 4 | 1184 | tagataccatccaaagccag | 40 | H. sapiens | 99 |
| 70383 | 4 | 2317 | gtaatcgatgtggaaaaccc | 41 | H. sapiens | 100 |
| 70386 | 4 | 2134 | ttcaaagtcaggaacgatct | 44 | H. sapiens | 101 |
| 70387 | 4 | 2862 | ttgctggattcatgcagcca | 45 | H. sapiens | 102 |
| 70388 | 4 | 2766 | agatgtaagaaatttctgca | 46 | H. sapiens | 103 |
| 70389 | 4 | 1861 | gaaactctgatggtgctgtg | 47 | H. sapiens | 104 |

TABLE 2-continued

Sequence and position of preferred target regions identified in PTPN12.

| SITEID | TARGET SEQ ID NO | TARGET SITE | SEQUENCE | REV COMP OF SEQ ID | ACTIVE IN | SEQ ID NO |
|---|---|---|---|---|---|---|
| 70390 | 4 | 597 | tatcagtttcattatgtgaa | 48 | H. sapiens | 105 |
| 70392 | 4 | 2453 | taatatgtgggactaacagc | 50 | H. sapiens | 106 |
| 70394 | 4 | 1505 | gaattcttgtgtggactgca | 52 | H. sapiens | 107 |
| 113396 | 4 | 167 | gatatatcccacagccactg | 54 | H. sapiens | 108 |
| 113398 | 4 | 281 | agattcagactatatcaatg | 56 | H. sapiens | 109 |
| 113399 | 4 | 512 | aatttcttgtgaggatgaac | 57 | H. sapiens | 110 |
| 113401 | 4 | 1205 | gttgcatatggtttcatcag | 59 | H. sapiens | 111 |
| 113402 | 4 | 1436 | ttgtatagctgataaaatct | 60 | H. sapiens | 112 |
| 113403 | 4 | 1686 | ggcaattcctcagatatcaa | 61 | H. sapiens | 113 |
| 113404 | 4 | 1831 | ttcactctgatgactcagac | 62 | H. sapiens | 114 |
| 113405 | 4 | 1935 | agtactgaaagcatttctac | 63 | H. sapiens | 115 |
| 113407 | 4 | 2361 | gaatggacatgattcaggga | 65 | H. sapiens | 116 |
| 113408 | 4 | 2822 | ttgccctggagttttagaaa | 66 | H. sapiens | 117 |
| 113410 | 11 | 41347 | tggcagcatctgtaggctaa | 68 | H. sapiens | 118 |
| 113414 | 11 | 106788 | tctgttttagaaaataccag | 72 | H. sapiens | 119 |
| 113416 | 11 | 128449 | agtgaacatagtgagtgtct | 74 | H. sapiens | 120 |
| 113425 | 14 | 302 | ctgcattaatatgttagtaa | 83 | H. sapiens | 121 |
| 113426 | 15 | 262 | cccttaggtatttggcatgt | 84 | H. sapiens | 122 |
| 113428 | 15 | 712 | gggccttgtaagttgatgtg | 86 | H. sapiens | 123 |

As these "preferred target regions" have been found by experimentation to be open to, and accessible for, hybridization with the antisense compounds of the present invention, one of skill in the art will recognize or be able to ascertain, using no more than routine experimentation, further embodiments of the invention that encompass other compounds that specifically hybridize to these sites and consequently inhibit the expression of PTPN12.

Example 16
Western Blot Analysis of PTPN12 Protein Levels

Western blot analysis (immunoblot analysis) is carried out using standard methods. Cells are harvested 16–20 h after oligonucleotide treatment, washed once with PBS, suspended in Laemmli buffer (100 ul/well), boiled for 5 minutes and loaded on a 16% SDS-PAGE gel. Gels are run for 1.5 hours at 150 V, and transferred to membrane for western blotting. Appropriate primary antibody directed to PTPN12 is used, with a radiolabeled or fluorescently labeled secondary antibody directed against the primary antibody species. Bands are visualized using a PHOSPHORIMAGER™ (Molecular Dynamics, Sunnyvale, Calif.).

What is claimed is:

1. A compound 20 to 80 nucleobases in length targeted to nucleobases 1771 through 1790 of a coding region of a nucleic acid molecule encoding human PTPN12 (SEQ ID NO: 4), wherein said compound comprises at least one modified internucleoside linkage, sugar moiety or nucleobase and specifically hybridizes with said region and inhibits the expression of human PTPN12.

2. The compound of claim 1 which is an antisense oligonucleotide.

3. The compound of claim 2 wherein the antisense oligonucleotide comprises at least one modified internucleoside linkage.

4. The compound of claim 3 wherein the modified internucleoside linkage is a phosphorothioate linkage.

5. The compound of claim 2 wherein the antisense oligonucleotide comprises at least one modified sugar moiety.

6. The compound of claim 5 wherein the modified sugar moiety is a 2'-o-methoxyethyl sugar moiety.

7. The compound of claim 2 wherein the antisense oligonucleotide comprises at least one modified nucleobase.

8. The compound of claim 7 wherein the modified nucleobase is a 5-methylcytosine.

9. The compound of claim 2 wherein the antisense oligonucleotide is a chimeric oligonucleotide.

10. A composition comprising the compound of claim 1 and a pharmaceutically acceptable carrier or diluent.

11. The composition of claim 10 further comprising a colloidal dispersion system.

12. The composition of claim 10 wherein the compound is an antisense oligonucleotide.

* * * * *